US009169481B2

(12) United States Patent
Cornish et al.

(10) Patent No.: US 9,169,481 B2
(45) Date of Patent: Oct. 27, 2015

(54) CELL-MEDIATED DIRECTED EVOLUTION

(75) Inventors: Virginia W. Cornish, New York, NY (US); Pamela P. Perlata-Yahya, Oakland, CA (US); Jonathan Eiseman Bronson, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1069 days.

(21) Appl. No.: 12/348,693

(22) Filed: Jan. 5, 2009

(65) Prior Publication Data
US 2009/0209038 A1  Aug. 20, 2009

Related U.S. Application Data

(63) Continuation of application No. PCT/US2007/015568, filed on Jul. 5, 2007.

(60) Provisional application No. 60/891,833, filed on Feb. 27, 2007, provisional application No. 60/819,531, filed on Jul. 7, 2006, provisional application No. 60/819,532, filed on Jul. 7, 2006.

(51) Int. Cl.
  *C12N 1/19* (2006.01)
  *C12N 15/10* (2006.01)
  *C07H 21/04* (2006.01)

(52) U.S. Cl.
  CPC ........ *C12N 15/1058* (2013.01); *C12N 15/1055* (2013.01); *C12N 15/1086* (2013.01)

(58) Field of Classification Search
  None
  See application file for complete search history.

(56) References Cited

U.S. PATENT DOCUMENTS

| | | | |
|---|---|---|---|
| 5,403,484 A | | 4/1995 | Ladner et al. |
| 5,571,698 A | | 11/1996 | Ladner et al. |
| 5,733,726 A | * | 3/1998 | Fu et al. ............................. 435/5 |
| 5,780,279 A | | 7/1998 | Matthews et al. |
| 5,837,500 A | | 11/1998 | Ladner et al. |
| 6,977,150 B2 | | 12/2005 | Forster et al. |
| 7,118,879 B2 | | 10/2006 | Ladner et al. |
| 7,148,054 B2 | | 12/2006 | del Cardayre et al. |
| 7,208,293 B2 | | 4/2007 | Ladner et al. |
| 7,240,160 B1 | | 7/2007 | Hetherington et al. |
| 7,487,063 B2 | | 2/2009 | Tubic et al. |
| 7,664,989 B2 | | 2/2010 | Joshi et al. |
| 7,893,007 B2 | | 2/2011 | Ladner et al. |
| 2002/0123101 A1 | | 9/2002 | Inoue et al. |
| 2004/0106154 A1 | | 6/2004 | Cornish |

FOREIGN PATENT DOCUMENTS

| | | |
|---|---|---|
| EP | 0 436 597 B1 | 4/1997 |
| WO | WO 2005/093073 | 10/2005 |

OTHER PUBLICATIONS

Kumar et al. Genome Research, 14:1975-1986, 2004.*
Lutz S, Patrick W, *Current Opinions in Biotechnology* 15, pp. 291-297 (2004).
Park S, Xi Y, Saven JG, *Curr. Opin. Struct. Biol.* 14, pp. 487-494 (2004).
Gordon DB, Horn GK, Mayo SL, Pierce NA, *J. Comp. Chem.* 24, pp. 232-243 (2003).
Camps M, Naukkarinen J, Johnson BP, Loeb LA, *PNAS* 100, pp. 9727-9732 (2003).
Abecassis et al. "High efficiency family shuffling based on multi-step PCR and in vivo DNA recombination in yeast: statistical and functional analysis of a combinatorial library between human cytochrome P450 1A1 and 1A2" 2000, *Nucleic Acids Res.*, 28(20):E88.
Abida et al. "Receptor-dependence of the transcription read-out in a small-molecule three-hybrid system" 2002, *Chembiochem.*, 3:887-95.
Aharoni et al. "High-throughput screens and selections of enzyme-encoding genes" 2005, *Curr. Opin. Chem. Biol.*, 9: 210-16.
Aharoni et al. "High-throughput screening of enzyme libraries: thiolactonases evolved by fluorescence-activated sorting of single cells in emulsion compartments" 2005, *Chem. Biol.*, 12(12):1281-9.
Alper et al. "Engineering yeast transcription machinery for improved ethanol tolerance and production" 2006, *Science*, 314:1565-8.
Althoff et al. "A bacterial small-molecule three-hybrid system" 2002, *Angew. Chem. Int. Ed. Engl.*, 114(13):2433-6.
Arnold "Combinatorial and computational challenges for biocatalyst design" 2001, *Nature*, 409(6817):253-7.
Baker et al. "An optimized dexamethasone-methotrexate yeast 3-hybrid system for high-throughput screening of small molecule-protein interactions" 2003, *Anal. Biochem.*, 315(1):134-7.
Baker et al. "Catalytically enhanced endocellulase Cel5A from *Acidothermus cellulolyticus*" 2005, *Appl. Biochem. Biotechnol.*, 121-124:129-48.
Baker et al. "Chemical complementation: a reaction-independent genetic assay for enzyme catalysis" 2002, *Proc. Natl. Acad. Sci. U.S.A.*, 99(26):16537-42.
Barbas et al. "Deoxyribose-5-phosphate aldolase as a synthetic catalyst" 1990, *J. Am. Chem. Soc.*, 112(5):2013-14.
Bartel et al. "Isolation of new ribozymes from a large pool of random sequences" 1993, *Science*, 261(5127):1411-8.
Baudin et al. "A simple and efficient method for direct gene deletion in *Saccharomyces cerevisiae*" 1993, *Nucleic Acids Res.*, 21(14):3329-30.
Becker et al. "A three-hybrid approach to scanning the proteome for targets of small molecule kinase inhibitors" 2004, *Chem. Biol.*, 11(2):211-23.
Becker et al. "Ultra-high-throughput screening based on cell-surface display and fluorescence-activated cell sorting for the identification of novel biocatalysts" 2004, Curr. Opin. Biotechnol., 15(4):323-9.

(Continued)

*Primary Examiner* — Nancy T Vogel
(74) *Attorney, Agent, or Firm* — Baker Botts, L.L.P.

(57) ABSTRACT

The present invention relates to systems which harness the molecular biology of a living cell to direct evolution of biological entities of interest. According to the invention, a host cell is engineered to facilitate mutation of a nucleic acid target corresponding to that entity and select for desirable mutants. As applied to populations of host cells, the invention provides a means to generate and contemporaneously select mutants of interest, allowing for the production of extremely diverse libraries enriched in the most 'fit' mutants.

16 Claims, 48 Drawing Sheets

(56) References Cited

OTHER PUBLICATIONS

Figure 1:
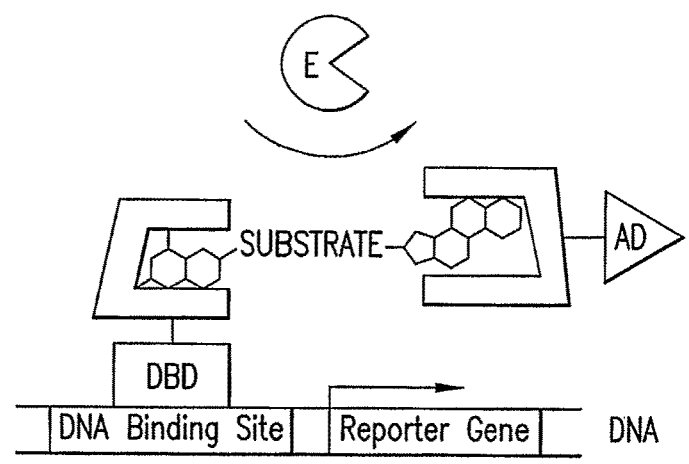

Beekwilder et al. "Production of resveratrol in recombinant microorganisms" 2006, *Appl. Environ. Microbiol.*, 72:5670-2.
Belfort et al. "Homing endonucleases: keeping the house in order" 1997, *Nucl. Acids Res.*, 25(17):3379-88.
Bell et al. "Genome sequence of the enterobacterial phytopathogen *Erwinia carotovora* subsp. atroseptica and characterization of virulence factors" 2004, *Proc. Natl. Acad. Sci. U.S.A.*, 101:11105-10.
Benkovic et al. "A perspective on enzyme catalysis" 2003, *Science*, 301(5637):1196-202.
Beste et al. "Small antibody-like proteins with prescribed ligand specificities derived from the lipocalin fold" 1999, *Proc. Natl. Acad. Sci. U.S.A.*, 96:1898-903.
Binz et al. "Engineering novel binding proteins from nonimmunoglobulin domains" 2005, *Nat. Biotechnol.*, 23(10):1257-68.
Binz et al. "High-affinity binders selected from designed ankyrin repeat protein libraries" 2004, *Nat. Biotechnol.*, 22(5):575-82.
Bloom et al. "Evolving strategies for enzyme engineering" 2005, *Curr. Opin. Struct. Biol.*, 15(4):447-52.
Bolon et al. ".Enzyme-like proteins by computational design" 2001, *Proc. Natl. Acad. Sci. U S A.*, 98:14274-9.
Braus "Aromatic amino acid biosynthesis in the yeast *Saccharomyces cerevisiae*: a model system for the regulation of a eukaryotic biosynthetic pathway" 1991, *Microbiol. Rev.*, 55(3):349-70.
Brower et al. "The synthesis of (4R-cis)-1,1-dimethylethyl 6-cyanomethyl-2, 2-dimethyl01,3-dioxane-4-acetate, a key intermediate for the preparation of CI-981, a highly potent, tissue selective inhibitor of HMG-CoA reductase" 33:2279-82, TEtrahedron Let. 1992.
Burcin et al. "A regulatory system for target gene expression" 1998, *Front. Biosci.*, 3:c1-7.
Buskirk et al. "Engineering a ligand-dependent RNA transcriptional activator" 2004, *Chem. Biol.*, 11(8):1157-63.
Buskirk et al. "In vivo evolution of an RNA-based transcriptional activator" 2003, *Chem Biol.*, 2003, 10(6):533-40.
Carter et al. "Book Review: Two-Hybrid systems methods and protocols" 2002, *ChemBioChem.*, 3(5):476-7.
Carter et al. "Investigation of the mechanism of resistance to third-generation cephalosporins by class C beta-lactamases by using chemical complementation" 2005, *Chembiochem.*, 6(11):2055-67.
Carter et al. "Yeast n-Hybrid systems for molecular evolution" 2002, *Directed Molecular Evolution of Proteins*.
Castle et al. "Discovery and directed evolution of a glyphosate tolerance gene" 2004, *Science*, 304:1151-4.
Chakraborty et al. "Analysis of the oligomerization of myogenin and E2A products in vivo using a two-hybrid assay system" 1992, *J. Biol. Chem.*, 267:17498-501.
Chen et al. "Deoxyribose-5-phosphate aldolase as a catalyst in asymmetric aldol condensation" 1992, *J.Am. Chem. Soc.*, 114(2):741-8.
Cherry et al., "Directed evolution of a fungal peroxidase" 1999, *Nat. Biotechnol.*, 17:379-84.
Chiang et al. "The structure superposition database" 2003, *Nucleic Acids Res.*, 31(1):505-10.
Chivers et al. "The CXXC motif: imperatives for the formation of native disulfide bonds in the cell" 1996, *EMBO J.*, 15: 2659-67.
Clackson "Redesigning small molecule-protein interfaces" 1998, *Curr. Opin. Struct. Biol.*, 8:451-8.
Colby et al. "Engineering antibody affinity by yeast surface display" 2004, *Methods Enzymol.*, 388:348-58.
Connolly et al. "Physical monitoring of mating type switching in *Saccharomyces cerevisiae*" 1988, *Mol. Cell. Biol.*, 8:2342-9.
Cornish "Biological chemistry: catalytic competition for cells" 2006, *Nature*, 440:156-7.
Cortajarena et al. "Protein design to understand peptide ligand recognition by tetratricopeptide repeat proteins" 2004, *Protein Eng. Des. Sel.*, 17(4):399-409.
Cosano et al. "Cloning and sequence analysis of the *Pichia pastoris* TRP1, IPP1 and HIS3 genes" 1998, *Yeast*, 14(9):861-7.
Coutinho et al. "Life with no sugars?" 1999, *J. Mol Microbiol. Biotechnol.*, 1(2):307-8.
Crout et al. "Glycosidases and glycosyl transferases in glycoside and oligosaccharide synthesis" 1998, *Curr. Opin. Chem. Biol.*, 2:98-111.
D'Costa et al. "Sampling the antibiotic resistome" 2006, *Science*, 311(5759):374-7.
Dahiyat et al. "De novo protein design: fully automated sequence selection" 1997, *Science*, 278(5335):82-7.
Danishefsky et al. "A strategy for the solid-phase synthesis of oligosaccharides" 1993, *Science*, 260:1307-9.
Davies et al. "Snapshots along an enzymatic reaction coordinate: analysis of a retaining beta-glycoside hydrolase" 1998, *Biochemistry*, 37(34):11707-13.
Davies et al. "The Enzymatic Synthesis of Glycosidic Bonds: "Glycosynthases" and Glycosyltransferases" 2001, *Trends Glycosci. Glycotechnol.*, 13(70):105-20.
Davies et al."Structure of the *Bacillus agaradherans* family 5 endoglucanase at 1.6 A and its cellobiose complex at 2.0 A resolution" 1998, *Biochemistry*, 37(7):1926-32.
de Felipe et al. "Correlation between ligand-receptor affinity and the transcription readout in a yeast three-hybrid system" 2004, *Biochemistry*, 43:10353-63.
Demartis et al. "A strategy for the isolation of catalytic activities from repertoires of enzymes displayed on phage" 1999, *J. Mol. Biol.*, 286: 617-33.
Denmark et al. "The First Catalytic, Diastereoselective, and Enantioselective Crossed-Aldol Reactions of Aldehydes We are grateful to the National Science Foundation for generous financial support (NSF CHE 9803124)" 2001, *Angew. Chem. Int. Ed. Engl.*, 40, 4759-62.
DeSantis et al. "Structure-based mutagenesis approaches toward expanding the substrate specificity of D-2-deoxyribose-5-phosphate aldolase" 2003, *Bioorg. Med. Chem.*, 11: 43-52.
Dove et al. "Activation of prokaryotic transcription through arbitrary protein-protein contacts" 1997, *Nature*, 386(6625):627-30.
Ducros et al. "Anatomy of glycosynthesis: structure and kinetics of the *humicola* insolens Ce17B E197A and E197S glycosynthase mutants" 2003, *Chem. Biol.*, 10(7):619-28.
Dwyer et al. "Computational design of a biologically active enzyme" 2004, *Science*, 304:1967-71.
Elias-Arnanz et al. "*Saccharomyces cerevisiae* mutants defective in plasmid-chromosome recombination" 1996, *Mol.Gen. Genet.*, 252:530-8.
Evans et al., 1982, *Topics in Stereochemistry*, 1-115.
Fa et al. "Expanding the substrate repertoire of a DNA polymerase by directed evolution" 2004, *J. Am. Chem. Soc.*, 126(6):1748-54.
Faijes et al. "Glycosynthase activity of *Bacillus licheniformis* 1,3-1,4-beta-glucanase mutants: specificity, kinetics, and mechanism" 2003, *Biochemistry*, 42(45):13304-18.
Faijes et al. "Oligosaccharide Synthesis by Coupled endo-Glycosynthases of Different Specificity: A Straightforward Preparation of Two Mixed-Linkage Hexasaccharide Substrates of 1,3/1,4-Glucanases" 2001, *Chem-Eur J.*, 7(21):4651-5.
Fairweather et al. "A 'glycosynthase' assisted synthesis of some epoxyalkyl β-C-oligosaccharides" 2000, *Aust. J. Chem.*, 53:913-16.
Fasullo et al. "Enhanced stimulation of chromosomal translocations and sister chromatid exchanges by either HO-induced double-strand breaks or ionizing radiation in *Saccharomyces cerevisiae* yku70 mutants" 2005, *Mutat. Res.*, 578(1-2):158-69.
Fernandez-Gacio et al. "Phage display as a tool for the directed evolution of enzymes" 2003, *Trends Biotechnol.*, 21(9):408-14.
Firestine "Using an AraC-based three-hybrid system to detect biocatalysts in vivo" 2000, *Nat. Biotechnol.*, 18(5):544-7.
Flitsch "Chemical and enzymatic synthesis of glycopolymers" 2000, *Curr. Opin. Chem. Biol.*, 4(6):619-25.
Forrest "Genetic algorithms: principles of natural selection applied to computation" 1993, *Science*, 261(5123):872-8.
Fort et al. "Highly Efficient Synthesis of β(1→4)-Oligo- and -Polysaccharides Using a Mutant Cellulase" 2000, *J. Am. Chem. Soc.*, 122(23):5429-37.
Foster "Evolutionary computation" 2001, *Nat. Rev. Genet.*, 2(6):428-36.

(56) References Cited

OTHER PUBLICATIONS

Franke et al. "Directed evolution of aldolases" 2004, *Methods Enzymol.*, 388:224-38.
Fraser-Reid et al. "Direct elaboration of pent-4-enyl glycosides into disaccharides" 1988, *J. Chem. Soc. Chem. Commun.*, 823-5.
Fraser-Reid et al. "n-Pentenyl Glycosides in Organic Chemistry: A Contemporary Example of Serendipity" 1992, *Synlett*, 927-42.
Fukuda et al. "Survival of recombinant erythropoietin in the circulation: the role of carbohydrates" 1989, *Blood*, 73(1):84-9.
Galarneau et al. "Beta-lactamase protein fragment complementation assays as in vivo and in vitro sensors of protein protein interactions" 2002, *Nat. Biotechnol.*, 20(6):619-22.
Gallagher et al. "An orthogonal dexamethasone-trimethoprim yeast three-hybrid system" 2007, *Anal. Biochem.*, 363(1):160-2.
Gendreizig et al. "Induced protein dimerization in vivo through covalent labeling" 2003, *J. Am. Chem. Soc.*, 125(49):14970-1.
Gerlt et al. "Divergent evolution of enzymatic function: mechanistically diverse superfamilies and functionally distinct suprafamilies" 2001, *Annu. Rev. Biochem.*, 70:209-46.
Gerlt et al. "Evolution of function in (beta/alpha)8-barrel enzymes" 2003, *Curr. Opin. Chem. Biol.*, 7:252-64.
Gherman et al. "Mixed quantum mechanical/molecular mechanical (QM/MM) study of the deacylation reaction in a penicillin binding protein (PBP) versus in a class C beta-lactamase" 2005, *J. Am. Chem. Soc.*, 126(24):7652-64.
Gijsen et al. "Recent Advances in the Chemoenzymatic Synthesis of Carbohydrates and Carbohydrate Mimetics" 1996, *Chem. Rev.*, 96(1):443-74.
Gijsen et al. "Sequential three and four substrate aldol reactions catalyzed by aldolases" 1995, *J. Am. Chem. Soc.*, 117(29)7585-91.
Giver et al. "Directed evolution of a thermostable esterase" 1998, *Proc. Natl. Acad. Sci. U.S.A.*, 95(22):12809-13.
Goldberg et al. "Identification of residues critical for catalysis in a class C beta-lactamase by combinatorial scanning mutagenesis" 2003, *Protein Sci.*, 12(8):1633-45.
Grabenhorst et al. "Genetic engineering of recombinant glycoproteins and the glycosylation pathway in mammalian host cells" 1999, *Glycoconj. J.*, 16(2):81-97.
Gray et al. "Bioethanol" 2006, *Curr. Opin. Chem. Biol.*, 10:141-6.
Greenberg et al. "Development of an efficient, scalable, aldolase-catalyzed process for enantioselective synthesis of statin intermediates" 2004, *Proc. Natl. Acad. Sci. U.S.A.*, 101, 5788-93.
Griffiths et al. "Directed evolution of an extremely fast phosphotriesterase by in vitro compartmentalization" 2003, *Embo. J.*, 22:24-35.
Grogan et al. "Homogeneous glycopeptides and glycoproteins for biological investigation" 2002, *Annu. Rev. Biochem.*, 71:593-634.
Groth et al. "Deoxyribose 5-phosphate aldolase. II. Purification and properties of the rat liver enzyme" 1967, *J. Biol. Chem.*, 242(1):155-9.
Hamilton "Enzymes in preparative mono- and oligo-saccharide synthesis" 2004, *Nat. Prod. Rep.*, 21:365-85.
Hamilton et al. "Humanization of yeast to produce complex terminally sialylated glycoproteins" 2006, *Science*, 313(5792):1441-3.
Hamilton et al. "Production of complex human glycoproteins in yeast" 2003, *Science*, 301:1244-6.
Haneda et al. "Chemo-enzymatic synthesis of calcitonin derivatives containing N-linked oligosaccharides" 1998, *Bioorg. Med. Chem. Lett.*, 8:1303-6.
Hanes et al. "In vitro selection and evolution of functional proteins by using ribosome display" 1997, *Proc. Natl. Acad. Sci. U.S.A.*, 94: 4937-42.
Hashimoto et al. "A Rapid and efficient synthesis of 1, 2-trans-b-linked glycosides via benzoyl-protected glycoryranoyl phospates" 1989, *J. Chem. Soc. Chem. Commun.*, 685-687.
Heathcock 1981, Comprehensive Organic Synthesis, 133.
Heathcock et al. "Stereoselective synthesis of 2-alkyl-3-hydroxy carbonyl compounds by aldol condensation" 1980, *J. Org. Chem.*, 45(6):1066-81.
Heathcock, 1991, Comprehensive Organic Synthesis, 181.

Hedstrom et al. "Converting trypsin to chymotrypsin: the role of surface loops" 1992, *Science*, 255(5049):1249-53.
Heine et al. "Analysis of the class I aldolase binding site architecture based on the crystal structure of 2-deoxyribose-5-phosphate aldolase at 0.99A resolution" 2004, *J. Mol. Biol.*, 343(4):1019-34.
Heine et al. "Observation of covalent intermediates in an enzyme mechanism at atomic resolution" 2001, *Science*, 294:369-74.
Helenius et al. "Intracellular functions of N-linked glycans" 2001, *Science*, 291:2364-9.
Henderson et al. 1999, *Comprehensive Natural Product Chemistry*, 367-441.
Hennig et al. "Crystal structure at 2.0 A resolution of phosphoribosyl anthranilate isomerase from the hyperthermophile *Thermotoga maritima*: possible determinants of protein stability" 1997, *Biochemistry*, 36:6009-16.
Henn-Sax et al. "Two (betaalpha)(8)-barrel enzymes of histidine and tryptophan biosynthesis have similar reaction mechanisms and common strategies for protecting their labile substrates" 2002, *Biochemistry*, 41:12032-42.
Henrissat "A classification of glycosyl hydrolases based on amino acid sequence similarities" 1991, *Biochem. J.*, 280 (Pt 2):309-16.
Henrissat et al. "New families in the classification of glycosyl hydrolases based on amino acid sequence similarities"1993, *Biochem. J.*, 293 (Pt.3):781-8.
Hermes et al. "Searching sequence space by definably random mutagenesis: improving the catalytic potency of an enzyme" 1990, *Proc. Natl. Acad Sci. U.S.A.*, 87:696-700.
Herskowitz "Life cycle of the budding yeast *Saccharomyces cerevisiae*" 1988, Microbiol. Rev., 52(4):536-53.
Hocker "Directed evolution of (betaalpha)(8)-barrel enzymes" 2005, *Biomol. Eng.*, 22(1-3):31-8.
Hommel et al. "Phosphoribosyl anthranilate isomerase catalyzes a reversible amadori reaction" 1995, *Biochemistry*, 34(16):5429-39.
Honda et al. "The first glycosynthase derived from an inverting glycoside hydrolase" 2006, *J. Biol. Chem.*, 281(3):1426-31.
Hoogenboom "Selecting and screening recombinant antibody libraries" 2005, Nat. Biotechnol., 23(9):1105-16.
Horinouchi et al. "Efficient production of 2-deoxyribose 5-phosphate from glucose and acetaldehyde by coupling of the alcoholic fermentation system of Baker's yeast and deoxyriboaldolase-expressing *Escherichia coli*" 2006, *Biosci. Biotechnol. Biochem.*, 70:1371-8.
Hrmova et al. "Mutated barley (1,3)-beta-D-glucan endohydrolases synthesize crystalline (1,3)-beta-D-glucans" 2002, J. Biol. Chem., 277:30102-11.
Hsu et al. "Directed evolution of D-sialic acid aldolase to L-3-deoxy-manno-2-octulosonic acid (L-KDO) aldolase" 2005, *Proc. Natl. Acad. Sci. U.S.A.*, 102:9122-6.
Huang et al. "A yeast genetic system for selecting small molecule inhibitors of protein-protein interactions in nanodroplets" 1997, *Proc. Natl. Acad. Sci. U.S.A.*, 94:13396-401.
Hussey et al. "Synthesis of a beta-estradiol-biotin chimera that potently heterodimerizes estrogen receptor and streptavidin proteins in a yeast three-hybrid system" 2003, *J. Am. Chem. Soc.*, 125(13):3692-3.
Jahn et al. "Expansion of the glycosynthase repertoire to produce defined manno-oligosaccharides" 2003, *Chem. Commun.(Camb.)*, 12:1327-9.
Jakeman et al. "On expanding the repertoire of glycosynthases: mutant β-galactosidases forming β-(1,6) linkages" 2002, *Can. J. Chem.*, 80:866-70.
Jenison et al. "High-resolution molecular discrimination by RNA" 1994, *Science*, 263(5152):1425-9.
Jennewein et al. "Directed evolution of an industrial biocatalyst: 2-deoxy-D-ribose 5-phosphate aldolase" 2006, Biotechnol. J., 1(5):537-48.
Jensen et al. "Directionality and regulation of cassette substitution in yeast" 1984, *Cold Spring Harb. Symp. Quan.t Biol.*, 49:97-104.
Jones "The molecular biology of the yeast *Saccharomyces*: metabolism and gene expression"1982,—Cold Spring Harbor Laboratory Cold Spring Harbor, NY.
Jue et al. "Determination of reducing sugars in the nanomole range with tetrazolium blue" 1985, *J. Biochem. Biophys. Methods.*, 11:109-15.

(56) References Cited

OTHER PUBLICATIONS

Jurgens et al. "Directed evolution of a (beta alpha)8-barrel enzyme to catalyze related reactions in two different metabolic pathways" 2000, *Proc. Natl. Acad. Sci. U.S.A.*, 97: 9925-30.
Kahne et al. "Glycosylation of unreactive substrates" 1989, *J. Am. Chem. Soc.*, 111:6881-2.
Kallenbach et al. "Three lymphoid-specific factors account for all junctional diversity characteristic of somatic assembly of T-cell receptor and immunoglobulin genes" 1992, *Proc. Natl. Acad. Sci.*, 89:2799-803.
Karimova et al. "A bacterial two-hybrid system based on a reconstituted signal transduction pathway" 1998, *Proc. Natl. Acad. Sci. U.S. A.*, 95(10):5752-6.
Khmelnitsky et al. "Synthesis of Water-Soluble Paclitaxel Derivatives by Enzymatic Acylation" 1997, J. Am. Chem. Soc., 119(47):11554-5.
Kim et al. "Directed evolution of a glycosynthase from *Agrobacterium* sp. increases its catalytic activity dramatically and expands its substrate repertoire" 2004, *J. Biol. Chem.*, 279(41):42787-93.
Knowles et al. "Tinkering with enzymes: what are we learning?" 1987, *Science*, 236(4806): 1252-8.
Koeller et al. "Enzymes for chemical synthesis" 2001, *Nature*, 409:232-40.
Koide et al. "Probing protein conformational changes in living cells by using designer binding proteins: application to the estrogen receptor" 2002, *Proc. Natl. Acad. Sci. U.S.A.*, 99(3):1253-8.
Korkegian et al. "Computational thermostabilization of an enzyme" 2005, Science, 308(5723):857-60.
Kornfeld et al. "Assembly of asparagine-linked oligosaccharides" 1985, *Annu. Rev. Biochem.*, 54:631-64.
Krogh et al. "Recombination proteins in yeast" 2004, *Annu. Rev. Genet.*, 38:233-71.
Kuhlman et al. "Design of a novel globular protein fold with atomic-level accuracy" 2003, *Science*, 302(5649):1364-8.
Lechner et al. "Structure and biosynthesis of prokaryotic glycoproteins" 1989, *Annu. Rev. Biochem.*, 58:173-94.
Leconte et al. "Polymerase evolution: efforts toward expansion of the genetic code" 2005, *J. Am. Chem. Soc.*, 127(36):12470-1.
Lefurgy et al. "Chemical complementation" 2006, *Enzyme Assays: High Throughput Screening, Genetic Selection and Fingerprinting*, 183-219.
Lemaire et al. "Nucleotide sequence of the ccIG gene of *Clostridium thermocellum* and characterization of its product, endoglucanase CelG" 1993, *J. Bacteriol.*, 175(11):3353-60.
Lin et al. "Dexamethasone—Methotrexate: An Efficient Chemical Inducer of Protein Dimerization in Vivo" 2000, *J. Am. Chem Soc.*, 122(17):4247-8.
Lin et al. "Directed evolution of a glycosynthase via chemical complementation" 2004, *J. Am. Chem. Soc.*, 126(46):15051-9.
Lin et al. "Screening and selection methods for large-scale analysis of protein function" 2002, *Angew. Chem. Int. Ed. Engl.*, 41:4402-25.
Liu et al. "Sequential aldol condensation catalyzed by DERA mutant Ser238Asp and a formal total synthesis of atorvastatin" 2004, *Tetrahedron Lett.*, 45:2439-41.
Live et al. "A strategy for probing the autonomy of cross-domain stereochemical communication in glycoconjugates" 2001, *Org. Lett.*, 3:851-4.
Ly et al. "Mutagenesis of glycosidases" 1999, *Annu. Rev. Biochem.*, 68:487-522.
Ma et al. "Plasmid construction by homologous recombination in yeast" 1987, *Gene*, 58(2-3):201-16.
Mackenzie et al. "Glycosynthases: mutant glycosidases for oligosaccharide synthesis" 1998, *J. Am. Chem. Soc*, 120(22):5583-4.
Mae et al. "Structure and regulation of the *Erwinia carotovora* subspecies *carotovora* SCC3193 cellulase gene celV1 and the role of cellulase in phytopathogenicity" 1995, *Mol. Gen. Genet.*, 247:17-26.
Magliery et al. "Combinatorial approaches to protein stability and structure" 2004, *Eur. J. Biochem.*, 271(9):1595-608.

Mahrwald "Diastereoselection in lewis-Acid-mediated aldol additions" 1999, *Chem. Rev.*, 99(5):1095-120.
Mahrwald et al. "Aldol addition of aldehydes—A stereoselective approach to syn-3-hydroxyaldehydes" 1997, *Tetrahedron Lett.*, 38(26):4543-4.
Malet et al. "From beta-glucanase to beta-glucansynthase: glycosyl transfer to alpha-glycosyl fluorides catalyzed by a mutant endoglucanase lacking its catalytic nucleophile" 1998, *FEBS Lett.*, 440(1-2):208-12.
Mastrobattista et al. "High-throughput screening of enzyme libraries: in vitro evolution of a beta-galactosidase by fluorescence-activated sorting of double emulsions" 2005, *Chem. Biol.*, 12:1291-1300.
Mayer et al. "Directed evolution of new glycosynthases from *Agrobacterium* beta-glucosidase: a general screen to detect enzymes for oligosaccharide synthesis" 2001, Chem. Biol., 8:437-43.
Mayer et al. "New glycosynthases: screening of an enzyme library generated by combined region-directed mutatgenesis/DNA-shuffling" 1999, *Faseb. J.*, 13:A1444.
Mayer et al. "The E358S mutant of *Agrobacterium* sp. beta-glucosidase is a greatly improved glycosynthase" 2000, *FEBS Lett.*, 466(1):40-4.
Merryman et al. "A bifunctional tRNA for in vitro selection" 2002, *Chem. Biol.*, 9:741-6.
Muddana et al. "Facile synthesis of cids: biotinylated estrone oximes efficiently heterodimerize estrogen receptor and streptavidin proteins in yeast three hybrid systems" 2004, *Org. Lett.*, 6(9):1409-12.
Nagano et al. "Barrel structures in proteins: automatic identification and classification including a sequence analysis of TIM barrels" 1999, *Pro. Sci.*, 8:2072-84.
Nakai et al. "Cloning and sequencing analysis of Trp1 gene of *Flammulina velutipes*" 2000, *FEMS Microbiol. Lett.*, 190(1):51-6.
Nashiru et al. "β-Mannosynthase: synthesis of β-mannosides with a mutant β-mannosidase" 2001, *Angew. Chem. Int. Ed. Engl.*, 40(2):417-20.
Nasmyth "Regulating the HO endonuclease in yeast" 1993, *Curr. Opin. Genet. Dev.*, 3(2):286-94.
Nasmyth K. "The determination of mother cell-specific mating type switching in yeast by a specific regulator of HO transcription" 1987, *Embo. J.*, 6:243-8.
Nilsson "Enzymatic synthesis of oligosaccharides" 1988, *Trends Biotechnol.*, 6: 256-64.
Nourrit et al. "The presence of direct repeats does not influence coding joint formation during V(D)J recombination" 1996, *Nuc. Acid Res.*, 24(20):3968-73.
O'Connor et al. "Probing the effect of the outer saccharide residues of N-linked glycans on peptide conformation" 2001, *J. Am. Chem. Soc.*, 123:6187-8.
Olsen et al. "Function-based isolation of novel enzymes from a large library" 2000, *Nat. Biotechnol.*, 18:1071-4.
Olsen et al. "Transplanting two unique beta-glucanase catalytic activities into one multienzyme, which forms glucose" 1996, *Biotechnol.*, (N Y), 14(1):71-6.
Pabo et al. "Design and selection of novel Cys2His2 zinc finger proteins" 2001, *Annu. Rev. Biochem.*, 70:313-40.
Park et al. "Characterization of *Erwinia carotovora* subsp. *carotovora* LY34 endo-1,4-beta-glucanase genes and rapid identification of their gene products" 1997, *Biochem. Biophys. Res. Commun.*, 241:636-41.
Park et al. "Design and evolution of new catalytic activity with an existing protein scaffold" 2006, *Science*, 311:535-8.
Patten et al. "Applications of DNA shuffling to pharmacetucials and vaccines" *Curr. Opin. Biotechnol.*, 8:724-33, 1997.
Paulsen "Advances in Selective Chemical Syntheses of Complex Oligosaccharides" 1982, *Angew. Chem. Int. Ed. Eng.*, 21(3):155-173.
Paulsen et al. "Progress in the selective chemical synthesis okf complex oligosaccharides" 1982, Angew. Chem. Int. Ed. Engl., 21:155-73.
Pedersen et al. "A method for directed evolution and functional cloning of enzymes" 1998, *Proc. Natl. Acad. Sci. U.S.A.*, 95(18):10523-8.
Pelletier et al. "An in vivo library-versus-library selection of optimized protein-protein interactions" 1999, Nat. Biotechnol., 17(7):683-90.

(56) References Cited

OTHER PUBLICATIONS

Perez et al. "Fluorogenic polypropionate fragments for detecting stereoselective aldolases" 2000, *Chemistry*, 6(22):4154-62.

Perfect et al. "Cloning the Cryptococcus neoformans TRP1 gene by complementation in *Saccharomyces cerevisiae*" 1992, *Gene*, 122:213-7.

Plante et al. "Synthesis and use of glycosyl phosphates as glycosyl donors" 1999, *Org. Lett.*, 1(2):211-4.

Pricer et al. "Deoxyribose aldolase from *Lactobacillus plantarum*" 1960, *J. Biol. Chem.*, 235:1292-8.

Raymond et al. "General method for plasmid construction using homologous recombination" 1999, *Biotechniques*, 26(1):134-8, 140-1.

Ro et al. "Production of the antimalarial drug precursor artemisinic acid in engineered yeast" 2006, *Nature*, 440(7086):940-3.

Roberts et al. "How restriction enzymes became the workhorses of molecular biology" 2005, *Proc. Natl. Acad. Sci. U S A.*, 102(17):5905-8.

Roberts et al. "RNA-peptide fusions for the in vitro selection of peptides and proteins" 1997, *Proc. Natl. Acad. Sci. U.S.A.*, 94:12297-302.

Roth et al. "Inhibitors of cholesterol biosynthesis. 3. Tetrahydro-4-hydroxy-6-[2-(1H-pyrrol-1-yl)ethyl]-2H-pyran-2-one inhibitors of HMG-CoA reductase. 2. Effects of introducing substituents at positions three and four of the pyrrole nucleus" 1991, *J. Med. Chem.*, 34(1):357-66.

Roth et al. "The discovery and development of atorvastatin, a potent novel hypolipidemic agent" 2002, *Prog. Med. Chem.*, 40:1-22.

Russ et al. "Natural-like function in artificial WW domains" 2005, *Nature*, 437(7058):579-83.

Rutledge et al. "Molecular recognition of protein surfaces: high affinity ligands for the CBP KIX domain" 2003, *J. Am. Chem. Soc.*, 125(47):14336-47.

Samland et al. "Microbial aldolases as C-C bonding enzymes—unknown treasures and new developments" 2006, *Appl. Microbiol. Biotechnol.*, 71(3):253-64.

Sassanfar et al. "An RNA motif that binds ATP" 1993, *Nature*, 364(6437):550-3.

Schmid et al. "Industrial biocatalysis today and tomorrow" 2001, *Nature*, 409(6817):258-68.

Schmidt "New methods of glycoside and oligosaccharide syntheses—are there alternatives to the Koenigs-Knorr method?" 1986, *Angew. Chem.*, 98:213-36.

Schmidt et al. "Evolutionary potential of (beta/alpha)8-barrels: functional promiscuity produced by single substitutions in the enolase superfamily" 2003, *Biochemistry*, 42: 8387-93.

Schmidt et al. "Facile synthesis α—and β-O-glycosyl imidates; preparation of glycosides and disaccharides" 1980, *Angew. Chem. Int.Ed. Engl.*, 19:731-2.

Schou et al. "Stereochemistry, specificity and kinetics of the hydrolysis of reduced cellodextrins by nine cellulases" 1993, *Eur. J. Biochem.*, 217(3):947-53.

Schultz et al. "From molecular diversity to catalysis: lessons from the immune system" 1995, *Science*, 269(5232):1835-42.

Sears et al. "Toward automated synthesis of oligosaccharides and glycoproteins" 2001, *Science*, 291(5512):2344-50.

Seeberger et al. "Solid Phase Synthesis of Oligosaccharides and Glycopeptides by the Glycal Assembly Method: A Five Year Retrospective" 1998, *Acc. Chem. Res.*, 31:685-95.

Senugupta et al. "Correlation between catalytic efficiency and the transcription read-out in chemical complementation: a general assay for enzyme catalysis" 2004, *Biochemistry*, 43:3570-81.

Silverman et al. "Multivalent avimer proteins evolved by exon shuffling of a family of human receptor domains" 2005, *Nat. Biotechnol.*, 23(12):1556-61.

Silverman et al. "Reverse engineering the (beta/alpha )8 barrel fold" 2001, *Proc. Natl. Acad. Sci. U.S.A.*, 98(6):3092-7.

Smith "Filamentous fusion phage: novel expression vectors that display cloned antigens on the virion surface" 1985, *Science*, 228(4705):1315-7.

Socolich et al. "Evolutionary information for specifying a protein fold" 2005, *Nature*, 437(7058):512-8.

Stemmer "DNA shuffling by random fragmentation and reassembly: in vitro recombination for molecular evolution" 1994, *Proc. Natl. Acad. Sci. U.S.A.*, 91(22):10747-51.

Sterner et al. "(Beta alpha)8-barrel proteins of tryptophan biosynthesis in the hyperthermophile *Thermotoga maritima*" 1995, *Embo. J.*, 14(18):4395-402.

Sterner et al. "Catalytic versatility, stability, and evolution of the (betaalpha)8-barrel enzyme fold" 2005, *Chem. Rev.*, 105:4038-55.

Sterner et al. "Phosphoribosylanthranilate isomerase and indoleglycerol-phosphate synthase: tryptophan biosynthetic enzymes from *Thermotoga maritima*" 2001, *Methods Enzymol.*, 331:270-80.

Storici et al. "Chromosomal site-specific double-strand breaks are efficiently targeted for repair by oligonucleotides in yeast" 2003, *Proc. Natl. Acad. Sci. U.S.A.*, 100:14994-9.

Storici et al. "The delitto perfetto approach to in vivo site-directed mutagenesis and chromosome rearrangements with synthetic oligonucleoties in yeast" 2006, *Methods Enzymol.*, 409:329-45.

Swers et al. "Shuffled antibody libraries created by in vivo homologous recombination and yeast surface display" 2004, *Nucleic Acids Res.*, 32(3):e36.

Szczebara et al. "Total biosynthesis of hydrocortisone from a simple carbon source in yeast" 2003, *Nat. Biotechnol.*, 21(2):143-9.

Tao et al. "Milestones in directed enzyme evolution" 2002, *Curr. Opin. Chem. Biol.*, 6(6):858-64.

Tao et al. "Optimized design and synthesis of chemical dimerizer substrates for detection of glycosynthase activity via chemical complementation" 2006, *Bioorg. Med. Chem.*, 14:6940-53.

Tawfik et al. "Man-made cell-like compartments for molecular evolution" 1998, *Nat. Biotechnol.*, 16(7):652-6.

Thiem "Applications of enzymes in synthetic carbohydrate chemistry" 1995, *FEMS Microbiol. Rev.*, 16(2-3): 193-211.

Thoma et al. "Structure and function of mutationally generated monomers of dimeric phosphoribosylanthranilate isomerase from *Thermotoga maritima*" 2000, *Structure*, 8(3):265-76.

Toshima et al. "Recent progress in O-glycosylation methods and its application to natural products synthesis" 1993, *Chem. Rev.*, 93:1503-31.

Tricone et al. "A novel thermophilic glycosynthase that effects branching glycosylation" 2000, *Bioorg. Med. Chem. Lett.*, 10(4):365-8.

Trincone et al. "Highly productive autocondensation and transglycosylation reactions with *Sulfolobus solfataricus* glycosynthase" 2005, *Chembiochem.*, 6(8):1431-7.

Tsang et al. "Specialization of the DNA-cleaving activity of a group I ribozyme through in vitro evolution" 1996, *J. Mol. Biol.*, 262(1):31-42.

Unverzagt "Chemoenzymatic synthesis of a sialylated undecasaccharide-asparagine conjugate" 1996, *Angew. Chem. Int. Ed. Engl.*, 35:2350-3.

van Lieshout et al. "Hydrolase and glycosynthase activity of endo-1,3-beta-glucanase from the thermophile *Pyrococcus furiosus*" 2004, *Archaea.*, 1(4):285-92.

Vann et al. "Enzyme-linked immunosorbent assay" 1990, Methods Enzymol., 184:537-41.

Varadarajan et al. "Engineering of protease variants exhibiting high catalytic activity and exquisite substrate selectivity" 2005, *Proc. Natl. Acad. Sci. U S A.*, 102(19):6855-60.

Varrot et al. "Atomic resolution structure of endoglucanase Cel5A in complex with methyl 4,4II,4III,4IV-tetrathio-alpha-cellopentoside highlights the alternative binding modes targeted by substrate mimics" 2001, *Acta. Crystallogr. D. Biol.Crystallogr.*, 57: 1739-42.

Varrot et al. "Direct experimental observation of the hydrogen-bonding network of a glycosidase along its reaction coordinate revealed by atomic resolution analyses of endoglucanase Cel5A" 2003, *Acta. Crystallogr. D. Biol. Crystallogr.*, 59(Pt 3):447-52.

Varrot et al. "Insights into ligand-induced conformational change in Cel5A from *Bacillus agaradhaerens* revealed by a catalytically active crystal form" 2000, *J. Mol. Biol.*, 297(3):819-28.

Velmurugan et al. "Stable propagation of "selfish" genetic elements" 2003, *J. Biosci.*, 25(5):623-36.

(56) References Cited

OTHER PUBLICATIONS

Vidal et al. "Reverse two-hybrid and one-hybrid systems to detect dissociation of protein-protein and DNA-protein interactions" 1996, *Proc. Natl. Acad. Sci. U.S.A.*, 93(19):10315-20.

Volkert et al. "Deoxyribonucleic acid plasmids in yeasts" 1989, *Microbiol. Rev.*, 53(3):299-317.

Wang et al. "Creating hybrid genes by homologous recombination" 2000, Dis. Markers., 16(1-2):3-13.

Wang et al. "Expanding the genetic code of *Escherichia coli*" 2001, *Science*, 292(5516):498-500.

Wang et al. "Generating molecular diversity by homologous recombination in *Escherichia coli*" 2005, *Pro. Eng. Des. & Sel.*, 18(8):397-404.

Wilson et al. "In vitro selection of functional nucleic acids" 1999, *Annu. Rev. Biochem.*, 68:611-47.

Winchester "Lysosomal metabolism of glycoproteins" 2005, *Glycobiology*, 15(6):1R-15R.

Wolf et al. "Distribution of protein folds in the three superkingdoms of life" 1999, *Gen. Res.*, 17-26.

Wymer et al. "Enzyme-catalyzed synthesis of carbohydrates" 2001, *Curr. Opin. Chem. Biol.*, 4(1):110-9.

Xia et al. "Directed evolution of novel polymerase activities: mutation of a DNA polymerase into an efficient RNA polymerase" 2002, *Proc. Natl. Acad. Sci. U.S.A.*, 99(10):6597-602.

Yachi et al. "Reaction of titanate-type aldehyde enolate with ketones to provide 3-hydroxyaldehydes" 1999, *J. Am. Chem. Soc.*, 121(40):9465-6.

Yamano et al. "Metabolic engineering for production of beta-carotene and lycopene in *Saccharomyces cerevisiae*" 1994, *Biosci. Biotechnol. Biochem.*, 58:1112-4.

Yang et al. "Protein-peptide interactions analyzed with the yeast two-hybrid system" 1995, *Nucl. Acids Res.*, 23(7):1152-6.

Yano et al. "Directed evolution of an aspartate aminotransferase with new substrate specificities" 1998, *Proc. Natl. Acad. Sci. U.S.A.*, 95(10):5511-5.

Yoshikuni et al. "Designed divergent evolution of enzyme function" 2006, *Nature*, 440(7087):1078-82.

Zechel et al. "Glycosidase mechanisms: anatomy of a finely tuned catalyst" 2000, Acc. Chem. Res., 33(1):11-8.

Zechel et al. "Mechanism, mutagenesis, and chemical rescue of a beta-mannosidase from cellulomonas fimi" 2003, *Biochemistry*, 42(23):7195-204.

Zhao et al. "Optimization of DNA shuffling for high fidelity recombination" 1997, *Nucleic Acids Res.*, 25(6):1307-8.

Cochran, et al., "Computational de novo design and characterization of a four-helix bundle protein that selectively binds a nonbiological cofactor", *J. Am. chem. Soc.*, 127(5):1346-7 (2005).

Cornish, "Biological chemistry: Catalytic competition for cells", *Nature*, 440(7081):156-157 (2006).

Dwyer, et al., "Computational design of a Zn2+ receptor that controls bacterial gene expression", PNAS, 100(20):11255-60 (2003).

Gallagher, et al., "An orthogonal dexamethasone-trimethoprim yeast three-hybrid system", *Anal. Biochem.*, 363(I):160-162 (2007).

Peralta-Yahya, et al., "Bringing the power of genetics to chemistry", published in *Chemical Biology*, 1:199-226 (2006) (previously cited).

Reina, et al., "Computer-aided design of a PDZ domain to recognize new target sequences", *Nat. Struct. Biol.*, 9(8):621-7 (2002).

Shifman, et al., "Modulating calmodulin binding specificity through computational protein design", *J. Mol. Biol.*, 323(3):417-423 (2002).

Tao, et al., "Characterization of a new glycosynthase cloned by using chemical complementation", *Chembiochem.*, 9(5):681-4 (Mar. 2008) (previously cited).

\* cited by examiner

|  | loop1<br>HXXXWYXQ | loop2<br>XXXX<br>XXXXXX<br>XXXXXXXX | loop3<br>XXXXXXX<br>XXXXXXXX | loop4<br>XEPXXXV<br>XEPXXXXXV |
|---|---|---|---|---|
| Cellulase<br>Chitosanase<br>Mannanase | HGLQWYGQ<br>HGTQWYAQ<br>HPHNWYPQ | MYTSSGGY<br>TYVQEGGY<br>LS----NG | DWH-ILSDN<br>DWH-MLSPG<br>EVHDTT--G | NEPN-GSD--V<br>NEPS-G----V<br>NEPYGNDSATV |
|  | loop5<br>GTXXWSX | loop6<br>XXXX | loop7<br>XXXXX | loop8<br>WXXXXXXXE<br>WXXXXXXXXE |
| Cellulase<br>Chitosanase<br>Mannanase | GTGTWSQ<br>GTRAWSS<br>DAPNWGO | GTHG<br>ASHR<br>YSQA | T--SAAT<br>T--QNYA<br>HDHSDGN | WSLTH---KDE<br>WNYSD---DHR<br>WSWSGNGGGVE |

FIG.6B

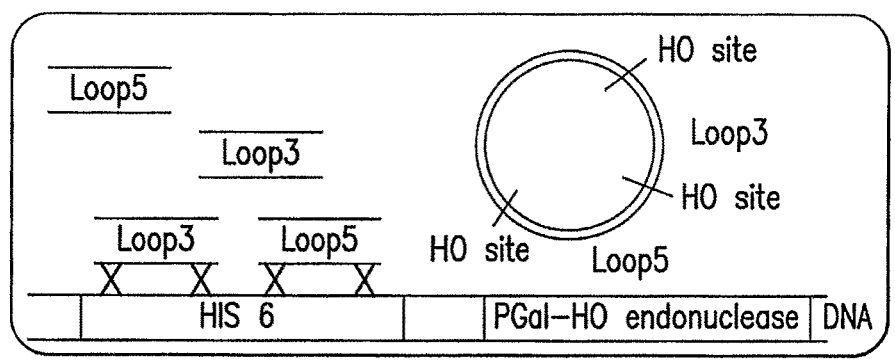
FIG.14A
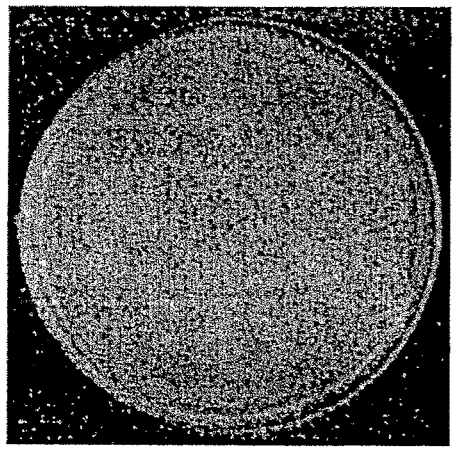 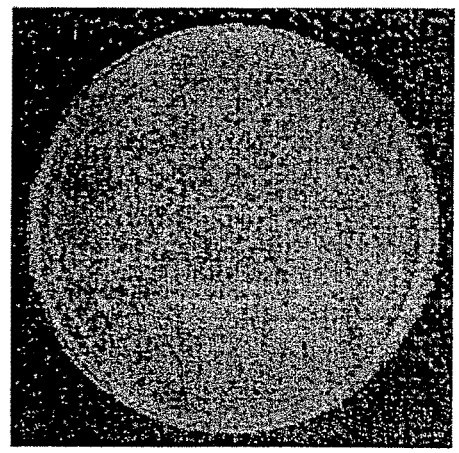
FIG.14B  FIG.14C

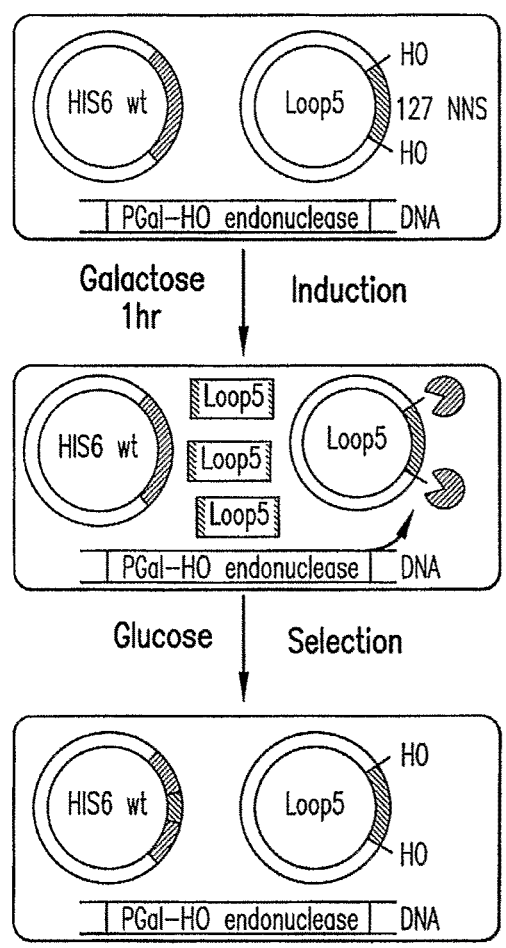
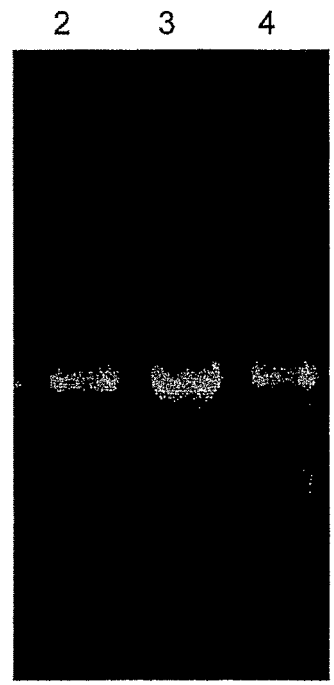
FIG. 14D
FIG. 14E (SEQ ID NO:1)

ATGGCCACGCCAGTAGAAACGCATGGTCAGCTGTCCATCGAAAACGGGCGACTGGT
GGATGAACAGGGGAAAAGGGTGCAACTGAGAGGGGTCAGTTCGCACGGTTTGCAGT
GGTTTGGCGACTATGTCAACAAAGACTCGATAAAATGGCTGCGTGACGACTGGGGG
ATCAATGTGTTTCGCGTTGCCATGTACACGGCGGAGAATGGTTATATTGCTAACCCT
TCCCTCGCCAATAAGGTAAAAGAGGCCGTTGCGGCGGCGCAAAGCCTCGGCGTCTA
CATCATCATCGACTGGCACATTTTGTCGGATAACGATCCCAATACTTATAAAGCACA
GGCAAAAATCTTCTTTGCCGAAATGGCTGGGCTGTATGGCAGCTCACCGAACGTGAT
TTATGAAATCGCCAATGAGCCAAACGGTGGCGTGACGTGGAACGGACAGATTCGGC
CTTATGCGCTGGAAGTGACTGACACCATCCGTAGCAAAGATCCTGATAACCTTATTA
TCGTCGGTACCGGCACCTGGAGTCAGGATATCCACGATGCAGCGGATAACCAACTG
CCCGATCTGAATACCCTATACGCGCTGCATTTCTATGCGGGCACGCACGGGCAATTC
CTGTGCGATCGTATTGACTATGCGCAAAGCCGTGGCGCGGCGATTTTCGTCAGCGAG
TGGGGCACCAGCGATGCATCCGGCAACGGTGGGCCGTTCCTGCCTGAATCGCAGAC
CTGGATCGATTTCCTGAATAACCGTGGCGTAAGCTGGGTGAACTGGTCACTAAGCGA
TAAGTCTGAGACGTCTGCGGCGCTGACTCCAGGGGCGAGCAAATCAGGCGGCTGGA
CGGAGCAGAATTTGTCGACGTCAGGCAAATTTGTCAGAGAGCAGATTCGTGCGGGG
GCGGGTCTGAGCGGTGGTGATCACCATCACCATCACCATTAA

FIG.21A (SEQ ID NO:3)

```
  1 - ATGGCCACGCCAGTAGAAACGCATGGTCAGCTGTCCATCGAAAACGGGCGACTGGTGGAT -  60
      - M  A  T  P  V  E  T  H  G  Q  L  S  I  E  N  G  R  L  V  D
 61 - GAACAGGGGAAAAGGGTGCAACTGAGAGGGGTCAGTTCGCACGGTTTGCAGTGGTTTGGC - 120
      - E  Q  G  K  R  V  Q  L  R  G  V  S  S  H  G  L  Q  W  F  G
121 - GACTATGTCAACAAAGACTCGATAAAATGGCTGCGTGACGACTGGGGGATCAATGTGTTT - 180
      - D  Y  V  N  K  D  S  I  K  W  L  R  D  D  W  G  I  N  V  F
181 - CGCGTTGCCATGTACACGGCGGAGAATGGTTATATTGCTAACCCTTCCCTCGCCAATAAG - 240
      - R  V  A  M  Y  T  A  E  N  G  Y  I  A  N  P  S  L  A  N  K
241 - GTAAAAGAGGCCGTTGCGGCGGCGCAAAGCCTCGGCGTCTACATCATCATCGACTGGCAC - 300
      - V  K  E  A  V  A  A  A  Q  S  L  G  V  Y  I  I  I  D  W  H
301 - ATTTTGTCGGATAACGATCCCAATACTTATAAAGCACAGGCAAAAATCTTCTTTGCCGAA - 360
      - I  L  S  D  N  D  P  N  T  Y  K  A  Q  A  K  I  F  F  A  E
361 - ATGGCTGGGCTGTATGGCAGCTCACCGAACGTGATTTATGAAATCGCCAATGAGCCAAAC - 420
      - M  A  G  L  Y  G  S  S  P  N  V  I  Y  E  I  A  N  E  P  N
421 - GGTGGCGTGACGTGGAACGGACAGATTCGGCCTTATGCGCTGGAAGTGACTGACACCATC - 480
      - G  G  V  T  W  N  G  Q  I  R  P  Y  A  L  E  V  T  D  T  I
481 - CGTAGCAAAGATCCTGATAACCTTATTATCGTCGGTACCGGCACCTGGAGTCAGGATATC - 540
      - R  S  K  D  P  D  N  L  I  I  V  G  T  G  T  W  S  Q  D  I
541 - CACGATGCAGCGGATAACCAACTGCCCGATCTGAATACCCTATACGCGCTGCATTTCTAT - 600
      - H  D  A  A  D  N  Q  L  P  D  L  N  T  L  Y  A  L  H  F  Y
601 - GCGGGCACGCACGGGCAATTCCTGTGCGATCGTATTGACTATGCGCAAAGCCGTGGCGCG - 660
      - A  G  T  H  G  Q  F  L  C  D  R  I  D  Y  A  Q  S  R  G  A
661 - GCGATTTTCGTCAGCGAGTGGGGCACCAGCGATGCATCCGGCAACGGTGGGCCGTTCCTG - 720
      - A  I  F  V  S  E  W  G  T  S  D  A  S  G  N  G  G  P  F  L
721 - CCTGAATCGCAGACCTGGATCGATTTCCTGAATAACCGTGGCGTAAGCTGGGTGAACTGG - 780
      - P  E  S  Q  T  W  I  D  F  L  N  N  R  G  V  S  W  V  N  W
781 - TCACTAAGCGATAAGTCTGAGACGTCTGCGGCGCTGACTCCAGGGGCGAGCAAATCAGGC - 840
      - S  L  S  D  K  S  E  T  S  A  A  L  T  P  G  A  S  K  S  G
841 - GGCTGGACGGAGCAGAATTTGTCGACGTCAGGCAAATTTGTCAGAGAGCAGATTCGTGCG - 900
      - G  W  T  E  Q  N  L  S  T  S  G  K  F  V  R  E  Q  I  R  A
901 - GGGGCGGGTCTGAGCGGTGGTGATCACCATCACCATCACCATTAA - 945
      - G  A  G  L  S  G  G  D  H  H  H  H  H  H  *
```

FIG.21B (SEQ ID NO:2)

ATGGCCACGCCAGTAGAAACGCATGGTCAGCTGTCCATCGAAAACGGGCGACTGGT
GGATGAACAGGGGAAAAGGGTGCAACTGAGAGGGGTCAGTTCGCACGGTTTGCAGT
GGTTTGGCGACTATGTCAACAAAGACTCGATGAAGTGGCTGCGTGATGACTGGGGG
ATTAATGTATTCCGCGTCGCCATGTACACGGCGGCGGATGGTTATATTTCGAATCCT
TCCCTCGCCAATAAGGTAAAAGAGGCCGTTGCGGCGGCGCAAAGCCTCGGCGTTTA
CATCATCATCGACTGGCACATTTTGTCGGATAACGATCCTAATATTTATAAAGCACA
GGCAAAAACCTTCTTTGCCGAAATGGCGGGGCTGTACGGTAATTCGCCGAACGTGAT
TTATGAAATCGCCAATGAACCTAACGGCGGCGTGACCTGGAACGGGCAGATTCGGC
CTTATGCGCTGGAAGTGACTGAAACTATCCGTAGTAAAGATCCTGATAATCTGATTA
TCGTTGGCACGGGTACCTGGAGTCAGGATATCCATGATGCGGCGGACAATCTGTTGC
CCGATCCGAATACGATGTACGCGCTGCATTTCTATGCGGGCACGCACGGGCAATTCC
TGTGCGATCGTATTGACTATGCGCAAAGCCGTGGCGCGGCGATTTTCGTCAGCGAGT
GGGGCACCAGCGATGCATCCGGCAACGGTGGGCCGTTCCTGCCTGAATCGCAGACC
TGGATCGATTTCCTGAATAACCGTGGCATAAGCTGGGTGAACTGGTCGCTTACCGAT
AAGTCAGAGGCGTCCGCCGCGCTGGCTCCAGGGGCGAGTAAATCAGGCGGTTGGAC
GGAGCAGAATTTGTCGGCGTCAGGAAAATTTGTCAGAGCACAGATTCGCGCGGCTG
CGAATCTAAGCGGTGGCGATCACCATCACCATCACCATTAA

FIG. 22A (SEQ ID NO:4)

```
  1 - ATGGCCACGCCAGTAGAAACGCATGGTCAGCTGTCCATCGAAAACGGGCGACTGGTGGAT -  60
    -  M  A  T  P  V  E  T  H  G  Q  L  S  I  E  N  G  R  L  V  D
 61 - GAACAGGGGAAAAGGGTGCAACTGAGAGGGGTCAGTTCGCACGGTTTGCAGTGGTTTGGC - 120
    -  E  Q  G  K  R  V  Q  L  R  G  V  S  S  H  G  L  Q  W  F  G
121 - GACTATGTCAACAAAGACTCGATGAAGTGGCTGCGTGATGACTGGGGGATTAATGTATTC - 180
    -  D  Y  V  N  K  D  S  M  K  W  L  R  D  D  W  G  I  N  V  F
181 - CGCGTCGCCATGTACACGGCGGCGGATGGTTATATTTCGAATCCTTCCCTCGCCAATAAG - 240
    -  R  V  A  M  Y  T  A  A  D  G  Y  I  S  N  P  S  L  A  N  K
241 - GTAAAAGAGGCCGTTGCGGCGGCGCAAAGCCTCGGCGTTTACATCATCATCGACTGGCAC - 300
    -  V  K  E  A  V  A  A  A  Q  S  L  G  V  Y  I  I  I  D  W  H
301 - ATTTTGTCGGATAACGATCCTAATATTTATAAAGCACAGGCAAAAACCTTCTTTGCCGAA - 360
    -  I  L  S  D  N  D  P  N  I  Y  K  A  Q  A  K  T  F  F  A  E
361 - ATGGCGGGGCTGTACGGTAATTCGCCGAACGTGATTTATGAAATCGCCAATGAACCTAAC - 420
    -  M  A  G  L  Y  G  N  S  P  N  V  I  Y  E  I  A  N  E  P  N
421 - GGCGGCGTGACCTGGAACGGGCAGATTCGGCCTTATGCGCTGGAAGTGACTGAAACTATC - 480
    -  G  G  V  T  W  N  G  Q  I  R  P  Y  A  L  E  V  T  E  T  I
481 - CGTAGTAAAGATCCTGATAATCTGATTATCGTTGGCACGGGGTACCTGGAGTCAGGATATC - 540
    -  R  S  K  D  P  D  N  L  I  I  V  G  T  G  T  W  S  Q  D  I
541 - CATGATGCGGCGGACAATCTGTTGCCCGATCCGAATACGATGTACGCGCTGCATTTCTAT - 600
    -  H  D  A  A  D  N  L  L  P  D  P  N  T  M  Y  A  L  H  F  Y
601 - GCGGGCACGCACGGGCAATTCCTGTGCGATCGTATTGACTATGCGCAAAGCCGTGGCGCG - 660
    -  A  G  T  H  G  Q  F  L  C  D  R  I  D  Y  A  Q  S  R  G  A
661 - GCGATTTTCGTCAGCGAGTGGGGCACCAGCGATGCATCCGGCAACGGTGGGCCGTTCCTG - 720
    -  A  I  F  V  S  E  W  G  T  S  D  A  S  G  N  G  G  P  F  L
721 - CCTGAATCGCAGACCTGGATCGATTTCCTGAATAACCGTGGCATAAGCTGGGTGAACTGG - 780
    -  P  E  S  Q  T  W  I  D  F  L  N  N  R  G  I  S  W  V  N  W
781 - TCGCTTACCGATAAGTCAGAGGCGTCCGCCGCGCTGGCTCCAGGGGCGAGTAAATCAGGC - 840
    -  S  L  T  D  K  S  E  A  S  A  A  L  A  P  G  A  S  K  S  G
841 - GGTTGGACGGAGCAGAATTTGTCGGCGTCAGGAAAATTTGTCAGAGCACAGATTCGCGCG - 900
    -  G  W  T  E  Q  N  L  S  A  S  G  K  F  V  R  A  Q  I  R  A
901 - GCTGCGAATCTAAGCGGTGGCGATCACCATCACCATCACCATTAA - 945
    -  A  A  N  L  S  G  G  D  H  H  H  H  H  H  *
```

FIG.22B

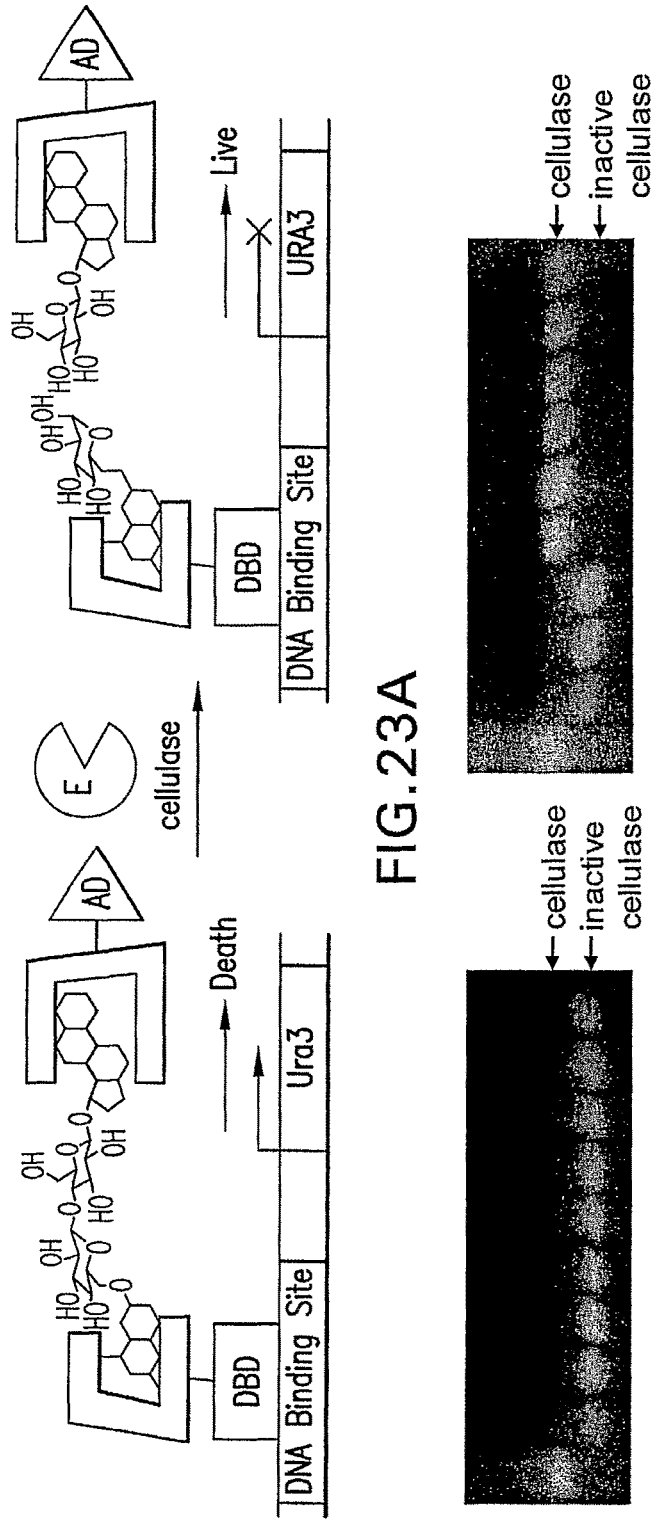

Methotrexate-Cellulose-Dexamethasone

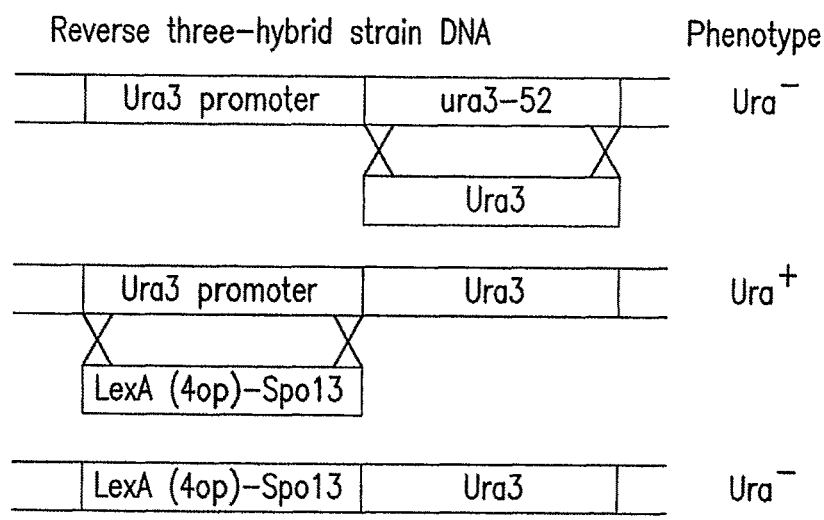
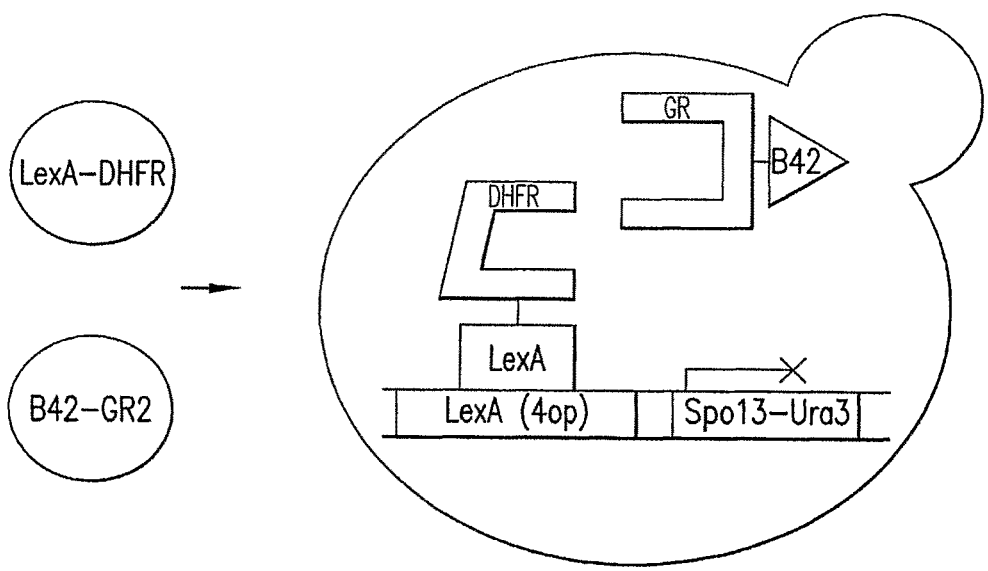
FIG.26A

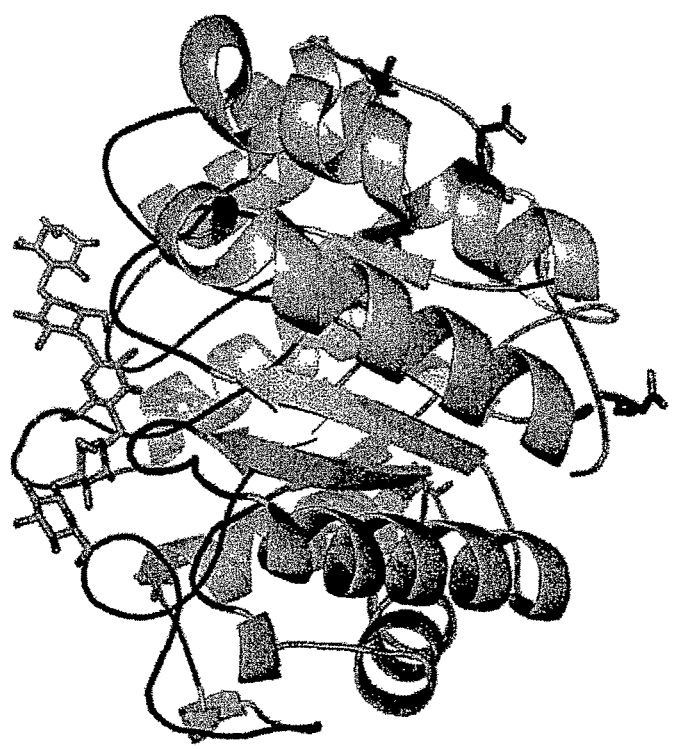
FIG. 28A Cel_3.6
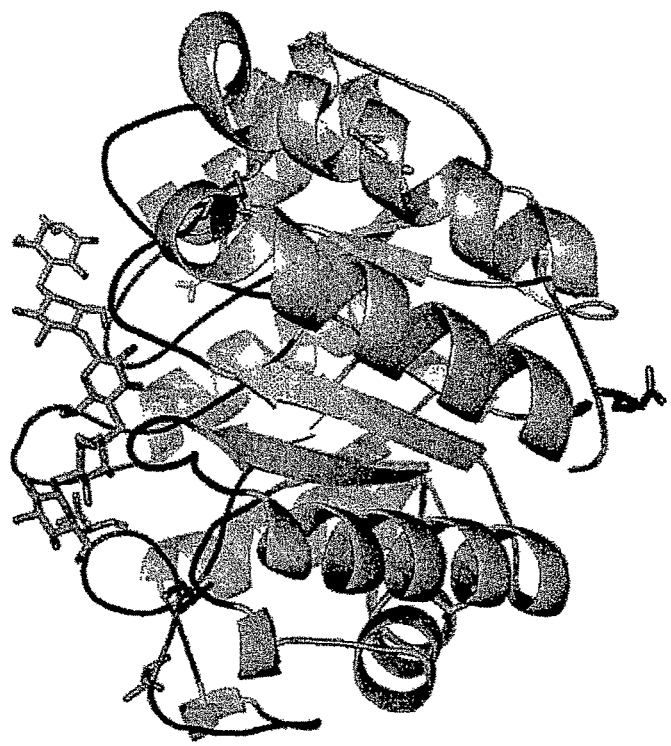
FIG. 28B Cel_5.3

Figure 2:
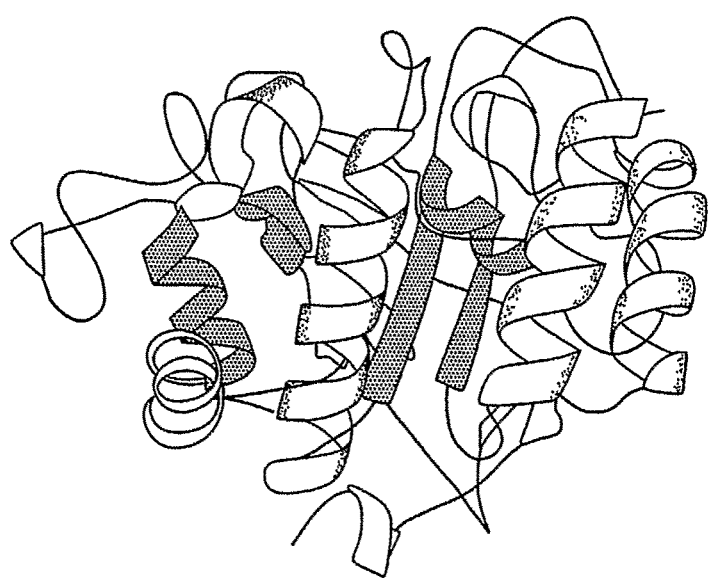
Figure 29A:
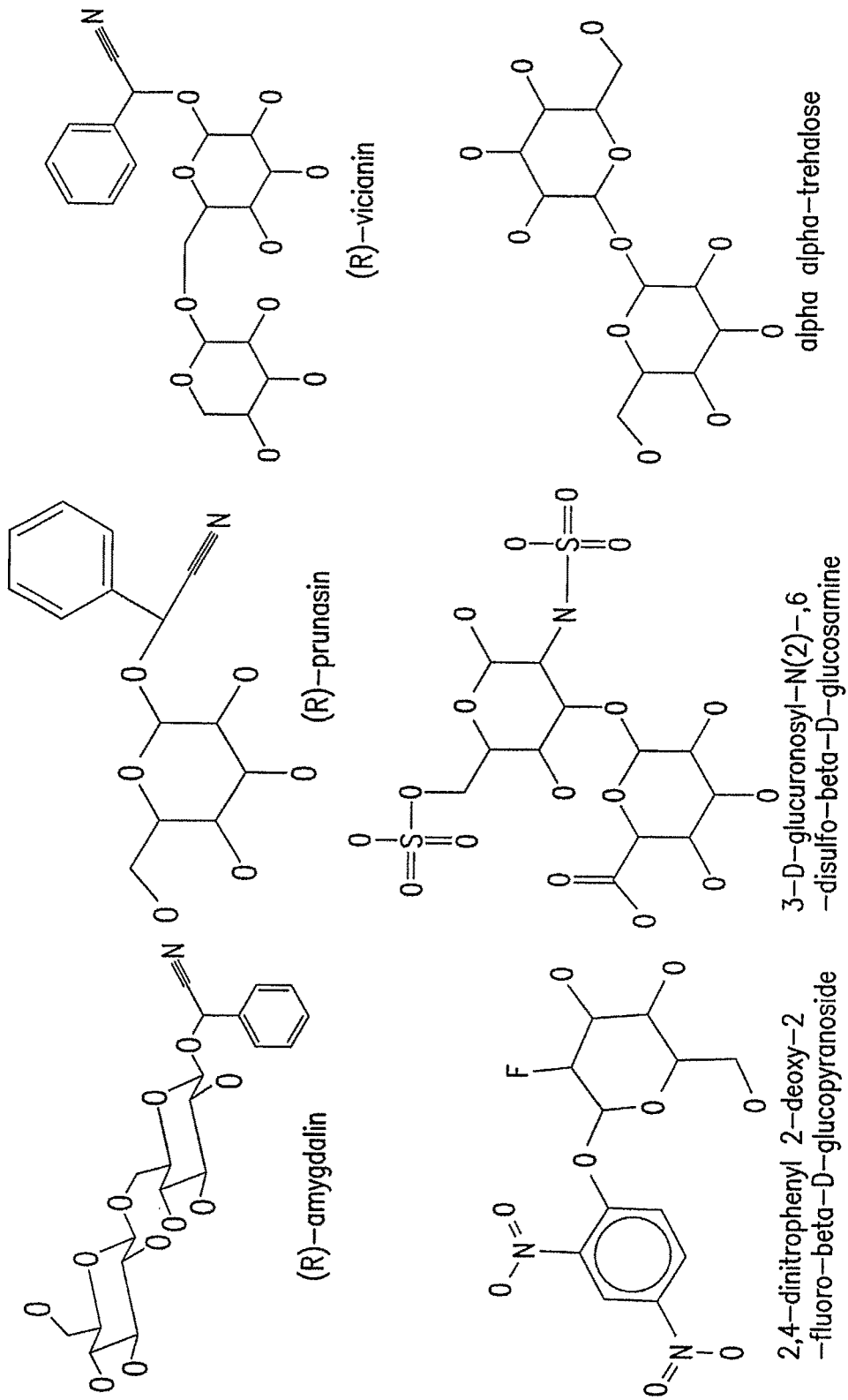
Figures 1, 29B:
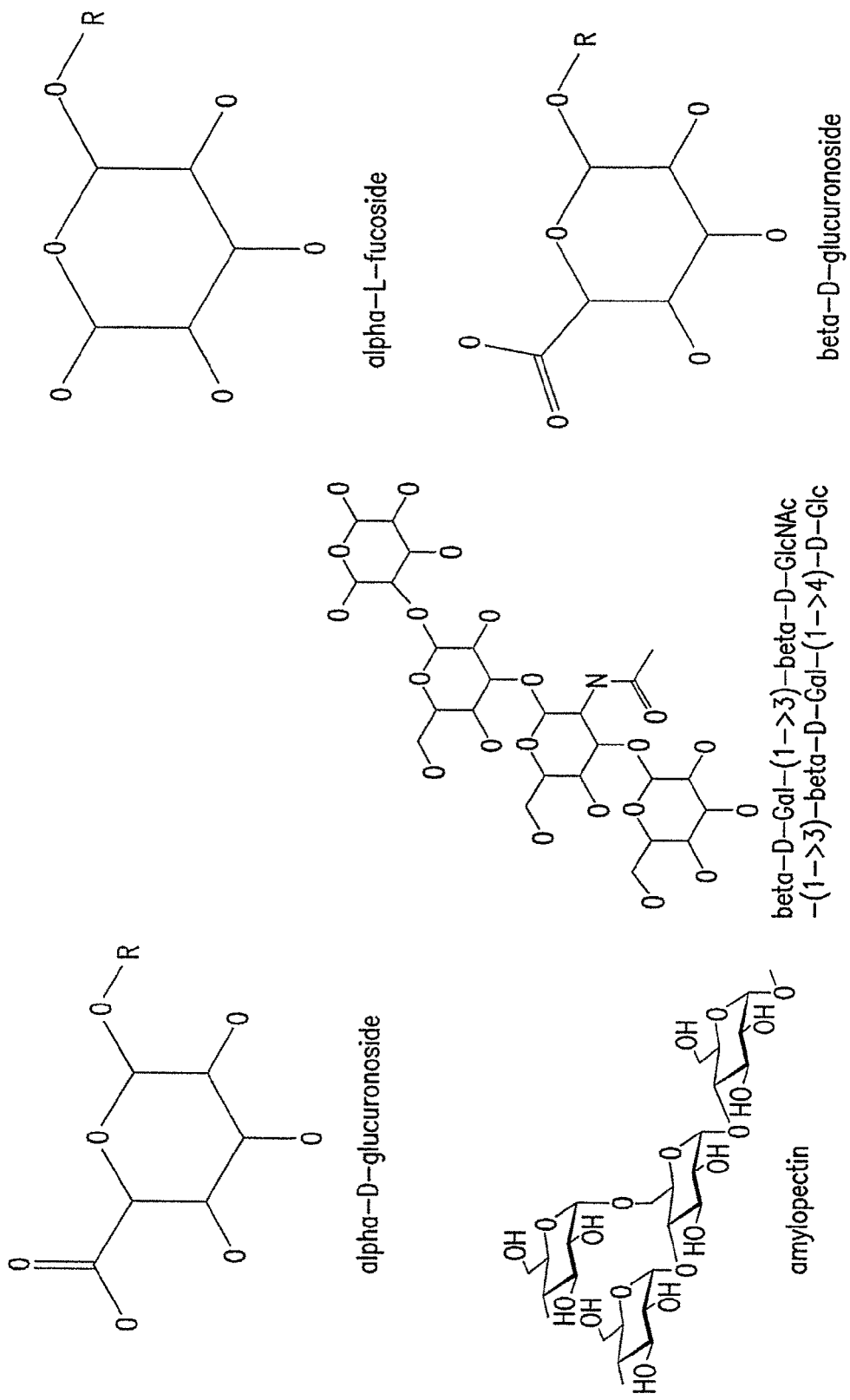
Figure 29D:
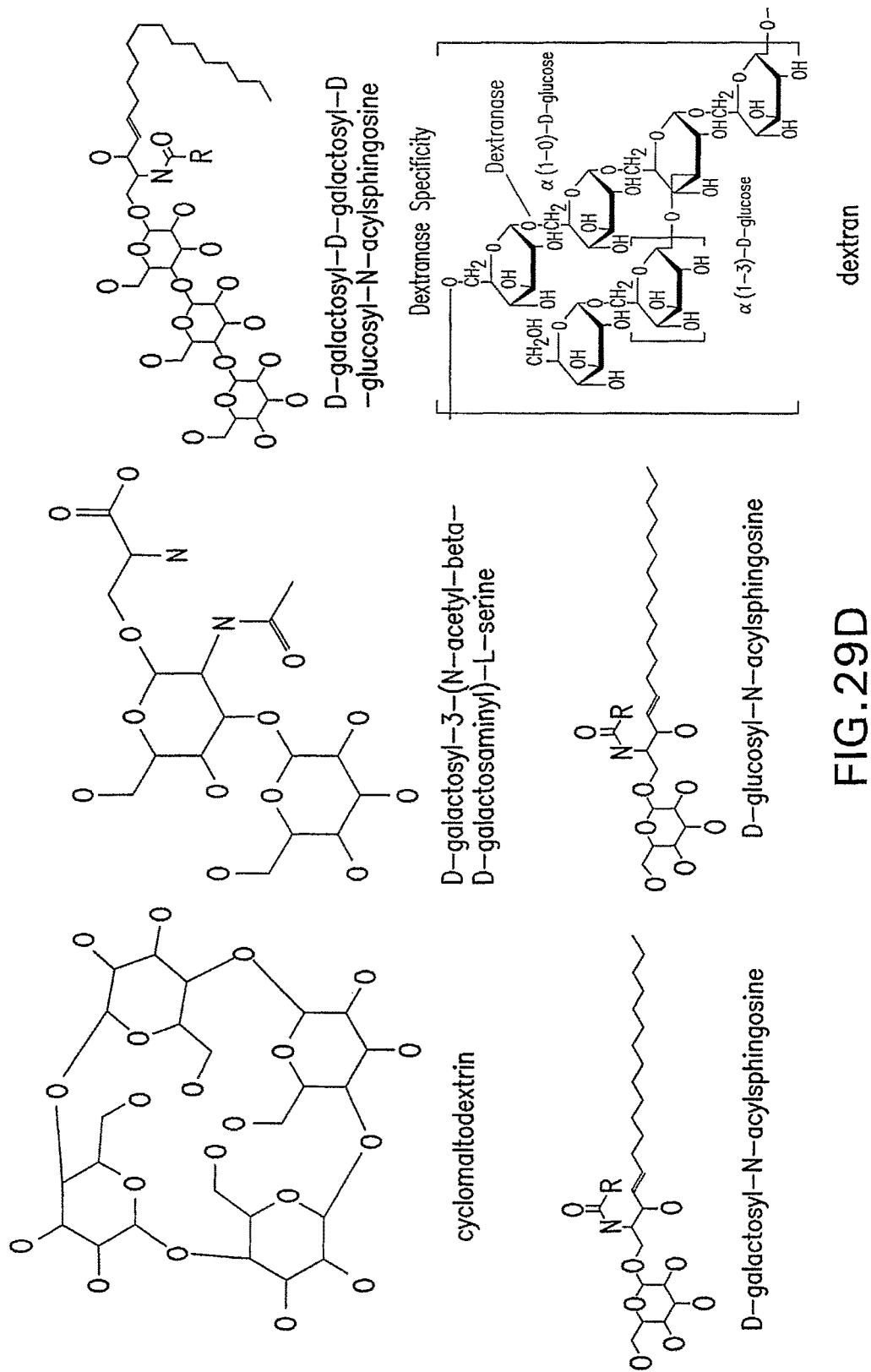
Figure 29E:
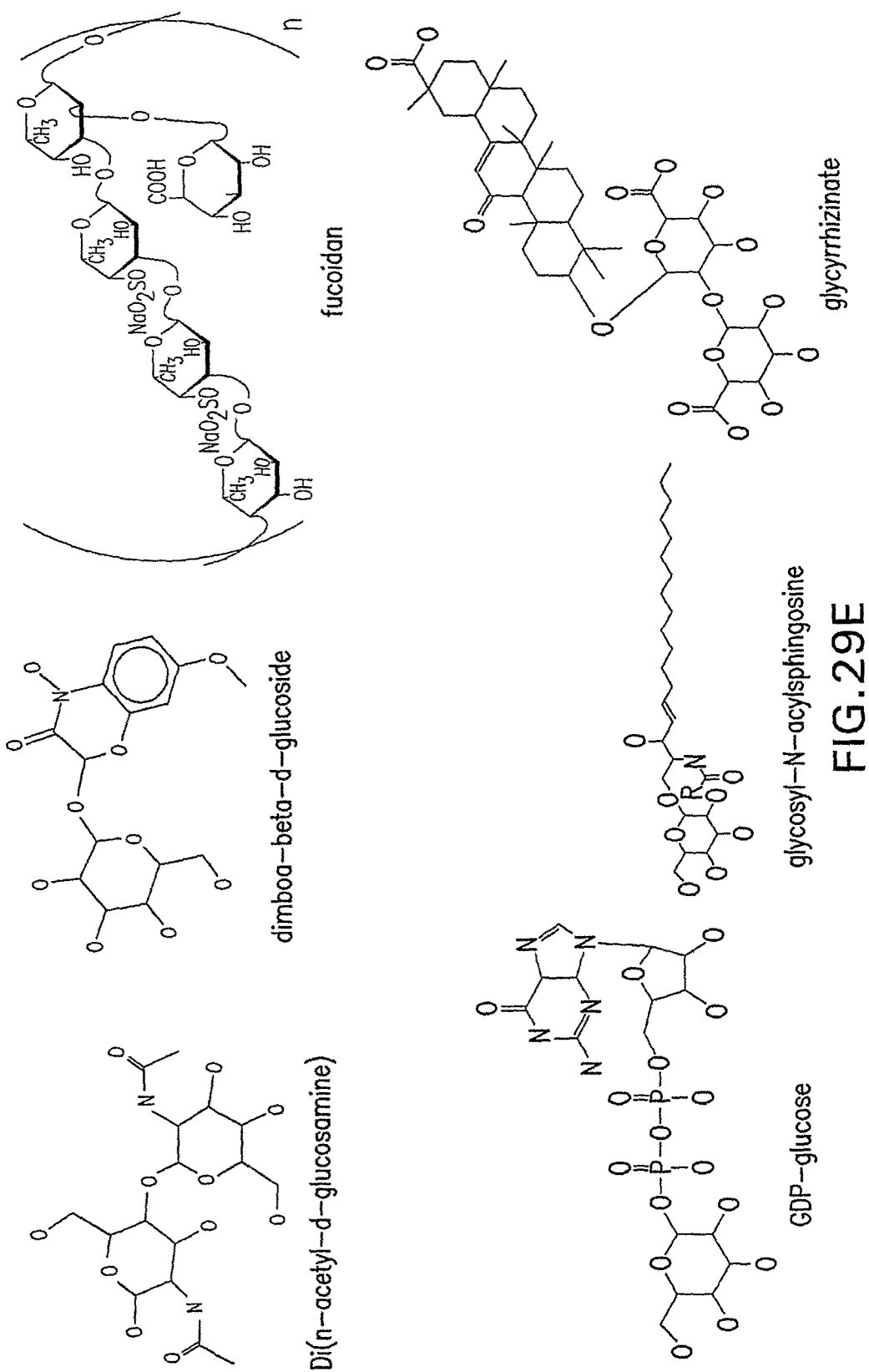
Figure 29F:
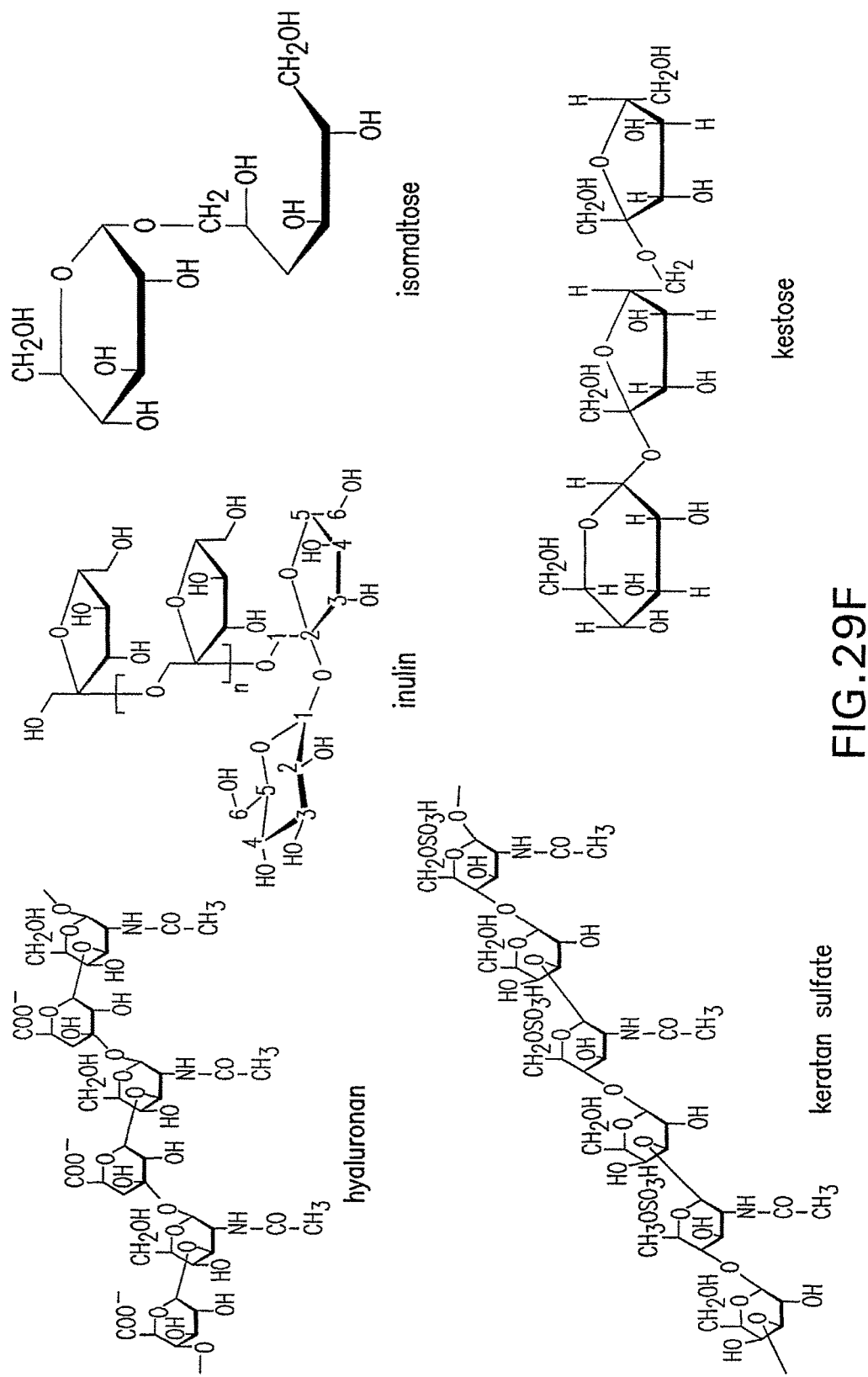
Figure 29G:
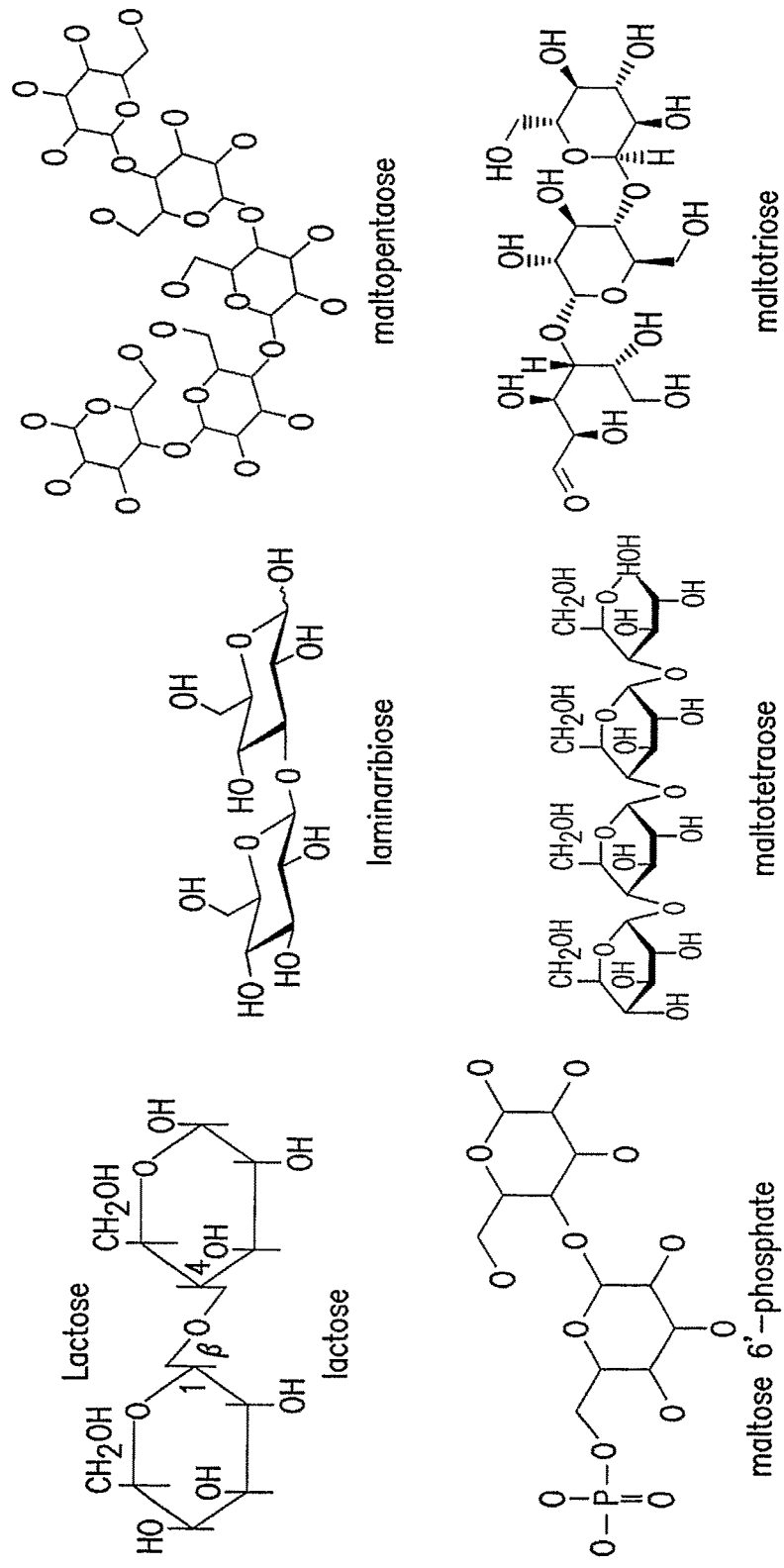
Figure 29I:
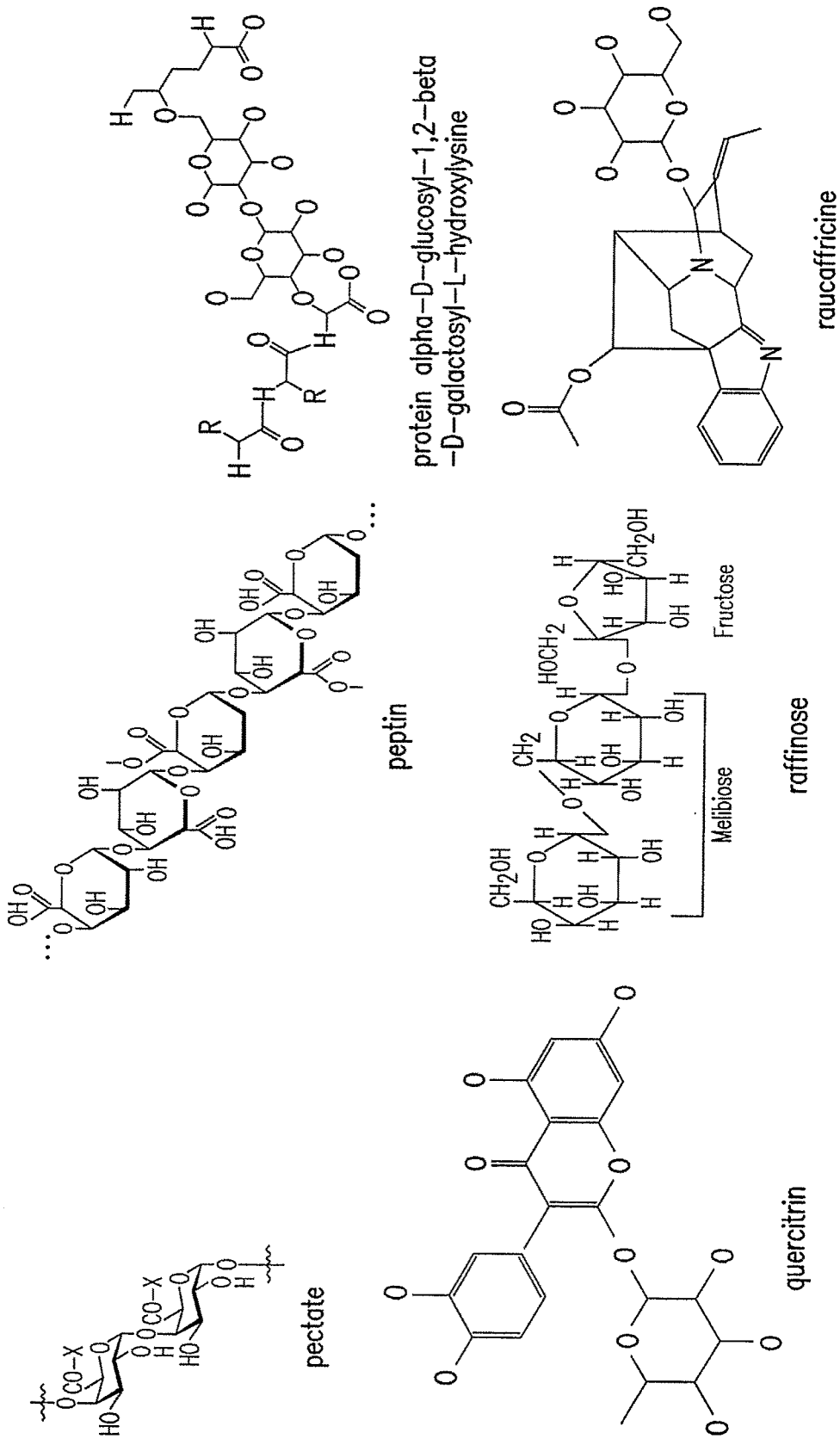
Figure 29J:
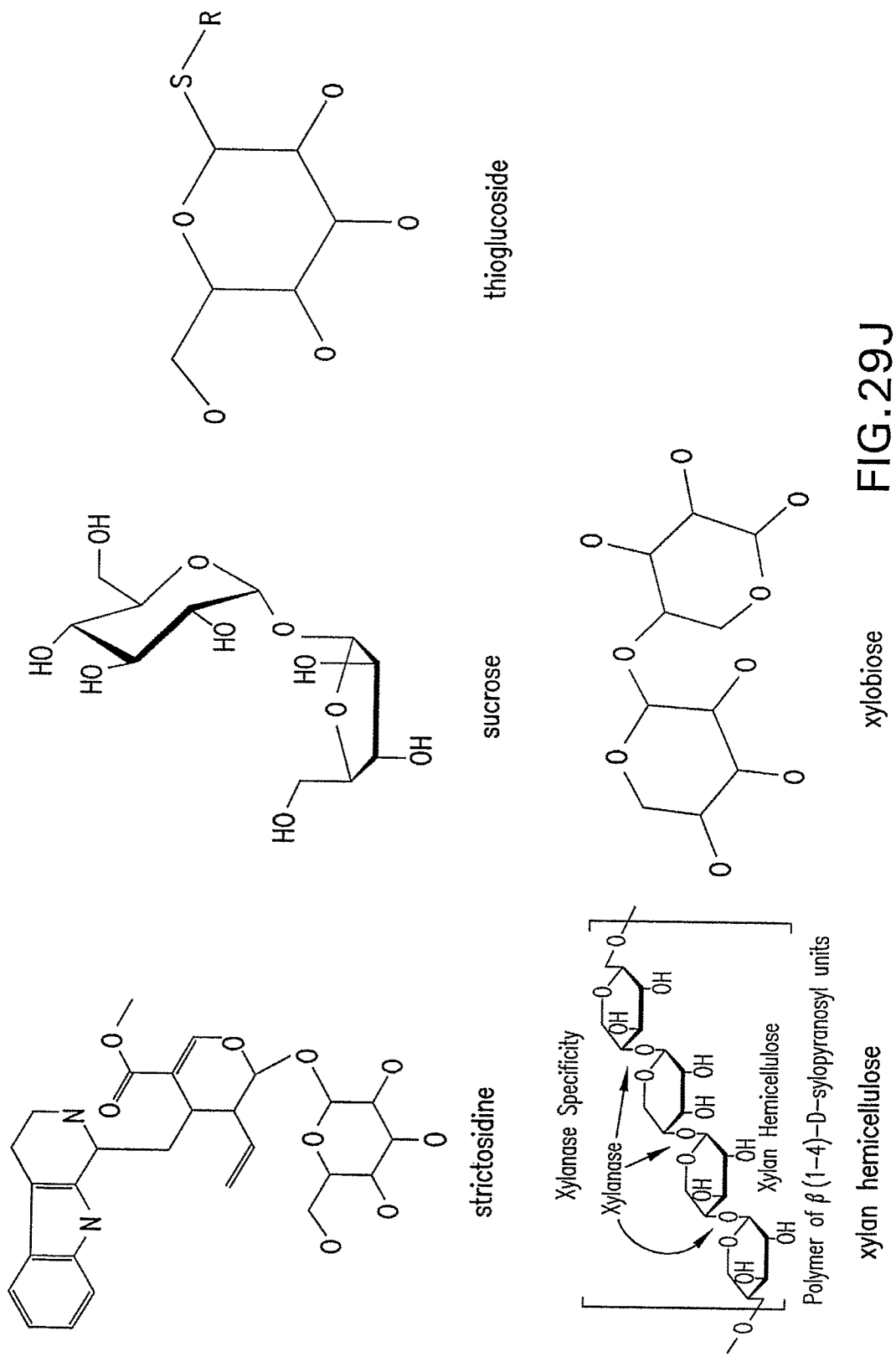
Figure 29K:
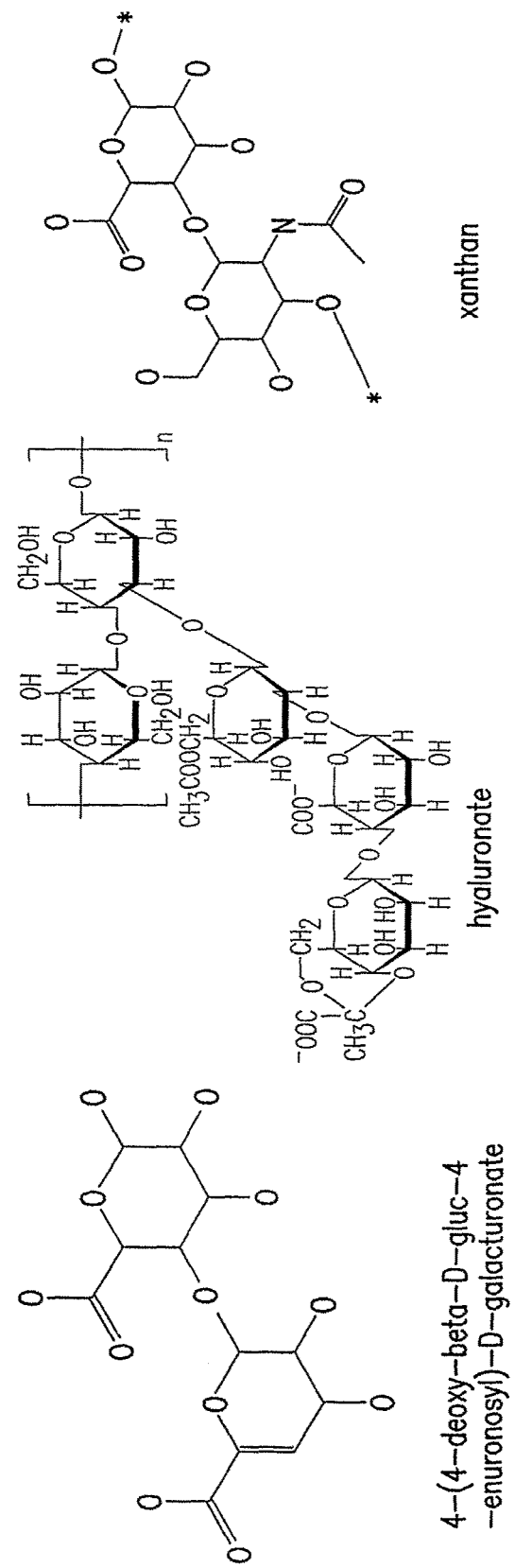

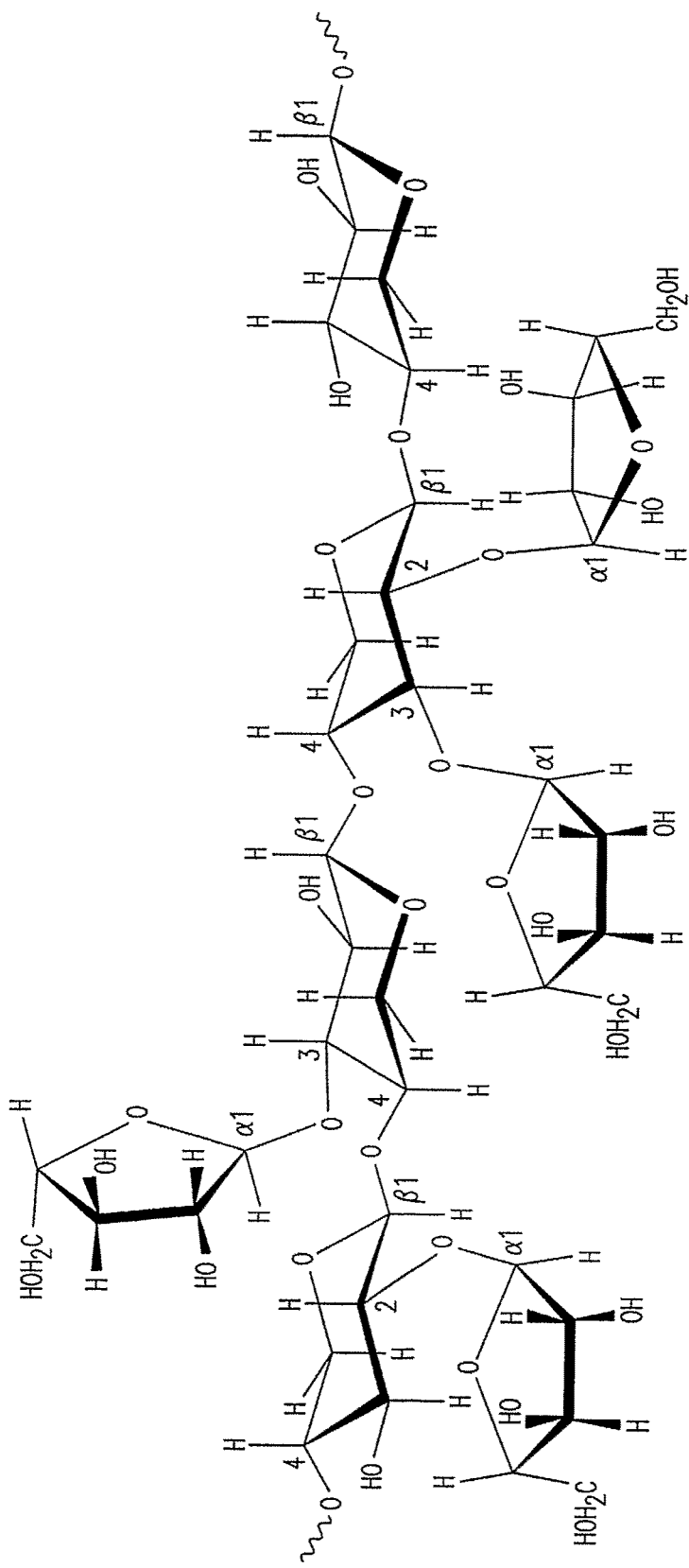
FIG. 29B-2 arabinoxylan

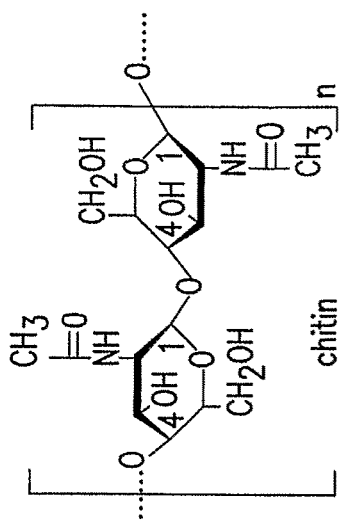
chitin
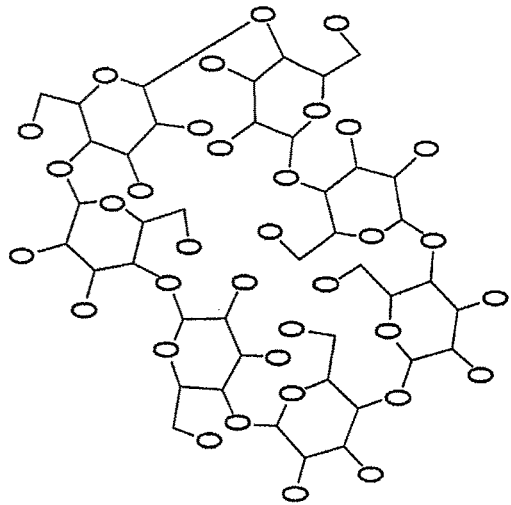
cyclodextrin
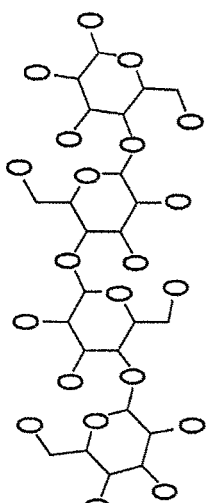
cellotetraose
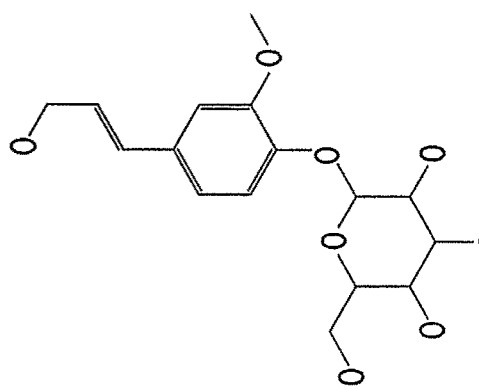
coniferin
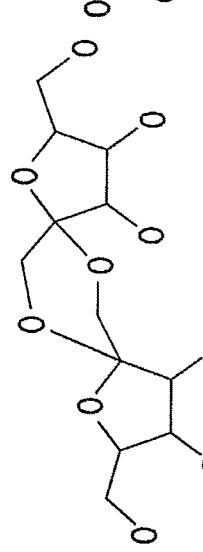
bis-D-fructose 2' 1 2, 1'-dianhydride
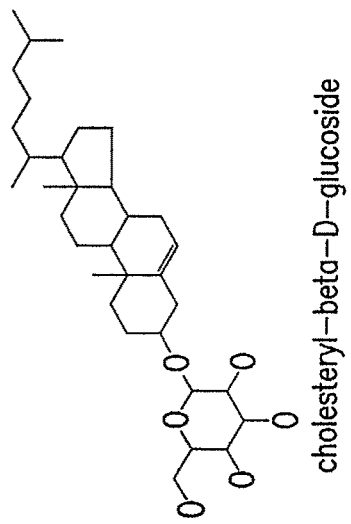
cholesteryl-beta-D-glucoside
FIG. 29C

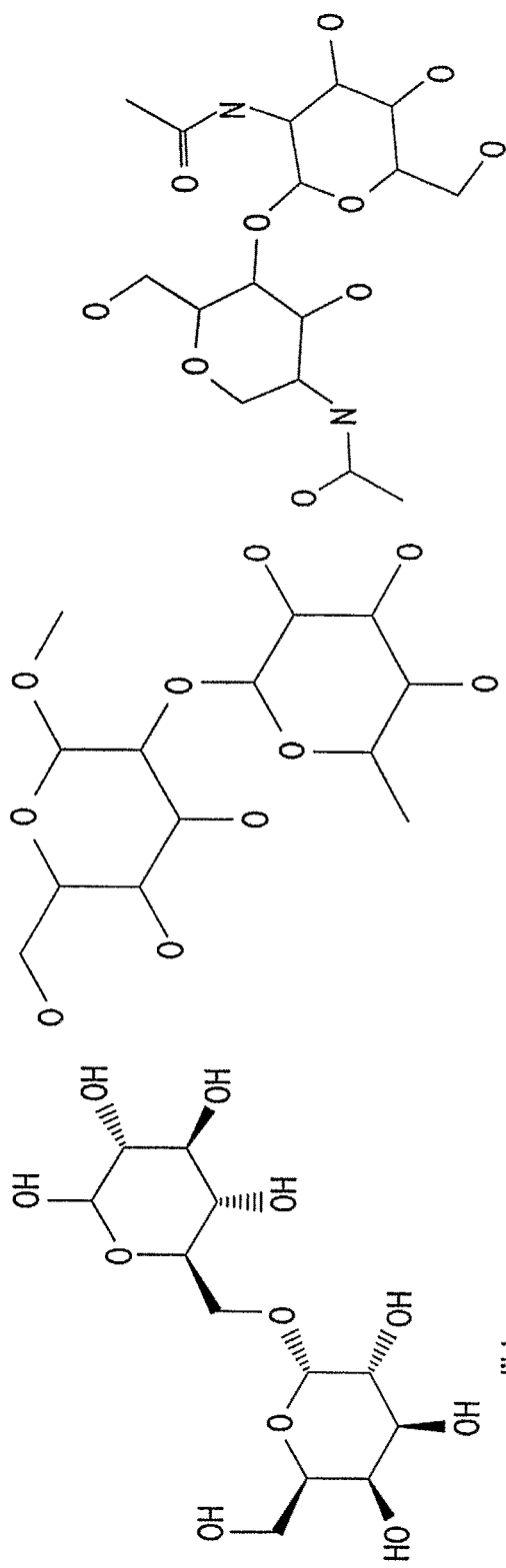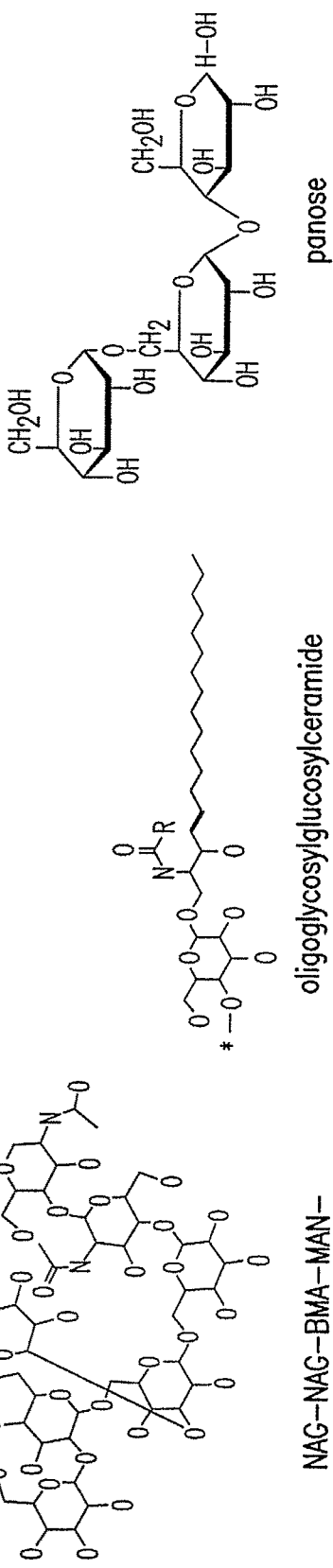
FIG.29H

CELL-MEDIATED DIRECTED EVOLUTION

PRIORITY CLAIM

This application is a continuation of International Application PCT/US07/15568, filed Jul. 5, 2007, which claims priority to U.S. Provisional Application No. 60/891,833, filed Feb. 27, 2007; U.S. Provisional Application No. 60/819,531 filed Jul. 7, 2006, and U.S. Provisional Application No. 60/819,532 filed Jul. 7, 2006, the contents of each of which are hereby incorporated by reference in their entireties.

GRANT INFORMATION

The subject matter herein was developed at least in part under National Institute of Health Grant No. 2R01GM062867-06, National Institute of Health Grant No. GM62867-01A1 and National Science Foundation Grant No. CHE 0350183, and a National Science Foundation Graduate Research Fellowship to Jonathan Bronson, so that the United States Government has certain rights herein.

SEQUENCE LISTING

The specification further incorporates by reference the Sequence Listing submitted herewith via EFS on Jan. 5, 2009. Pursuant to 37 C.F.R. §1.52(e)(5), the Sequence Listing text file, identified as "0700503723.TXT," is 117,428 bytes and was created on Jan. 5, 2009.

1. INTRODUCTION

The present invention relates to systems which harness the molecular biology of a living cell to direct evolution of biological entities of interest. According to the invention, a host cell is engineered to facilitate mutation of a nucleic acid target corresponding to that entity and select for desirable mutants. As applied to populations of host cells, the invention provides a means to generate and contemporaneously select mutants of interest, allowing for the production of extremely diverse libraries enriched in the most "fit" species of mutants. The methods of the invention, which include the generation of secondary libraries by genetic exchange (e.g. sexual reproduction) between "evolved" libraries, are calculated to be capable of producing libraries having a diversity of $10^{24}$ or greater. In specific, non-limiting embodiments, the present invention provides for directed evolution of hydrolases useful to the energy sector.

2. BACKGROUND OF THE INVENTION

2.1 Directed Evolution

As compared to evolution in nature, a slow process in which mutations occur randomly and apt mutants persist through natural selection, directed evolution is a strategic approach for rapidly creating and selecting useful mutants in the laboratory. Directed evolution holds promise for creating designer enzymes for use as reagents in biomedical research and medical diagnostics, and perhaps even as therapeutics.

Briefly, the history of the development of directed evolution is as follows. In the 1990's, the ability to reverse transcribe and amplify RNA directly was successfully exploited to select for RNA molecules with de novo binding and catalytic functions from very large (>$10^{12}$ unique molecules) random libraries of RNA (Wilson and Szostak, 1999, Annu. Rev. Biochem. 68: 611-647; Jenison et al., 1994, Science 263: 1425-1429; Tsang and Joyce, 1996, J. Mol. Biol. 262: 31-42; Sassanfar and Szostak, 1993, Nature 364: 550-553). Beginning with the introduction of phage display technology in 1985 (Smith, 1985, Science 228: 1315-1317), the development to robust methods (Merryman et al., 2002, Chem. Biol. 9: 741-746; Hanes and Pluckthun, 1997, Proc. Natl. Acad. Sci. USA. 94: 4937-4942; Roberts and Szostak, 1997, Proc. Natl. Acad. Sci. USA. 94: 12297-12302; Colby et al., 2004, Methods Enzymol. 388: 348-358; Arnold, 2001, Nature 409: 253-257) for directly or indirectly "tagging" a protein with its DNA sequence for very large library sizes brought momentum to the protein directed evolution field (Arnold, 2001, Nature 409: 253-257; Lin and Cornish, 2002, Angew. Chem. Int. Ed. Engl. 41: 4402-4425; Aharoni et al., 2005, Curr. Opin. Chem. Biol. 9: 210-216; Magliery and Regan, 2004, Eur. J. Biochem. 271: 1595-1608). These methods lend themselves naturally to selections for binding—for example, by repeated passage of the protein-DNA complex over a small-molecule ligand affinity matrix. The last several years have now seen multiple reports from different laboratories of the de novo directed evolution of binding proteins from large libraries (>$10^8$; Binz et al., 2005, Nat. Biotechnol. 23: 1257-1268). In 1999, Skerra and coworkers reported the de novo selection of a lipocalin with a 65 nM dissociation constant for fluorescein (Beste et al., 1999, Proc. Natl. Acad. Sci. USA. 96: 1898-1903). De novo binding proteins have also been reported using libraries of fibronectin, thioredoxin, and ankyrin and TPR repeat proteins (Chivers et al., 1996, EMBO J. 15: 2659-2667; Cortajarena et al., 2004, Protein Eng. Des. Sel. 17: 399-409; Rutledge et al., 2003, J. Am. Chem. Soc. 125: 14336-14347; Binz et al., 2004, Nat. Biotechnol. 22: 575-582).

The foregoing reports utilize a similar strategy. An existing, well-studied protein fold that naturally binds to diverse targets is used as a privileged binding "scaffold". Flexible loops in the protein that comprise most of the ligand-binding pocket are randomized to all 20 amino acids to create very large libraries (>$10^{20}$). Active protein variants are selected from a subset of ca. $10^8$ of these variants based on binding to an affinity matrix using methods like phage display to link each protein variant to its mutatable and amplifiable DNA code.

While directed evolution of binding proteins has met with early success, directed evolution of catalytic proteins—enzymes—has been difficult. The problem for enzyme catalysis is that these methods like phage display that effectively create a protein-DNA complex are difficult to adapt to select for catalytic turnover (Arnold, 2001, Nature 409: 253-257; Lin and Cornish, 2002, Angew. Chem. Int. Ed. Eng. 41: 4402-4425). Bringing the power of directed evolution to bear on more demanding applications in enzyme catalysis, such as changing the substrate specificity of an existing enzyme, appears to require larger library sizes that cannot be achieved even with automation of these traditional assays. Proof of the feasibility of changing enzyme substrate specificity when large library sizes (ca. $10^8$) can be achieved comes from the application of traditional genetic complementation assays to directed evolution. For example, Yano and coworkers were able to increase the activity of aspartate aminotransferase with β-branched substrates by five orders of magnitude using an *Escherichia coli* (*E. coli*) β-branched amino acid auxotroph, with multiple rounds of selection from libraries of $10^6$-$10^7$ variants (Yano et al., 1998, Proc. Natl. Acad. Sci. USA. 95: 5511-5515).

One of the early examples of test tube directed evolution was carried out with the classic TIM barrel triose-phosphate isomerase (Hermes et al., 1990, Proc. Natl. Acad. Sci. 87:696-

700). More recently the wealth of sequence data and sophisticated understanding of structure-function relationships in TIM barrel enzymes has been exploited to interconvert existing TIM barrel enzymes with dramatic changes in substrate specificity and catalytic activity (Schmidt et al., 2003, Biochemistry 42: 8387-8393; Jurgens et al., 2000, Proc. Natl. Acad. Sci. USA. 97: 9925-9930; Silverman et al., 2001, Proc Natl Acad Sci USA. 98: 3092-309775-78; Hsu et al., 2005, Proc. Natl. Acad. Sci. USA. 102: 9122-9126).

Most recently, an αβ/βα metallohydrolase that hydrolyzes the thioester bond in S-D-lactoylglutathione was converted to a related αβ/βα metallohydrolase with β-lactamase activity by mutagenesis and randomization of four key active site loops from libraries of $10^7$-$10^8$ variants using an ampicillin-resistance growth selection in $E.\ coli$ (Park et al., 2006, Science 311: 535-538). These complementation assays, however, limit directed evolution for the most part to the specific substrates and reactions already carried out by Nature (for an exception, see Wang et al., 2001, Science 292: 498-500). De novo test tube directed evolution of catalytic function may be predicted to require even larger library sizes.

2.2 Chemical Complementation

For the handful of reactions for which there are high-throughput selections for function (for example, the synthesis of a detectable reaction product), directed evolution has been used to change enzyme substrate specificity using large libraries (about $10^8$). For reactions which do not themselves provide a means for selection, the technique of "chemical complementation" has been developed to create suitable selection mechanisms (see, for example, United States Patent Application Publication No. 20040106154 by Cornish; Abida et al., 2002, Chembiochem 3:887-895; Baker et al., 2002, Proc. Natl. Acad. Sci. 99:16537-16542; Baker et al., 2003, Anal. Biochem 315:134-137; Lin et al., J. Am. Chem. Soc. 126:15051-15059; de Fillipe et al., 2004, Biochemistry 43:10353-10363; Senugupta et al., 2004, Biochemistry 43:3570-3581; Carter et al., 2005, Chembiochem. 6:2055-2067).

In chemical complementation, enzyme catalysis is linked to cell survival or phenotype via covalent coupling of two small molecule three-hybrid ligands that reconstitute a transcriptional activator such that the chemistry can be readily varied. A heterodimeric small molecule bridges a DNA-binding domain (DBD)-receptor fusion protein and an activation domain (AD)-receptor fusion protein. When the DNA binding Domain and Activation Domain are joined by the small molecule bridge, the DNA-binding domain can bind to a corresponding binding site in a host cell which is operably linked to a reporter gene, and transcription of the reporter gene can occur. Catalytic activity of an enzyme E can be detected where the small molecule bridge is a substrate of the enzyme (see FIG. 1). Enzyme catalysis of formation of a bond between the two small molecule ligands to create such a bridge is detected as activation of an essential reporter gene; whereas enzyme catalysis resulting in bond cleavage and destruction of the bridge may be detected by repression of a toxic reporter gene. The assay can be applied to new chemical reactions simply by synthesizing new small molecule substrates to bridge the DBD and AD domains.

2.3 Systems for Screening for Catalytic Activity

Several technologies have been developed to address the need for high-throughput screening of mutants for catalytic activity. As one example, methods like phage display and cell surface display have been further modified to detect catalysis by attaching not only the mutant protein, but also the substrate and product for the chemical reaction to the phage or cell surface (Pedersen et al., 1998, Proc. Natl. Acad. Sci. USA. 95: 10523-10528; Demartis et al., 1999, J. Mol. Biol. 286: 617-633; Olsen et al., 2000, Nat. Biotechnol. 18: 1071-1074). In another approach, as used by Tawfik and Griffiths, emulsion technology is used to create water droplets of crude cell extracts that encapsulate not only the protein and its encoding DNA but also multiple substrate and product molecules (Tawfik and Griffiths, 1998, Nat. Biotechnol. 16: 652-656; Aharoni et al., 2005, Chem. Biol. 12: 1281-1289; Mastrobattista et al., 2005, Chem. Biol. 12: 1291-1300). For a review, see Cornish, 2006, Nature 440:156-157.

2.4 The Need for More Active Cellulase

According to the United States Department of Energy, over 85 percent of the energy used in the United States comes from fossil fuels (Apr. 30, 2006, www.energy.gov). A viable alternative energy source would reduce dependence on non-renewable fossil fuel resources. Ethanol derived from corn or sugarcane fermentation is the most common renewable fuel today (Id.) However, increasing energy needs can be expected to make these raw materials limited in the future. Therefore, generation of ethanol via biomass conversion is an attractive alternative.

Currently, it is not cost effective to generate ethanol from biomass due to the high enzyme cost required for cellulose degradation. A ten-fold decrease in the enzyme cost, equivalent to a ten-fold increase in cellulase catalytic activity, is needed to make generation of ethanol from biomass commercially viable. Since cellulose is estimated to constitute virtually half of the biomass, increasing the specific activity of cellulases ten-fold arguably would be the most straightforward solution to the energy crisis. However, industrial efforts to generate cellulase mutants with increased catalytic activity either by rational design or by screening random mutants individually for increased activity (limited to $10^4$-$10^6$ mutants even with automation techniques) have met with limited success.

3. SUMMARY OF THE INVENTION

In particular non-limiting embodiments, the present invention provides for a system for directing evolution of a biological entity of interest comprising a plurality of host cells, such that each host cell:

(i) contains a nucleic acid target corresponding to the entity of interest;

(ii) contains at least one diversifying nucleic acid ("DINA") which can be used to direct mutation of the target; and (iii) exhibits at least one mutator function which increases the likelihood that the target will be mutated by the DINA; wherein a plurality of host cells contain a plurality of different DINAs, and wherein said system further comprises a means for selecting for a mutant entity of interest target exhibiting a desired activity.

The present invention further provides for a method for directing evolution of a nucleic acid target, especially a protein, especially an enzyme, of interest which utilizes the foregoing system, whereby the plurality of host cells are subjected to conditions such that the mutator function operates to direct mutation of the target by the DINA and then host cells expressing a mutated target with altered activity are selected, with the optional step of permitting genetic exchange between genetically non-identical host cells (for example, but not limited to, sexual reproduction) followed by selection.

The present invention also provides for a primary population of host cells (a "primary library") which contains, as a result of operation of the mutator function(s) and DINAs, a diversity of mutant targets. Still further, the present invention provides for a secondary population ("secondary library") of host cells resulting from genetic exchange between two or more primary populations of cells.

Accordingly, the present invention provides for the creation of extremely large primary and secondary libraries of mutant targets of interest, by calculation having a diversity potentially of $10^{24}$ and even higher, with "less fit" species of mutants being eliminated by selection, so that the selected library would contain a practically sustainable number of "more fit" species of mutants.

The entity of interest may be, for example and not by way of limitation, a protein, a functional RNA, a promoter element, an intron, a ribosome binding site, an endonuclease recognition site, or a repressor element. In other non-limiting embodiments, the entity of interest may be a metabolite, and the nucleic acid target corresponding to that metabolite may be an enzyme that produces it. Moreover, the invention may be used to essentially concurrently evolve more than one target, and therefore, in a specific non-limiting embodiment, may evolve a plurality of members of a molecular pathway that produces a metabolite of interest.

In particular, non-limiting embodiments, the system of the invention may be used to change the level or nature of the activity of a target enzyme, where the change, for example, is an increase or decrease in the activity of the enzyme, an alteration in the conditions required for enzyme activity, or a change in the substrate specificity of the enzyme.

In certain non-limiting embodiments of the invention, the basis for selection, rather than being the target itself, is the result of chemical complementation. According to such embodiments, mutation of the target results in a change in the amount of a compound which bridges DNA-binding and activation domains of a two-site receptor fusion protein and, as a consequence, a change in the amount of expression of reporter gene product, which forms the basis for selection.

In one specific non-limiting embodiment of the invention, the system comprises a yeast cell as the host cell, and the mutator function is a yeast HO endonuclease which acts to "shuffle" variant DINAs, for example in 2μ plasmids, where DINAs can replace one or more portion of a target by homologous recombination. The HO endonuclease operating on a plurality of DINAs efficiently increases the diversity of substitutions possible. The host yeast cell is then cultured under conditions which select for a desirable activity of a mutant target; for example, where the activity confers a survival advantage.

In particular, non-limiting embodiments, the present invention provides for systems for directed evolution of biomass converting enzymes, such as enzymes of interest to the energy sector.

In specific, non-limiting embodiments, the present invention provides for a system for directed evolution of cellulase which employs chemical complementation to link cellulase enzyme catalysis to cell survival. A selection step, which allows more than $10^8$ mutants to be tested (because mutants with enhanced activity have a survival advantage) increases the probability of producing a mutant with significantly enhanced cellulase activity. Indeed, the methods of the invention have generated a number of cellulase variants with approximately five-fold increases in activity compared to the parent enzymes. Accordingly, in various embodiments, the present invention provides for systems for directed evolution of cellulases (and other hydrolases), as well as novel cellulases with enhanced activity. Directed evolution may be facilitated by cell-mediated selection as well as, in non-limiting embodiments, cell-mediated mutation and/or genetic exchange. In non-limiting embodiments, the novel cellulases of the invention may be employed in industrial processes involving cellulose breakdown, such as the generation of ethanol as an energy source.

4. BRIEF DESCRIPTION OF THE FIGURES

FIG. 1. Chemical complementation. A heterodimeric small molecule bridges a DNA-binding Domain (DBD)-receptor fusion protein and an Activation Domain (AD)-receptor fusion protein, activating transcription of a reporter gene downstream from the cognate DNA-binding site in vivo.

FIG. 2. Cartoon of the 3-D structure of a canonical TIM barrel enzyme, taken from PDB 1a3h, prepared using Pymol (DeLano Scientific).

Figure 3A:
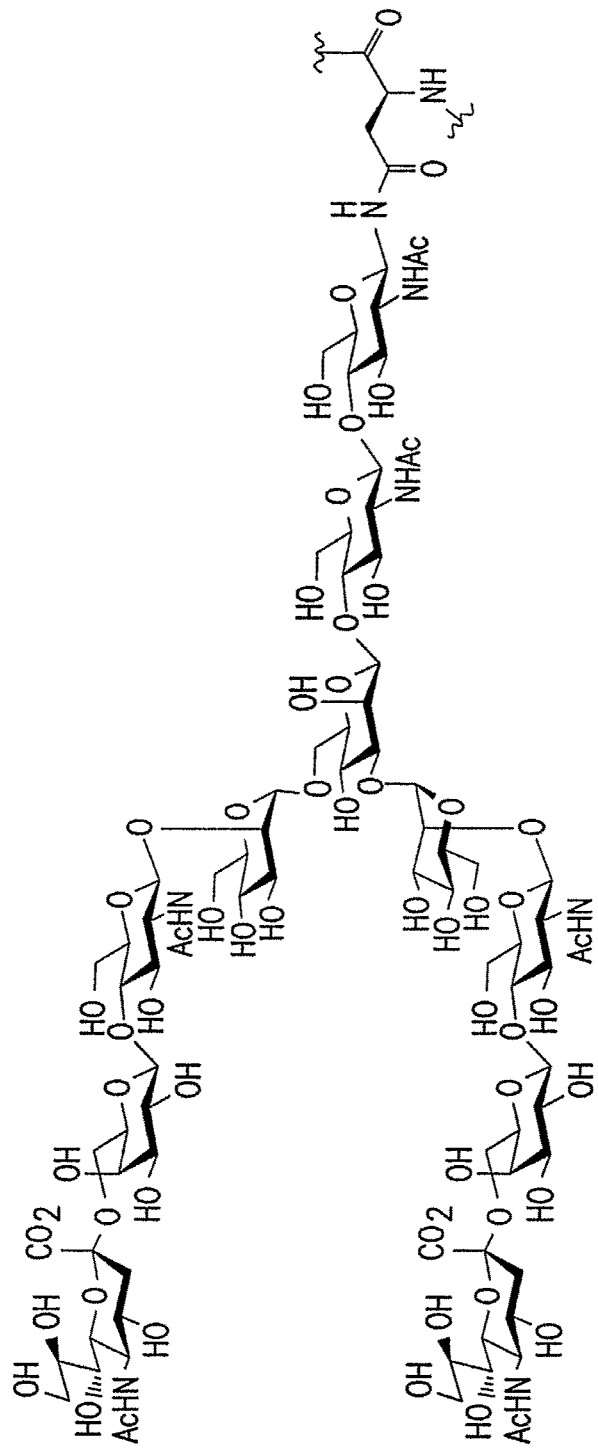
Figure 3B:
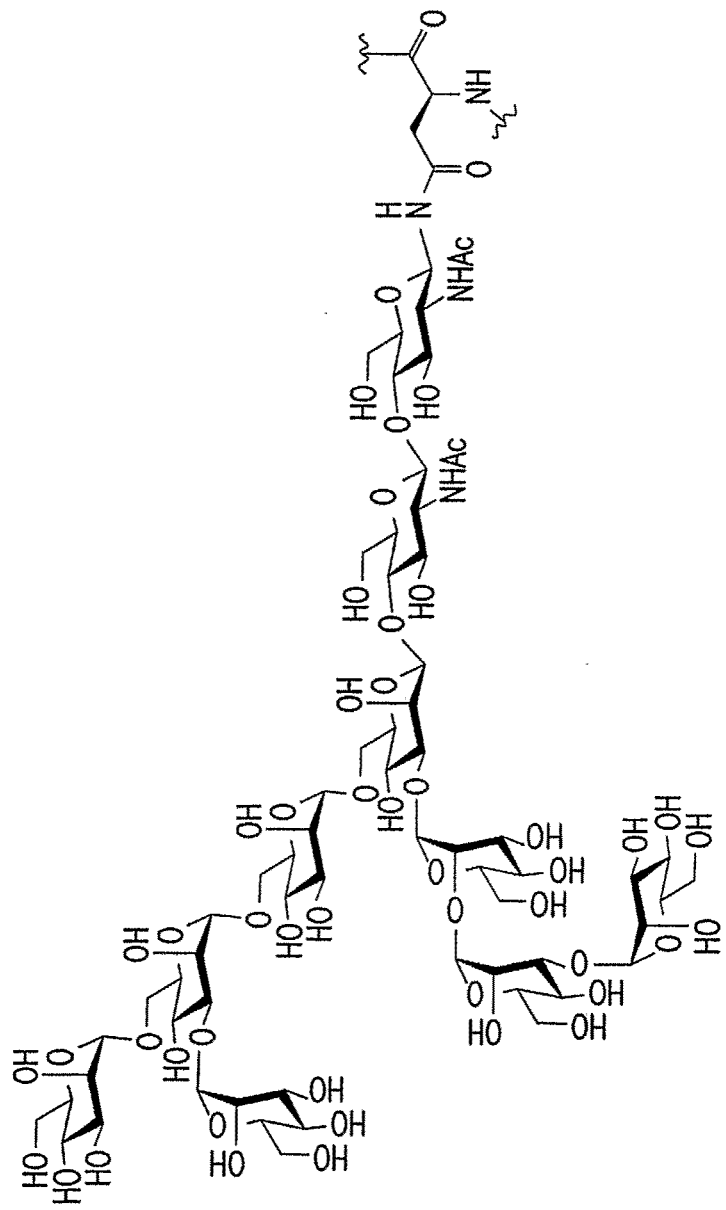
Figure 3C:
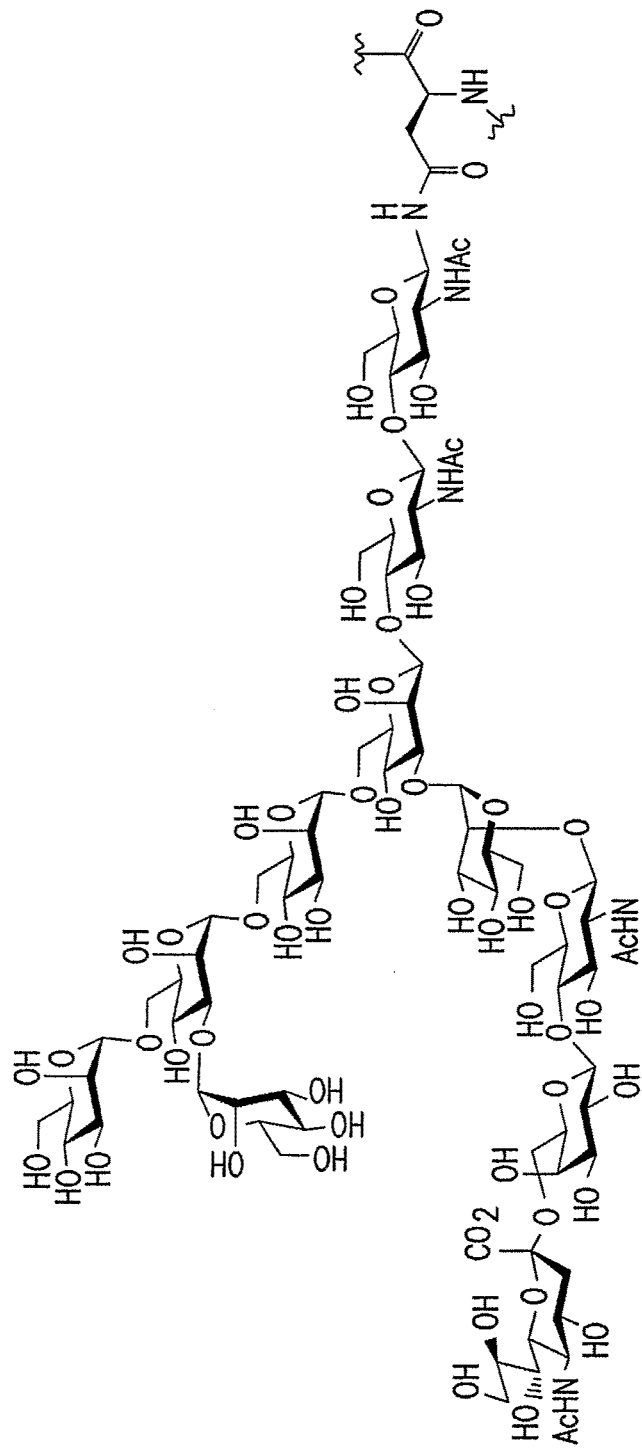

FIG. 3A-C. Extracellular N-glycans in vertebrates display three N-glycan subtypes: A. complex, B. high mannose, and C. hybrid. The figure is adapted from Grogan et al., 2002, Annu. Rev. Biochem. 71:593-634.

Figure 4:
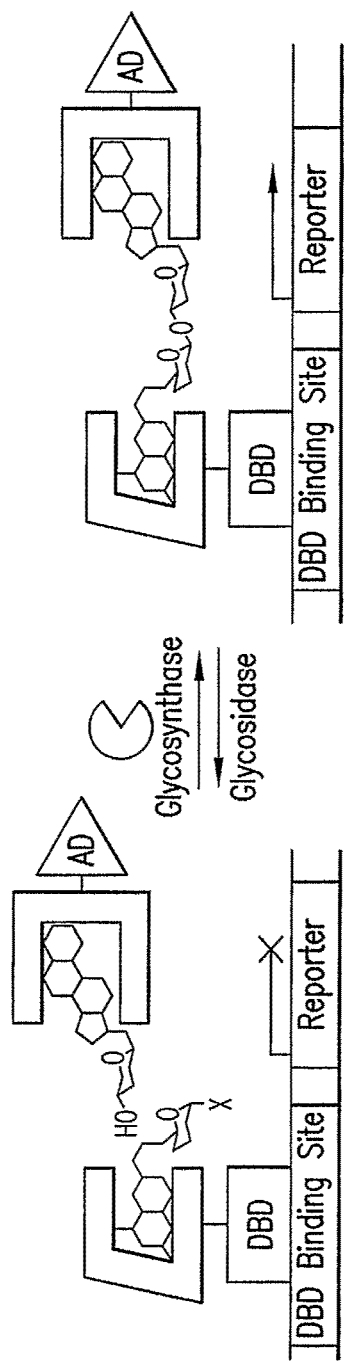

FIG. 4. Application of chemical complementation to detect glycosynthase and glycosidase activity.

Figure 5A:
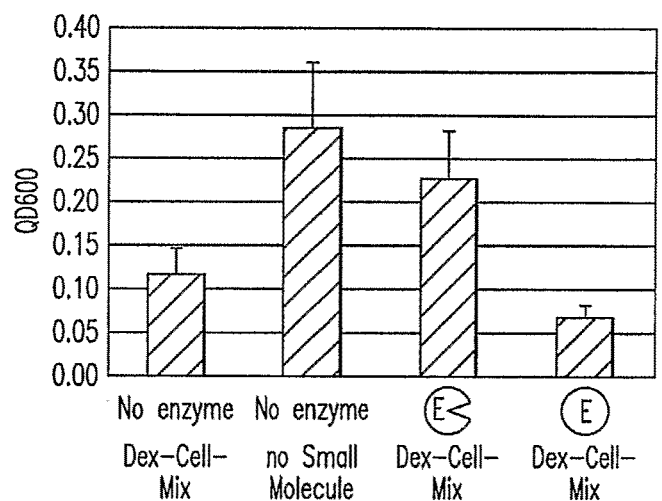
Figure 5B:
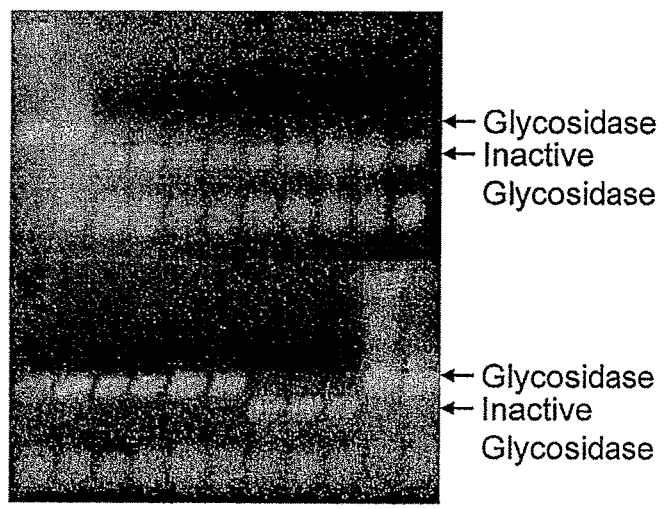

FIG. 5A-B. Chemical complementation links cellulase activity to URA3 reporter gene transcription in vivo. A. Yeast cells containing the DBD-DHFR and AD-GR fusion proteins and the URA3 reporter gene expressing either no enzyme, glycosidase (pacman) or an inactive glycosidase (circle) were grown in selective media with and without 1 μM Dex-Cel-Lac-Mtx. B. Starting with a 1:100 mixture of active:inactive glycosidase variants (top gel, restriction digest of 9 enzymes from independent colonies; bottom gel, restriction enzymes from the 9 fastest growing colonies after selection) the URA3 selection achieved a 200-fold enrichment in active glycosidase from a single round of selection.

Figure 6A:
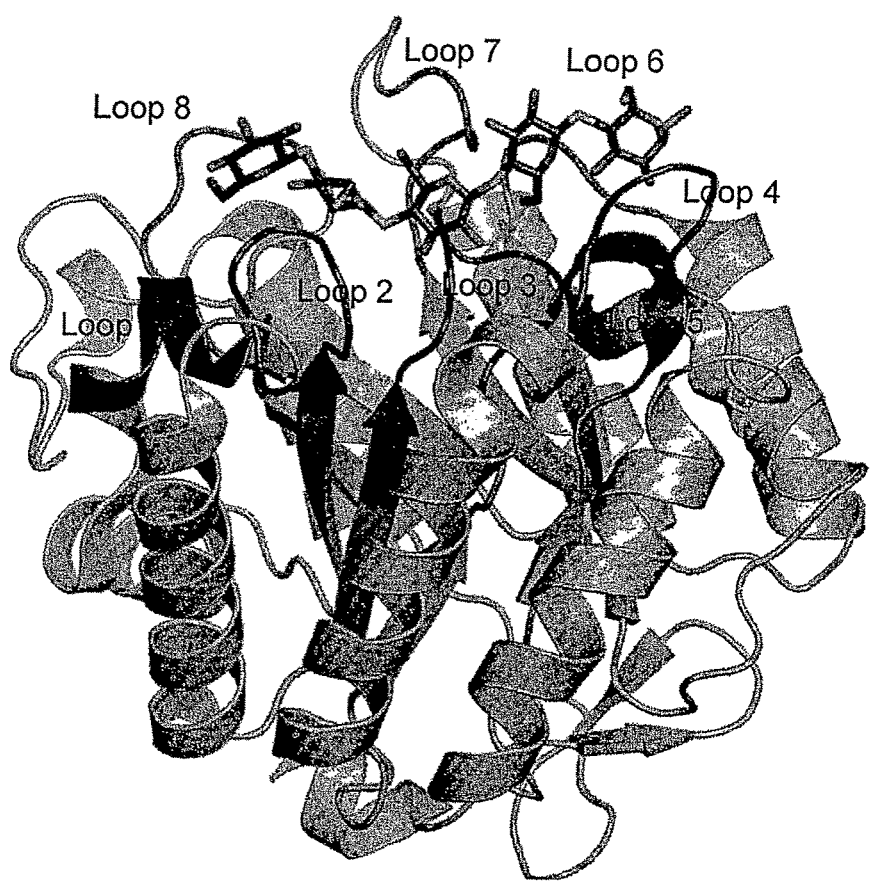

FIG. 6A-B. A. Structure of the complex of the *Bacillus agaradhaerens* Cel5A (SwissProt: O85465; pdb: 1h5v) with methyl 4,4II,4III,4Iv-tetrathio-α-cellopentoside. The cassettes that have direct contact with the substrate are highlighted in red. Figure was prepared using Pymol (DeLano Scientific). B. Designed loop libraries from the sequences of family 5 glycosidases. Cellulase: *B. agaradhaerens* Cel5A (SwissProt: O85465; pdb: 1h5v); Chitosanase: *Streptomyces griseus* HUT 6037 chitosanase II (SwissProt: Q83VL5, 32% identity with Cel5A); Mannanse: *Thermobifida fusca* KW3 mannosidase (SwissProt: Q9ZF13; pdb: 1bqc, 14% identify with Cel5A).

Figure 7:
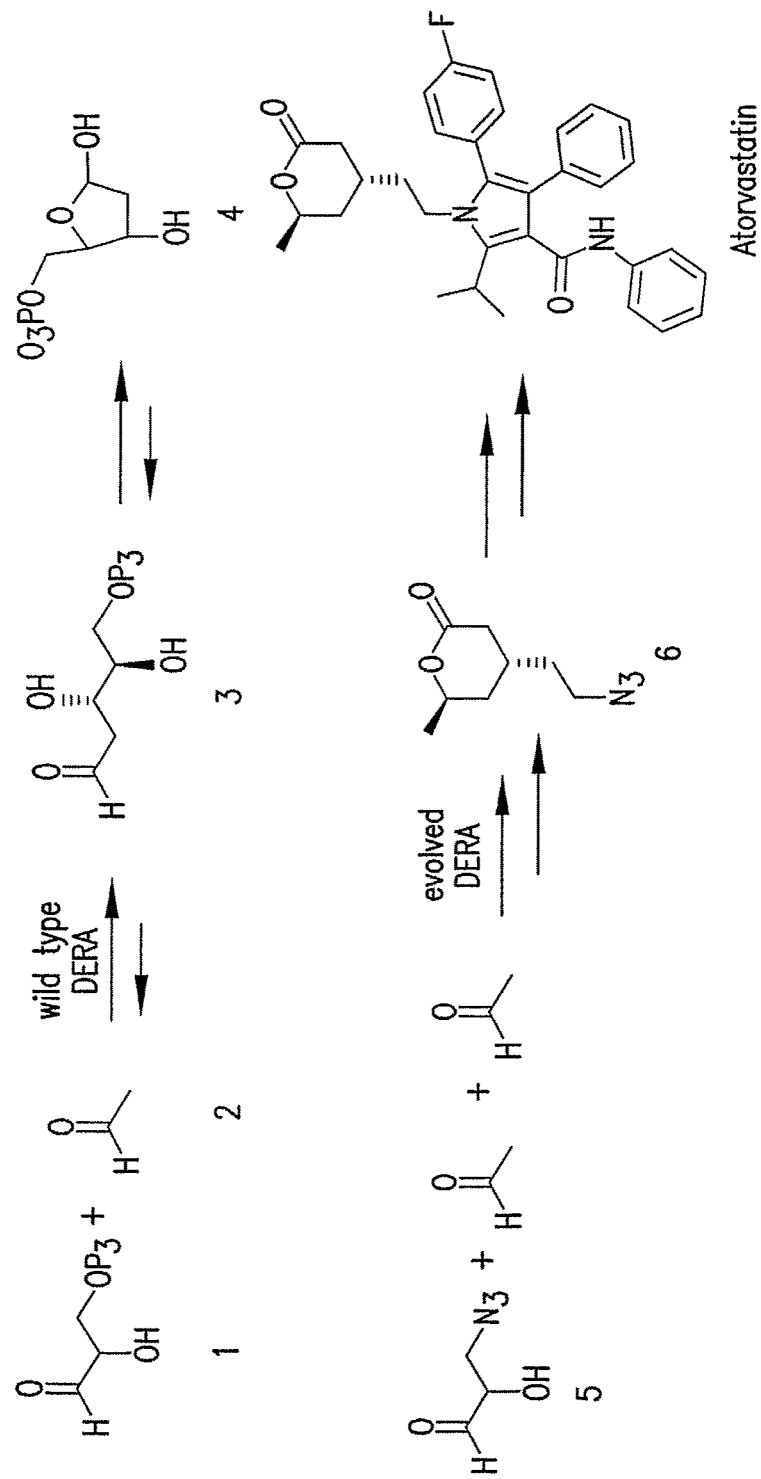

FIG. 7. DERA naturally catalyzes the aldol addition reaction between acetaldehyde and D-glyceraldehyde-3-phosphate. Evolved DERA variants with expanded substrate specificity are being sought, for example, for the synthesis of key chiral intermediate (6) in the synthesis of statins.

Figure 8:
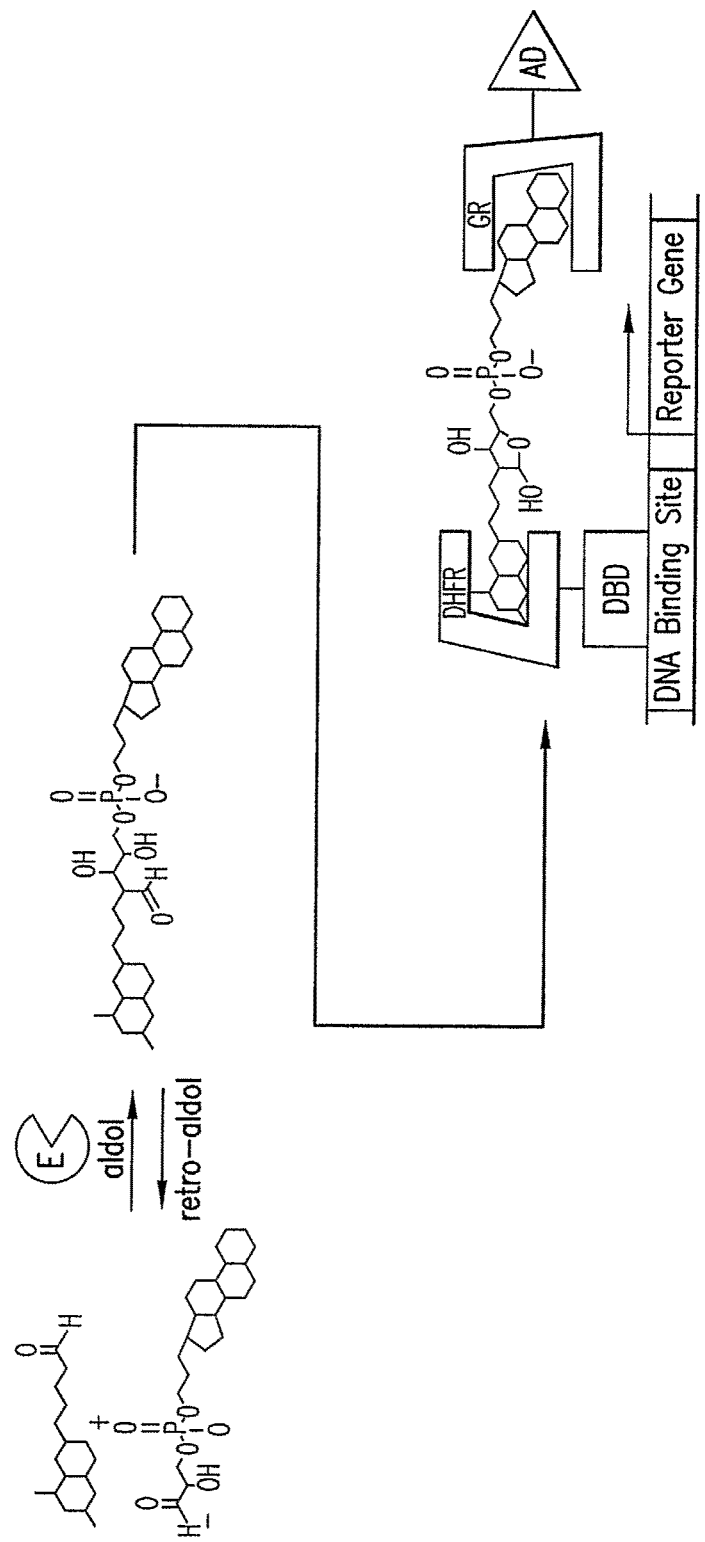

FIG. 8. Detection of aldolase activity via chemical complementation. DERA should catalyze the addition of Dex-"acetaldehyde" and Mtx-"glyceraldehyde". Spontaneous cyclization of the aldol product should result in a stable Dex-Mtx aldol product that should dimerize the DBD-DHFR and AD-GR fusion proteins, activating the transcription of a downstream reporter gene.

Figure 9:
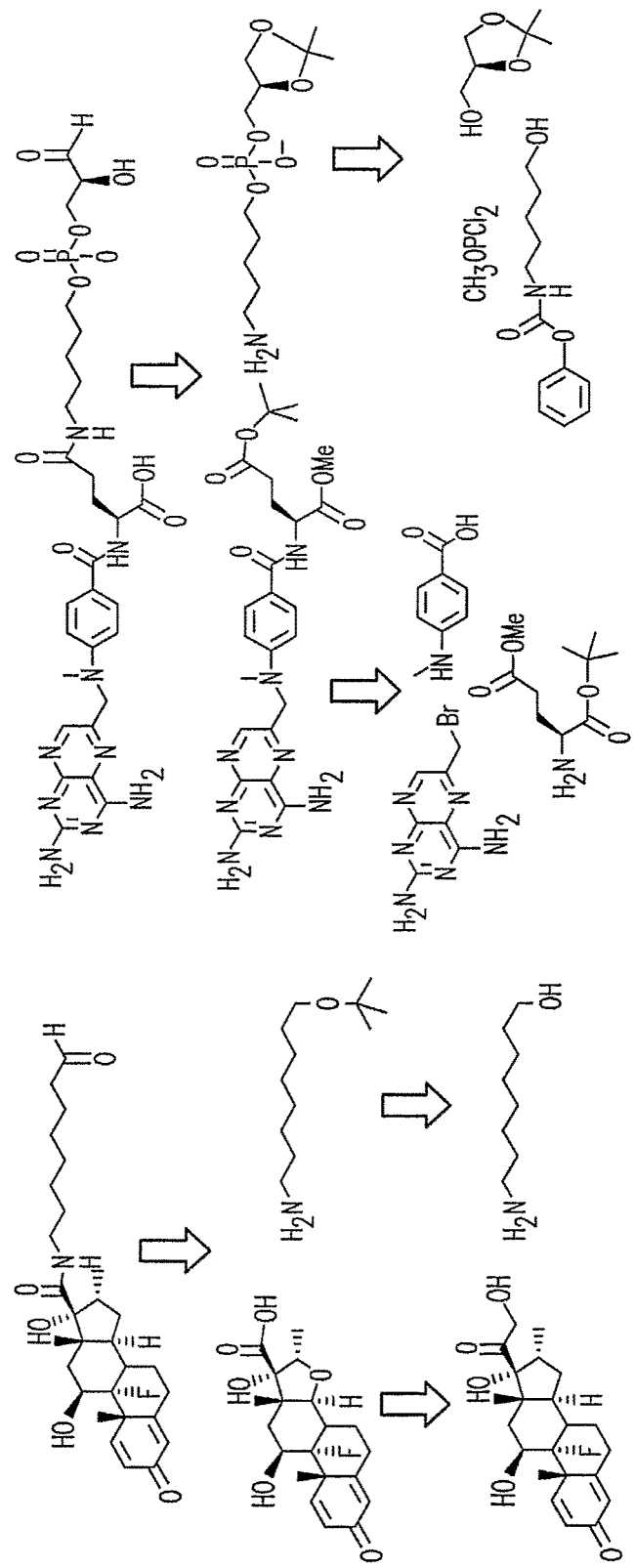

FIG. 9. Retro synthetic scheme of Dex-AAld and Mtx-GAld.

Figure 10:

FIG. 10. Representation of the substrate binding pocket of the *E. coli* D-2-deoxyribose-5-phosphate aldolase (PDB:

1jcj) showing the points of attachment for the Dex and Mtx ligands. There is a large open cavity that should readily accommodate derivatization of the 3-phosphate with Mtx. Four point mutations (L20A, Y49A, V73A and F76A) are proposed to create an opening for the linker from acetaldehyde to Dex. These positions are not implicated in catalysis and are not expected to disrupt protein fold. This figure was prepared using Pymol (DeLano Scientific).

Figure 11A:
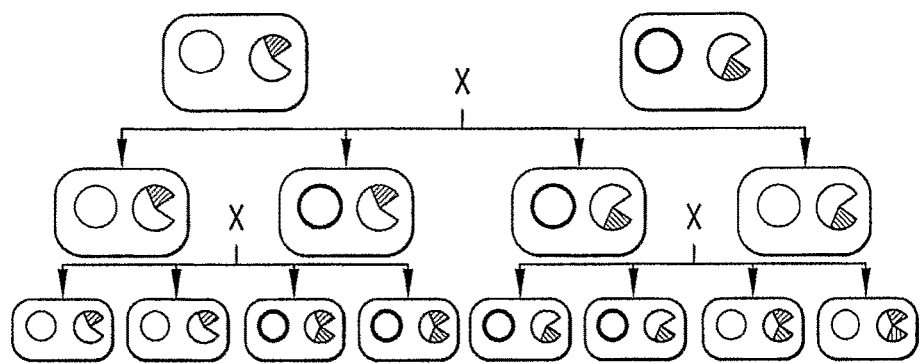
Figure 11B:
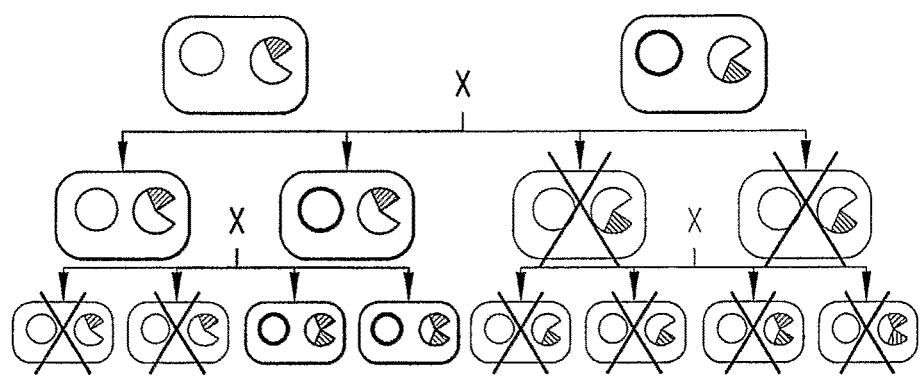

FIG. 11A-B. Simplified schematic diagram showing the effects of mutation and selection. Each rounded rectangular cell contains a plasmid which is either light grey or dark grey and an enzyme (middle grey circle missing a quadrant) having one or more mutation (identified as a light grey or dark grey quadrant). A. Mutation. Beginning with $10^8$ cells each encoding a different protein variant, if there were mutations at each round of cell division, there would be about $10^{16}$ cells containing $10^{16}$ different protein variants after a week of growth assuming doubling time of 6 hours. The problem, however, is that $10^{16}$ cells would require about 100,000 L of cell culture. B. Mutation and selection. The cell elegantly solves this problem through simultaneous mutation and selection. As illustrated here, if there were simultaneous mutations and selection at each round of cell division (cartooned as first selecting for light grey mutations, then light and dark grey mutations), simplistically after the same week of growth, there would be only $10^8$ cells containing the most fit $10^8$ protein variants, such that only the more fit of the two cells survived.

Figure 12A:
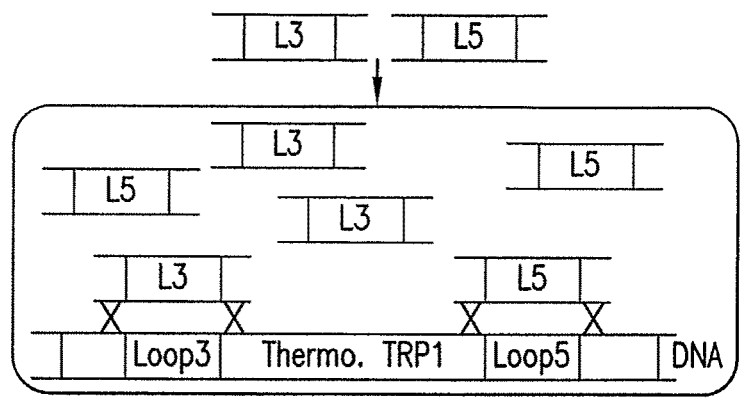
Figure 12B:
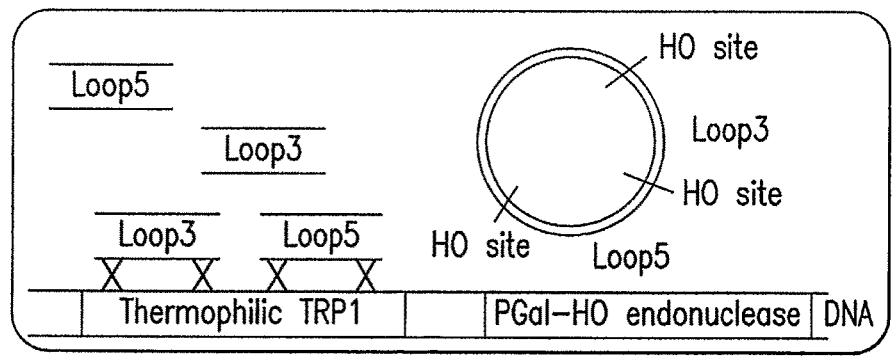

FIG. 12A-B. In vivo mutagenesis. A. Loop libraries by homologous recombination. Active-site loops in the TIM barrel structure of the thermophilic TRP1 may be mutagenized by homologous recombination of synthetic oligonucleotides encoding random loop libraries introduced via electroporation into yeast cells. B. In vivo mutagenesis with HO endonuclease. Removing the transformation step, the short oligonucleotide loop (DINA) libraries can be generated in vivo by galactose induced cleavage of a 2μ plasmid encoding the loop libraries embedded in HO endonuclease sites at each round of cell division. By tuning the levels of HO endonuclease induction, only a portion of the ca. 60 copies of 2μ plasmid present in each cell may be cleaved, allowing the loop library template plasmid to be replicated and restored at each cell division.

Figure 13A:
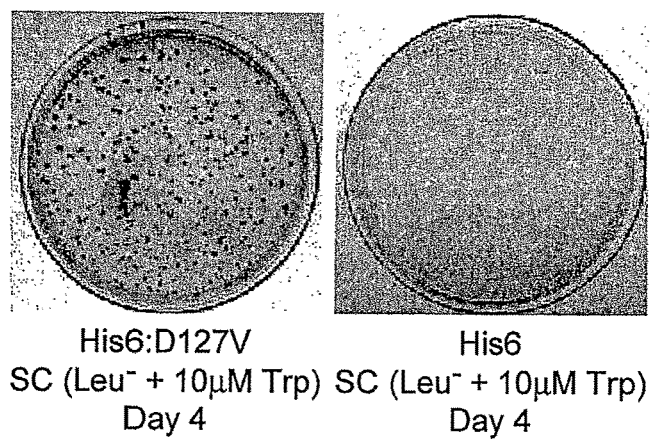
Figure 13B:
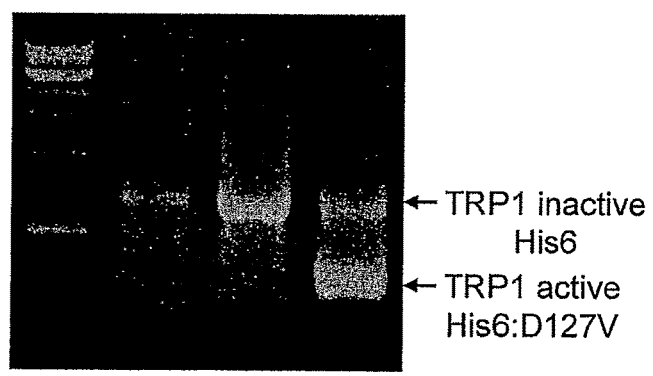

FIG. 13A-B. The TRP1 complementation selection distinguishes between the inactive HIS6 and the active HIS6: D127V variants in yeast. A. HIS6:D127V, but not HIS6, is able to complement a TRP1 deficiency, growing on SC media lacking leucine and supplemented with only 10 μM tryptophan. B. TRP1 mock selection. A 100:1 mixture of plasmid DNA encoding either inactive (His6) or active (His6:D127V) enzyme was grown under either nonselective or selective conditions to complement a TRP1 deficiency. After seven days of selection, total pooled plasmid DNA was analyzed on a DNA gel following restriction digest (HIS6:D127V contains a unique restriction site). Lane 1: 1 kb ladder; lane 2: selection on SC(LT−); lane 3: selection on SC(L−); lane 4: selection on SC(L−+10 μM tryptophan).

Figure 15B:
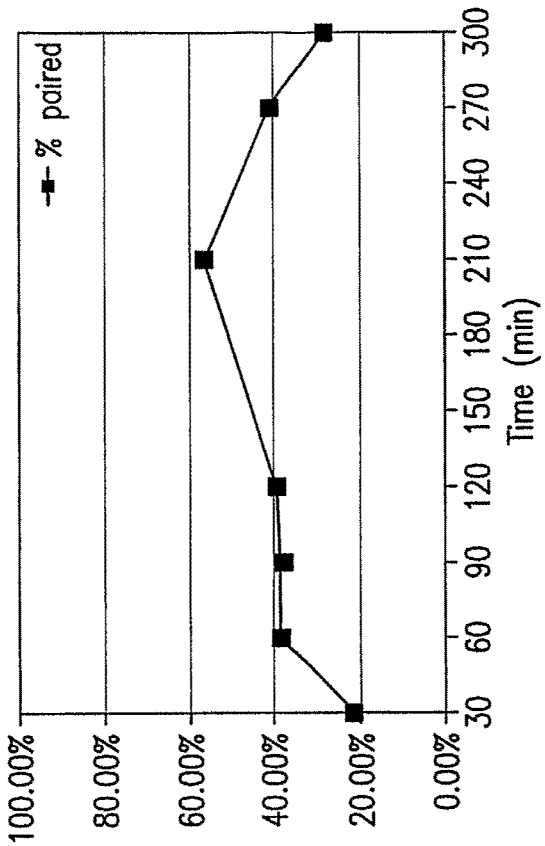
Figure 15A:
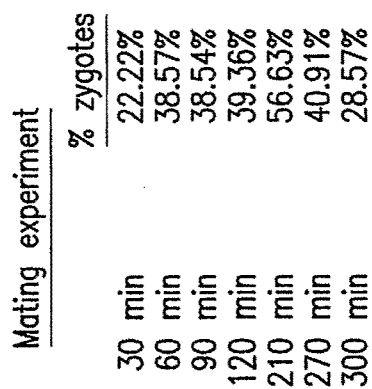

FIG. 14A-E. A. Schematic of HO-induced DNA cassette recombination to mutate the HIS6 gene and confer ability to grow in low TRP medium, where HO endonuclease is expressed under the control of a galactose-inducible promoter. B. HIS6 recombinants in host cells induced with galactose. C. HIS6 recombinants in host cells which were not induced with galactose. D. Schematic of protocol for the steps taken to carry the HO induced DNA cassette recombination. E. DNA gel with restriction digest of the pool of HIS6 variants after HO induced recombination and TRP1 selection. Lane 2: BssSI PCR digest of DNA pool induced with galactose for 30 min., Lane 3: non-digested PCR of HIS6 DNA pool Lane 4::BssSI PCR digest of DNA pool induced with galactose for 60 min FIG. 15A-B. Results of an experiment to determine efficiency of mating of MATα strain VM44 and MATa strain VM55, showing percent zygotes over time. (A) shows numerical results and (B) depicts those results in graph format.

Figure 16:
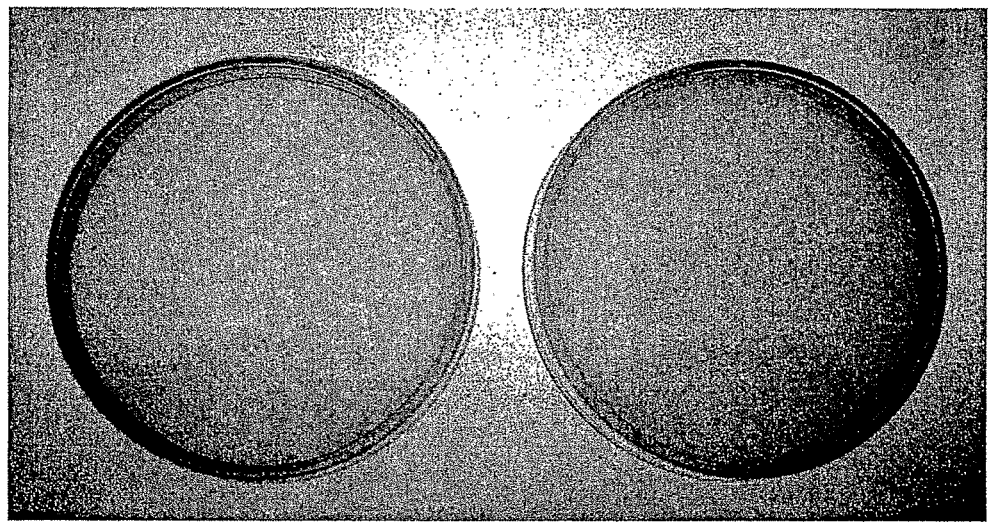

FIG. 16. After galactose induction an equal dilution of cells is plated on selection media. Left is VM44 transformed with library 1. Right is VM45 transformed with library 2.

Figure 17:
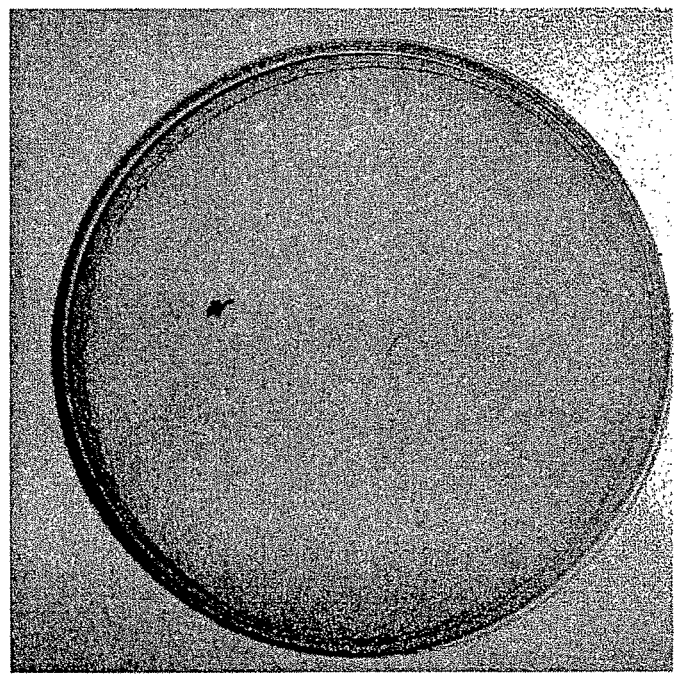

FIG. 17. After mating overnight a dilution of cells is plated on selection media.

Figure 18:
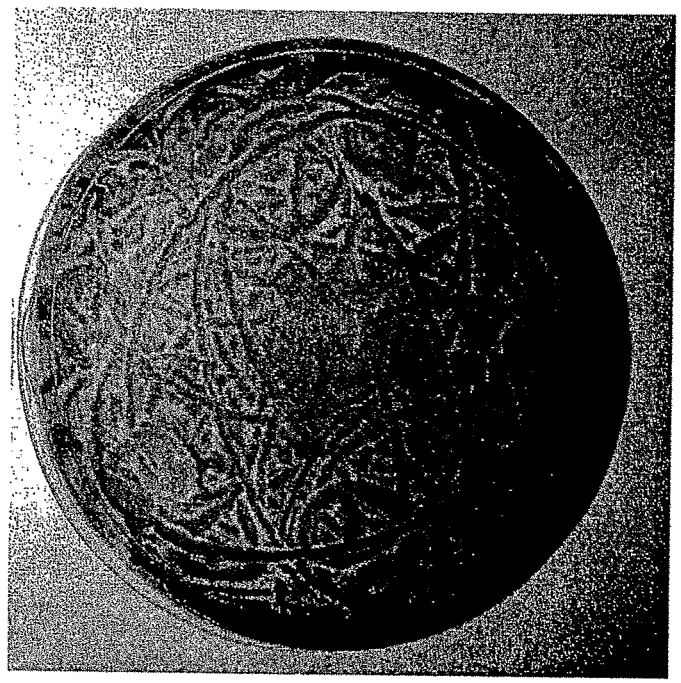

FIG. 18. After four day selection, a dilution of cells is plated on selection media.

Figure 19:
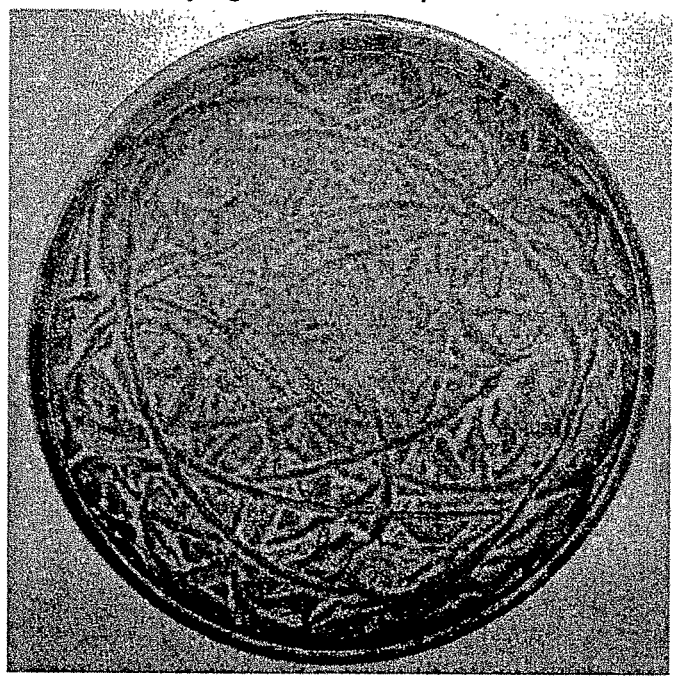

FIG. 19. After sporulation and separation, a dilution of cells is plated on selection media.

Figure 20:
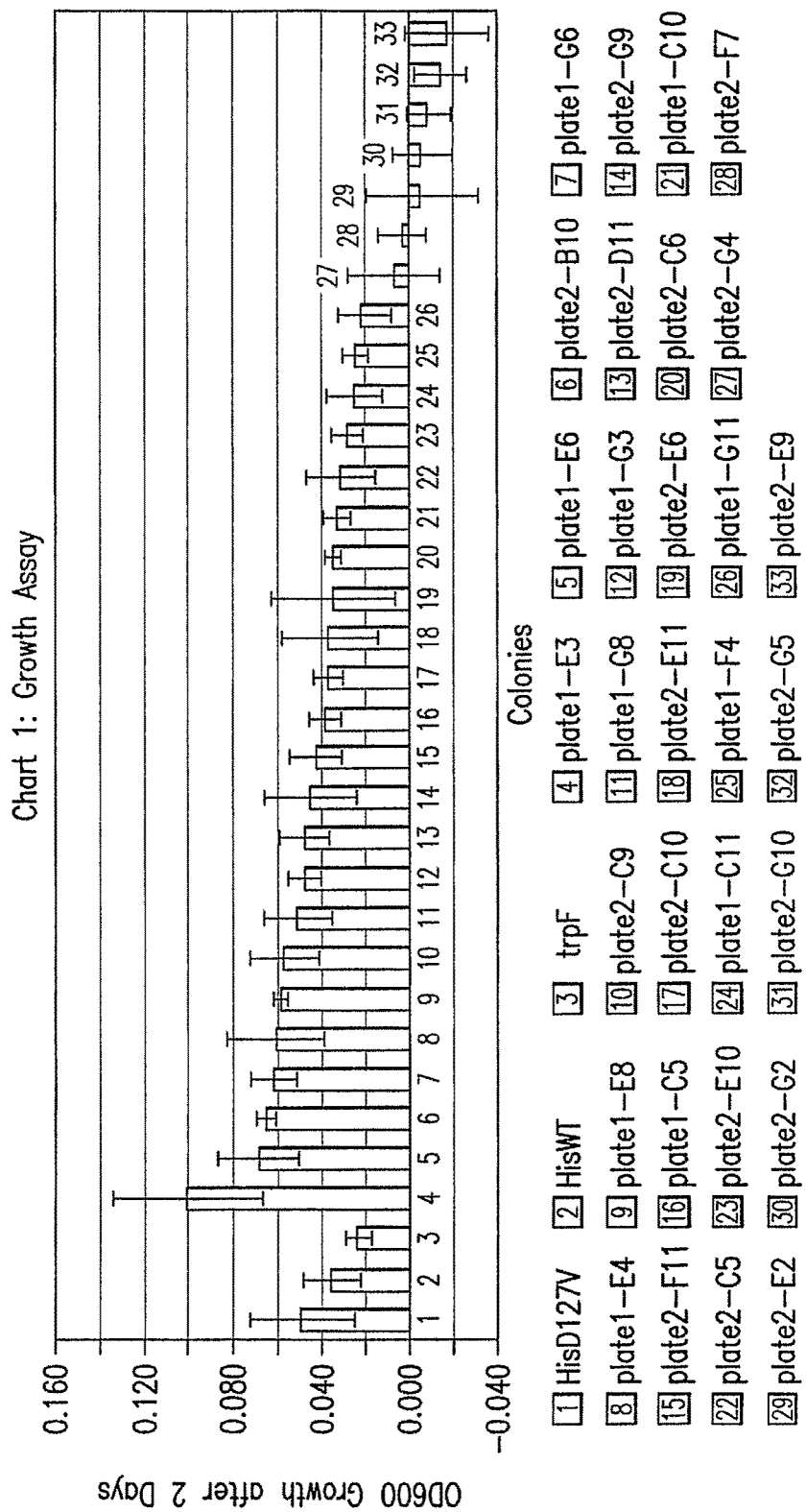

FIG. 20. Growth after two days in selection medium in triplicate, the first three bars on the left representing, respectively, His D127V, His WT, and ΔtrpF, the remaining bars showing activity of variants generated by the mutation plus mating experiments.

FIG. 21A-B. A. Nucleic acid sequence of cellulase coding region of colony 1 (Cellulase 4) (SEQ ID NO:1). B. Amino acid sequence predicted from A (SEQ ID NO:3).

FIG. 22A-B. A. Nucleic acid sequence of cellulase coding region of Colony 2 (Cellulase 1) (SEQ ID NO:2). B. Amino acid sequence predicted from B (SEQ ID NO:4).

FIG. 23A-C. A. Application of chemical complementation to detect cellulase activity. B. Starting from a 1:100 mixture active:inactive cellulase mutants (top gel, restriction digest of 9 enzymes from independent colonies, bottom gel, restriction enzymes from the 9 fastest growing colonies after selection) the URA3 selection achieved a 200-fold enrichment in active glycosidase from a single round of selection. C. Steady state kinetic parameters of the parent cellulase and the improved mutant using p-nitrophenyl cellobioside.

Figure 24:
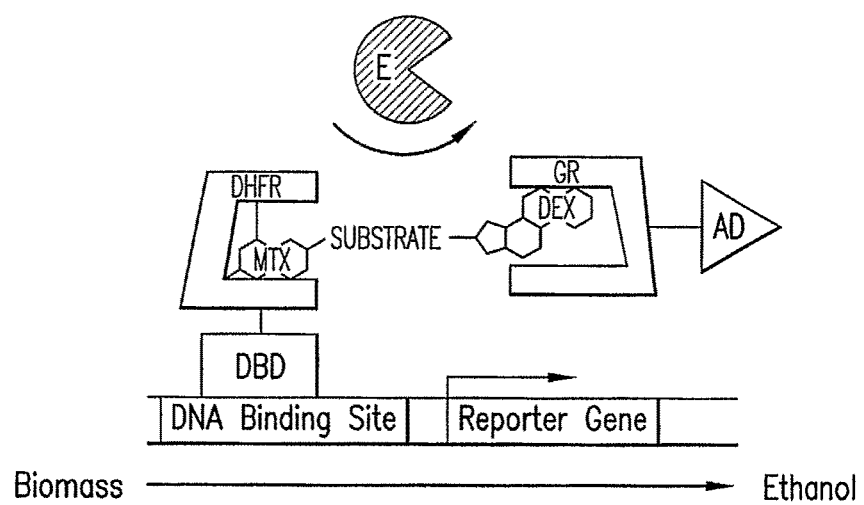

FIG. 24. Chemical complementation offers a selection for cellulase catalysis, an important target for the conversion of biomass to ethanol.

Figure 25:
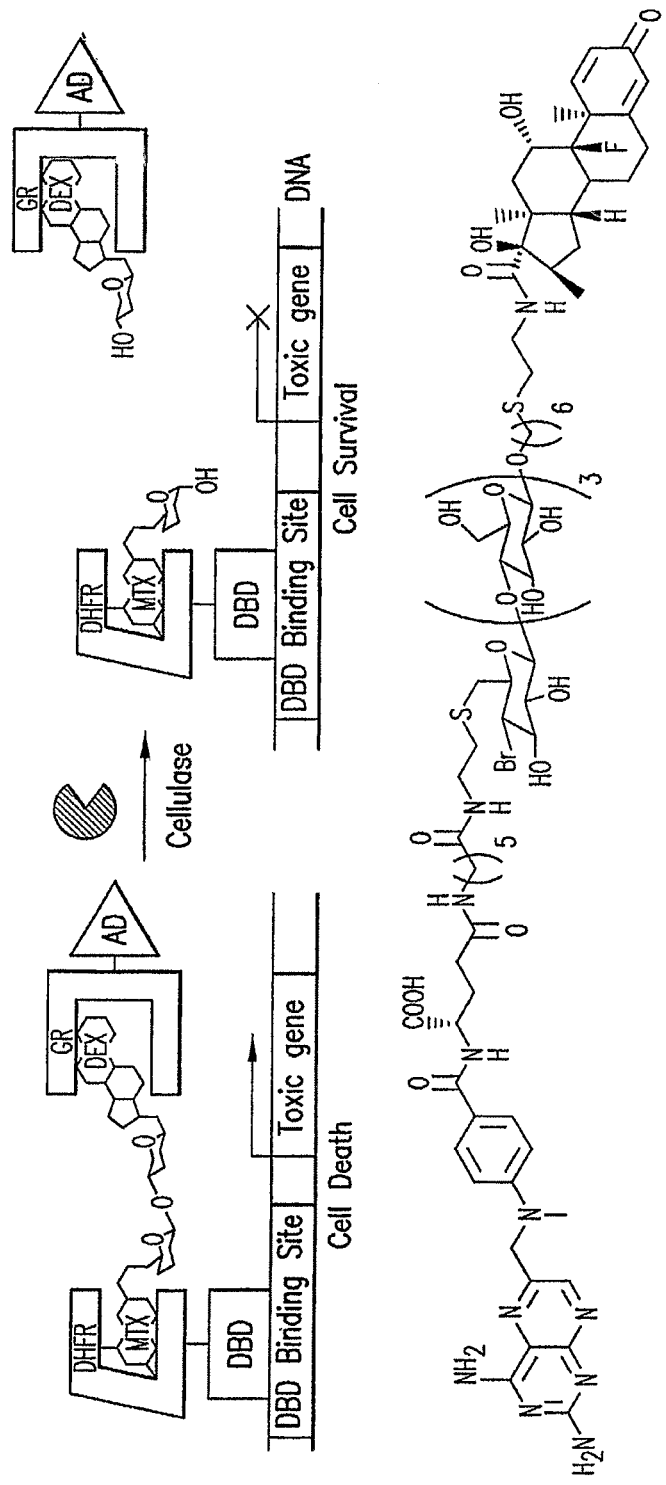

FIG. 25. Chemical complementation provides a growth selection for cellulase catalysis. In the presence of Mtx-Cel-Dex the transcriptional activator is reconstituted, activating transcription of a toxic reporter gene, thus leading to cell death. Introduction of an active cellulase which is able to cleave the β-1,4-glucosidic bond present in the cellulose linker in Mtx-Cel-Dex halts transcription of the toxic reporter gene, thus leading to cell survival. Bottom: The structure of the Mtx-Cel-Dex molecule.

Figure 26B:
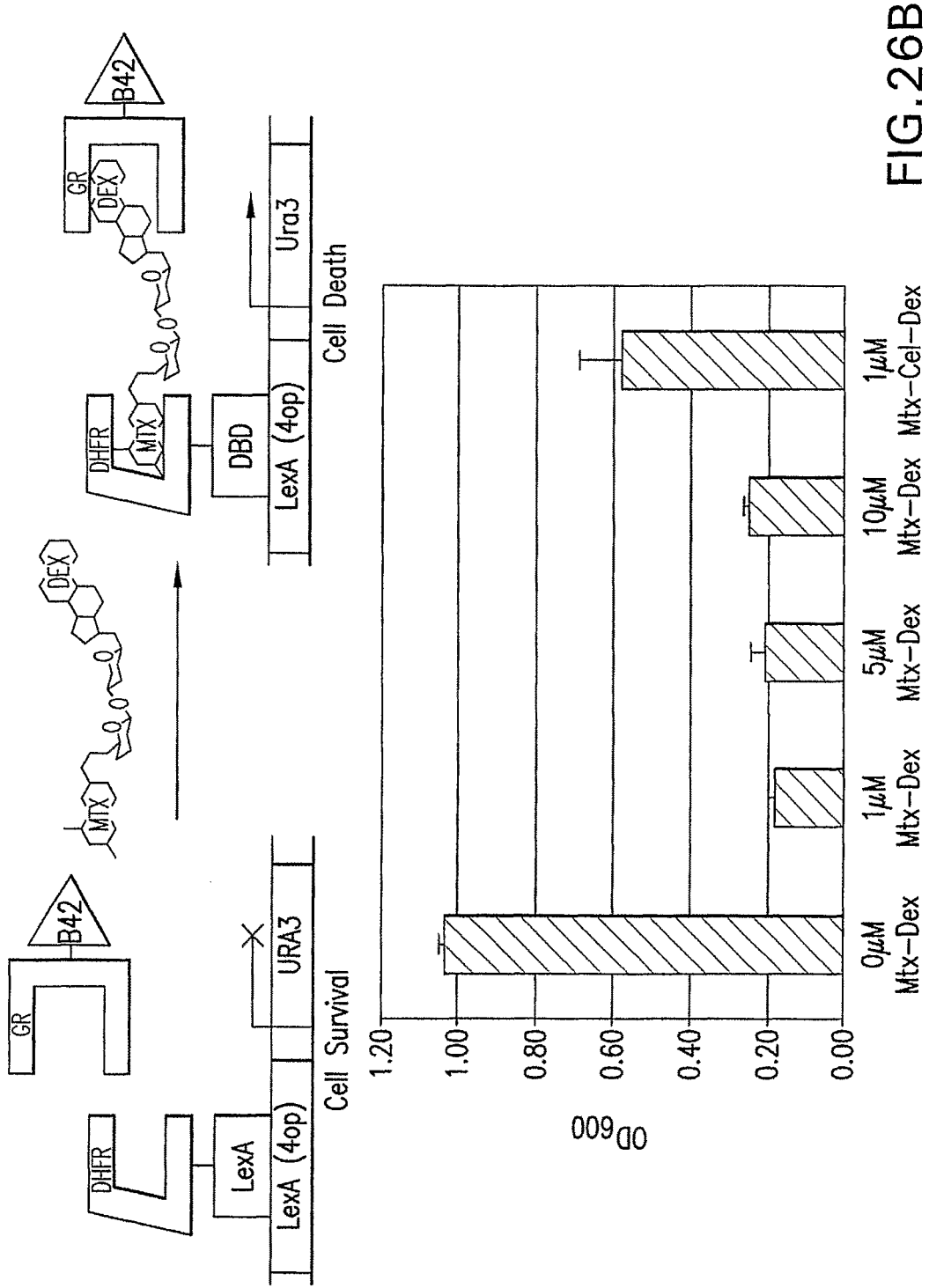

FIG. 26A-B. Reverse three-hybrid strain. A. Schematic construction of the reverse yeast-three-hybrid strain. B. The reverse three-hybrid strain was grown under URA3 counter selection conditions in the presence of 0, 1, 5, 10 μM Mtx-Dex, and 1 μM Mtx-Cel-Dex. The presence of small molecule leads to cell death, measured as a decrease in cell density at OD600.

Figure 27A:
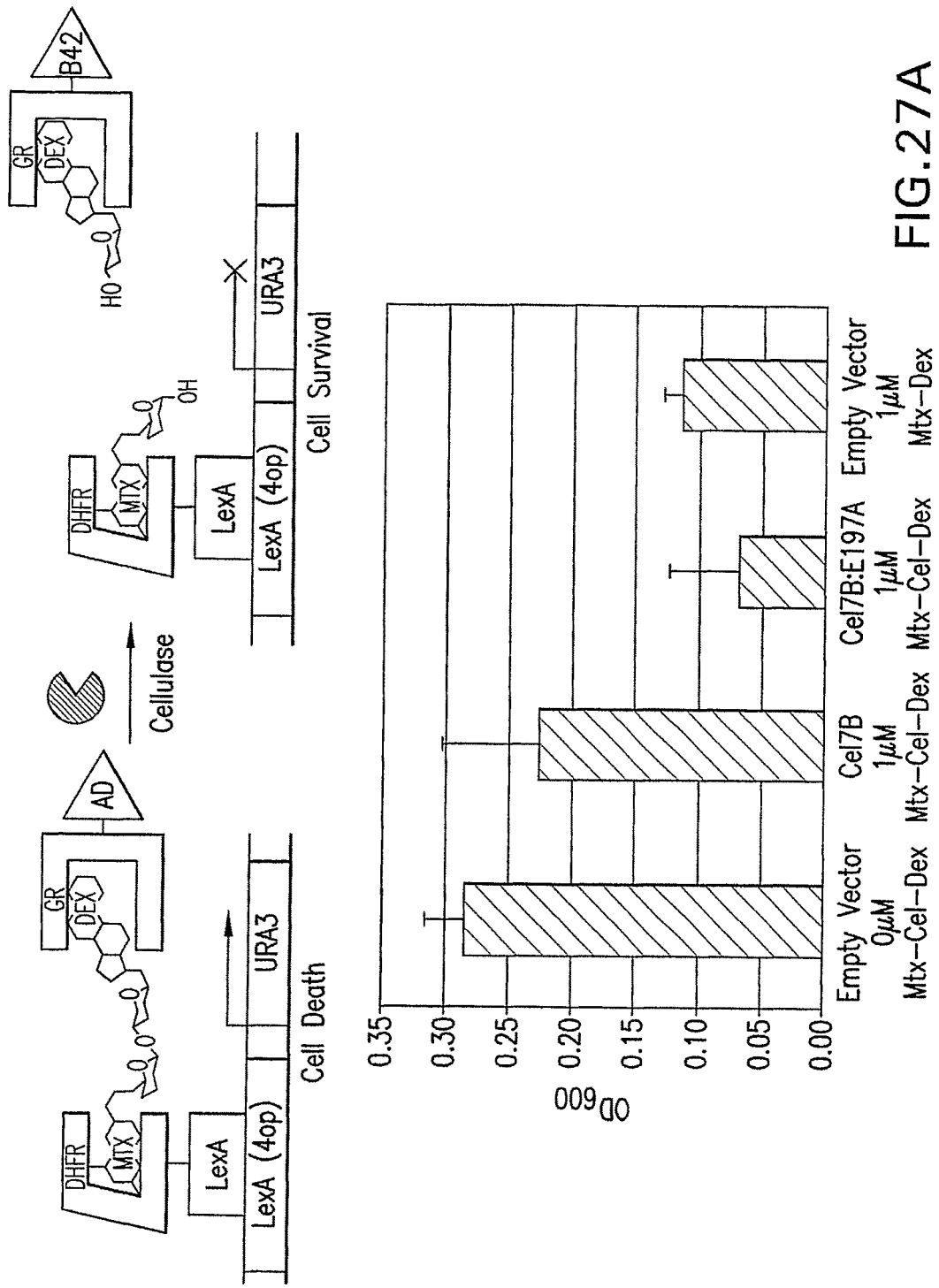
Figure 27B:
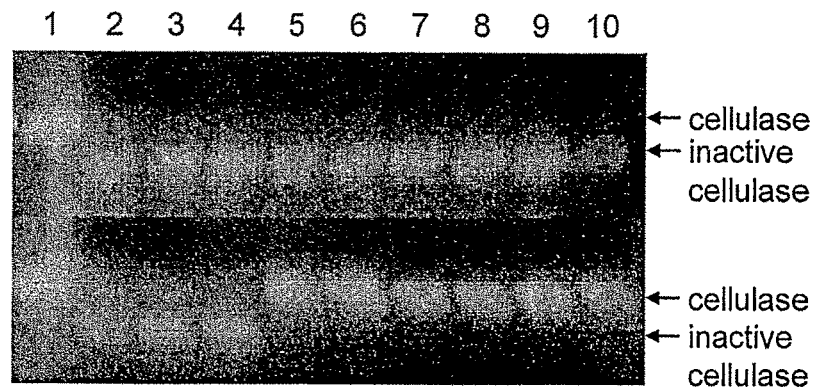
Figure 27C:
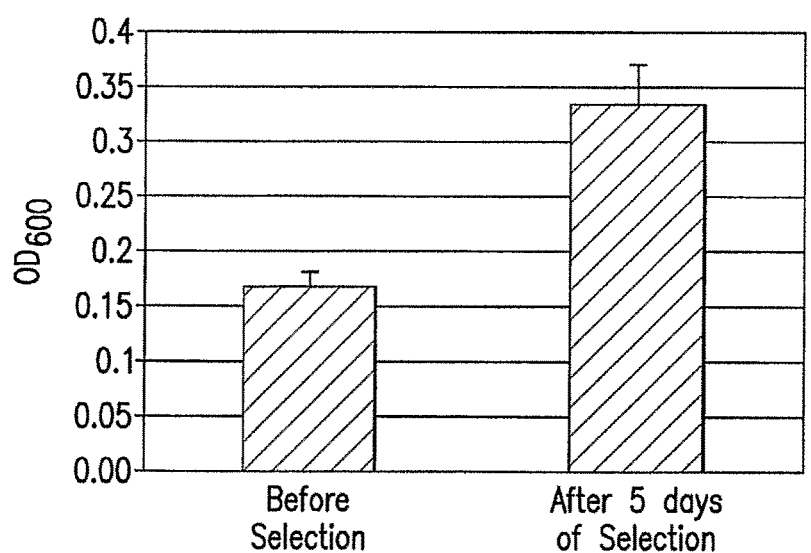

FIG. 27A-C. Detection of cellulase activity and cellulase enrichment assay using the URA3 counter selection. A. The reverse three-hybrid strain is grown under counter selection conditions in the presence of empty vector, the *Humicola insolens* cellulase Cel7B and the inactive cellulase variant Cel7B:E197A. Under counter selection conditions, the presence of empty vector and 0 μm Mtx-Cel-Dex leads to cell survival, the presence of cellulase and 1 μM Mtx-Cel-Dex leads to cell survival, while the presence of inactive cellulase Cel7B:E197A in the presence of 1 µM Mtx-Cel-Dex leads to cell death. Finally, presence of empty vector in the presence of 1 µM Mtx-Dex leads to cell death. B. Starting from a 1:100 mixture of active:inactive cellulase mutants, the URA3 counter selection achieved a 200-fold enrichment in active cellulase from a single round of selection. Lane 1, active cellulase control. Top gel, lanes 2-10, restriction digest of 9 enzymes from independent colonies isolated before selection. Bottom gel, lanes 2-10, restriction digest of 9 independent colonies isolated after selection. C. Twenty-two cellulase variants isolated before selection and twenty-two variants isolated after five days of selection were tested for aldehyde formation using carboxymethylcellulose (CMC) in crude cell extracts. Aldehyde formation was measured as absorption at 660 nm. The mean activity of cellulase variants isolated before and after 5 days of selection is plotted. The error bars represent the variance from the mean. The cellulase activity on CMC from cellulase variants isolated after 5 days of selection is higher than that of cellulases isolated before selection. This difference is statistically significant ($p<0.005$).

FIG. 28A-B. Homology model of Cellulase 1 (CELL-VAR2, see Table 1A and Cel_5. (Cellulase 2 in Table 1A) using *B. agaradharens* Cel5A (PDB: 1H5V). Lett. Cellulase 1 (CELLVAR2) differs by nine mutations (pink), when compared to the most active starting cellulase, CelN. Right. Cel5.7 (Celluase 2) differs by eight mutations (pink), when compared to the CelN.

FIG. 29. Substrates of enzymes useful in biomass conversion.

5. DETAILED DESCRIPTION OF THE INVENTION

For clarity of disclosure, and not by way of limitation, the detailed description of the invention is divided into the following subsections:
(i) host cells;
(ii) targets;
(iii) mutator functions;
(iv) diversifying nucleic acids;
(v) genetic exchange;
(vi) selection;
(vii) libraries;
(viii) exemplary in vivo directed evolution systems;
(ix) exemplary enzymes for evolution;
(x) directed evolution systems for improving enzymes for biomass conversion; and
(xi) cellulase variants.

5.1 Host Cells

Systems of the invention comprise a host cell containing a nucleic acid target corresponding to a biological entity of interest. In particular, non-limiting embodiments (see below) the target may be a gene ("target gene") encoding a protein of interest ("target protein"), operably linked to a promoter element.

The host cell may be a prokaryotic or eukaryotic cell, including, but not limited to, a yeast cell, a bacterial cell, an insect cell, a plant cell, a unicellular slime mold cell, an invertebrate cell (e.g., a worm cell), a vertebrate cell and/or a mammalian cell. In specific, non-limiting embodiments of the invention, the yeast cell is a yeast that contains a HO-endonuclease, for example *Saccharomyces cerevisiae*, *Candidat glabrata*, *Kluveromyces delphiensis*, or *Saccharomyces castellii*.

In non-limiting embodiments of the invention, and in conjunction with the ability to select for desirable mutant targets, the host cell has a phenotype that provides a selection mechanism. The phenotype may be manifested by native host cells ("endogenous phenotype") or may be produced by genetic engineering or similar artificial means ("exogenous phenotype").

For example, the host cell may have a nutritional requirement which the desirable mutant target directly or indirectly provides, or a particular compound may be toxic to the host cell, and the desirable mutant target may directly or indirectly alleviate said toxicity. In the foregoing, "directly" means that the mutant target itself is acting, and "indirectly" means that the mutant target is causing another agent to act. As a non-limiting example of indirect action, the mutant target may produce a small molecule bridging compound that links DNA-binding and activation domains in a chemical complementation assay, thereby producing a reporter gene which satisfies a nutritional requirement or degrades a toxic protein (or the converse if the mutant target cleaves a bridging molecule). In one specific, non-limiting embodiment, where the host cell is a yeast cell, the reporter gene may be URA3, which encodes a toxic product.

The host cell further comprises at least one diversifying nucleic acid ("DINA"). Said one or more DINA may be exosomal or may be integrated into genomic DNA. The DINA may be introduced into the host cell by any means known in the art, including, but not limited to, transformation, transfection, electroporation, microinjection, etc. In particular non-limiting embodiments of the invention, one or more DINA may be introduced into a parental host cell, which is then propagated to produce a population of progeny host cells containing the DINA(s); in some instances, the DINA(s) may have undergone mutation between cellular generations.

In certain non-limiting embodiments, the host cell may further comprise elements supporting chemical complementation, for example, (i) a DNA binding site linked to a reporter gene; (ii) a nucleic acid encoding a receptor for a first small molecule linked to a DNA binding domain (DBD) which specifically binds to the DNA binding site, operably linked to a promoter element; and (iii) a nucleic acid encoding a receptor for a second small molecule linked to an activation domain, operably linked to a promoter element. Said promoters may be distinct or shared. The first small molecule, second small molecule, or a molecule comprising the first small molecule and second small molecule connected by a linker (e.g., a substrate bridge) may be introduced into the cell or may be generated by the target and/or mutants thereof. The first small molecule joined to the second small molecule forms the basis for association between DNA binding and activation domains of a fusion protein and is also referred to herein as a "bridging compound."

5.2 Targets

The present invention provides for a means for directing evolution of an entity of interest via a nucleic acid (DNA or RNA, preferably DNA) target corresponding to that entity. "Corresponding" refers to the relationship between nucleic acid and the target, as can be seen below. Suitable entities of interest (which can be molecules found in nature (wild-type) or naturally occurring or engineered mutants thereof) include, but are not limited to:
a protein (especially an enzyme), where the corresponding target is a target gene encoding said protein or a portion thereof;

a promoter, where the target is the promoter itself or a portion thereof;

a functional RNA, where the target is the RNA itself or a DNA which may be transcribed to produce the functional RNA, or a portion thereof;

an intron, where the target is the DNA or RNA version of the intron, or a portion thereof;

a ribosome binding site, where the target is the DNA or RNA version of the ribosome binding site, or a portion thereof; an endonuclease recognition site, where the target is the DNA site or a portion thereof;

a repressor element, where the target is the repressor element or a portion thereof;

a metabolite; or a plurality or combination of the above, where the ultimate entity of interest is a product of their association (e.g. the entity of interest is a metabolite and the target is one or more component of a pathway that generates the metabolite).

The size of the target may be understood to be dictated by the nature of the target. "A portion thereof" is defined herein to mean a region which represents less than 100 percent, less than 90 percent, less than 80 percent, less than 70 percent, less than 60 percent, less than 50 percent, less than 40 percent, less than 30 percent, less than 20 percent, less than 10 percent, or less than 5 percent of the size of the target.

Examples of functional RNAs are provided in Alper et al., 2006, Science 314:1565-1568; Buskirk et al., 2003, Chemistry & Biology 10:533-540; and Buskirk et al., 2004, Chemistry & Biology 11: 1157-1163).

The nucleic acid target is alternatively referred to herein as a target gene. Where the target gene is not native to the host cell, it may be referred to as a heterologous target gene. The target gene may comprise a region, or "replaceable segment", which is desirably mutated by the DINA. The replaceable segment may optionally comprise a region which is engineered to facilitate mutation by the DINA, for example, but not by way of limitation, via the incorporation of a homologous nucleic acid sequence and/or an endonuclease site.

Examples of metabolites which may be entities of interest include but are not limited to the antimalarial drug precursor artemisinic acid (Ro et al., 2006. Nature 440:940-943; hydrocortisone (Szczebara et al., 2003, Nature Biotechnol. 21:143-149; resveratrol (Beekwilder et al., 2006, Appl. Environmental Microbiol. 72:5670-5672; and beta-carotene and lycopene (Yamano et al., 1994, Biosci. Biotechnol. Biochem. 58:1112-1114).

In particular non-limiting embodiments, the target is a protein, especially an enzyme. It should be understood, however, that although the examples present herein usually refer to protein targets, analogous techniques may be used to evolve other classes of entities of interest (targets) as discussed above.

Virtually any protein may serve as the target in the present invention, provided that such protein may directly or indirectly (as described herein) provide a potential basis for selection. A protein of interest is alternatively referred to herein as the "target protein." The target protein may be a specific enzyme, the activity of which is desirably increased, decreased, or otherwise modified. The target gene of the target protein may encode a protein scaffold which is common to a number of enzymes, having one or more segment that may be replaced ("replaceable segment") without compromising the structure and/or stability of the enzyme, optionally engineered to comprise a marker sequence which facilitates its replacement (e.g., a sequence homologous to a portion of a DINA and/or an endonuclease specific recognition element). In non-limiting embodiments of the invention, the size of the replaceable segment may be between about 4 and 75 amino acids (between 12 and about 300 nucleotides in the corresponding target gene), or between about 5 and 10 amino acids (between 15 and 30 nucleotides in the target gene), or between about 5 and 25 amino acids (between 15 and 75 nucleotides in the target gene), or between about 10 and 50 amino acids (between 30 and 150 nucleotides in the target gene).

Homology, as that term is used herein, refers to a sequence which is at least about 75, at least about 80, at least about 85, at least about 90, at least about 95 or at least about 98 percent homologous relative to a comparison sequence, as may be determined by standard software such as BLAST or FASTA. A homologous region of a nucleic acid may be at least about 8, at least about 10 nucleotides, at least about 15 nucleotides, at least about 20 nucleotides, at least about 25 nucleotides, at least about 30 nucleotides, at least about 40 nucleotides, or at least about 50 nucleotides, in length.

In one preferred non-limiting embodiment, the present invention utilizes as a target protein a TIM barrel scaffold. Over 10% of enzymes whose structures are deposited in the protein data bank (PDB) have the TIM barrel scaffold (Hocker, 2005, Biomol. Eng. 22:31-38). TIM barrel enzymes are promiscuous in their activity, catalyzing five of the six Enzyme Commission (EC) reaction classes—oxidations and reductions, transferase reactions, lyase reactions, hydrolase reactions, and isomerase reactions (Sterner and Hocker, 2005, Chem. Rev. 105:4038-4055). As illustrated in FIG. 2, the classic TIM barrel structure is comprised of eight internal, parallel β-strands connected by loops to eight surrounding α-helices (Gerlt and Babbitt, 2001, Annu. Rev. Biochem. 70:209-246). Although any one of the eight loops may comprise or constitute a replaceable segment, because structural integrity appears to be maintained by the N-terminal half of the barrel and residues important for substrate binding and catalytic activity are found in the C-terminal half of the barrel in the loops and at the ends of the β-strands, loops in the C-terminal half of the barrel are preferred locations for replaceable segments. Randomization of the β-strand termini and loops may be used to support new or altered enzyme functions without, in theory, impairing the structural integrity of the protein. The sequence, structure, and function of TIM barrel enzymes are well characterized (Gerlt and Raushel, 2003, Curr. Opin. Chem. Biol. 7:252-264). In particular non-limiting embodiments, a subclass of TIM barrel may be used as the target gene, for example, but not by way of limitation, a TIM barrel glycosidase or a TIM barrel aldolase.

The target gene may be operably linked to a suitable promoter, which may be an endogenous host cell promoter or a promoter introduced by genetic engineering, such as a heterologous promoter (a promoter not associated with the target gene in nature). The promoter may be an inducible promoter, or may be constitutively active.

A host cell may comprise more than one target, where each target may be the same or may be different (for example, members of a molecular pathway).

5.3 Mutator Functions

The host cells of the invention comprise one or more mutator function. At least one mutator function increases the likelihood that the target will be mutated by the DINA. An additional optional, "ancillary" mutator function may increase the diversity of potential mutations.

The mutator function may be native to the host cell ("endogenous mutator function") or may be engineered ("exogenous mutator function").

One non-limiting example of a mutator function is homologous recombination (reciprocal recombination).

Another non-limiting example of a mutator function is a function that facilitates homologous recombination (e.g., the formation of double strand breaks by the HO endonuclease of yeast; other homing endonucleases may be used to provide said mutator function; see, for example, Belfort & Roberts, 1997, Nucl. Acids Res. 25(17):3379-3388).

Yet another non-limiting example of a mutator function is gene conversion (non-reciprocal recombination).

A non-limiting example of an ancillary mutator function is a tendency to commit replication errors such as is produced by an error-prone polymerase.

Another non-limiting example of an ancillary mutator function is the ability to decrease expression of a DNA damage-binding (DDB) protein (e.g., a repressible promoter controlling the expression of a DDB-encoding gene).

Another non-limiting example of an ancillary mutator function is a transposable element.

A mutator function or ancillary mutator function may occur as a result of interaction of nucleic acids or as a result of interaction between one or more nucleic acid and one or more protein.

In non-limiting embodiments of the invention, the mutator function or ancillary mutator function is executed by one or more protein, wherein the expression of at least one such protein is controlled by an operably linked promoter element. Said promoter may be constitutively active or may be inducible or otherwise conditionally active (e.g., can be inhibited by binding of a repressor element). Most preferably, the promoter permits "titration" of the amount of mutator function operating. In a specific, non-limiting embodiment, the promoter is the Gal1 promoter.

In various specific non-limiting embodiments of the invention, the mutator function(s) comprise(s) (i) a gene encoding an HO endonuclease operably linked to a promoter element, wherein the endonuclease product of this gene acts at HO-specific recognition sequences flanking one or more diversifying nucleic acid present in the host cell genome or (preferably) in an episome, and/or at one or more HO-specific recognition sequence comprised in a replaceable segment of the target gene; (ii) a gene encoding a I-SceI gene operably linked to a promoter element, wherein the product of this gene acts at one or more I-SceI site-specific recognition sequence in the target gene (for example, using the delitto perfetto system described in Storici et al., 2003, Proc. Natl. Acad. Sci. U.S.A. 100: 14994-14999); or (iii) genes encoding Rag1, Rag2, and optionally terminal deoxynucleotidyltransferase (TdT), which act at specific recognition sequences flanking one or more replaceable segment within the target gene and/or one or more diversifying nucleic acid sequence in the host cell.

5.4 Diversifying Nucleic Acids

As set forth above, a diversifying nucleic acid ("DINA") may be comprised in the host cell genome or in an episomal sequence (e.g., a 2μ plasmid). For example, one or more DINA may be comprised in the host cell genome outside of the target gene, or maintained in episomal form. In various non-limiting embodiments of the invention, a DINA comprises or is flanked by (i) a region homologous to one or more target gene sequence (so as to facilitate recombination) (e.g., is homologous to a replaceable segment) and/or (ii) a recognition sequence recognized by an enzyme that promotes recombination (e.g., an endonuclease, for example HO endonuclease, Rag1 or Rag2). A diversity of DINAs, referred to herein as a "DINA library" may be generated and provided to a population of host cells. For example, a diverse DINA library may be generated by standard chemical or genetic engineering techniques (e.g., error prone PCR), and may be introduced into a host cell either directly (e.g., by transformation) or via insertion into plasmids, phage, virus, or a transposable element. Where such a library comprises diverse loops for introduction into a protein scaffold, it is referred to as a "loop library."

A DINA may be approximately commensurate in length relative to the portion of the target intended to be modified (for example, the "replaceable segment", e.g., a "loop" in a protein scaffold), may be smaller or may be larger (for example, comprising sequence homologous to a region outside of the replaceable segment). More than one DINA may be used to replace or be inserted into a replaceable segment of the target gene. Accordingly, the length of a DINA may be between about 12 and about 500 nucleotides, or between about 9 and 15 nucleotides, or between about 15 and 30 nucleotides, or between about 15 and 75 nucleotides, or between about 30 and 150 nucleotides, or between about 50 and 200 nucleotides. The DINA may comprise a portion homologous to a target sequence and/or replaceable segment of the target gene or a portion homologous to a region of the target gene which is not part of a replaceable segment, where said portions may be at least about 8, at least about 10 nucleotides, at least about 15 nucleotides, at least about 20 nucleotides, at least about 25 nucleotides, at least about 30 nucleotides, at least about 40 nucleotides, or at least about 50 nucleotides in length; the homologous portion may promote homologous recombination with the target gene. Accordingly, the DINA itself may be sufficiently homologous as to promote a homologous recombination or gene conversion event.

5.5 Genetic Exchange

According to certain non-limiting embodiments of the invention, genetically non-identical host cells are permitted to engage in genetic exchange between their genomes, under conditions in which homologous recombination and/or gene conversion can occur. Genetic exchange may be achieved, for example and not by limitation, by sexual reproduction or cell fusion followed by division (e.g., protoplast fusion or plasmodia formation). Genetic exchange in an environment that provides a selection mechanism (see below) maintains an extremely diverse "virtual" library (by calculation, for example, having $10^{24}$ members) to manageable size for culture.

Where the present invention is used to produce a diversified plurality ("library") of host cells, genetic exchange may occur between members of the library. Alternatively, a plurality of libraries may be prepared separately and then combined to allow genetic exchange to occur between members of different libraries.

5.6 Selection

Selection, according to the invention, may be achieved by any method known in the art. As stated above, selection may operate directly upon the activity of the target or mutant target or indirectly, for example via chemical complementation or via the product of a gene downstream from the protein of interest (or mutants thereof) in a functionally-linked pathway. Chemical complementation is described, for example, in United States Patent Application Publication No. US 2004/0106154 by Cornish.

Without limitation, selection may be made based on, for example: (i) the ability of a host cell to thrive in a particular nutritional context (e.g., medium lacking a particular anabolic component); (ii) the ability of a host cell to survive in the presence or absence of a particular agent (e.g., the presence of a conditional toxin such as neomycin or hygromycin B); (iii) host cell volume; (iv) the production of a detectable product (e.g., a fluorescent protein such as green fluorescent protein as an antigen "tag"); (iv) host cell size; (v) host cell mobility; (vi) host cell invasiveness; (vii) host cell adhesiveness, etc.

5.7 Libraries

The term "library" as used herein refers to a collection of host cells containing a plurality of mutated versions of the target protein. The "diversity" may be quantitated as the number of individual host cells estimated to be required to represent all the different mutant target proteins expressed by the library.

Libraries may be categorized as "primary libraries" which are the result of operation of the invention and where genetic exchange may or may not occur between members of the library, or "secondary libraries" which are the result of allowing or promoting genetic exchange between two or more primary libraries prepared according to the invention.

For example, a primary library size equal to the product of the transformation efficiency and the number library variants capable of being produced by the DINA(s) and mutator function(s) in one cell may be generated, and a secondary library having a size equal to the product of the sizes of the parent primary libraries undergoing genetic exchange may be generated.

As a non-limiting example of how diversity in a primary library may be expanded according to the present invention, if one cell has one plasmid containing 10 discrete DINAs, each flanked with HO sites, each mutating one or more amino acids at different replaceable segments of a target protein, the target gene in that cell could be mutated in $10^{23}$ different ways because each targeted region of DNA could either remain wild type or mutate; because there are two states that a targeted region of DNA can be in and 10 DINAs, there would be $2^{10}=10^{24}$ different combinations of wild type and mutated regions (one of which is everything stays wild type, hence a possible $10^{23}$ mutants). In order to realize all $10^{23}$ combinations, a parent cell would theoretically need to divide to generate $10^{23}$ different progeny cells, each carrying the DINA-containing plasmid. Accordingly, if $10^8$ cells are transformed with different plasmids having 10 unique DINAs, then those cells can be grown and induced to create a library of up to $10^3 \times 10^8$ (~$10^{11}$). As a non-limiting example of how diversity in a secondary library may be generated, if three groups of cells each containing a (primary) library of $10^8$ generate a secondary library through genetic exchange, a diversity of up to $10^8 \times 10^8 \times 10^8$ (=$10^{24}$) in the resulting secondary library may be generated.

Moreover, this method naturally lends itself to searching sequence space via genetic algorithms (i.e. by performing simultaneous mutagenesis and selection), so the potential library can be efficiently searched by using far fewer actual (selected) library members

5.8 Exemplary In Vivo Directed Evolution Systems

The present invention provides for a system for directing evolution of a entity of interest, for example a protein, espe cially an enzyme, of interest ("the target protein"), comprising a plurality of host cells, such that each host cell:

(i) contains, in its genome, a nucleic acid corresponding to the entity of interest (e.g., encoding the target protein) ("the target gene"), optionally operably linked to a promoter element;

(ii) contains at least one diversifying nucleic acid ("DINA") which can be used to direct mutation of the target gene; and (iii) exhibits at least one mutator function which increases the likelihood that the target gene will be mutated by the DINA; wherein a plurality of host cells contain a plurality of different DINAs, and wherein said system further comprises a means for selecting for a mutant entity of interest exhibiting a desired activity.

In one set of non-limiting embodiments, the present invention provides for a system for directing evolution of an entity of interest (e.g. a target protein) comprising a plurality of host cells, such that each host cell:

(i) contains, in its genome, a nucleic acid corresponding to the entity of interest (e.g., encoding the target protein) ("the target gene"), optionally operably linked to a promoter element;

(ii) contains at least one diversifying nucleic acid ("DINA") which can be used to direct mutation of the target gene;

(iii) exhibits at least one mutator function which increases the likelihood that the target gene will be mutated by the DINA;

(iv) a DNA binding site linked to a reporter gene;

(v) a nucleic acid encoding a receptor for a first small molecule linked to a DNA binding domain that specifically binds to the DNA binding site, operably linked to a promoter element; and (vi) a nucleic acid encoding a receptor for a second small molecule linked to an activation domain, operably linked to a promoter element, wherein, whether or not the DNA binding domain and the activation domain are joined (to cause expression of the reporter gene) is related to mutation of the target gene;

wherein a plurality of host cells contain a plurality of different DINAs; and wherein said system further comprises a means for selecting for a mutant entity exhibiting a desired activity based on the product of the reporter gene. For example, where the entity of interest is a protein, if the target gene is mutated in vivo to form a mutant protein with bond-forming activity, and a first small molecule and a second small molecule are provided to said host cell, the mutant protein links the first small molecule and the second small molecule, causing expression of the reporter gene. Alternatively, where the entity of interest is a protein, if the target gene is mutated in vivo to form a mutant protein with bond-cleaving activity, and a first small molecule linked to a second small molecule is provided to said host cell, the mutant protein cleaves the first small molecule from the second small molecule, thereby inhibiting or preventing expression of the reporter gene.

In a further non-limiting embodiment, the present invention provides for a system of directing evolution of an entity of interest (e.g., a target protein) comprising a plurality of host cells, such that each host cell:

(i) contains, in its genome, a nucleic acid corresponding to the entity of interest (e.g., encoding the target protein) ("the target gene"), optionally operably linked to a promoter element;

(ii) contains at least one diversifying nucleic acid ("DINA") comprising a flanking pair of endonuclease specific recognition sequences, which can be used to direct mutation of the target gene; and (iii) exhibits at least one mutator function which increases the likelihood that the target gene will be mutated by the DINA; wherein the mutator function is an endonuclease which cleaves at the specific recognition sequences, and wherein a plurality of host cells contain a plurality of different DINAs, and wherein said system further comprises a means for selecting for a mutant entity of interest exhibiting a desired activity.

In a still further non-limiting embodiment, the present invention provides for a system of directing evolution of an entity of interest (e.g., a target protein) comprising a plurality of host cells, such that each host cell:

(i) contains, in its genome, a nucleic acid corresponding to the entity of interest (e.g., encoding the target protein) ("the target gene"), optionally operably linked to a promoter element;

(ii) contains at least one diversifying nucleic acid ("DINA") comprising a flanking pair of endonuclease specific recognition sequences, which can be used to direct mutation of the target gene;

(iii) exhibits at least one mutator function which increases the likelihood that the target gene will be mutated by the DINA; wherein the mutator function is an endonuclease which cleaves at the specific recognition sequences, and wherein a plurality of host cells contain a plurality of different DINAs;

(iv) a DNA binding site linked to a reporter gene;

(v) a nucleic acid encoding a receptor for a first small molecule linked to a DNA binding domain that specifically binds to the DNA binding site, operably linked to a promoter element; and (vi) a nucleic acid encoding a receptor for a second small molecule linked to an activation domain, operably linked to a promoter element, wherein, whether or not the DNA binding domain and the activation domain are joined (to cause expression of the reporter gene) is related to mutation of the target gene;

wherein a plurality of host cells contain a plurality of different DINAs; and wherein said system further comprises a means for selecting for a mutant entity exhibiting a desired activity based on the product of the reporter gene. For example, where the entity of interest is a protein, if the target gene is mutated in vivo to form a mutant protein with bond-forming activity, and a first small molecule and a second small molecule are provided to said host cell, the mutant protein links the first small molecule and the second small molecule, causing expression of the reporter gene. Alternatively, where the entity of interest is a protein, if the target gene is mutated in vivo to form a mutant protein with bond-cleaving activity, and a first small molecule linked to a second small molecule is provided to said host cell, the mutant protein cleaves the first small molecule from the second small molecule, thereby inhibiting or preventing expression of the reporter gene.

The present invention further provides for methods of using said systems to produce libraries, and the primary and secondary libraries so produced.

5.9 Exemplary Enzymes for Evolution

For example and not by way of limitation, the systems and methods of the present invention may be applied toward directed evolution of the following families of enzymes (and see section 5.10 below, relating to enzymes useful in biomass conversion).

5.9.1. Directed Evolution of Glycosidase/Glycosynthases

Despite their fundamental role in biological processes and potential use as therapeutics, it still remains difficult to synthesize carbohydrates, glycoproteins, and glycolipids. In the past two decades, there has been tremendous progress in the chemical synthesis of complex carbohydrates (Paulsen, 1982, Angew Chem. Int. Ed. Engl. 21, 155-173; Plante, et al., 1999, Org. Lett., 1, 211-214; Hashimoto, et al., 1989, J. Chem. Soc. Chem. Commun., 685-687; Schmidt, R. R. and Michel, J., 1980, Angew. Chem. Int. Ed. Engl. 19, 731-732; Schmidt, 1986, Angew. Chem., 98, 213-236; Fraser-Reid, et al., 1992, Synlett, 927-942; Fraser-Reid, et al., 1988, J. Chem. Soc. Chem. Commun., 823-825; Kahne, et al., 1989, J. Am. Chem. Soc., 111, 6881-6882; Toshima and Tatsuta, 1993, Chem. Rev. 93, 1503-1531) (Seeberger and Danishefsky, 1998, Acc. Chem. Res. 31, 685-695; Danishefsky, et al., 1993, Science, 260, 1307-1309) However, chemical synthesis is still quite demanding other than for a handful of laboratories most skilled in the art. Natural glycosyltransferase and glycosidase enzymes are also used for carbohydrate synthesis (Flitsch, 2000, Curr. Opin. Chem. Biol. 4, 619-625; Koeller, and Wong, 2001, Nature, 409, 232-240). However, the human enzymes are often required, and many of these are difficult to express recombinantly, with several not even commercially available (Crout and Vic, 1998, Curr. Opin. Chem. Biol., 2, 98-111; Sears and Wong, 2001, Science, 291, 2344-2350; Thiem, J., 1995, FEMS Microbiol. Rev., 16, 193-211; Nilsson, 1988, Trends Biotechnol. 6, 256-264; Hamilton, 2004, Nat. Prod. Rep. 21, 365-385). Therefore, it is desirable to use directed evolution to develop a family of well behaved TIM barrel enzymes that could be used for the routine synthesis of carbohydrates and their conjugates for biomedical research by laboratories not specializing in carbohydrate synthesis and perhaps even for large-scale production of therapeutics.

In a first set of non-limiting embodiments, the present invention provides for the development of a family of "glycosynthase"/glycosidase pairs that can be used for the synthesis of N-linked glycans (FIG. 3A-C). N-linked glycosylation of proteins occurs in the Endoplasmic Reticulum and Golgi Apparatus and is integral to protein trafficking via the secretory pathway and serves as an important extracellular ligand for cell-cell communication (Helenius and Aebi, 2001, Science, 291, 2364-2369; Lechner and Wieland, 1989, Annu. Rev. Biochem., 58, 173-194; Kornfeld and Kornfeld, 1985, Annu. Rev. Biochem. 54, 631-664; Grogan, et al., 2002, Annu. Rev. Biochem. 71, 593-634; *Essentials of glycobiology*, eds. Varki, et al., Cold Spring Harbor Laboratory Press Cold Spring Harbor, N.Y., 1999). A core oligosaccharide is transferred to the side chain of Asn from a lipid precursor. This core N-linked glycan is then built-up through differential cleavage, modification, and further glycosylation to produce N-linked glycans of diverse structure (Kornfeld and Kornfeld, 1985, Annu. Rev. Biochem., 54, 631-664). Because of the complexity of N-linked glycan structure and the difficulty of reconstituting the lipid precursor and human enzymes for in vitro synthesis, N-linked glycoproteins have proven particularly challenging to synthesize. Currently N-linked glycoproteins are synthesized recombinantly (and in impure form) in mammalian cell lines (Grabenhorst, et al., 1999, Glycoconj. J., 16, 81-97). Partial reconstitution of the human glycosylation pathway in yeast shows promise (Hamilton, et al., 2003, Science, 301, 1244-1246) (the yeast pathway produces different glycosylation patterns), but also suffers from heterogeneity in the final product. Glycopeptides can be prepared by synthetic chemistry—often in concert with recombinant enzymes—or by in vitro reconstitution of the transglycosylation reaction using Endo-M with subsequent enzymatic elaboration (Sears and Wong, 2001, Science, 291, 2344-2350; Grogan, et al., 2002, Annu. Rev. Biochem. 71, 593-634; Live, et al., 2001, Org. Lett. 3, 851-854; Unverzagt, C., 1996, Angew Chem. Int. Ed. Engl. 35, 2350-2353; O'Connor, et al., 2001, J. Am. Chem. Soc., 123, 6187-6188; Haneda, et al., 1998, Bioorg. Med. Chem. Lett. 8, 1303-1306). These methods, however, remain sufficiently challenging, so that the state of the art cannot routinely synthesize N-linked glycoproteins with defined structural variations to study the role of N-linked glycosylation on myriad biological pathways. Erythropoietin, for example, which has three N-linked and one O-linked glycans, is used therapeutically with heterogeneous glycosylation, even though this heterogeneity is known to affect its therapeutic efficacy (Fukuda, et al., 1989, Blood, 73, 84-89). With robust chemical methods for coupling the first carbohydrate as the glycosylamine to Asp, in various embodiments, the present invention provides for engineering a family of designer enzymes that allow N-linked glycans of diverse structure to then be built-up one sugar at a time. Alternatively, these designer enzymes could be used to selectively cleave and then build back up from a core oligosaccharide transferred using Endo-M. The genesis of such as family may begin with directed evolution of a glycosynthase/glycosidase pair for the β-1,4-Man-GlcNAc linkage found in the pentasaccharide core of all N-linked glycans (Grogan, et al., 2002, Annu. Rev. Biochem., 71, 593-634; *Essentials of glycobiology*, eds. Varki, et al., Cold Spring Harbor Laboratory Press Cold Spring Harbor, N.Y., 1999). Without favorable neighboring group participation from the 2'-hydroxyl group of mannose, this linkage cannot be synthesized directly in high yield with existing chemical methods. There are no recombinant glycosyltransferases of glycosidases commercially available for the synthesis or selective hydrolysis of this linkage.

Chemical complementation was adapted as a selection for glycosynthase activity (FIG. 4), starting with the published Cel7B:E197A glycosynthase variant from *Humicola insolens*. The effectiveness of chemical complementation in this context was experimentally determined (see Section 8, below).

Directed Evolution of a β-1,4-Man-GlcNAc Glycosynthase/Glycosidase Pair

Directed evolution may be carried out via chemical complementation to modify the substrate specificity of a glycosynthase and a glycosidase for the synthesis and hydrolysis, respectively, of the β-1,4-Man-GlcNAc linkage found in the core of N-linked glycans. As the protein scaffold, family 5 glycosidases—monomeric TIM barrel enzymes, with known specificity for β-1,4-linked oligomers of Glu, Man, and GlcNAc, may be used. Chemical complementation may be adapted for β-1,4-Man-GlcNAc substrate specificity simply through the synthesis of the necessary Mtx-Man-F donor, Dex-(GlcNAc)$_2$ acceptor, and Mtx-Man-(GlcNAc)$_2$-Dex trisaccharide substrates. Directed evolution, for example, but not by way of limitation, from TIM barrel loop libraries may then be performed using yeast LEU2 and URA3 5-FOA growth selections. The activity and substrate specificity of evolved protein variants may then be characterized in vitro. Further, the best β-1,4-Man-GlcNAc glycosynthase and glycosidase variants may then be incorporated into a synthesis of an N-linked glycopeptide.

Substrate Synthesis.

Chemical complementation may be adapted to detect synthesis of the β-1,4-Man-GlcNAc linkage with the LEU2 selection using Dex-(GlcNAc)$_2$ and Mtx-Man-F as substrates. With subsequent enzymatic synthesis of Dex-(GlcNAc)$_2$-Man-Mtx, chemical complementation may then be used to detect hydrolysis of the β-1,4-Man-GlcNAc linkage using the URA3 counter selection. Man monosaccharide may be used as the α-fluoro donor because ultimately it may be desirable to add the Man monosaccharide to the GlcNAc-GlcNAc disaccharide in the N-linked glycan core. Use of the monosaccharide may also simplify the synthesis of the substrate. If need be, however, one could start with a disaccharide Glu-Man-F donor and then subsequently modify it to accept a monosaccharide Man-F donor.

TIM Barrel Libraries.

Family 5 endo-glycosidases may be used as the protein scaffold for these directed evolution experiments (Henrissat and Bairoch, 1993, Biochem. J., 293 (Pt. 3), 781-788; Henrissat, 1991, Biochem. J., 280 (Pt. 2), 309-316) (FIG. 6A). Family 5 glycosidases are monomeric TIM barrel enzymes, and the endo-type enzymes in this family should readily incorporate the Dex and Mtx CIDs required for chemical complementation. The sequences of over 500 family 5 glycosidases are known. There are 157 known cellulases, with 10 different high-resolution structures in the PDB; 24 mannosidases, with 5 high-resolution structures; and 1 chitosonase (Coutinho and Henrissat, 1999). The in vitro activities and substrate specificities of several of these family 5 glycosidases have been extensively characterized (Coutinho and Henrissat, 1999).

Chemical complementation may be used to "clone" a new glycosynthase with β-1,4-Man-GlcNAc synthesis activity simply by screening active-site Glu to Gly variants of these known family 5 glycosidases using chemical complementation.

Activity of this cloned β-1,4-Man-GlcNAc glycosynthase TIM barrel may be improved by randomizing the β-strand termini and loops involved in substrate recognition and catalysis. For illustration, FIG. 6B presents the loop libraries the could be used in the *B. agaradhaerens* Cel5A (O85465, 1h5v) based on alignment with the *S. griseus* chitosanase II (Q83VL5, wild-type enzyme shows weak transglycosylation activity to accept (GLcNAc)3 as the acceptor substrate) and *T. fusca* mannosidase (Q9ZF13, 1bqc). The design of these libraries is based largely on recent successes in the de novo directed evolution of binding proteins (Beste, et al., 1999, Proc. Natl. Acad. Sci., USA, 96, 1898-1903; Binz, et al., 2004, Nat. Biotechnol., 22, 575-582; Silverman, et al., 2005, Nat. Biotechnol., 23, 1558-1561) and changes in substrate specificity with traditional genetic assays and extensive characterization of the TIM barrel scaffold (Dwyer, et al., 2004, Science, 304, 1967-1971). A "privileged scaffold" is used for enzyme catalysis. The libraries are focused on the loops that directly contact the substrate and do not disrupt the structural integrity of the protein scaffold. Very diverse libraries of random sequence may be used, even though these libraries vastly exceed the amount of sequence space that can be searched even with a selection.

Chemical Complementation Selections.

LEU2 selection may be used for glycosynthase activity and URA3 5-FOA may be used for counter selection for glycosidase activity. The stringency of both selections can be readily tuned, simply by varying the concentration of leucine or 5-FOA in the yeast media, to select for improvements in activity. False positives may be ruled out simply by carrying out a secondary three-hybrid screen with and without small-molecule substrate.

Characterization of Evolved Protein Variants.

The activity of successful clones may be confirmed in vitro with purified enzyme based on confirmation of the product by HPLC purification and LRMS and $^1$H NMR and specific activity measurements (Lin, et al., 2004, J. Am. Chem. Soc., 126, 15051-15059). It may also be desirable to carry out further NMR experiments to confirm the regio- and stereochemistry of the products. Michaelis-Menten parameters may be determined by measuring fluoride anion release in the case of the glycosynthases and by measuring the release of p-nitrophenol from a tetrasaccharide linked to nitrophenol for the glycosidases (Lin., et al., 2004, J. Am. Chem. Soc., 126, 15051-15059; Ly and Withers, 1999, Annu. Rev. Biochem. 68, 487-522).

5.9.2 Directed Evolution of Aldolases

The aldol reaction is one of the key carbon-carbon bond forming reactions in organic synthesis (Evans, et al., 1982, Topics in Stereochemistry, 1-115; Mahrwald, 1999, Chem. Rev., 99, 1095-1120; Heathcock, 1981, Comprehensive Organic Synthesis, 133 Heathcock, 1991, Comprehensive Organic Synthesis, 181). Aldolases, natural enzymes that catalyze this reaction, have emerged as important tools for aldol synthesis, particularly on the industrial scale (Henderson and Toone, 1999, Comprehensive Natural Product Chemistry, 367-441) (Wymer and Toone, 2001, Curr. Opin. Chem. Biol., 4, 110-119) (Gijsen, et. al., 1996, Chem. Rev. 96, 443-474). Aldolases typically catalyze aldol addition reactions with defined regio- and stereo-chemistry. Significantly, this control of reactivity is independent of neighboring group effects and instead depends on the orientation of the donor and acceptor substrates in the enzyme active site (Franke, et al., 2004, Methods Enzymol, 388, 224-238). On the industrial scale, enzymes offer advantages over synthetic catalysts or auxiliaries that can be expensive to prepare and can generate toxic waste products.

According to the present invention, chemical complementation may be used to carry out directed evolution of D-2-deoxyribose-5-phosphate aldolase (DERA) variants with expanded substrate specificity for chemical synthesis. DERA is the only natural aldolase known to be able to carry out the aldol condensation of two aldehydes (Barbas, et al., 1990, J. Am. Chem. Soc., 112, 2013-2014; Chen, et al., 1992, J. Am. Chem. Soc., 114, 741-748; Gijsen and Wong, 1995, J. Am. Chem. Soc. 117, 7585-7591), a task that has been difficult to solve through synthetic methods (Heathcock, et al., 1980, J. Org. Chem., 45, 1066-1081; Mahrwald, et al., 1997, Tetrahedron Lett., 38, 4543-4544; Yachi, et al., 1999, J. Am. Chem. Soc. 121; Denmark and Ghosh, 2001, Angew. Chem. Int. Ed. Engl. 40, 4759-4762). The E. Coli DERA enzyme has a TIM barrel fold, it is a monomer, its substrate specificity is well defined, and several high-resolution structures are available (Heine, et al., 2001, Science, 294, 369-374; Heine, et al., 2004, J. Mol. Biol. 343, 1019-1034). Current approaches to improve the catalytic activity or change the substrate specificity of DERA rely on in vitro screens, where only ca. $10^3$-$10^4$ variants can be tested at a time (Greenberg, et al., 2004, Proc. Natl. Acad. Sci. USA, 101, 5788-5793), although efforts are being made to engineer genetic selections for DERA activity (DeSantis, et al., 2003, Bioorg. Med. Chem. 11, 43-52). Finally, there is significant interest in modifying the substrate specificity of DERA for a tandem synthesis with 3-azidopropinaldehyde and two acetaldehyde units for the formation of the key chiral lactone 6 present in the cholesterol-lowering drugs Lipitor® (atorvastatin) and Crestor® (rosuvastatin) (Greenberg, et al., 2004, Proc. Natl. Acad. Sci. USA, 101, 5788-5793; DeSantis, et al., 2003, Bioorg. Med. Chem. 11, 43-52; Liu and Wong, 2004, Tetrahedron Lett. 45, 2439-2441) (FIG. 7).

By analogy to the adaptation of chemical complementation to detect glycosynthase and glycosidase activity, chemical complementation may be modified to detect aldolase activity simply by adding a vector encoding DERA and the appropriate Dex and Mtx aldehyde substrates (FIG. 8). Aldol addition may be used to generate the Dex-aldol-Mtx product leading to dimerization of the DBD-DHFR and AD-GR fusion proteins and activation of the LEU2 reporter gene. Because the reaction is reversible, aldol substrates are designed such that upon aldol addition a cyclic product will be formed, which is not a substrate for DERA (Barbas, et al., 1990, J. Am. Chem. Soc., 112, 2013-2014; Chen, et al., 1992, J. Am. Chem. Soc., 114, 741-748; Gijsen and Wong, 1995, J. Am. Chem. Soc. 117, 7585-7591). Alternatively, retro-aldolase activity may be selected for using the URA3 counter selection.

Substrate Synthesis. Based on the natural DERA substrates acetaldehyde and D-glyceraldehyde-3-phosphate (Heine, et al., 2001, Science, 294, 369-374), the Dex-"acetaldehyde" (Dex-AAld) and Mtx-"glyceraldehyde" (Mtx-GAld) substrates shown in FIG. 9 may be used to detect DERA activity using chemical complementation. A phosphodiester "glyceraldehyde" acceptor substrate may be used in order to achieve better cell permeability properties than a phosphate derivative. The recent directed evolution of DERA to accept D-glyceraldehyde with a 2.5-fold improvement in catalytic efficiency using an in vitro screen establishes the feasibility of evolving a DERA variant with altered substrate specificity and the need for further improvement (DeSantis, et al., 2003, Bioorg. Med. Chem., 11, 43-52). Alternatively, a DERA recently cloned from a soil bacterium that appears to have broader substrate specificity (Greenberg, et al., 2003, Bioorg. Med. Chem., 1143-52) may be used. Based on inspection of a high-resolution structure of the E. coli DERA with product bound (Heine, et al., 2001, Science, 294, 369-374), Dex-AAld and Mtx-GAld may be readily accommodated to DERA with hydrocarbon linkers if four point mutations outside the catalytic site are made (FIG. 10). The activity of the substrates with purified enzyme may be verified in vitro based on product synthesis as judged by HPLC. The Mtx substrate may also be tested for cell permeability based on competition of Dex-Mtx transcription activation (this does not work for Dex substrates, see Abida et al.). DERA may also be used to synthesize the Dex-aldol-Mtx product to ensure that it is cell permeable and activates transcription in our yeast three-hybrid strain.

Directed Evolution of DERA Variants with Specificity for Unphosphorylated Substrates.

Directed evolution may be used to produce DERA variants that work efficiently with a Mtx-GAld substrate in which the phosphodiester is replaced with a simple methylene linker. Briefly, loop libraries of the DERA TIM barrel may be selected for increased activity with the unphosphorylated acceptor substrate using the LEU2 growth selection. Evolved variants may be purified and characterized in vitro based on their activity with known fluorogenic substrates (Greenberg, et al., 2004, Proc. Natl. Acad. Sci., 101, 5788-5793). The best-evolved variants may be tested for their ability to synthesize lactone 6 using 3-azidopropinaldehyde or 3-chloropropinaldehyde as an acceptor substrate.

Directed Evolution of a "C-Glycosynthase".

Features of the glycosynthase and aldolase TIM barrels may be combined to create a "C-glycosynthase". Directed evolution may be used to produce a DERA variant that can catalyze addition of a Dex-AAld substrate to a Mtx-Lac-F electrophile, building in the randomized TIM barrel loops that interact with the Lac-F electrophile.

5.10 Directed Evolution Systems for Improving Enzymes for Biomass Conversion

The systems and methods described in the foregoing sections may be used to "evolve" enzymes for use in biomass conversion. A list of enzymes, and their substrates, relevant to biomass conversion, ("BCEs") which may be "evolved" according to the present invention, are set forth in Tables 5A and 5B at the end of the Examples section of this document, and in FIG. 29.

In non-limiting embodiments of the invention, a BCE may be evolved in a system whereby a library of BCE variants is generated (where diversity is generated in vitro and/or in vivo) and then selected by survival in cell culture, using chemical complementation whereby the DNA binding domain ("DBD") and the activation domain ("AD") are joined via the substrate for the BCE. In non-limiting embodiments, the DBD may be comprised in a first fusion molecule which further comprises a first receptor for a first ligand, the AD may be comprised in a second fusion molecule which further comprises a second receptor for a second ligand, and the substrate for the BCE may be comprised in a fusion molecule which comprises the first ligand and the second ligand, such that cleavage of the substrate prevents DBD and AD from being joined and triggering expression of a directly or conditionally toxic reporter gene.

DBD molecules which may be used according to the invention include, but are not limited to LexA, the GAL4 DBD (e.g., residues 1-147) (Yang et al., 1995, Nucl. Acids Res. 23:1152-1156); ZFHD1 and zinc finger DBDs (Pabo et al., 2001, Annu. Rev. Biochem. 70:313-340).

AD molecules which may be used according to the invention include, but are not limited to, B42, the GAL4 AD (e.g., residues 768-881) (Yang et al., 1995, Nucl. Acids Res. 23:1152-1156), NF-κB, and HSV VP16 AD (Burcin et al., 1998, Front. Biosci. 3:c1-7) and the AD used in Chakraborty et al., 1992, J. Biol. Chem. 267:17498-17501).

Receptor/ligand pairs which may be utilized according to the invention include, but are not limited to, DHFR/antifolate (e.g., DHFR/trimethoprim; see Gallagher et al., 2007, Anal. Biochem. 363(1):160-162); glucocorticoid receptor/steroid (or glucocorticoid receptor/agonist or glucocorticoid receptor/antagonist); TET-repressor/tetracycline; penicillin binding proteins/penicillin or cephalosporin (fluorescently labeled penicillins are commercially available, such as BOCILLIN FL and BOCILLIN 650/665 (Molecular Probes, Inc., Oregon)); acetylcholinesterase/acetylcholine (fluorescently labeled acetylcholine is commercially available, such as Amplex Red acetylcholine (Molecular Probes Inc., Oregon)); carboxypeptidase A/MTX; cyclophilin prolyl isomerase/cyclosporin; FK506-binding protein (FKBP)/FK506 and rapamycin; beta-lactamase/clavulinate; DNA binding site/DNA binding protein; DNA alkyltransferase/$O^6$-benzylguanine-$O^6$ alkylated guanine (Gendreizig et al., 2003, J. Am. Chem. Soc. 125(49):14970-14971); estrogen receptor/estrone (Muddana and Peterson, 2004, Org. Lett. 6(9):1409-1412); streptavidin/biotin (Hussey et al., 2003, J. Am. Chem. Soc. 125(13):3692-3693); and hemoglobin/heme. For cyclophilin prolyl isomerase/cyclosporin and FK506-binding protein (FKBP)/FK506 and rapamycin, strategies for redesigning ligand/protein interfaces and modified structures are set forth in Clackson, 1998, Curr. Opin. Struct. Biol. 8:451-458.

BCEs which may be "evolved" according to said system include any enzyme which degrades a naturally occurring substrate, including but not limited to carbon-oxygen lyase enzymes, including but not limited to enzymes listed in Tables 5A and 5B, below, and/or that operate on substrates set forth in Table 5A, Table 5B, and/or FIG. 29.

Where diversity is generated in vitro, for example by the creation of a diversified phage or plasmid library, standard techniques may be used.

Where diversity is generated in vivo, a system as set forth herein may be employed which utilizes a plurality of host cells, wherein each host cell contains a nucleic acid encoding the BCE; contains at least one DNA which can be used to direct mutation of the BCE, and exhibits at least one mutator function.

The foregoing systems may be used to generate a plurality of primary libraries comprising mutants of a BCE, which then may, through genetic exchange (e.g., sexual reproduction) may be used to produce a secondary library of substantially amplified diversity.

5.11 Cellulase Variants

The present invention provides for cellulase variants having increased activity relative to their parent cellulase. The present invention provides for isolated nucleic acids comprising sequences encoding said variants and portions thereof, as well as purified proteins. See for example, Table 1A, which includes SEQ ID NOS:1-60.

In one set of non-limiting embodiments, the present invention provides for a nucleic acid encoding the cellulase variant of Colony 1 described in Section 13, below (termed "CELLVAR1", Cellulase 4 in Table 1A, below), wherein the nucleic acid sequence comprises SEQ ID NO:1 (FIG. 21A), or comprises the nucleic acid sequence of residues 1 through 924 of SEQ ID NO:1, or the nucleic acid sequence of residues 61 through 924 of SEQ ID NO:1, or the nucleic acid sequence of residues 109 through 924 of SEQ ID NO:1, or the nucleic acid sequence of residues 115 through 924 of SEQ ID NO:1; or a nucleic acid which hybridizes to any of the foregoing under stringent conditions, defined as e.g., hybridization in 0.5 M $NaHPO_4$, 7 percent sodium dodecyl sulfate ("SDS"), 1 mM ethylenediamine tetraacetic acid ("EDTA") at 65° C., and washing in 0.1×SSC/0.1 percent SDS at 68° C. (Ausubel et al., 1989, Current Protocols in Molecular Biology, Vol. I, Green Publishing Associates, Inc., and John Wiley & Sons, Inc. New York, at p. 2.10.3). The present invention further provides for a nucleic acid which is at least 90 percent, at least 95 percent, at least 96 percent, at least 97 percent, at least 98 percent, or at least 99 percent homologous to one or more of SEQ ID NO:1 (FIG. 21A) or residues 1 through 924 of SEQ ID NO:1 or residues 61 through 924 of SEQ ID NO:1 or residues 109 through 924 of SEQ ID NO:1, or residues 115 through 924 of SEQ ID NO:1, where homology may be determined relative to a second sequence using standard software such as BLAST or FASTA, and where said homologous nucleic acid encodes a protein having cellulase activity. Of note, CELLVAR1 had previously been believed to show a 33-fold improvement over its parental strains, but this was later determined to have been an error, as a parental strain that was not considered in that determination had a high level of activity.

In further non-limiting embodiments, the present invention provides for a nucleic acid encoding an amino acid sequence as set forth for CELLVAR1 in SEQ ID NO:3 (FIG. 21B), or for a nucleic acid sequence comprising a nucleic acid sequence encoding the amino acid sequence of residues 1 through 308 of SEQ ID NO:3, or residues 25 through 300 of SEQ ID NO:3, or residues 21 through 308 of SEQ ID NO:3, or residues 37-308 of SEQ ID NO:3, or residues 39-308 of SEQ ID NO:3, optionally further encoding additional residues of SEQ ID NO:3 and/or amino acid sequence not found in SEQ ID NO:3, and where the protein encoded by said nucleic acid has cellulase activity.

In another set of non-limiting embodiments, the present invention provides for a nucleic acid encoding the cellulase variant of Colony 2 described in Section 8, below (termed "CELLVAR2"), wherein the nucleic acid sequence comprises SEQ ID NO:2 (FIG. 22A), or comprises the nucleic acid sequence of residues 1 through 924 of SEQ ID NO:2, or the nucleic acid sequence of residues 61 through 924 of SEQ ID NO:2, or the nucleic acid sequence of residues 109 through 924 of SEQ ID NO:2, or the nucleic acid sequence of residues 115 through 924 of SEQ ID NO:2; or a nucleic acid which hybridizes to any of the foregoing under stringent conditions, defined as e.g., hybridization in 0.5 M $NaHPO_4$, 7 percent sodium dodecyl sulfate ("SDS"), 1 mM ethylenediamine tetraacetic acid ("EDTA") at 65° C., and washing in 0.1×SSC/ 0.1 percent SDS at 68° C. (Ausubel et al., 1989, Current Protocols in Molecular Biology, Vol. I, Green Publishing Associates, Inc., and John Wiley & Sons, Inc. New York, at p. 2.10.3). The present invention further provides for a nucleic acid which is at least about 90 percent, at least 95 percent, at least 96 percent, at least 97 percent, at least 98 percent, or at least 99 percent homologous to one or more of SEQ ID NO:2 (FIG. 22A) or residues 1 through 924 of SEQ ID NO:2 or residues 61 through 924 of SEQ ID NO:2, or residues 109 through 924 of SEQ ID NO:2, or residues 115 through 924 of SEQ ID NO:2, where homology may be determined relative to a second sequence using standard software such as BLAST or FASTA, and where said homologous nucleic acid encodes a protein having cellulase activity.

In further non-limiting embodiments, the present invention provides for a nucleic acid encoding an amino acid sequence as set forth for CELLVAR2 in SEQ ID NO:4 (FIG. 22B), or for a nucleic acid sequence comprising a nucleic acid sequence encoding the amino acid sequence of residues 1 through 308 of SEQ ID NO:4, or residues 25 through 300 of SEQ ID NO:4, or residues 21 through 308 of SEQ ID NO:4, or residues 37-308 of SEQ ID NO:4, or residues 39-308 of SEQ ID NO:4, optionally further encoding additional residues of SEQ ID NO:4 and/or amino acid sequence not found in SEQ ID NO:4, and where the protein encoded by said nucleic acid has cellulase activity.

Additional non-limiting examples of cellulase variants according to the invention are set forth in Table 1A, below, which includes nucleic acid and amino acid sequences as well as, in certain instances, kinetic data showing enzyme activity (summarized in Table 1B). Further, the present invention provides for cellulase variants having a nucleic acid sequence which is least about 90 percent, at least 95 percent, at least 96 percent, at least 97 percent, at least 98 percent, or at least 99 percent homologous to a nucleic acid sequence of a variant as set forth in Table 1A, where homology may be determined relative to a second sequence using standard software such as BLAST or FASTA, and where said homologous nucleic acid encodes a protein having cellulase activity. In still further non-limiting embodiments, the present invention provides for a nucleic acid encoding an amino acid sequence as set forth for a cellulase variant in Table 1A, and where the protein encoded by said nucleic acid has cellulase activity.

Any of the foregoing cellulase variant-encoding nucleic acids may be operably linked to a promoter, which may be a native cellulase promoter or a promoter which is not a native cellulase promoter (i.e., a heterologous promoter). Any suitable promoter, including constitutively active promoters, inducible promoters, eukaryotic promoters, prokaryotic promoters, viral promoters, etc., may be used. Further, said CELLVAR1 or CELLVAR2-encoding nucleic acids may further be modified or operably linked to other elements which aid expression. For example, but not by way of limitation, amino acid residues 1-20, or 1-36, or 1-38 of SEQ ID NO:3 or SEQ ID NO:4 may be replaced by a heterologous (e.g., artificial or designed based on the signal sequence of another protein) signal sequence. Any of the foregoing nucleic acids may be comprised in a vector molecule. The invention further provides for a host cell containing a vector molecule which comprises a nucleic acid encoding CELLVAR1 or CELL-VAR2, where the host cell may be a eukaryotic or prokaryotic cell, and in particular may be a bacterial cell, a yeast cell, an insect cell, or a mammalian cell.

The present invention further provides for a CELLVAR1 protein with cellulase activity comprising the amino acid sequence (SEQ ID NO:3) or portions thereof such as amino acid residues 1 through 308 of SEQ ID NO:3, or amino acid residues 25 through 300 of SEQ ID NO:3, or amino acid residues 21 through 308 of SEQ ID NO:3, or amino acid residues 37 through 308 of SEQ ID NO:3, or amino acid residues 39-308 of SEQ ID NO:3, optionally further encoding additional residues of SEQ ID NO:3 and/or amino acid sequence not found in SEQ ID NO:3 (e.g., a heterologous signal sequence).

The present invention further provides for a CELLVAR2 protein with cellulase activity comprising the amino acid sequence (SEQ ID NO:4) or portions thereof such as amino acid residues 1 through 308 of SEQ ID NO:4, or amino acid residues 25 through 300 of SEQ ID NO:4, amino acid residues 21 through 308 of SEQ ID NO:4, or amino acid residues 37 through 308 of SEQ ID NO:4, or amino acid residues 39-308 of SEQ ID NO:4, optionally further encoding additional residues of SEQ ID NO:4 and/or amino acid sequence not found in SEQ ID NO:4 (e.g., a heterologous signal sequence).

The present invention still further provides for a cellulase variant with cellulase activity comprising an amino acid sequence as set forth in Table 1A, and for cellulase variants having cellulase activity which are at least about 90 percent, at least 95 percent, at least 98 percent, or at least 99 percent homologous thereto.

Such proteins may be produced using the nucleic acid molecules disclosed above and protein expression methods known in the art.

The foregoing cellulases may be used to break down cellulose, for example as part of a method to produce ethanol.

In a specific, non-limiting embodiment of the invention e.g., see Section 14, below), the following chemical complementation system may be used: a DNA binding domain such as LEX a may be fused to the Mtx receptor protein dihydrofolate reductase (DBD-DHFR) and an activation domain such as B42 may be fused to the Dex receptor protein glucocorticoid receptor (AD-GR). In the presence of Mtx-Dex, AD-GR is recruited to DBD-DHFR, which is bound upstream of the reporter gene, effectively reconstituting the transcriptional activator, and leading to transcription of the downstream reporter gene. To adapt the yeast three-hybrid system to read out cellulase catalysis, the linkage between Mtx and Dex may be replaced with the substrate for the reaction, cellulose, and the cellulase enzyme may be added as the fourth component to the system. Both the DBD-DHFR and AD-GR fusion proteins may be expressed from a Gal1 promoter in a 2µ plasmid, and the reporter gene may be URA3, which in the presence of 5-fluoroorotic acid (5-FOA) produces 5-fluorouracil (5-FU) and so is toxic. Cell survival is achieved by cleavage of the heterodimeric small molecule, disrupting expression of the URA3 gene. Said chemical complementation may be used in a diversifying system to generate cellulase variants of increased activity, which further comprises at least one DINA and at least one mutator function, as described above. Furthermore, a first primary library generated by said chemical complementation/diversifying system may be used to generate a secondary library by genetic exchange with a second primary library generated by said chemical complementation/diversifying system, for example by sexual reproduction. Analogous systems may be used to improve activity of other hydrolases or other enzymes which cleave their substrates.

TABLE 1A

```
CELLULASE 1 = CELLVAR2
(3.7 fold improvement over starting genes)]
Kcat =                4.3 x 10^3 sec^-1
Km =                  3.2 x 10^-3 M
Kcat/Km =             1.4 x 10^6 sec^-1M^-1
Nucleic acid sequence cellulase 1 (CELLVAR2):
                                        SEQ ID NO:2
ATGGCCACGCCAGTAGAAACGCATGGTCAGCTGTCCATCGAAAACGGGCG
ACTGGTGGATGAACAGGGGAAAGGGTGCAACTGAGAGGGGTCAGTTCGC
ACGGTTTGCAGTGGTTTGGCGACTATGTCAACAAAGACTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTAAAAGAGG
CCGTTGCGGCGGCGCAAAGCCTCGGCGTTTACATCATCATCGACTGGCAC
ATTTTGTCGGATAACGATCCTAATATTTATAAAGCACAGGCAAAAACCTT
CTTTGCCGAAATGGCGGGGCTGTACGGTAATTCGCCGAACGTGATTTATG
AAATCGCCAATGAACCTAACGGCGGCGTGACCTGGAACGGGCAGATTCGG
CCTTATGCGCTGGAAGTGACTGAAACTATCCGTAGTAAAGATCCTGATAA
TCTGATTATCGTTGGCACGGGTACCTGGAGTCAGGATATCCATGATGCGG
CGGACAATCTGTTGCCCGATCCGAATACGATGTACGCGCTGCATTTCTAT
GCGGGCACGCACGGGCAATTCCTGTGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCATAAGCTGGGTGAACTGGTCGCTTACCGATAAGTCAGA
GGCGTCCGCCGCGCTGGCTCCAGGGGCGAGTAAATCAGGCGGTTGGACGG
AGCAGAATTTGTCGGCGTCAGGAAATTTGTCAGAGCACAGATTCGCGCG
GCTGCGAATCTAAGCGGTGGCGATCACCATCACCATCACCATTAA Amino acid sequence cellulase 1 (CELLVAR2):
                                        SEQ ID NO:4
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKTFFAEMAGLYGNSPNVIYEIANEPNGGVTWNGQIR
PYALEVTETIRSKDPDNLIIVGTGTWSQDIHDAADNLLPDPNTMYALHFY
AGTHGQFLCDRIDYAQSRGAAIFVSEWGTSDASGNGGPPFLPESQTWIDFL
NNRGISWVNWSLTDKSEASAALAPGASKSGGWTEQNLSASGKFVRAQIRA
AANLSGGDHHHHHH*

CELLULASE 2
(5.7-fold improvement over starting genes)]
Kcat =                5.2 x 10^3 sec^-1
Km =                  2.5 x 10^-3 M
Kcat/Km =             2.1 x 10^6 sec^-1M^-1
Nucleic acid sequence cellulase 2
                                        (SEQ ID NO:5)
ATGGCCACACCGGTGGAAACGCATGGCCAACTGTCCATTGAAAATGGGCG
ACTGGTGGATGAACAGGGGAAAGGGTGCAACTGAGAGGGGTCAGTTCGC
ACGGTTTGCAGTGGTTTGGCGACTATGTCAACAAAGACTCGATGAAGTGG
CTGCGTGATGACTGGGGGATTAATGTATTCCGCGTCGCATGTACACGGC
GGCGGATGGTTATATTTCGAATCCTTCCCTCGCCAATAAGGTCAAAGAAG
CCGTTGCGGTGGCACAAAGCCTCGGCGTTTACATCATCATCGACTGGCAT
ATCTTGTCGGATAACGATCCCAATATTTATAAAGCACAGGCAAAAACCTT
CTTTGCCGAAATGGCGGGGCTGTACGGTAATTCGCCGAACGTGATTTATG
AAATCGCCAATGAACCTAACGGCGGCGTGACATGGAACGGGCAGATTCGG
CCTTATGCGCTGGATGTTACTGACACTATCCGTAGCAAAGATCCTGATAA
CCTTATTATCGTCGGCAGCGGGACCTGGAGCCAGGACATCCATGACGCGG
CGGATAATCAGCTGCCCGATCCGAATACGCTACGCGCTGCATTTCTAT
GCGGGTACGCACGGGCAGTTCCTGCGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGTGTAAGCTGGGTAAACTGGTCACTAAGCGATAAGTCTGA
GACGTCTGCGGCGCTGACTCCAGGGGCGAGTAAATCAGGCGGTTGGACGG
AGCAGAATCTGTCGACGTCAGGAAAATTTGTCAGAGAGCAGATTCGTGCA
GGTGCGAATCTGGGCGGTGGCGATCACCATCACCATCACCATTAA Amino acid sequence cellulase 2
                                        (SEQ ID NO:6)
ATPVETHGQLSIENGRLVDEQGKRVQLRGVSSHGLQWFGDYVNKDSMKWL
RDDWGINVFRVAMYTAADGYISNPSLANKVKEAVAVAQSLGVYIIIDWHI
LSDNDPNIYKAQAKTFFAEMAGLYGNSPNVIYEIANEPNGGVTWNGQIRP
YALDVTDTIRSKDPDNLIIVGSGTWSQDIHDAADNQLPDPNTLYALHFYA
GTHGQFLRDRIDYAQSRGAAIFVSEWGTSDASGNGGPPFLPESQTWIDFLN
NRGVSWVNWSLSDKSETSAALTPGASKSGGWTEQNLSTSGKFVREQIRAG
ANLGGGDHHHHHH*

CELLULASE 3
Kcat =                5 x 10^3 sec^-1
Km =                  3.6 x 10^-3 M
Kcat/Km =             1.4 x 10^6 sec^-1M^-1
Nucleic acid sequence cellulase 3
                                        (SEQ ID NO:7)
ATGGCCACGCCAGTAGAAACGCATGGTCAGCTGTCCATCGAAAACGGGCG
ACTGGTGGATGAACAGGGGAAAGGGTGCAACTGAGAGGGGTCAGTTCGC
ACGGTTTGCAGTGGTTTGGCGACTATGTCAACAAAGACTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTAAAAGAGG
CCGTTGCGGCGGCGCAAAGCCTCGGCGTTTACATCATCATCGACTGGCAC
ATTTTCGGATAACGATCCCAATATTTATAAAGCACAGGCAAAAACCTT
CTTTGCCGAAATGGCGGGGCTGTACGGTAATTCGCCGAACGTGATTTATG
AAATCGCCAATGAACCTAACGGCGGCGTGACCTGGAACGGGCAGATTCGG
CCTTATGCGCTGGAAGTGACTGAAACTATCCGTAGTAAAGATCCTGATAA
TCTGATTATCGTTGGCACGGGTACCTGGAGTCAGGATATCCATGATGCGG
CGGACAATCTGTTGCCCGATCCGAATACGATGTACGCGCTGCATTTCTAT
GCGGGCACGCACGGGCAATTCCTGTGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCATAAGCTGGGTGAACTGGTCGCTTACCGATAAGTCAGA
GGCGTCCGCCGCGCTGGCTCCAGGGGGCGAGTAA Amino acid sequence cellulase 3
                                        (SEQ ID NO:8)
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKTFFAEMAGLYGNSPNVIYEIANEPNGGVTWNGQIR
PYALEVTETIRSKDPDNLIIVGTGTWSQDIHDAADNLLPDPNTMYALHFY
AGTHGQFLCDRIDYAQSRGAAIFVSEWGTSDASGNGGPPFLPESQTWIDFL
NNRGISWVNWSLTDKSEASAALAPGGE- CELLULASE 4 = CELLVAR1
Kcat =                1.6 x 10^4 sec^-1
Km =                  1.3 x 10^-3 M
Kcat/Km =             1.1 x 10^7 M^-1sec^-1
Nucleic acid sequence cellulase 4 (CELLVAR1)
                                        (SEQ ID NO:1)
ATGGCCACGCCAGTAGAAACGCATGGTCAGCTGTCCATCGAAAACGGGCG
ACTGGTGGATGAACAGGGGAAAGGGTGCAACTGAGAGGGGTCAGTTCGC
ACGGTTTGCAGTGGTTTGGCGACTATGTCAACAAAGACTCGATGAAATGG
CTGCGTGACGACTGGGGGATCAATGTGTTTCGCGTTGCCATGTACACGGC
GGAGAATGGTTATATTGCTAACCCTTCCCTCGCCAATAAGGTAAAAGAGG
CCGTTGCGGCGGCGCAAAGCCTCGGCGTCTACATCATCATCGACTGGCAC
ATTTTGTCGGATAACGATCCCAATACTTATAAAGCACAGGCAAAAATCTT
CTTTGCCGAAATGGCTGGGCTGTATGGCAGCTCACCGAACGTGATTTATG
AAATCGCCAATGAGCCAAACGGTGGCGTGACGTGGAACGGACAGATTCGG
CCTTATGCGCTGGAAGTGACTGACACCATCCGTAGCAAAGATCCTGATAA
CCTTATTATCGTCGGTACCGGCACCTGGAGTCAGGATATCCACGATGCAG
CGGATAACCAACTCCCCGATCTGAATACCCTATACGCGCTGCATTTCTAT
GCGGGCACGCACGGGCAATTCCTGTGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCTAAGCTGGGTGAACTGGTCACTAAGCGATAAGTCTGA
GACGTCTGCGGCGCTGACTCCAGGGGCGAGCAAATCAGGCGGCTGGACGG
AGCAGAATTTGTCGACGTCAGGCAAATTTGTCAGAGAGCAGATTCGTGCG
GGGGCGGGTCTGAGCGGTGGTGATCACCATCACCATCACCATTAA Amino acid sequence cellulase 4 (CELLVAR1)
                                        (SEQ UD NO:3)
MATPVETHGQLSIENGRLVDEQGKRVQLRGVSSHGLQWFGDYVNKDSIKW
LRDDWGINVFRVAMYTAENGYIANPSLANKVKEAVAAAQSLGVYIIIDWH
```

TABLE 1A-continued

ILSDNDPNTYKAQAKIFFAEMAGLYGSSPNVIYEIANEPNGGVTWNGQIR
PYALEVTDTIRSKDPDNLIIVGTGTWSQDIHDAADNQLPDLNTLYALHFY
AGTHGQFLCDRIDYAQSRGAAIFVSEWGTSDASGNGGPFLPESQTWIDFL
NNRGVSWVNWSLSDKSETSAALTPGASKSGGWTEQNLSTSGKFVREQIRA
GAGLSGGDHHHHHH*

CELLULASE 5
Kcat = $6.7 \times 10^3$ sec$^{-1}$
Km = $1.5 \times 10^{-3}$ M
Kcat/Km = $4.5 \times 10^6$ M$^{-1}$sec$^{-1}$
Nucleic acid sequence cellulase 5
(SEQ ID NO:9)
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGCGACTATGTCAACAAAGACTCGATAAAATGG
CTGCGTGACGACTGGGGGATCAATGTGTTTCGCGTTGCCATGTACACGGC
GGAGAATGGTTATATTGCTAACCCTTCCCTCGCCAATAAGGTAAAAGAGG
CCGTTGCGGCGGCACAAAGCCTCGGCGTCTACATCATCATCGACTGGCAC
ATTTTGTCGGATAACGATCCCAATACTTATAAAGCACAGGCAAAAATGTT
CTTTTGCCGAAATGGCTGGGCTGTATGGCAGCTCACCGAACGTGATTTATG
AAATCGCCAATGAGCCAAACGGTGGCGTGACGTGGAACGGACAGATTCGG
CCTTATGCGCTGGAAGTGACTGACACCATCCGTAGCAAAGATCCTGATAA
CCTTATTATCGTCGGTACCGGCACCTGGAGTCAGGATATCCACGATGCAG
CGGATAACCAACTGCCCGATCTGAATACCCTATACGCTGCATTTCTAT
GCGGGCACGCACGGGCAGTTCCTGTGCGATCGTATTGATTATGCGCAAAG
CCGTGGCGCGGCGATTTCGTCAGCGAGTGGGGGACCAGCGATGCATCCG
GCAACGGTGGGCCGTTCCTGCCGAATCGCAGACCTGGATCGATTTCCTG
AATAACCGTGGCGTAAGCTGGGTGAACTGGTCACTAAGCGATAAGTCTGA
GACGTCTGCGGCGCTGACTCCAGGGGCGAGCAAATCAGGCGGCTGGACGG
AGCAGAATTTGTCGACGTCAGGCAAATTTGTCAGAGAGCAGATTCGTGCG
GGGGCGGGTCTGAGCGGTGGTGATCACCATCACCATCACCATTAA Amino acid sequence cellulase 5
(SEQ ID NO:10)
MATPVETHGQLSIENGRLVDEQGKRVQLRGVSSHGLQWFGDYVNKDSIKW
LRDDWGINVFRVAMYTAENGYIANPSLANKVKEAVAAAQSLGVYIIIDWH
ILSDNDPNTYKAQAKIFFAEMAGLYGSSPNVIYEIANEPNGGVTWNGQIR
PYALEVTDTIRSKDPDNLIIVGTGTWSQDIHDAADNQLPDLNTLYALHFY
AGTHGQFLCDRIDYAQSRGAAIFVSEWGTSDASGNGGPFLPESQTWIDFL
NNRGVSWVNWSLSDKSETSAALTPGASKSGGWTEQNLSTSGKFVREQIRA
GAGLSGGDHHHHHH*

CELLULASE 6
Kcat = $2.1 \times 10^2$ sec$^{-1}$
Km = $0.96 \times 10^{-3}$ M
Kcat/Km = $2.2 \times 10^5$ M$^{-1}$sec$^{-1}$
Nucleic acid sequence cellulase 6
(SEQ ID NO:11)
ATGGCCACGCCAGTAGAAACACATGGCCAACTGTCCATCGAAAATGGGCG
ACTGGTGGATGAACAGGGGAAAAGGGTGCAACTGAGAGGGGTCAGTTCGC
ACGGTTTGCAGTGGTTTGGCGACTATGTCAACAAAGATTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTAAAAGAGG
CCGTTGCGGCGGCACAAAGCCTCGGCGTTTACATCATCATCGACTGGCAT
ATCTTGTCGGATAACGATCCTAATATTTATAAAGCACAGGCAAAACCTT
CTTTTGCTGAAATGGCTGGGCTGTATGGCAGCTCACCGAACGTGATTTATG
AAATCGCCAATGAGCCAAACGGTGGCGTGACCTGGAACGGGCAGATTCGG
CCTTATGCGCTGGAAGTGACTGACACCATCCGTAGCAAAGATCCTGATAA
CCTTATTATCGTCGGCAGCGGGACCTGGAGCCAGGATATCCATGATGCAG
CGGATAACCAACTGCCCGATCTGAATACCGTACGCTGCATTTCTAT
GCGGGCACGCACGGGCAGTTCCTGCGCGATCGTATCGATTATGCACAAAG
CCGCGGTGCCGCGATTTTGTCAGCGAGTGGGGCACAAGCGATGCGTCCG
GCAATGCCGGGCCGTTCCTGCCTGAATCGCAGACCTGGATCGATTTCCTG
AATAACCGTGGCGTAAGCTGGGTGAACTGGTCGCTTACCGATAAATCAGA
GGCGTCCGCCGCGCTGGCTCCGGGAGCGAGCAAATCTGGTGGCTGGACGG
AGCAGAATCTGTCGACGTCAGGCAAATTTGTCAGAGAGCAGATTCGTGCA
GGTGCGAATCTGGGCGGTGGCGATCACCATCACCATCACCATTAA Amino acid sequence cellulase 6
(SEQ ID NO:12)
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNTYKAQAKTFFAEMAGLYGSSPNVIYEIANEPNGGVTWNGQIR
PYALEVTDTIRSKDPDNLIIVGSGTWSQDIHDAADNQLPDPNTLYALHFY
AGTHGQFLRDRIDYAQSRGAAIFVSEWGTSDASGNGGPFLPESQTWIDFL
NNRGVSWVNWSLTDKSEASAALAPGASKSGGWTEQNLSTSGKFVREQIRA
GANLGGGDHHHHHH*

CELLULASE 7
Kcat = $1.1 \times 10^2$ sec$^{-1}$
Km = $1.4 \times 10^{-2}$ M
Kcat/Km = $8.12 \times 10^3$ M$^{-1}$sec$^{-1}$
Nucleic acid sequence cellulase 7
(SEQ ID NO:13)
ATGGCCACGCCAGTAGAAACGCATGGCCAACTGTCCATCGAAAATGGGCG
ACTGGTGGATGAGCAGGGGAAAAAGAGTGCAACTGAGAGGGAATCAGCTCGA
ACGGGTTGCAGTGGTTTGGTGACTACGTCAACAAAGATTCGATGAAGTGG
CTGCGTGATGACTGGGGGATTAACGTATTCCGTGTTGCCATGTACACGGC
GGCGGATGGTTATATTTCGAATCCTTCCCTCGCCAATAAGGTCAAAGAGG
CCGTTGCGGTGGCACAAAGCCTCGGCGTCTACATCATCATCGACTGGCAT
ATCTTGTCGGATAACGATCCTAATATTTATAAAGCACAGGCAAAAACCTT
CTTTTGCCGAAATGGCGGGGCTGTACGGTAATTCGCCGAACGTGATTTATG
AAATCGCCAATGAACCTAACGGCGGCGTGACATGGAACGGGCAAATTCGG
CCTTATGCGCTGGATGTTACTGACACCATCCGTAGCAAAGATCCCGATAA
CCTCATTATCGTCGGTACCGGCACCTGGAGTCAGGATATCCACGATGCAG
CGGATAACCAACTGCCCGATCCGAATACGCTGTATGCGCTGCATTTCTAT
GCCGGTACGCACGGGCAGTTCCTGCGCGATCGCATTGACTATGCACAAAG
CCGCGGTGCCGCAATTTTCGTCAGCGAGTGGGGAACAAGCGATGCGTCCG
GCAACGGTGGGCCGTTCCTGCCAGAATCGCAAACCTGGATCGATTTCCTG
AATAACCGTGGCATAAGCTGGGTTAACTGGTCGCTTACCGATAAATCAGA
GGCGTCTGCGGCGCTGGCACCGGGAGCGAGCAAATCTGGCGGTTTGGACA
GAGCAGAATTTGTCGGCGTCAGGAAATTTGTCAGAGCACAGATTCGCGC
GGCTGCGAATCTGGGCGGTGGCGATCACCATCACCATCACCATTAA Amino acid sequence cellulase 7
(SEQ ID NO:14)
MATPVETHGQLSIENGRLVDEQGKRVQLRGISSNGLQWFGDYVNKDSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALDVTDTIRSKDPDNLIIVGTGTWSQDIHDAADNQLPDPNTLYALHFY
AGTHGQFLRDRIDYAQSRGAAIFVSEWGTSDASGNGGPFLPESQTWIDFL
NNRGISWVNWSLTDKSEASAALAPGASKSGGWTEQNLSASGKFVRAQIRA
AANLGGGDHHHHHH*

CELLULASE 8
Kcat = $8.4 \times 10^2$ sec$^{-1}$
Km = $4.3 \times 10^{-3}$ M
Kcat/Km = $2 \times 10^5$ M$^{-1}$sec$^{-1}$
Nucleic acid sequence cellulase 8
(SEQ ID NO:15)
ATGGCCACGCCAGTAGAAACGCATGGCCAACTGTCCATTGAAAATGGGCG
ACTGGTGGATGAACAGGGGAAAAGGGTGCAACTGAGAGGGGTCAGTTCGC
ACGGTTTGCAGTGGTTTGGTGACTACGTCAACAAAGATTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTAAAAGAGG
CCGTTGCGGCGGCGCAAAGCCTCGGCGTTTACATCATCATCGACTGGCAT
ATCTTGTCGGATAACGATCCTAATATTTATAAAGCACAGGCAAAAACCTT
CTTTTGCCGAAATGGCGGGGCTGTACGGTAATTCGCCGAACGTGATTTATG
AAATCGCCAATGAACCTAACGGCGGCGTGACATGGAACGGGCAAATTCGG
CCTTATGCGCTGGAAGTGACTGAAACTATCCGTAGTAAAGATCCTGATAA
CCTTATTATCGTCGGCAGCGGGACCTGGAGCCAGGACATCCATGATGCGG
CAGACAATCAGTTGCCCGATCCGAATACGATGTACGCGCTGCATTTCTAT
GCCGGCACGCACGGGCAGTTCCTGCGCGATCGTATCGATTATGCACAAAG
CCGCGGCGCCGCGATTTTTGTCAGCGAGTGGGGCACAAGCGATGCGTCCG
GCAACGGCGGACCGTTCCTGCCTGAATCGCAGACCTGGATCGATTCCTGA
ACAACCGTGGTGTGAGCTGGGTTAACTGGTCGCTTACCGATAAGTCAGAG
GCGTCTGCGGCGCTGGCACCGGGAGCGAGCAAATCAGGTGGCTGGACGGA
GCAGAATCTGTCGACGTCAGGCAAATTTGTCAGAGAGCAGATTCGTCAG
GTGCGAATCTGGGCGGTGGCGATCACCATCACCATCACCATTAA Amino acid sequence cellulase 8
(SEQ ID NO:16)
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKTFFAEMAGLYGNSPNVIYEIANEPNGGVTWNGQIR
PYALEVTETIRSKDPDNLIIVGSGTWSQDIHDAADNQLPDPNTMYALHFY
AGTHGQFLRDRIDYAQSRGAAIFVSEWGTSDASGNGGPFLPESQTWIDFL
NNRGVSWVNWSLTDKSEASAALAPGASKSGGWTEQNLSTSGKFVREQIRA
GANLGGGDHHHHHH*

CELLULASE 9
Kcat = $7.1 \times 10^2$ sec-1
Km = $4.6 \times 10^{-3}$ M
Kcat/Km = $1.5 \times 10^5$ M$^{-1}$sec$^{-1}$

TABLE 1A-continued

Nucleic acid sequence cellulase 9
(SEQ ID NO:17)
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGTGACTACGTCAACAAAGATTCGATGAAATGG
CTGCGCGATGACTGGGGGATTAACGTATTCCGTGTTGCCATGTACACGGC
AGCGGATGGCTATATTTCCAATCCTTCCCTTGCGAATAAGGTCAAAGAAG
CCGTTGCGGTGGCACAAAGCCTCGGCGTTTACATCATCATGGACTGGCAC
ATTTTGTCGGATAACGATCCTAATATTTATAAAGCACAGGCAAAAACCTT
CTTTGCCGAAATGGCGGGGCTGTACGGTAATTCGCCGAACGTGATTTATG
AAATCGCCAATGAGCCAAACGGTGGCGTGACCTGGAACGGGCAGATTCGG
CCTTATGCGCTGGAAGCCACTGACACCATCCGTAGCAAAGATCCCGATAA
CCTTATTATCGTCGGCAGCGGGACCTGGAGCCAGGATATCCATGATGCGG
CAGACAATCAGTTGCCCGATCCGAATACTCTGTATGCGCTGCATTTCTAT
GCGGGTACGCACGGGCAGTTCCTGCGCGATCGTATTGACTATGCACAAAG
CCGCGGTGCTGCAATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCGTAAGCTGGGTGAACTGGTCGCTTACCGATAAGTCAGA
GGTGTCCGCCCGCTGGCTCCAGGGGCGAGTAAATCAGGCGGTTGGACGG
AGCAGAATCTGTCGACGTCAGGAAAATTTGTCAGAGCACAGATTCGCGCG
GCTGCGAATCTAAGCGGTGGCGATCACCATCACCATCACCATTAA Amino acid sequence cellulase 9
(SEQ ID NO:18)
MATPVETHGQLSIENGRLVDEQGKRVQLRGVSSHGLQWFGDYVNKDSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALEATDTIRSKDPDNLIIVGSGTWSQDIHDAADNQLPDPNTLYALHFY
AGTHGQFLRDRIDYAQSRGAAIFVSEWGTSDASGNGGPFLPESQTWIDFL
NNRGVSWVNWSLTDKSEVSAALAPGASKSGGWTEQNLSTSGKFVRAQIRA
AANLSGGDHHHHHH*

CELLULASE 10
Kcat = 87 sec$^{-1}$
Km = 0.76 × 10$^{-3}$ M
Kcat/Km = 1.1 × 10$^{5}$ M$^{-1}$sec$^{-1}$
Nucleic acid sequence cellulase 10
(SEQ ID NO:19)
ATGGCCACGCCAGTAGAAACACATGGCCAACTGTCCATCGAAAACGGGCG
ACTGGTGGATGAACAGGGGAAAAGGGTGCAACTGAGAGGGGTCAGTTCGC
ACGGTTTGCAGTGGTTTGGTGACTATGTCAACAAAGACTCGATGAAGTGG
CTGCGCGATGACTGGGGGATTAACGTATTCCGTGTTGCCATGTACACGGC
AGCGGATGGCTATATTTCCAATCCTTCCCTTGCGAATAAGGTCAAAGAAG
CCGTTGCGGTGGCACAAAGCCTCGGCGTTTACATCATCATCGACTGGCAC
ATTTTGTCGGATAACGATCCTAATATTTATAAAGCACAGGCAAAAACCTT
CTTCGCCGAAATGGCTGGGCTGTACGGTAACTCGCCGAACGTGATTTATG
AAATCGCCAATGAAGCTAACGGTGGCGTGACCTGGAACGGGCAAATTCGG
CCTTATGCGCTGGAAGTGACTGAAACTATCCGTAGTAAAGATCCTGATAA
CCTTATTATCGTCGGCAGCGGGACCTGGAGCCAGGACATCCATGATGCGG
CGGACAATCTGTTGCCCGATCCGAATACGATGTACGCGCTGCATTTCTAT
GCGGGTACGCACGGGCAGTTCCTGCGCGATCGCATTGATTATGCACAAAG
CCGCGGTGCCGCGATTTTTGTCAGCGAGTGGGGCACAAGCGATGCGTCCG
GCAATGGCGGACCGTTCCTGCCTGAATCGCAGACCTGGATCGATTTCCTG
AATAACCGTGGCGTAAGCTGGGTTAACTGGTCGCTTACCGATAAATCAGA
GGCGTCTGCGGCGCTGGCTCCAGGGGCGAGCAAATCAGGTGGCTGGACGG
AGCAGAATTTGTCAACGTCAGGCAAATTTGTCAGAGCAGATTCGTGCG
GGTGCAGACCTGAGTGGTGGCGTTCACCATCACCATCACCATTAA Amino acid sequence cellulase 10
(SEQ ID NO:20)
MATPVETHGQLSIENGRLVDEQGKRVQLRGVSSHGLQWFGDYVNKDSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALEVTETIRSKDPDNLIIVGSGTWSQDIHDAADNLLPDPNTMYALHFY
AGTHGQFLRDRIDYAQSRGAAIFVSEWGTSDASGNGGPFLPESQTWIDFL
NNRGVSWVNWSLTDKSEASAALAPGASKSGGWTEQNLSTSGKFVREQIRA
GADLSGGVHHHHHH*

CELLULASE 11
Nucleic acid sequence cellulase 11
(SEQ ID NO:21)
ATGGCCACACCGGTGGAAACACATGGCCAACTGTCCATCGAAAATGGGCG
ACTGGTGGATGAGCAGGGGAAAAGGGTGCAACTGAGAGGGGTCAGTTCGC
ACGGGTTGCAGTGGTTTGGTGACTACGTCAACAAAGACTCGATGAAGTGG
CTGCGCGATGACTGGGGGATTAACGTATTCCGTGTTGCCATGTACACGGC
AGCGGATGGCTATATTTCCAATCCTTCCCTTGCGAATAAGGTCAAAGAAG
CCGTTGCGGTGGCACAAAGCCTCGGCGTTTACATCATCATCGACTGGCAC
ATTTTGTCGGATAACGATCCTAATATTTATAATGCACAGGCAAAAACCTT
CTTTGCTGAAATGGCGGGGCTGTACGGTAATTCGCCGAACGTGATTTATG
AAATCGCCAATGAGCCAAACGGTGGCGTGACCTGGAACGGACAGATTCGG
CCTTATGCGCTGGAAGTGACTGACACCATCCGTAGCAAAGATCCCGATAA
CCTCATTATCGTCGGTACCGGCACCTGGAGTCAGGATATCCACGATGCAG
CGGATAACCAACTGCCCGATCCGAATACCCTATACGCGCTGCATTTCTAT
GCGGGCACGCACGGGCAGTTCCTGCGCGATCGTATCGATTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCGTAAGCTGGGTGAACTGGTCGCTTACCGATAAGTCAGA
GGCGTCTGCCGCGCTGGCTCCAGGGGCGAGCAAATCTGGCGGTTGGACAG
AGCAGAATTTGTCGGCGTCGCAGGAAAATTTGTCAGAGCACAGATTCGCGCG
GCTGCGAATCTAAGCGGTGGCGATCACCATCACCATCACCATTAA Amino acid sequence cellulase 11
(SEQ ID NO:22)
MATPVETHGQLSIENGRLVDEQGKRVQLRGVSSHGLQWVGDYVNKDSMKW
LRDDWGINVFRVAMYTAADGYISNPSLANKVKEAVAVAQSLGVYIIIDWH
ILSDNDPNIYNAQAKTFFAEMAGLYGNSPNVIYEIANEPNGGVTWNGQIR
PYALEVTDTIRSKDPDNLIIVGTGTWSQDIHDAADNQLPDPNTLYALHFY
AGTHGQFLRDRIDYAQSRGAAIFVSEWGTSDASGNGGPPFLPESQTWIDFL
NNRGVSWVNWSLTDKSEASAALAPGASKSGGWTEQNLSASGKFVRAQIRA
AANLSGGDHHHHHH*

CELLULASE 12
Nucleic acid sequence cellulase 12
(SEQ ID NO:23)
ATGGCCACGCCAGTAGAAACACATGGCCAACTGTCCATCGAAAACGGGCG
ACTGGTGGATGAACAGGGGAAAAGGGTGCAACTGGGAGGGGTCAGTTCGC
ACGGTTTGCAGTGGTTTGGTGACTATGTCAACAAAGACTCGATGAAGTGG
CTGCGCGATGACTGGGGGATTAACGTATTCCGTGTTGCCATGTACACGGC
AGCGGATGGCTATATTTCCAATCCTTCCCTTGCGAATAAGGTCAAAGAAG
CCGTTGCGGTGGCACAAAGCCTCGGCGTCTACATCATCATCGACTGGCAC
ATTTTGTCGGATAACGATCCTAATATTTATAAAGCACAGGCAAAAACCTT
CTTCGCCGAAATGGCTGGGCTGTATGGTAACTCGCCGAACGTGATTTATG
AAATCGCCAATGAACCTAACGGTGGCGTGACCTGGAACGGGCAAATTCGG
CCTTATGCGCTGGAAGTGACTGAAACTATCCGTAGTAAAGATCCTGATAA
CCTTATTATCGTCGGCAGCGGGACCTGGAGCCAGGACATCCATGATGCGG
CGGACAATCTGTTGCCCGATCCGAATACGATGTACGCGCTGCATTTCTAT
GCGGGTACGCACGGGCAGTTCCTGCGCGATCGCATTGATTATGCACAAAG
CCGCGGTGCCGCGATTTTTGTCAGCGAGTGGGGCACAAGCGATGCGTCCG
GCAATGGCGGACCGTTCCTGCCTGAATCGCAGACCTGGATCGATTTTCTG
AATAACCGTGGCGTAAGCTGGGTTAACTGGTCGCTTACCGATAAATCAGA
GGCGTCTGCGGCGCTGGCTCCAGGGGCGAGCAAATCAGGTGGCTGGACGG
AGCAGAATTTGTCAACGTCAGGCAAATTTGTCAGAGCAGATTCGTGCG
GGTGCAGACCTGAGTGGTGGCGTTCACCATCACCATCACCATTAA Amino acid sequence cellulase 12
(SEQ ID NO:24)
MATPVETHGQLSIENGRLVDEQGKRVQLGGVSSHGLQWFGDYVNKDSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALEVTETIRSKDPDNLIIVGSGTWSQDIHDAADNLLPDPNTMYALHFY
AGTHGQFLRDRIDYAQSRGAAIFVSEWGTSDASGNGGPFLPESQTWIDFL
NNRGVSWVNWSLTDKSEASAALAPGASKSGGWTEQNLSTSGKFVREQIRA
GADLSGGVHHHHHH*

CELLULASE 13
Nucleic acid sequence cellulase 13
(SEQ ID NO:25)
ATGGCCACGCCAGTAGAAACGCATGGCCAGCTGTCCATCGAAAACGGGCG
ACTGGTGGATGAACAGGGGAAAAGGGTGCAACTGAGAGGGGTCAGTTCGC
ACGGTTTGCAGTGGTTTGGTGACTACGTCAACAAAGATTCGATGAAATGG
CTGCGCGATGACTGGGGGATTAACGTATTCCGTGTTGCCATGTACACGGC
AGCGGATGGCTATATTTCCAATCCTTCCCTTGCGAATAAGGTCAAAGAAG
CCGTTGCGGTGGCACAAAGCCTCGGCGTTTACATCATCATCGACTGGCAC
ATTTTGTCGGATAACGATCCTAATATTTATAAAGCACAGGCAAAAACCTT
CTTTGCCGAAATGGCGGGGCTGTACGGTAATTCGCCGAACGTGATTTATG
AAATCGCCAATGAGCCAAACGGTGGCGTGACCTGGAACGGGCAGATTCGG
CCTTATGCGCTGGAAGCCACTGACACCATCCGTAGCAAAGATCCCGATAA
CCTTATTATCGTCGGCAGCGGGACCTGGAGCCAGGATATCCATGATGCGG
CAGACAATCAGTTGCCCGATCCGAATACTCTGTATGCGCTGCATTTCTAT
GCGGGTACGCACGGGCAGTTCCTGCGCGATCGTATTGACTATGCACAAAG
CCGCGGTGCTGCAATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCGTAAGCTGGGTGAACTGGTCGCTTACCGATAAGTCAGA
GGTGTCCGCCCGCTGGCTCCAGGGGCGAGTAAATCAGGCGGTTGGACGG
AGCAGAATCTGTCGACGTCAGGAAAATTTGTCAGAGCACAGATTCGCGCG
GCTGCGAATCTAAGCGGTGGCGATCACCATCACCATCACCATTAA TABLE 1A-continued Amino acid sequence cellulase 13
(SEQ ID NO:26)
MATPVETHGQLSIENGRLVDEQGKRVQLRGVSSHGLQWFGDYVNKDSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALEATDTIRSKDPDNLHVGSGTWSQDIHDAADNQLPDPNTLYALHFYA
GTHGQFLRDRIDYAQSRGAAIFVSEWGTSDASGNGGPFLPESQTWIDFLN
NRGVSWVNWSLTDKSEVSAALAPGASKSGGWTEQNLSTSGKFVRAQIRAA
ANLSGGDHHHHHH*

CELLULASE 14
Nucleic acid sequence cellulase 14
(SEQ ID NO:27)
ATGGCCACGCCAGTAGAAACGCATGGCCAACTGTCCATTGAAAATGGGCG
ACTGGTGGATGAGCAGGGAAAAGAGTGCAACTGAGAGGGGTCAGTTCGC
ACGGTTTGCAGTGGTTTGGCGACTATGTCAACAAAGATTCGATGAGATGG
CCGCGCGATGACTGGGGGATTGACGTATTCCGTGTTGCCATGTACACGGC
GGCGGATGGTTATATTTCGAATCCTTCCCTCGCCAATAAGGTCAAAGAAG
CCGTTGCGGTGGCACAAAGCCTCGGCGTTCATCATCATCGACTGGCAC
ATTTTGTCGGATAACGATCCCAATACTTATAAAGCACAGGCAAAAACCTT
CTTTTGCCGAAATGGCGGGGCTGTATGGCAGCTCACCGAACGTGATTTATG
AAATCGCCAATGAGCCAAACGGTGGCGTGACACGGAACGGGCAAATTCGG
CCTTATGCGCTGGATGTGACTGAAACTATCCGTAGTAAAGATCCTGATAA
TCCGATTATCGTCGGCAGCGGGACCTGGAGCCAGGACATCCACGATGCGG
CGGACAATCTGTTGCCCGATCCGAATACGATGTACGCGCTGCATTTCTAT
GCCGGTACGCACGGGCAGTTCCTGTGTGATCGTATCGATTATGCGCAAAG
CCGCGGTGCTGCAATTTTCGTCAGCGAGTGGGGCACAAGCGATGCGTCCG
GCAACGGTGGGCCGTTCCTGCCTGAATCGCAGACCTGGATCGATTTCCTG
AACAACCGTGGTGTGAGCTGGGTTAACTGGTCGCTTACCGATAAATCAGA
GGCGTCTGCGGCGCTGGCACCGGGAGCGAGCAAATCTGGCGGTTGGACAG
AGCAGAATTTGTCGGCGTCAGGAAAATTTGTCAGAGCACAGATTCGCGCG
GCTGCGAATCTAAGCGGTGGCGATCACCATCACCATCACCATTAA Amino acid sequence cellulase 14
(SEQ ID NO:28)
MATPVETHGQLSIENGRLVDEQGKRVQLRGVSSHGLQWFGDYVNKDSMRW
PRDDWGIDVFRVAMYTAADGYISNPSLANKVKEAVAVAQSLGVYIIIDWH
ILSDNDPNTYKAQAKTFFAEMAGLYGSSPNVIYEIANEPNGGVTRNGQIR
PYALDVTETIRSKDPDNPIIVGSGTWSQDIHDAADNLLPDPNTMYALHFY
AGTHGQFLCDRIDYAQSRGAAIFVSEWGTSDASGNGGPFLPESQTWIDFL
NNRGVSWVNWSLTDKSEASAALAPGASKSGGWTEQNLSASGKFVRAQIRA
AANLSGGDHHHHHH*

CELLULASE 15
Nucleic acid sequence cellulase 15
(SEQ ID NO:29)
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGTGACTATGTCAACAAAGATTCGATGAAATGG
CTGCGTGACGACTGGGGGATCAATGTGTTTCGCGTTGCCATGTACACGGC
GGAGAATGGTTATATTGCTAACCCTTCTCTCGCCAATAAAGTAAAAGAGG
CTGTTGCGGCGGCGCAAAGCCTTGGCGTCTACATCATCATCGACTGGCAT
ATCTTGTCGGATAACGATCCTAATATTTATAAAGCACAGGCAAAAACCTC
CTTTTGCCGAAATGGCGGGGCTGTATGGTAACTCGCCGAACGTGATTTATG
AAATCGCCAATGAGCCAAACGGCAGTGTGACATGGAACGGGCAAATTCGG
CCTTATGCGCTGGAAGCACTGACACCATCCGTAGCAAAGATCCCGATAA
CCTTATTATCGTCGGCAGCGGGACCTGGAGCCAGGACATCCATGATGCGG
CGGACAATCTGTTGCCCGATCCGAATACGCTGTACGCGCTGCATTTCTAT
GCGGGCACGCACGGGCAGTTCCTCTGCGCGATCGCATTGATTATGCACAAAG
CCGCGGTGCCGCGGATTTTGTCAGCGAGTGGGGCACAAGCGATGCGTCCG
GCAACGGTGGGCCGTTCGTGCCTGAATCGCAGACCTGGATCGATTTCCTG
AACAACCGTGGTGTGAGCTGGGTTAACTGGTCGCTTACCGATAAATCAGA
GGCGTCTGCGGCGCTGACTCCAGGGGCGAGTAAATCAGGCGGTTGGACGG
AGCAGAATTCTGTCGACGTCAGGCAAATTTGTCAGAGAGCAGATTCGTGCA
GGTGCGAATCTAAGCGGTGGCGATCACCATCACCATCACCATTAA Amino acid sequence cellulase 15
(SEQ ID NO:30)
MATPVETHGQLSIENGRLVDEQGKRVQLRGVSSHGLQWFGDYVNKDSMKW
LRDDWGINVFRVAMYTAENGYIANPSLANKVKEAVAAAQSLGVYIIDWH
ILSDNDPNIYKAQAKTSFAEMAGLYGNSPNVIYEIANEPNGSVTWNGQIR
PYALEATDTIRSKDPDNLIIVGSGTWSQDIHDAADNLLPDPNTLYALHFY
AGTHGQFLRDRIDYAQSRGAAIFVSEWGTSDASGNGGPFLPESQTWIDFL
NNRGVSWVNWSLTDKSEASAALTPGASKSGGWTEQNLSTSGKFVREQIRA
GANLSGGDHHHHHH CELLULASE 16
Nucleic acid sequence cellulase 16
(SEQ ID NO:31)
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGCGACTATGTCAACAAAGACTCGATGAAGTGG
CTGCGTGACGACTGGGGGATTAACGTATTCCGTGTTGCCATGTACACGGC
AGCGGATGGCTATATTTCCAATCCTTCCCTCGCCAATAAGGTAAAAGAGG
CCGTTGCGGTGGCACAAAGCCTCGGCGTTTACATCATCATCGACTGGCAC
ATTTTGTCGGATAACGATCCTAATATTTATAAAGCACAGGCAAAAACCTT
CTTTTGCCGAAATGGCGGGGCTGTATGGTAACTCGCCGAACGTGATTTATG
AAATCGCCAATGAACCTAACGGTGGCGTGACCTGGAACGGGCAAATTCGG
CCTTATGCGCTGGATGTTACTGAAACTATCCGTAGTAAAGATCCTGATAA
TCTGATTATCGTTGGCACGGGTACCTGGAGTCAGGATATTCATGACGCGG
CGGATAATCAGCTGCCCGATCCGAATACGCTGTACGCGCTGCATCTCTAT
GCCGGTACGCACGGGCAATTCCTGTGCGATCGTATTGACTATGCGCAAAG
CCGCGGCGCCGCGATTTTTGTCAGCGAGTGGGGGCACCAGCGATGCGTCCG
GCAATGGCGGGCCGTTCCTGCCTGAATCGCAGACCTGGATCGATTTCCTG
AATAACCGTGGCGTAAGCTGGGTGAACTGGTCGCTTACCGATAAGTCAGA
GGCGTCCGCCGCGCTGGCTCCAGGGCGCGAGTAAATCAGGTGGCTGGACGG
AGCAGAATATGTCGACGTCAGGCAAATTTGTCAGAGAGCAGATTCGTGCA
GGTGCGAATCTAAGCGGTGGCGATCACCATCACCATCACCATTAA Amino acid sequence cellulase 16
(SEQ ID NO:32)
MATPVETHGQLSIENGRLVDEQGKRVQLRGVSSHGLQWFGDYVNKDSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALDVTETIRSKDPDNLIIVGTGTWSQDIHDAADNQLPDPNTLYALHLY
AGTHGQFLCDRIDYAQSRGAAIFVSEWGTSDASGNGGPFLPESQTWIDFL
NNRGVSWVNWSLTDKSEASAALAPGASKSGGWTEQNMSTSGKFVREQIRA
GANLSGGDHHHHHH*

CELLULASE 17
Nucleic acid sequence cellulase 17
(SEQ ID NO:33)
ATGGCCACGCCAGTAGAAACGCATGGTCAGCTGTCCATCGAAAACGGGCG
ACTGGTGGACGAACAGGGGAAAAGGGTGCAACTGAGAGGGGTCAGTTCGC
ACGGTTTGCAGTGGTTTGGCGACTATGTCAACAAAGACTCGATGAAGTGG
CTGCGTGATGACTGGGGGATCAATGTGTTTCGCGTTGCCATGTACACGGC
GGCGGATGGTTATATTTCGAATCCTTCCCTCGCCAATAAGGTAAAAGAGG
CCGTTGCGGCGGCACAAAGCCTCGGCGTTTACATCATCATCGACTGGCAC
ATTTTGTCGGATAACGATCCCAATACTTATAAAGCGCAGGCAAAAACCTT
CTTTGCTGAAATGGCGGGGCTGTATGGCAGCTCACCGAACGTGATTTATG
AAATCGCCAATGAGCCAAACGGTGACCTGGAACGGGCAAGATTCGG
CCTTATGCGCTGGAAGTGACTGACACCATCCGTAGCAAAGATCCTGATAA
CCTTATTATCGTCGGTACCGGCACCTGGAGTCAGGATATCCACGATGCAG
CGGATAACCAACTGCCCGATCCGAATACCCTATACGCGCTGCATTTCTAT
GCGGGCACGCACGGGCAGTTCCTGTGTGATCGTATTGACTATGCGCAAAG
CCGTGGCGCGGCGATTTTCGTCTGCGAGTGGGGGCACCAGCGATGCGTCCG
GCAATGGCGGGCCGTTCCTGCCTGAATCGCAGACCTGGATCGATTTCCTG
AATAACNGTGGCGTAAGCTGGGTGAACTGGTCGCTTAGCGATAAATCAGA
GGCGTCCGCCGCGCTGGCTCCAGGCGCGAGTAAATCAGGTGGCTGGACGG
AGCAGAATCTGTCGACGTCAGGCAAATTTGTCAGAGAGCAGATTCGTGCA
GGTGCGAATCTGGGCGGTGGCGATCACCATCACCATCACCATTAA Amino acid sequence cellulase 17
(SEQ ID NO:34)
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNTYKAQAKTFFAEMAGLYGSSPNVIYEIANEPNGGVTWNGQIR
PYALEVTDTIRSKDPDNLIIVGTGTWSQDIHDAADNQLPDPNTLYALHFY
AGTHGQFLCDRIDYAQSRGAAIFVCEWGTSDASGNGGPFLPESQTWIDFL
NNXGVSWVNWSLSDKSEASAALAPGASKSGGWTEQNLSTSGKFVREQIRA
GANLGGGDHHHHHH*

CELLULASE 18
Nucleic acid sequence cellulase 18
(SEQ ID NO:35)
ATGGCCACGCCAGTAGAAACGCATGGCCAACTGTCCATTGAAAATGGGCG
ACTGGTGGATGAGCAGGGAAAAGAGTGCAACTGAGAGGAATCAGTCCGA
ACGGGTTGCAGTGGTTGGTGATTACGTAAACAAAGATTCGATGAAGTGG
CCGCGTGATGACTGGGGGATTAATGTGTTTCGCGTTGCCATGTACACGGC
GGCGGATGGTTATATTTCGAATCCTTCCCTCGCCAATAAGGTCAAAGAAG
CCGTTGCGGTGGCACAAAGCCTCGGCGTCTACATCATCATCGACTGGCAT
ATTTTGTCGGACAACGATCCTAATATTTATAAAGCACAGGCAAAAACCTT
CTTTTGCCGAAATGGCGGGGCTGTATGGCAACTCGCCGAATGTGATTTATG
GAATCGCCAATGAGCCAAACGGCGGCGTGACATGGAACGGGCAAATTCGG
CCTTATGCGCTGGAAGTGACTGAAACTATCCGTAGTAAAGATCCTGATAA TABLE 1A-continued

```
TCTGATTATCGTCGGCAGCGGGACCTGGAGCCAGGATATTCATGACGCGG
CGGATAATCAGCTGCCGGATCCGAATACGCTGTACGCGCTGCATTTCTAT
GCTGGCATGCACGGGCAATTCCTGTGCGATCGTATTGACTATGCGCAAAG
CCGTGGCGCGGCGATTTTCGTCATCGAGTGGGGCACCAGCGATGCATCCG
GCAACGGTGGGCCGTTCCTGCCTGAATCGCAGACCTGGATCGATTTCCTG
AACAACCGTGGGATAAGCTGGGTAAACTGGTGACTAAGCGATAAGTCTGA
GACGTCTGCGGCGCTGGCTCTAGGGGCGAGTAAATCAGGCGGCTGGAGAG
AGGAGAGATTTGTCGGCGTCAGGAAAATTTGTCAGAGAGCAGATTCGTGCA
GGTGCGAATCTGGGCGGTGGCGATCACCATCACCATCACCATTAA
```

Amino acid sequence cellulase 18
(SEQ ID NO:36)
```
MATPVETHGQLSIENGRLVDEQGKRVQLRGISSNGLQWVFGDYVNKDSMKW
PRDDWGINVFRVAMYTAADGYISNPSLANKVKEAVAVAQSLGVYIIIDWH
ILSDNDPNIYKAQAKTFFAEMAGLYGNSPNVIYGIANEPNGGVTWNGQIR
PYALEVTETIRSKDPDNLIIVGSGTWSQDIHDAADNQLPDPNTLYALHFY
AGMHGQFLCDRIDYAQSRGAAIFVIEWGTSDASGNGGPFLPESQTWIDFL
NNRGISWVNWSLSDKSETSAALALGASKSGGWTEQNLSASGKFVREQIRA
GANLGGGDHHHHHH*
```

CELLULASE 19
Nucleic acid sequence cellulase 19
(SEQ ID NO:37)
```
ATGGCCACGCCAGTAGAAACGCATGGTCAGCTGTCCATCGAAAACGGGCG
ACTGGTGGATGAACGGGGAAAAGGGTGCAACTGAGAGGGGTCAGTTCAC
ACGGTTTACAGTGGTTTGGCGACTATGTCAACAAAGACTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTCAAAGAAG
CCGTTGCGGCGGCGCAAAGCCTCGGCGTTTACATCATCATCGACTGGCAC
ATTTTGTCGGATAACGATCCTAATATTTATAAAGCACAGGCAAAAATCTT
CTTTGCCGAAATGGCGGGGCTGTACGGTAATTCGCCGAACGTGATTTATG
AATTCGCCAATGAACCTAACGGCGGCGTGACCTGGAACGGGCAGATTCGG
CCTTATGCGCTGGAAGTGACTGAAACTATCCGTAGTAAAGATCCTGATAA
TCTGATTATCGTCGGTACCGGCACCTGGAGTCAGGATATCCACGATGCAG
CGGATAACCAACTGCCCGATCGTAATACCCTATACGGCTGCATTTCTAT
GCGGGCACGCACGGGCAATTCCTGTGCGATCGTATTGACTATGCGCAAAG
CCGTGGCGCGGCGATTTTCGTCCGCGAGTGGGGCACCAGCGATGCATCCG
GCAACGGTGGGCCGTTCCTGCCTGAATCGCAGACCTGGATCGATTTCCTG
AATAACCGTGGCGTAAGCTGGGTGAACTGGTCGCTTACCGATAAGTCTGA
GACGTCTGCGGCGCTGACTCCAGGGGCGAGCAAATCAGGCGGCTGGACGG
AGCAGAATTTGTCGGCATCAGGAAAATTTGTCAGAGCACAGATTCGCGCG
GCTGCGAATCTAAGCGGTGGCGATCACCATCACCATCACCATTAA
```

Amino acid sequence cellulase 19
(SEQ ID NO:38)
```
MATPVETHGQLSIENGRLVDERGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKIFFAEMAGLYGNSPNVIYEFANEPNGGVTWNGQIR
PYALEVTETIRSKDPDNLIIVGTGTWSQDIHDAADNQLPDLNTLYALHFY
AGTHGQFLCDRIDYAQSRGAAIFVREWGTSDASGNGGPFLPESQTWIDFL
NNRGVSWVNWSLTDKSETSAALTPGASKSGGWTEQNLSASGKFVRAQIRA
AANLSGGDHHHHHH*
```

CELLULASE 20
Nucleic acid sequence cellulase 20
(SEQ ID NO:39)
```
ATGTTTCGCGTTGCCATGTACACGGCGGCGGATGGTTATATTTCGAATCC
TTCCCTCGCCAATAAGGTCAAAGAAGCCGTTGCGGTGCGCAAAGCCTCG
GCGTCTACATCATCATCGACTGGCACATTTTGTCGGATAACGATCCTAAT
ATTTATAAAGCACAGGCAAAAACCTTCTTTGCCGAAATGGCGGGGCTGTA
CGGTAATTCGCCGAACGTGATTTATGAAATCGCCAATGAACCTAACGGCG
GCGTGACCTGGAACGGGCAGATTCGGCTTATGCGCTGGAAGTGACTGAA
ACTATCCGTAGCAAAGATCCTGATAACCTTATCATCGTCGGCAGCGGAC
CTGGAGCCAGGACATCCATGACGCGGCGGATAATCAGCTGCCCGATCCGA
ATACGCTGTACGCGCTGCATTTCTATGCGGGCACGCACGGGCAGTTCCTG
CGCGATCGTACTGACTATGCGAAAGCCGTGGCGCGGCGATTTTCGTCAG
CGAGTGGAGCACCAGCGATGCATCCGGCAACGGTGGGCCGTTCCTGCCTG
AATCGCAGACCTGGATTCCTGAATAACCGTGGCATAAGCTGGGTG
AACTGGTCGCTTACCGATAAGTCAGAGCGTCCGCCGCGCTGGCTCCAGG
GGCGAGTAAATCAGGCGGTTGGACGGAGCAGAATTTGTCGACGTCAGGCA
AATTTGTCAGAGAGCAGATTCGTGCGGGGCGGGTCTGAGCGGTGGCGAT
CACCATCACCATCACCATTAA
```

Amino acid sequence cellulase 20
(SEQ ID NO:40)
```
MFRVAMYTAADGYISNPSLANKVKEAVAVAQSLGVYIIIDWHILSDNDPN
IYKAQAKTFFAEMAGLYGNSPNVIYEIANEPNGGVTWNGQIRPYALEVTE
TIRSKDPDNLIIVGSGTWSQDIHDAADNQLPDPNTLYALHFYAGTHGQFL
RDRTDYAQSRGAAIFVSEWSTSDASGNGGPFLPESQTWIDFLNNRGISWV
NWSLTDKSEASAALAPGASKSGGWTEQNLSTSGKFVREQIRAGAGLSGGD
HHHHHH*
```

CELLULASE 21
Nucleic acid sequence cellulase 21
(SEQ ID NO:41)
```
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCAC
ACGGTTTGCAGTGGTTTGGCGACTATGTCAACAAAGACTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTAAAAGAGG
CCGTTGCGGCGGCGCAAAGCCTCGGCGTTTACATCATCATCGACTGGCAT
ATCTTGTCGGATAACGATCCCAATATTTATAAAGCACAGGCAAAAACCTT
CTTTGCCGAAATGGCGGGGCTGTACGGTAATTCGCCGAACGTGATTTATG
AAATCGCCAATGAACCTAACGGCGGCGTGACCTGGAACGGGCAGATTCGG
CCTTATGCGCTGGAAGTGACTGAAACTATCCGTAGTAAAGATCCTGATAA
TCTGATTATCGTTGACACGGGTACCTGGAGTCAGGATATCCATGATGCGG
CGGACAATCTGTTGCCCGATCCGAATACGACGTACGCGCTGCATTTCTAT
GCGGGCACGCACGGGCAGTTCCTGCGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCATAAGCTGGGTGAACTGGTCGCTTACCGATAAGTCTGA
GACGTCTGCGGCGCTGACTCCAGGGGCGAGCAAATCAGGCGGCTGGACGG
AGCAGAATTTGTCGACGTCAGGCAAATTTGTCAGAGAACAGATTCGTGCG
GGGGCGGGTCTGAGCGGTGGCGATCACCATCACCATCACCATTAA
```

Amino acid sequence cellulase 21
(SEQ ID NO:42)
```
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKTFFAEMAGLYGNSPNVIYEIANEPNGGVTWNGQIR
PYALEVTETIRSKDPDNLIIVDTGTWSQDIHDAADNLLPDPNTTYALHFY
AGTHGQFLRDRIDYAQSRGAAIFVSEWGTSDASGNGGPPFLPESQTWIDFL
NNRGISWVNWSLTDKSETSAALTPGASKSGGWTEQNLSTSGKFVREQIRA
GAGLSGGDHHHHHH*
```

CELLULASE 22
Nucleic acid sequence cellulase 22
(SEQ ID NO:43)
```
ATGGCCACGCCAGTAGAAACGCATGGTCAGCTGTCCATCGAAAACGGGCG
ACTGGTGGATGAACAGGGGAAAAGGGTGCAATTGAGAGGGGTCAGTTCGC
ACGGTTTGCAGTGGTTTGGCGACTATGTCAACAAAGACTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTCAAAGAGG
CCGTTGCGGCGGCGCAAAGCCTCGGCGTTTACATCATCATCGACTGGCAT
ATCTTGTCGGATAACGATCCCAATATTTATAAAGCACAGGCAAAAACCTT
CTTTGCCGAAATGGCGGGGCTGTACGGTAATTCGCCGAACGTGATTTATG
AAATCGCCAATGAGCCAAACGGTGGCGTGACGTGGAACGGACAGATTCGG
CCTTATGCGCTGGAGGTGACTGACACTATCCGTAGCAAAGATCCTGATAA
CCTTATTATCGTCGGCAGCGGGACCTGGAGCCAGGACATCCATGACGCGG
CGGATAATCAGCTGCCCGATCCGGATACGCTGTACGCGCTGCATTTCTAT
GCGGGCACGCACGGGCAATTCCTGTGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCATAAGCTGGGTGAACTGGTCGCTTACCGATAAGTCAGA
GGCGTCCGCCGCGCTGGCTCCAGGGGCGAGTAAATCAGGCGGCTGGACGG
AGCAGAATTTGTCGACGTCAGGCAAATTTGTCAGAGAGCAGATTCGTGCG
GGGGCGGGTCTGAGCGGTGGCGATCACCATCACCATCACCATTAA
```

Amino acid sequence cellulase 22
(SEQ ID NO:44)
```
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKTFFAEMAGLYGNSPNVIYEIANEPNGGVTWNGQIR
PYALEVTDTIRSKDPDNLIIVGSGTWSQDIHDAADNQLPDPDTLYALHFY
AGTHGQFLCDRIDYAQSRGAAIFVSEWGTSDASGNGGPFLPESQTWIDFL
NNRGISWVNWSLTDKSEASAALAPGASKSGGWTEQNLSTSGKFVREQIRA
GAGLSGGDHHHHHH*
```

CELLULASE 23
Nucleic acid sequence cellulase 23
(SEQ ID NO:45)
```
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGCGACTATGTCAACAAAGACTCGATGAAGTGG
CTGCGTGATGACTGGGGGATTAATGTATTCCGCGTCGCCATGTACACGGC
GGCGGATGGTTATATTTCGAATCCTTCCCTCGCCAATAAGGTAAAAGAGG
CCGTTGCGGCGGCGCAAAGCCTCGGCGTTTACATCATCATCGACTGGCAC
ATTTTGTCGGATAACGATCCCAGTATTTATAAAGCACAGGCAAAAACCTT
CTTTGCCGAAATGGCGGGGCTGTACGGTAATTCGCCGAACGTGATTTATG
```

TABLE 1A-continued

```
AAATCGCCAATGAACCTAACGGCGGCGTGACATGGAACGGGCAGATTCGG
CCTTATGCGCTGGAAGTGACTGAAACTATCCGTAGTAAAGATCCTGATAA
TCTGATTATCGTTGGCACGGGTACCTGGAGTCAGGATATCCATGATGCGG
CGGACAATCTGTTGCCCGATCCGAATACGATGTACGCGCTGCATTTCTAT
GCGGGCACGCACGGACAATTCCTGTGCGATCGTATTGACTATGCGCAAAG
CCGTGGCGCGGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCATAA
```

Amino acid sequence cellulase 23
(SEQ ID NO:46)
```
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPSIYKAQAKTFFAEMAGLYGNSPNVIYEIANEPNGGVTWNGQIR
PYALEVTETIRSKDPDNLIIVGTGTWSQDIHDAADNLLPDPNTMYALHFY
AGTHGQFLCDRIDYAQSRGAAIFVSEWGTSDASGNGGPFLPESQTWIDFL
NNRGISWVNWSLTDKSEASAALAPGASKSGGWTEQNLSASGKFVRAQIRA
AANLSGGDHHHHHH*
```

CELLULASE 24
Nucleic acid sequence cellulase 24
(SEQ ID NO:47)
```
ATGGCCACGCCAGTAGAAACGCATGGCCAACTGTCCATCGAAACGGGCG
ACTGGTGGATGAACAGGGGAAAAGGGTGCAACTGAGAGGGGTCAGTTCGC
ACGGTTTGCAGTGGTTTGGTGACTACGTCAACAAAGATTCGATGAAATGG
CTGCGCGATGACTGGGGGATTAACGTATTCCGTGTTGCCATGTACACGGC
GGAGAATGGTTATATTTCGAATCCTTCCCTCGCCAATAAGGTAAAAGAAG
CCGTTGCGGTGGCACAAAGCCTCGGCGTCTACATCATCATCGACTGGCAT
ATCTTGTCGGATAACGATCCTAATATTTATAAAGCACAGGCAAAAATCTT
CTTTGCCGAAATGGCGGGGCTGTATGGCAACTCGCCGAACGTGGTTTATG
AAATCGCCAATGAACCTGACGGCGGCGTGACCTGGAACGGGCAAATTCGG
CCTTATGCGCTGGAAGCCACTGACACTATCCGTAGCAAAGATCCTGATAA
CCTTATTATCGTCGGTACCGGCACCTGGAGTCAGGACATCCATGATGCGG
CGGACAATCTGTTGCCCGATCCGAATACGATGTACGCGCTGCATTTCTAT
GCGGGTACACACGGGCAGTTCCTGCGCGATCGTATCGATTATGCGCAAAG
CCGCGGTGCCGCGATTTTTGTCAGCGAGTGGGGCACCAGCGATGCATCCG
GCAACGGCGGACCGTTCCTGCCTGAATCGCAGACCTGGATCGATTTCCTG
AACAACCGTGGCGTAAGCTGGGTGAACTGGTCGCTTACCGATAAATCAGA
GGCGTCTGCGGCGCTGGCACCGGGGGCGAGCAAATCTGGCGGTTGGACGG
AGCAGAGATTTGTCGGCGTCAGGAAATTTGTCAGAGCACAGATTCGCGCG
GCTGCGAATCTAAGCGGTGGCGATCACCATCACCATCACCATTAA
```

Amino acid sequence cellulase 24
(SEQ ID NO:48)
```
MATPVETHGQLSIENGRLVDEQGKRVQLRGVSSHGLQWFGDYVNKDSMKW
LRDDWGINVFRVAMYTAADGYISNPSLANKVKEAVAAAQSLGVYIIIDWH
ILSDNDPNIYKAQAKIFFAEMAGLYGNSPNVVYEIANEPDGGVTWNGQIR
PYALEATDTIRSKDPDNLIVGSGTWSQDIHDAADNLLPDPNTMYALHFY
AGTHGQFLRDRIDYAQSRGAAIFVSEWGTSDASGNGGPFLPESQTWIDFL
NNRGVSWVNWSLTDKSEASAALAPGASKSGGWTEQNLSASGKFVRAQIRA
AANLSGGDHHHHHH*
```

CELLULASE 25
Nucleic acid sequence cellulase 25
(SEQ ID NO:49)
```
ATGGCCACGCCAGTAGAAACGCATGGCCAACTGTCCATTGAAAATGGGCG
ACTGGTGGATGAACAGGGGAAAAGGGTGCAACTGAGAGGGGTCAGTTCGC
ACGGTTTGCAGTGGTTTGGTGACTACGTCAACAAAGATTCGATGAAATGG
CTGCGCGATGACTGGGGGATCAATGTGTTTCGCGTTGCCATGTACACGGC
GGAGAATGGTTATATTTCCAATCCTTCCCTTGCGAATAAGGTCAAAGAAG
CCGTTGCGGCGGCGCAAAGCCTCGGCGTTTACATCATCATCGACTGGCAC
ATTTTGTCGGATAACGATCCCAATACTTATAAAGCACAGGCAAAAATCTT
CTTTGCCGAAATGGCGGGGCTGTACTGTAATTCGCCGAACGTGATTTATG
AAATCGCCAATGAGCCAAACGTGGCGTGACCTGGAACGGGCAGATTCGG
CCTTATGCGCTGGAAGTGACTGACACCATCCGTAGCAAAGATCCCGATAA
CCTCATTATCGTCGGTACCGGCACCTGGAGTCAGGATATCCACGATGCAG
CGGATAACCAACTGCCCGATCCGAATACCCTATACGCGCTGCATTTCTAT
GCTGGCACGCACGGACAGTTCCTGCGCGATCGCATTGACTATGCGCAAAG
CCGCGGTGCCGCGATTTTTGTCAGCGAGTGGGGCACCAGCGATGCATCCG
GCAATGGCGGGCCGTTCCTGCCAGAATCGCAAACCTGGATCGATTTCCTG
AATAACCGTGGCGTAAGCTGGGTGAACTGGTCGCTTACCGATAAGTCAGA
GGCGTCTGCGGCGCTGACTCCAGGGGCGAGTAAATCAGGCGGTTGGACGG
AGCAGAATCTGTCGACGTCAGGAAATTTGTCAGAGCACAGATTCGCGCG
GCTGCGAATCTGGGCGGTGGCGATCACCATCACCATCACCATTAA
```

Amino acid sequence cellulase 25
(SEQ ID NO:50)
```
MATPVETHGQLSIENGRLVDEQGKRVQLRGVSSHGLQWFGDYVNKDSMKW
LRDDWGINVFRVAMYTAENGYISNPSLANKVKEAVAAAQSLGVYIIIDWH
ILSDNDPNIYKAQAKTFFAEMAGLYGNSPNVIYEIANEPNGGVTWNGQIR
PYALEVTDTIRSKDPDNLIIVGTGTWSQDIHDAADNQLPDPNTLYALHFY
AGTHGQFLRDRIDYAQSRGAAIFVSEWGTSDASGNGGPFLPESQTWIDFL
NNRGVSWVNWSLTDKSEASAALTPGASKSGGWTEQNLSTSGKFVRAQIRA
AANLGGGDHHHHHH*
```

CELLULASE 26
Nucleic acid sequence cellulase 26
(SEQ ID NO:51)
```
ATGGCCACGCCAGTAGAAACACATGGCCAACTGTCCATCGAAAATGGGCG
ACTGGTGGACGAACAGGGGAAAGGGTGCAACTGAGAGGGGTCAGTTCGC
ACGGTTTGCAGTGGTTTGGCGACTATGTCAACAAAGACTCGATGAAGTGG
CTGCGCGATGACTGGGGTATAAATGTGTTCCGCGTCGCTATGTACACGGC
GGAGAATGGTTATATTTCGAATCCTTCCCTCGCCAATAAGGTAAAAGAGG
CCGTTGCGGCGGCGCAAAGCCTTGGCATCTACATCATTATCGACTGGCAC
ATTTTGTCGGATAACGATCCTAATATTTATAAAGCGCAGGCAAAAACCTT
CTTTGCTGAAATGGCGGGGCTGTATGGTAATTCGCCGAACGTGATTTATG
AAATCGCCAATGAACCTAACGGCGGCGTGACATGGAACGGGCAGATTCGG
CCTTATGCGCTGGAAGCCACTGACACCATCCGTAGCAAAGATCCCGATAA
CCTCATTATCGTCGGTACCGGCACCTGGAGTCAGGATATTCATGACGCGG
CAGACAATCAGCTGCCCGATCCGAATACGCTGTACGCGCTGCATTTCTAT
GCGGGTACGCACGGGCAGTTCCTGCGCGATCGTATCGATTATGCGCAAAG
CCGCGGTGCTGCAATTTTCGTCAGCGAGTGGGGCACCAGCGATGCATCCG
GCAACGGTGGGCCGTTCCTGCCTGAATCGCAGACCTGGATCGATTTCCTG
AACAACCGTGGTGTGAGCTGGGTTAACTGGTCGCTTACCGATAAATCAGA
GGCGTCGCCGCGCTGGCTCCAGGGGCGAGTAAATCAGACGGTTGGACGG
AGCAGAATCTGTCGACGTCAGGAAATTTGTCAGAGCACAGATTGGCGCG
GCTGCGAATCTAAGCGGTGGCGATCACCATCACCATCACCATTAA
```

Amino acid sequence cellulase 26
(SEQ ID NO:52)
```
MATPVETHGQLSIENGRLVDEQGKRVQLRGVSSHGLQWFGDYVNKDSMKW
LRDDWGINVFRVAMYTAENGYISNPSLANKVKEAVAAAQSLGIYIIIDWH
ILSDNDPNIYKAQAKTFFAEMAGLYGNSPNVIYEIANEPNGGVTWNGQIR
PYALEATDTIRSKDPDNLIIVGTGTWSQDIHDAADNQLPDPNTLYALHFY
AGTHGQFLRDRIDYAQSRGAAIFVSEWGTSDASGNGGPFLPESQTWIDFL
NNRGVSWVNWSLTDKSEASAALAPGASKSDGWTEQNLSTSGKFVRAQIRA
AANLSGGDHHHHHH*
```

CELLULASE 27
Nucleic acid sequence cellulase 27
(SEQ ID NO:53)
```
ATGGCCACGCCAGTAGAAACGCATGGTCAGCTGTCCATCGAAAATGGGCG
ACTGGTGGATGAACAGGGGAAAAGGGTGCAACTGAGAGGGGTCAGTTCGC
ACGGTTTGCAGTGGTTTGGCGACTATGTCAACAAAGACTCGATGAAATGG
CTGCGTGATGACTGGGGGATTAATGTATTCCGTGTTGCCATGTACACGGC
AGCGGATGGCTATATTTCCAATCCTTCCCTTGCGAATAAGGTCAAAGAAG
CCGTTGCGGTGGCACAAAGCCTTGGCATCTACATCATCATCGACTGGCAC
ATTTTGTCGGATAACGATCCTAATATTTATAAAGCGCAGGCAAAAACCTT
CTTTGCTGAAATGGCGGGGCTGTACGGTAATTCGCCGAACGTGATTTATG
AAATCGCCAATGAACCTAACGGCGGCGTGACATGGAACGGGCAGATTCGG
CCTTATGCGCTGGATGTTACTGACACCATCCGTAGCAAAGATCCTGATAA
CCTTATTATCGTCGGTACCGGCACCTGGAGTCAGGATATTCATGACGCGG
CGGATAATCAGCTGCCCGATCCGAATACGCTGTACGCGCTGCATTTCTAT
GCGGGCACGCACGGGCAGTTCCTGCGCGATCGCATTGACTATGCACAAAG
CCGCGGTGCTGCAATTTTCGTCAGCGAGTGGGGCACAAGCGATGCATCCG
GCAACGGTGGGCCGTTCCTGCCTGAATCGCAGACCTGGATCGATTTCCTG
AATAACCGTGGTATAAGCTGGGTAAACTGGTCGCTTACCGATAAGTCTGA
GACATCCGGCGCTGGCACCGGGAGCGAGCAAATCTGGTGGTTGGACAG
AGCAGAATTCGTCGGCGTCAGGAAATTTGTCAGAGCAGGTTCGTGCG
GGTGCAGACCTGAGTGGTGGCGATCACCATCACCATCACCATTAA
```

Amino acid sequence cellulase 27
(SEQ ID NO:54)
```
MATPVETHGQLSIENGRLVDEQGKRVQLRGVSSHGLQWFGDYVNKDSMKW
LRDDWGINVFRVAMYTAADGYISNPSLANKVKEAVAVAQSLGIYIIIDWH
ILSDNDPNIYKAQAKTFFAEMAGLYGNSPNVIYEIANEPNGGVTWNGQIR
PYALDVTDTIRSKDPDNLIIVGTGTWSQDIHDAADNQLPDPNTLYALHFY
AGTHGQFLRDRIDYAQSRGAAIFVSEWGTSDASGNGGPFLPESQTWIDFL
NNRGISWVNWSLTDKSETSAALAPGASKSGGWTEQNSSASGKFVREQVRA
GADLSGGDHHHHHH*
```

CELLULASE 28
Nucleic acid sequence cellulase 28
(SEQ ID NO:55)
```
ATGGCCACGCCAGTAGAAACGCATGGCCAACTGTCCATCGAAAATGGGCG
ACTGGTGGATGAGCAGGGGAAAAGAGTGCAACTGAGAGGGGTCAGTTCGC
ACGGTTTGCAGTGGTTTGGTGACTATGTCAACAAAGACTCGATGAAGTGG
CTGCGTGATGACTGGGGGATTAACGTATTCCGTGTTGCCATGTACACGGC
AGCGGATGGCTATATTTCCAATCCTTCCCCTTGCGAATAAGGTCAAAGAAG
CCGTTGCGGTGGCACAAAGCCTCGGCGTCTACATCATCATCGACTGGCAT
```

TABLE 1A-continued

```
ATCTTGTCGGATAACGATCCTAATATTTATAAAGCACAGGCAAAAACCTT
CTTTGCCGAAATGGCGGGGCTGTACGGTAATTCGCCGAACGTGATTTATG
AAATCGCCAATGAACCTAACGGCGGCGTGACATGGAACGGGCAAATTCGG
CCTTATGCGCTGGAAGTGACTGACACTATCCGTAGCAAAGATCCTGATAA
CCTTATTATCGTCGGCAGCGGGACCTGGAGCCAGGACATCCATGATGCGG
CAGACAATCAGTTGCCCGATCCGAATACGCTGTACGCGCTGCATTTCTAT
GCGGGCACGCACGGGCAATTCCTGTGCGATCGTATTGACTATGCGCAAAG
CCGTGGCGCGGCGATTTTCGTCAGCGAGTGGGGCACCAGCGATGCATCCG
GCAACGGCGGACCGTTCCTGCCTGAATCGCAAACCTGGATCGATTTCCTG
AATAACCGTGGCATAAGCTGGGTTAACTGGTCGCTTAGCGATAAGTCTGA
GACGTCTGCGGCGCTGACTCCAGGGGCGAGTAAATCAGGCGGTTGGACGG
AGCAGAATCTGTCGGCGTCAGGAAAACTTGTCAGAGCACAGATTCGTGCA
GGTGCGAATCTGGGCGGTGGCGATCACCATCACCATCACCATTAA
```

Amino acid sequence cellulase 28
(SEQ ID NO:56)
MATPVETHGQLSIENGRLVDEQGKRVQLRGVSSHGLQWFGDYVNKDSMKW
LRDDWGINVFRVAMYTAADGYISNPPLANKVKEAVAVAQSLGVYIIIDWH
ILSDNDPNIYKAQAKTFFAEMAGLYGNSPNVIYEIANEPNGGVTWNGQIR
PYALEVTDTIRSKDPDNLIIVGSGTWSQDIHDAADNQLPDPNTLYALHFY
AGTHGQFLCDRIDYAQSRGAAIFVSEWGTSDASGNGGPFLPESQTWIDFL
NNRGISWVNWSLSDKSETSAALTPGASKSGGWTEQNLSASGKLVRAQIRA
GANLGGGDHHHHHH*

CELLULASE 29
Nucleic acid sequence cellulase 29
(SEQ ID NO:57)
```
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGTGACTACGTCAACAAAGGTTCGATGAAATGG
CTGCGCGATGACTGGGGGATTAACGTATTCCGTGTTGCCATGTACACGGC
GGCGGATGGTTATATTTCGAATCCTTCCCTCGCCAATAAGGTAAAAGAAG
CCGTTGCGGTGGCACAAAGCCTCGGCGTCTACATCATCATCGACTGGCAT
ATCTTGTCGGATAACGATCCTAATATTTATAAAGCACAGGCAAAAACCTT
CTTTGCCGAAATGGCGGGGCTGTACGGTAATTCGCCGAACGTGATTTATG
AAATCGCCAATGAACCTAACGGCGGCGTGACATGGAACGGGCAAATTCGG
CCTTATGCGCTGGAAGTGACTGAAACTATCCGTAGTAAAGATCCTGATAA
TCTGATTATCGTTGGCACGGGTACCTGGAGTCAGGATATTCATGACGCGG
CGGATAATCAGCTGCCCGATCCGAATACGATGTACGCGCTGCATTTCTAT
GCGGGTACGCACGGGCAGTTCCTGCGCGATCGCATTGATTATGCACAAAG
CCGCGGTGCCGCGATTTTCGTCAGCGAGTGGGGCACCAGCGATGCATCCG
GCAACGGTGGGCCGTTCCTGCCTGAATCGCAGACCTGGATCGATTTCCTG
AATAACCGTGGCGTAAGCTGGGTGAACTGGTCGCTTACCGATAAATCANA
GGCGTCCGCCGCGCTGGCTCCAGGGGCGAGTAAATCTGGCGGTTGGACGG
ANCANAATCTGTCGACGTCAGGCAAATTTGTCANANAGCAGATTCGTGCA
GGTGCGAATCTGGGCGGTGGCGATCACCATCACCATCACCATTAA
```

Amino acid sequence cellulase 29
(SEQ ID NO:58)
MATPVETHGQLSIENGRLVDEQGKRVQLRGVSSHGLQWFGDYVNKGSMKW
LRDDWGINVFRVAMYTAADGYISNPSLANKVKEAVAVAQSLGVYIIIDWH
ILSDNDPNIYKAQAKTFFAEMAGLYGNSPNVIYEIANEPNGGVTWNGQIR
PYALEVTETIRSKDPDNLIIVGTGTWSQDIHDAADNQLPDPNTMYALHFY
AGTHGQFLRDRIDYAQSRGAAIFVSEWGTSDASGNGGPFLPESQTWIDFL
NNRGVSWVNWSLTDKSXASAALAPGASKSGGWTXXNLSTSGKFVXXQIRA
GANLGGGDHHHHHH*

CELLULASE 30
Nucleic acid sequence cellulase 30
(SEQ ID NO:59)
```
ATGGCCACGCCAGTAGAAACGCATGGTCAGCTGTCCATCGAAAACGGGCG
ACTGGTGGATGAACAGGGGAAAAGGGTGCAACTGAGAGGGGTCAGTTCGC
ACGGTTTGCAGTGGTTTGGTGACTACGTCAACAAAGATTCGATAAAATGG
CTGCGTGACGACTGGGGGATCAATGTGTTTCGCGTTGCCATGTACACGGC
GGAGAATGGTTATATTGCTAACCCTTCTCTCGCCAATAAGGTAAAAGAGG
CCGTTGCGGCGGCGAAAGCCTCGGCGTTTACATCATCATCGACTGGCAT
ATCTTGTCGGATAACGATCCTAATATTTATAAAGCACAGGCAAAAACCTT
CTTTGCCGAAATGGCTGGGCTGTACGGTAATTCGCCGAACGTGATTTATG
AAATCGCCAATGAACCTAACGGCGGCGTGACATGGAACGGGCAAATTCGG
CCTTATGCGCTGGAAGTGACTGACACCATCCGTAGCAAAGATCCCGATAA
CCTCATTATCGTCGGTACCGGCACCTGGAGTCAGGATATTCATGACGCAG
CGGATAACCAACTGCCCGATCCGAATACCCTATACGCGCTGCATTTCTAT
GCCGGTACGCACGGGCAGTTCCTGCGCGATCGTATTGACTATGCACAAAG
CCGCGGTGCCGCGATTTTCGTCAGCGAGTGGGGCACAAGCGATGCGTCCG
GCAACGGCGGACCGTTCCTGCCTGAATCGCAGACCTGGATCGATTTCCTG
AATAACCGTGGCGTAAGCTGGGTGAACTGGTCGCTTACCGATAAGTCAGA
GACGTCTGCGGCGCTGGCACCCGGGAGCGAGCAAATCTGGCGGTTGGACAG
AGCAGAATTTGTCGGCGTCAGGCAAATTTGTCAGAGAGCAGATTCGTGCA
GGTGCGAATCTGGGCGGTGGCGATCACCATCACCATCACCATTAA
```

Aminoacid sequence cellulase 30
(SEQ ID NO:60)
MATPVETHGQLSIENGRLVDEQGKRVQLRGVSSHGLQWFGDYVNKDSIKW
LRDDWGINVFRVAMYTAENGYIANPSLANKVKEAVAAAQSLGVYIIIDWH
ILSDNDPNIYKAQAKTFFAEMAGLYGNSPNVIYEIANEPNGGVTWNGQIR
PYALEVTDTIRSKDPDNLIIVGTGTWSQDIHDAADNQLPDPNTLYALHFY
AGTHGQFLRDRIDYAQSRGAAIFVSEWGTSDASGNGGPFLPESQTWIDFL
NNRGVSWVNWSLTDKSETSAALAPGASKSGGWTEQNLSASGKFVREQIRA
GANLGGGDHHHHHH*

TABLE 1B

| Cellulase # | Kcat (sec$^{-1}$) | Km (M) | Kcat/Km (M-1sec$^{-1}$) |
|---|---|---|---|
| 1 | $4.3 \times 10^3$ | $3.2 \times 10^{-3}$ | $1.4 \times 10^6$ |
| 2 | $5.2 \times 10^3$ | $2.5 \times 10^{-3}$ | $2.1 \times 10^6$ |
| 3 | $5 \times 10^3$ | $3.6 \times 10^{-3}$ | $1.4 \times 10^6$ |
| 4 | $1.6 \times 10^4$ | $1.3 \times 10^{-3}$ | $1.1 \times 10^7$ |
| 5 | $6.7 \times 10^3$ | $1.5 \times 10^{-3}$ | $4.5 \times 10^6$ |
| 6 | $2.1 \times 10^2$ | $1.0 \times 10^{-3}$ | $2.2 \times 10^5$ |
| 7 | $1.1 \times 10^2$ | $1.4 \times 10^{-2}$ | $8.1 \times 10^3$ |
| 8 | $8.4 \times 10^2$ | $4.3 \times 10^{-3}$ | $2.0 \times 10^5$ |
| 9 | $7.1 \times 10^2$ | $4.6 \times 10^{-3}$ | $1.5 \times 10^5$ |
| 10 | 87 | $0.8 \times 10^{-3}$ | $1.1 \times 10^5$ |

The present invention is illustrated by the following non-limiting working examples. The contents of the working examples is hereby incorporated by reference into this detailed description of the invention section.

6. EXAMPLE

In Vivo Mutagenesis with HO Endonuclease

Directed evolution requires two steps—mutagenesis of the DNA encoding the protein of interest, followed by selection of the fittest variants. Both these steps may be carried out by a living cell. Harnessing the cell's powerful mutagenesis and selection machineries for "unnatural" chemistry has real advantages for searching very large library sizes and ultimately being able to achieve the de novo directed evolution of enzymes (FIG. 11).

The key to the directed evolution of ever more dramatic changes in function is the ability to search very large libraries of protein variants. Changes in enzyme substrate specificity typically have required libraries of about $10^8$ protein variants (Yano, et al., 1998, Proc. Natl. Acad. Sci. USA, 95, 5511-5515; Park, et al., 2006, Science, 3111, 535-538). It is reasonable to assume that the de novo directed evolution of enzyme activity requires even larger library sizes. So what limits library size? Hypothetically, beginning with $10^8$ cells, each containing DNA encoding a unique protein variant (a library size currently achievable by DNA transformation in yeast). If the yeast has a doubling time of 6 hours, and the DNA could be mutated at each round of cell division, after 1 week there would be ca. $10^{16}$ cells, with $10^{16}$ different protein variants (FIG. 11A). The problem is that given there are about $10^8$ cells/mL in a rapidly growing and dividing yeast cell culture ("late log phase"), $10^{16}$ cells would require 100,000 L of material! This thought experiment nicely illustrates that the problem is not really technical issues like DNA transformation efficiency, but simply the volume of material required (for in vitro systems there is a similar limit imposed by the amount of DNA that can realistically be produced). The cell's elegant solution to this problem is to carry out mutation and selection simultaneously. For example, simplistically, if only the fitter variant survived at each round of cell division, after a week of mutation and selection, there would be only $10^8$ cells containing the $10^8$ fittest protein variants (FIG. 11B). Thus, as detailed below, a yeast strain may be engineered that can carry out both mutation and selection for "unnatural" chemistry to allow a virtual search of very large library sizes.

The following relates to developing an in vivo mutagenesis system with a traditional TRP1 yeast genetic selection, although such a system may be extended to incorporate chemical complementation technology. By analogy to ampicillin-resistance selections in *E. coli*, TRP1 is one of the classic selectable markers used in yeast genetics (Jones and Fink, 1982, *The molecular biology of the yeast sacchromyces* (eds. Strahern, J., Jones, E. &Broach, J.) 181-299, Cold Spring Harbor Laboratory, Cold Spring Harbor; Braus, G. H., 1991, Microbiol. Rev., 55, 349-370). TRP1 encodes phosphoribosyl anthranilate isomerase (PRAI), which carries out the isomerisation of phosphoribosyl anthranilate to carboxyphenylamino deoxyribulose phosphate—the third step in tryptophan biosynthesis from chorismic acid (Braus, G. H., 1991, Microbiol. Rev., 55, 349-370). Thus, a yeast trp1 auxotroph can be used to select for PRAI activity simply by growing cells on media lacking tryptophan (Perfect, et al., 1992, Gene, 122, 213-217; Nakai, et al., 2000, FEMS Microbiol. Lett. 190, 51-56; Cosano, et al., 1998, Yeast, 14, 861-867). PRAI is a TIM barrel enzyme, and its sequence, structure, and function are very well characterized (Sterner, et al., 1995, Embo. J., 14, 4395-4402; Thoma, et al., 2000, Structure, 8, 265-276; Henn-Sax, et al., 2002, Biochemistry, 41, 12032-12042; Sterner, et al., 2001, Methods Enzymol, 331, 270-280). The enzyme is well behaved, and the activity of the purified protein can be readily monitored in vitro based on the change in fluorescence at 400 nm upon conversion of substrate to product (Hommel and Kirschner, 1995, Biochemistry, 34, 5429-5439).

A system may be developed to direct evolution so as to increase the activity of the thermophilic PRAI from *Thermotoga maritima* at ambient temperature (the *T. maritima* PRAI is impaired about 10-fold in its catalytic efficiency at ambient temperature compared with the *S. cerevisiae* enzyme (Thoma, et al., 2000, Structure, 8, 265-276; Hommel and Kirschner, 1995, Biochemistry, 34, 5429-5439) and so is expected to begin with a weak selective advantage in the yeast auxotroph). Alternatively the directed evolution of phosphoribosyl imidazolecarboxamide isomerase (HIS6) to PRAI (TRP1) (Jurgens, et al., 2000, Proc. Natl. Acad. Sci. USA, 97, 9925-9930) reported previously could be used.

Because of the efficiency of homologous recombination in *S. cerevisiae* (Krogh and Symington, 2004, Annu. Rev. Genet., 38, 233-271) (homologous recombination is significantly less efficient, for example in *E. coli*), TIM barrel loop libraries may be produced in vivo simply by transforming linear oligonucleotides encoding the loop libraries into yeast containing DNA encoding the PRAI TIM barrel. Homologous recombination is used routinely as a tool in yeast genetics for creating "knock-outs" by replacing a segment of the chromosomal DNA with a homologous piece of linear synthetic DNA by recombination (Baudin, et al., 1993, Nucleic Acids Res., 31, 3329-3330). Homologous recombination has long been used to create plasmid in yeast (Ma, et al., 1987, Gene, 58, 201-216) (homologous recombination has been used to engineer yeast three-hybrid strains (Baker, et al., 2003, Anal. Biochem. 315, 134-137)). More quantitatively, Sexson and co-workers showed that using 30-base pair homologous ends he could achieve efficient plasmid reconstitution via homologous recombination in yeast (Raymond, et al., 1999, Biotechniques, 26, 134-138; 140-131). Building on this work, homologous recombination has been exploited for in vivo "DNA shuffling" (Swers, et al., 2004, Nucleic Acids Res. 32, e36; Cherry, et al., 1999, Nat. Biotechnol., 17, 379-384; Abecassis, et al., 2000, Nucleic Acids Res. 28, E88). The TIM barrel scaffold lends itself readily to loop mutagenesis by homologous recombination since the β-sheet and α-helix on either side of each loop provide sufficient homology regions for efficient recombination. Currently, the synthesis of libraries in which multiple, nonadjacent loops are randomized by in vitro PCR methods is cumbersome, expensive, and low yielding (see Beste et al.). Synthesis of the TIM barrel loop libraries may be used to create a family of libraries in which different combinations of the loops are randomized at different stages in the selection process (FIG. 12A).

To produce a suitable host cell, the gene encoding the PRAI from *T. maritima* may be placed under control of the tunable MET promoter into a yeast trp1 auxotroph, for example by homologous recombination. Random loop libraries for loops 3 and 5, which form much of the substrate-binding pocket for PRAI (Thoma, et al., 2000, Structure, 8, 265-276; Hennig, et al., 1997, Biochemistry, 36, 6009-6016), may be prepared. Linear oligonucleotides ca. 100 base pairs in length encoding the randomized loops surrounded on either side by 30-base pair PRAI homology regions may be prepared from synthetic oligonucleotides by standard molecular biology methods. These oligonucleotide loop libraries may be transformed into yeast by electroporation. The efficiency of homologous recombination may be confirmed by sequencing PRAI genes obtained by colony PCR from colonies grown under nonselective conditions. Then the loop libraries may be used to increase the activity of the *T. maritima* PRAI at ambient temperatures with a trp1 growth selection.

In Vivo Mutagenesis with HO Endonuclease. As discussed above. much larger library sizes could be accessed, however, if the mutagenesis could be carried out entirely inside the cell, with a round of mutagenesis and selection at each cell division. Since the mutagenized DNA would not have to be reintroduced to the cell at each round of mutagenesis, in vivo mutagenesis would remove the limit on library sizes currently imposed by DNA transformation efficiency. Classic yeast genetic experiments in which the HO endonuclease is placed under control of the tunable Gal promoter provide a route to achieving this goal (Nasmyth, K., 1987, Embo. J. 6, 243-248; Connolly, et al., 1988, Mol. Cell. Biol. 8, 2342-2349; Elias-Arnanz, et al., 1996, Mol. Gen. Genet, 252, 530-538). In studies of yeast recombination, it has been shown that the highly-specific HO endonuclease, which naturally is involved in mating-type switching in yeast, can be knocked-out and then reintroduced into the yeast chromosome under control of the Gal promoter without impairing yeast viability (Connolly, et al., 1988, Mol. Cell. Biol. 8, 2342-2349; Nasmyth, K., 1993, Curr. Opin. Genet. Dev., 3, 286-294; Jensen and Herskowitz, 1984, Symp. Quant. Biol., 49, 97-104). HO endonuclease can then be induced after each cell division to cleave a 2µ plasmid engineered to have a 28-base pair-HO endonuclease recognition site (Connolly, et al., 1988, Mol. Cell. Biol. 8, 2342-2349). By tuning the timing and concentration of galactose induction, the extent of plasmid cleavage can be controlled such that a percentage of the plasmid should remain uncleaved (Galactose Induction Protocol., www.bio.brandeis.edu/haberlab/jehsite/protocol.html) and so be copied and restored to the ca. 60-copies per cell typical for 2µ plasmids at each cell division (Volkert, et al., 1989, Microbiol. Rev. 53, 299-317).

Accordingly, linear loop libraries may be generated in vivo simply by constructing a 2µ plasmid encoding each loop library embedded in HO endonuclease cleavage sites. Loop libraries may be generated afresh after each cell division simply by cycling HO endonuclease induction.

7. EXAMPLE

Establishment of a Yeast Host Strain

Based on a published report that a HIS6:D127V mutant could complement a TRP1 deficiency in *E. coli*, the directed evolution of HIS6 may be used to increase its activity with the analogous indole substrate based on TRP1 complementation in yeast. The data presented herein show that the HIS6:D127V enzyme can also complement a TRP1 deficiency in yeast, validating the proof of principle target.

HIS6:D127V has been previously identified to complement a TRP1 deficiency. Since this evolution was carried out in *E. coli*, it was first determined whether the TRP1 selection in yeast could differentiate between the inactive HIS6 and the active HIS6:D127V variants. After 4 days of selection on solid media, HIS6 did not complement a TRP1 deficiency, while the HIS6:D127V variant did, surviving on plates containing 10 µM tryptophan (FIG. 13A). The TRP1 selection was then used to carry out a mock selection. Starting from a 1:100 ratio of active (HIS6:D127V) to inactive (HIS6) gene, the TRP1 selection achieved >100-fold increase in TRP1 activity after seven days of selection (FIG. 13B). The results validate the conversion of HIS6 to HIS6:D127V to complement a TRP1 deficiency in yeast.

8. EXAMPLE

Use of Chemical Complementation to Detect Glycosynthase and Glycosidase Activities

8.1 Detection of Glycosynthase Activity

Experimental Results.

First, it was shown that chemical complementation could link Cel7B:E197A glycosynthase activity to transcription of a LEU2 reporter gene in the presence of the Dex-cellobiose (Dex-Cel) and Mtx-lactose-F substrates (Mtx-Lac-F). Then the LEU2 selection was used to enrich for the Cel7B:E197A glycosynthase from a 1:100 mixture of active:inactive glycosynthase variants, giving a 400-fold enrichment in a single round of selection. Finally, the LEU2 selection was used to select the most active variants from a saturation library at position E197 in Cel7B. Significantly, false positives (ca. 50% of the clones) could be readily ruled out by a simple secondary three-hybrid screen with and without the Dex-Cel and Mtx-Lac-F substrates. Two of the most active variants, Cel7B:E197S and an unencoded Cel7B:N196D,E197A double mutant, were purified and their activity was determined in vitro based on product synthesis as verified by HPLC and the specific activity of fluoride ion release as reported (Lin, et al., 2004, J. Am. Chem. Soc., 126, 15051-15059). The Cel7B:E197S variant was found to have a five-fold increase in glycosynthase activity (Table 2). It should be emphasized that this variant had high activity with unmodified substrates, suggesting that use of the Dex and Mtx linkers in the chemical complementation selection should not impair the activity of evolved variants with the desired in vitro substrates.

TABLE 2

Glycosynthase activities and protein purification yields for Cel17B variants

|  | E197A | E197S | N196D/E197A |
|---|---|---|---|
| specific activity mol[F]/(min-mol [E$_o$]) | 8 ± 2 | 40 ± 5 | 7 ± 1 |
| protein purification yield: nmol/L | 6.1 | 4.6 | 7.3 |

For the results in Table 2, glycosynthase activity for tetrasaccharide synthesis from α-lactosyl fluoride and p-nitrophenyl β-cellobioside (PNPC) was measured for the *Humicola isolens* Vel17B variants in sodium phosphate buffer, pH 7.0, at room temperature. Specific activities were determined by measuring the fluoride ion release rate by a fluoride ion selective electrode. The protein purification yields were determined by western analysis from total cell culture.

8.2 Detection of Glycosidase Activity

Using chemical complementation for the directed evolution of glycosidases required synthesis of the Mtx-Lac-Cel-Dex tetrasaccharide substrate, which was achieved using the Cel7B:E197A glycosynthase enzyme. Mtx-Lac-Cel-Dex was purified by HPLC and confirmed by UV spectroscopy and LRMS. LacZ transcription assays confirmed that this tetrasaccharide substrate was cell permeable and able to activate transcription in a yeast three-hybrid system. A counter selection method was required. A counter selection is more demanding because enzyme catalysis must relieve transcription of a toxic reporter gene. The chemical complementation system was adapted to provide a URA3 counter selection for bond cleavage reactions (Huang, et al., 1997, Proc. Natl. Acad. Sci. USA, 94, 13396-13401; Vidal, et al., 1996, Proc. Natl. Acad. Sci. USA, 93, 10315-10320). Briefly, the URA3 gene product converts 5-fluoroorotic acid (5-FOA) to 5-fluorouracil (5-FU), which is toxic, allowing for counter selection in the presence of 5-FOA (a classic yeast genetics experiment). Synthesis of the URA3 gene from a weak SPO13 promoter attenuates toxicity. Toxicity is then controlled by transcription activation of the URA3 gene by the artificial yeast three-hybrid transcriptional activator. First, the URA3 yeast three-hybrid counter-selection strain was developed using a Dex-Mtx CID with a simple methylene linker. Then, it was shown that a 5-FOA selection could distinguish the active Cel7B glycosidase from the inactive Cel7B:E197A variant in this strain background (FIG. 5A). Finally, the URA3 counter selection was used to enrich 200-fold for the Cel7B glycosidase from a 1:100 mixture of active:inactive glycosidase variants (FIG. 5B). These results establish that chemical complementation can be used to detect glycosidase activity, serving as the basis for directed evolution experiments.

9. VALIDATION OF HO-INDUCED DNA CASSETTE RECOMBINATION IN VIVO

The following experiment was performed to test the system schematically depicted in FIG. 14A. According to this system, short oligonucleotide (DINA) libraries may be generated in vivo by galactose-induced cleavage of a 2µ plasmid encoding the loop libraries embedded in HO endonuclease sites at each round of cell division.

To determine both the level of HO-induced recombination and the background level of recombination under non-inducing conditions, recombination of a DNA cassette encoding the D127V mutation into the wt HIS6 gene was scored based on growth in a yeast trp1 knockout strain (strain VM46Y). The wtHIS6 gene is encoded on a standard yeast expression plasmid under control of the MET promoter. The D127V cassette is encoded on a second plasmid, with 30-bp of homology to the HIS6 gene on either side of the D127V mutant and HO cleavage sites on either side of the cassette. The yeast strain is a trp1 knockout with HO endonuclease under control of the GAL promoter integrated into the chromosome. VM46Y was grown under both inducing and non-inducing conditions, and then the percent recombinants was measured as the ratio of cells growing on T plates (10 µM Trp, only HIS6:D127V grows under these conditions) versus non-selective plates (both HIS6 and HIS6:D127V grow under these conditions).

Briefly, an overnight culture of VM46Y taken from a a fresh patch was used to seed a culture that was then grown to an $OD_{600}$=0.6. These cells were then either induced by 1 hour growth in 2% lactate followed by 1 hour growth in 2% galactose ("induced cells") or grown under non-inducing conditions by 1 hour growth in 2% lactate plus 2% glucose followed by 1 hour growth in 2% glucose ("non-induced cells").

The results of these experiments is shown in FIG. 14B-C. Based on serial dilutions, the percent recombinants were measured as induced cells=2% and non-induced cells=0.004%. It was estimated that the true number of recombinants is probably higher, because the HIS6:D127V complementation of the yeast trp1 auxotroph is incomplete. Specifically, when a plasmid with a LEU2 selectable marker encoding the HIS6:D127V variant is transformed into the yeast trp1 auxotroph, the ratio of cells growing on a $L^-$ versus a $LT^-$ plate is not 1:1 as would be expected, but rather is 50:1. Given that HIS6:D127V complementation of the trp1 auxotroph is only 2%, the true recombination in induced cells may be estimated to be 100% and in non-induced cells may be estimated to be 0.2%.

To further evaluate the extent of recombination, the following experiment, performed in liquid culture rather than on selective medium, was performed.

Strain VM39 is a trp-auxotroph, containing the Ho-endonuclease under control of the galactose promoter, and carrying the plasmid coding for HIS6 wildtype. VM39 was transformed with a pool of plasmids ("library plasmid") coding the D127NNS cassette with 30 bp of homology to the HIS6 gene on either side of the D127NNS mutant and the HO cleavage sites in either side of the cassette. A silent restriction site (BssSI) was incorporated 5 base pairs away from the 127 position in the cassettes to more easily analyze the pool of HIS6D127 variants after selection.

After transformation of the VM39 cells with the pool of plasmids, the transformed cells were incubated for 1 hr at 30° C. in YPD at 200 rpm for recovery. Next, the cells were pelleted, washed with distilled water, and resuspended in 2 ml induction media (synthetic medium containing galactose and lacking leucine and uracil) and shaken for 1 hr at 30° C. (see FIG. 14D for schematized protocol). Then, the cells were pelleted, washed with sterile distilled water, and resuspended in 2 ml selection media (synthetic media containing glucose and 10 uM tryptophan) and shaken at 30° C. for 8 days. Finally, 100 ul of the selection media were used to inoculate a 5 ml amplification culture (synthetic media containing glucose and lacking leucine) to amplify the winners of the TRP1 selection. After 5 days the DNA from the cells in the amplification culture was extracted and used as a template to PCR the pool of HIS6 variants. The PCR of the pool of HIS6 variants after selection was digested overnight with BssBI. FIG. 14E shows a DNA gel of the pool of HIS6 variants after digestion with BssBI.

As FIG. 14E shows, after 8 days of selection, the pool of HIS6 variants that underwent 60 min of galactose induction has been enriched for the HIS6:D127NNS variants when compared to the pool of HIS6 variants induced with galactose for only 30 min. Since the His6:D127NNS variants carry a BssSi restriction site, it is possible to identify them in a pool of HIS6 wildtype strains by digestion with BssSi which generates a smaller DNA fragment. The enrichment occurs because during the 60 min of galactose induction, the HO endonuclease is expressed form the galactose promoter and effectively cleaves the cassettes. The recombination machinery of yeast then effectively recombine the cassettes at the 127 position in the His6 wild type incorporating not only the NNs mutation but also the BssSI restriction site.

10. EXAMPLE

Generation of a Secondary (Diversified) Library by Mating (Diversified) Primary Libraries Testing of Mating and Sporulation.

Strain VM44 is a MATα type, trp-auxotroph, containing the HO-endonuclease under control of the galactose promoter, and the HisA wild-type plasmid with a leucine marker. Strain VM45 is the MATa type version of VM44. MATa and MATα cells mate with each other and create zygotes. These zygotes spawn diploids that contain both MATa and MATα mating types and cease to mate. To test the efficiency of mating liquid cultures, an overnight culture of each VM44 and VM45 was grown to saturation. $OD_{600}$ readings determined cell counts and equal cell amounts were then mixed into 2 ml of media, in a 14 ml culture tube. The tubes shook at 30°, 200 RPMs and then 1:10 dilutions with sterile water were taken at several time intervals; 30 min, 60 min, 90 min, 120 min, 210 min, 270 min, 300 min. Using a microscope at 400× total magnification, zygotes vs. non zygotes were counted in at least 10 large hemocytometer squares, per dilution. Each dilution is calculated as the average of the 10 squares. FIG. 15 shows the percentage of zygotes which peaks around 210 min.

Based on the above experiment, it was concluded that these strains need no more than 6 hours to fully mate. To test the efficiency of sporulation in triplicate, an overnight culture of each VM44 and VM45 was grown to saturation. $OD_{600}$ readings determined cell counts and equal cell amounts were mixed into 2 ml of media, in a 14 ml culture tube. The tubes were then shaken at 30°, 200 RPMs for 6 hours to ensure full mating. $OD_{600}$ readings were established and the newly mated culture was used to inoculate to $OD_{600}$=0.100, three 14 ml culture tubes with 2 ml of 10% YPD media (which is yeast extract-peptone, media with 10% glucose). These tubes were shaken at 22°, 350 RPM until the $OD_{600}$=0.600-0.800, which is about 16 to 18 hours. Each tube was pelleted and washed twice with sterile water, and then re-suspended with 2 ml SPO2 sporulation media (0.5% KAc). Each tube went back into 22° shaker at 350 RPM for another 48 hours. The cells were than washed with water, diluted 1:10, and viewed under 400× total magnification with a hemocytometer to determine the number of spores versus unsporulated cells. Each tube was calculated as the average of 10 hemocytometer squares counted. The three tubes were then averaged to determine the percent sporulation in triplicate after 48 hours, which is 47%.

Mating Of Primary (Diversified) Libraries.

The following experiment was performed, whereby two primary libraries (diversified by in vivo recombination) were combined such that mating and sporulation could occur, thereby producing a secondary library of amplified diversity, with a goal of producing a HIS mutant with improved Trp activity. VM44 was transformed with library 1, a pool of plasmids that randomized sites for loop 5 (S125NNS, D127NNS) and loop 8 (I221NNS, G223NNS, F226NNS). VM45 was transformed with library 2, a pool of plasmids that randomized sites for loop 2 (H48NNS, V50NNS, L52NNS, A55NNS, I56NNS), the loops being flanked by HO endonuclease cleavage sites. After transformation the cells were incubated for 1 hr at 30° C. in YPD at 200 rpm for recovery. Next, the cells were pelleted, washed with distilled water, and resuspended in 5 ml pre-induction media (synthetic medium containing 2% lactate and lacking leucine and uracil) and shaken for 1 hr at 30° C. Then, the cells were pelleted, washed with sterile distilled water, and resuspended in 5 ml induction media (synthetic media containing galactose and lacking leucine and uracil, to induce production of the HO-endonuclease) and shaken for 1 hr at 30° C. Finally, the cells were pelleted, washed with sterile distilled water, and resuspended in 5 ml selection media (synthetic media containing glucose and 10 uM of tryptophan) and shaken at 30° C. for 2 more hours. 100 ul of a dilution of $OD_{600}$=0.300 from each tube was plated on selection plates (synthetic media plates containing glucose and 10 uM of tryptophan). FIG. 16 is a picture of these plates taken after 4 days of 30° C. incubation.

Each 5 ml cell culture was than mixed together in 50 ml flask and shook overnight at 30°, 200 RPM to ensure full mating. 100 ul of a dilution of $OD_{600}$=0.300 from each tube was plated on selection plates. FIG. 17 is a picture of these plates taken after 4 days of 30° incubation. All the cells were used to inoculate a large 1L culture of selection media to $OD_{600}$=0.100 and shaken at 30°, 200 RPM. $OD_{600}$ readings were taken at several time intervals to determine whether selection was working. The selection increased to $OD_{600}$=3.35 after four days which implied that the selection worked well. 100 ul of a dilution of $OD_{600}$=0.300 from each tube was plated on selection plates. FIG. 18 is a picture of these plates taken after 4 days of 30° incubation.

$OD_{600}$=1.00 number was used to inoculate to $OD_{600}$=0.100, 10% YPD media. The flask was shaken at 22°, 350 RPM until the $OD_{600}$=0.600-0.800, which is about 16 to 18 hours. The cells were then pelleted and washed twice with sterile water, and then re-suspended with SPO2 sporulation media (0.5% KAc). The flask went back into 22° shaker at 350 RPM for another 96 hours. A sample of cells was then washed with water, diluted 1:10, and viewed under 400× total magnification with a hemocytometer to determine the number of spores versus unsporulated cells. The sporulation efficiency after 96 hours was calculated as the average of 10 hemocytometer squares counting spores vs. non-spores, which is 94%. The spores were separated by pelleting the cells down, washing them with sterile water and resuspending the cells in 1 ml of sterile water. 50 ul of Zymolase (24 Units/ul) was added and incubated in 37° waterbath for 1 hr to break the ascus. To complete separation, the cells were washed with 1% SDS solution and sonicated for five minutes. 100 ul of a dilution of $OD_{600}$=0.300 from each tube was plated on selection plates. FIG. 19 is a picture of these plates taken after 4 days of 30° incubation.

In order to further analyze the results, the cells were used to prepare a maxiprep so the pool of plasmids could be electroporated into Lucigen E cloni. Supercompetent cells. Another maxiprep was prepared from the *E. coli* and transformed back into a generic trp-yeast strain (Δtrp1). This was done to minimize the incidences of false positives. 118 colonies were picked and grown overnight in SC(L−) (synthetic media lacking leucine) in 2×96 well plates. The overnight culture was used to dilute 1:10 into selection media (synthetic media with 5 uM tryptophan) and $OD_{600}$ were read after 2 days. The growth of these colonies were compared to HisWT and HisD127 mutants and colonies which grew faster than HisD127V were isolated for to compare growth in triplicate. As seen in FIG. 20, several colonies grow better then the HisD127V mutant, which implies that they have higher TrpF catalytic activity.

11. EXAMPLE

Directed Evolution of Glycosidase Activity

Using chemical complementation for the directed evolution of glycosidases required synthesis of the Mtx-Lac-Cel-Dex tetrasaccharide substrate, which was achieved using the Cel7B:E197A glycosynthase enzyme. Mtx-Lac-Cel-Dex was purified by HPLC and confirmed by UV spectroscopy and LRMS. LacZ transcription assays confirmed that this tetrasaccharide substrate was cell permeable and able to activate transcription in a yeast three-hybrid system. A counter selection method was required. A counter selection is more demanding because enzyme catalysis must relieve transcription of a toxic reporter gene. The chemical complementation system was adapted to provide a URA3 counter selection for bond cleavage reactions (see FIG. 23A for schematic drawing; Huang, et al., 1997, Proc. Natl. Acad. Sci. USA, 94, 13396-13401; Vidal, et al., 1996, Proc. Natl. Acad. Sci. USA, 93, 10315-10320). Briefly, the URA3 gene product converts 5-fluoroorotic acid (5-FOA) to 5-fluorouracil (5-FU), which is toxic, allowing for counter selection in the presence of 5-FOA (a classic yeast genetics experiment). Synthesis of the URA3 gene from a weak SPO13 promoter attenuates toxicity. Toxicity is then controlled by transcription activation of the URA3 gene by the artificial yeast three-hybrid transcriptional activator. First, the URA3 yeast three-hybrid counter-selection strain was developed using a Dex-Mtx CID with a simple methylene linker. Then, it was shown that a 5-FOA selection could distinguish the active Cel7B glycosidase from the inactive Cel7B:E197A variant in this strain background (FIG. 5A). Finally, the URA3 counter selection was used to enrich 200-fold for the Cel7B glycosidase from a 1:100 mixture of active:inactive glycosidase variants (FIG. 5B). These results establish that chemical complementation can be used to detect glycosidase activity, serving as the basis for directed evolution experiments.

12. EXAMPLE

Directed Evolution of Cellulase I

As above, chemical complementation was adapted to detect cellulase activity, utilizing a URA3 counter selection for bond cleavage reactions, allowing detection of cellulase activity (FIG. 23A; Vidal et al., 1996, Proc Natl Acad Sci USA. 93: 10315-10320; Huang and Schreiber, 1997, Proc Natl Acad Sci USA. 94: 13396-13401). Also as above, using the URA3 counter selection, 200-fold enrichment for *Humicola insolens* Cellulase7B from a 1:100 mixture of active: inactive cellulase mutants was (FIG. 23B). Further, URA3 counter selection was applied to the directed evolution of cellulases and a cellulase variant was identified having 2.6 fold increased activity when compared to the parent gene (FIG. 23C).

13. EXAMPLE

Directed Evolution of Cellulase II

Materials and Methods

Construction of Reporter Yeast Strain for Cellulase Selection. The Ura3 ORF from pMW112 was amplified using primers VC1077 and VC1640 and was, by homologous recombination, introduced into the ura3-52 locus of the yeast strain FY251 (MATa trp1Δ63 his3Δ200 ura3-52 leu2Δ1 Gal+) and selected on 5-floroorotic acid plates to give strain VC2169. Next, the plasmids pKB521 and pBC398[1] carrying the DNA-binding domain-dihydrofolate reductase fusion protein (LexA-eDHFR) and the glucocorticoid receptor-activation domain protein fusion (GR-B42), were transformed into VC2169 to give strain PPY9. The pUra3-LexA(4op)-Pspo13-Spo13(15aa)-Ura3 fragment was created by fusion PCR of the LexAop(8×) fragment from pMW112, amplified using primers VC1671 and VC1672, and the Pspo13-Spo13(15aa)-Ura3 fragment from MaV95[2] (Invitrogen), amplified using primers VC1669 and VC1670. The pUra3-LexA(4op)-Pspo13-Spo13(15aa)-Ura3construct was introduced into p425Met25 to create pPPY2176. Finally the pUra3-LexA(4op)-Pspo13-Spo13(15aa)-Ura3 fragment from pPPY2176 was amplified using primers VC1677 and VC1678 and integrated into PPY9 to create VPPY12, the reporter yeast strain for cellulase selection. The successful integration was confirmed by PCR and phenotypically.

Cellulase Mutagenesis.

The DNA shuffling vector, pPPY2148, was constructed by digesting p425Met25 (ATCC) with HindIII and PstI and introducing an 800 bp stuffer flanked by SfiI sites. The catalytic domain of four family 5 cellulases with 77-90% sequence identity, *E. carotovora* CelN (Olsen et al., 1996, Biotechnology (NY) 14:71-76), CelVI (Mae and Palva, 1995, Mol Gen Genet. 247:17-26), CelA (Park et al., 1997, Biochem Biophys Res Commun. 241:636-641) and CelT (cloned from the *E. carotovora* subs. *atroceptica* (Bell et al., 2004, Proc Natl Acad Sci USA. 101: 11105-11110) genomic DNA) were cloned into pPY2148 to create plasmids pPPY2230, pPPY2232, pPPY2234 and pPPY2236 respectively. A [6]His-tag was added at the C-terminus of the four parent genes to facilitate protein purification after selection. The catalytic domain of these cellulases was identified by sequence comparison with the catalytic domain of *Bacillus agaradhaerens* Cel5A, which has 68% sequence identity at the amino acid level with the parent genes and which three dimensional X-ray structure is available (Davies et al., 1998, Biochemistry 37: 1926-1932; Davies et al., 1998, Biochemistry 37: 11707-11713; Varrot et al., 2000, J Mol Biol. 297: 819-828; Varrot et al., 2001, Acta Crystallogr D Biol Crystallogr. 57: 1739-1742; Varrot and Davies, 2003, Acta Crystallogr D Biol Crystallogr. 59: 447-452). The cellulase genes were shuffled using standard procedures with slight variations (Zhao and Arnold, 1997, Nucleic Acids Res. 25: 1307-1308). To introduce the shuffled product into the shuffling vector via homologous recombination, 30 bp homology to the shuffling vector was introduced at the 5' and 3' end of the shuffled product by carrying an extra amplification step of the shuffling product primers VC1658-VC1659. 7.5 ng of shuffled product (1.4E11 shuffled product molecules assuming each base pair is 330M and the shuffled product was 1000 bp) was used as a template in a 100 ul amplification reaction. The product was purified in a 2% agarose gel.

Yeast Transformation and Cellulase Selection.

The reverse three hybrid strain was transformed using standard high transformation efficient procedures (Colby et al., 2004, *Methods Enzymol.* 388: 348-358). After recovery for an hour in YPD, the cells were centrifuge for 10 sec at 10,000 rpm, washed with sterile distilled water. The pellet was then resuspended in selection media (SC(HTL⁻), 2% galactose, 0.2% 5-FOA, 1 uM Dex-Cel-Lac-Mtx) for a final volume of 2 ml. A sample of the selection was plated under non-selective conditions on day 9.

In Vitro Kinetics.

Ten colonies selected on day 8 and 9 were characterized in vitro using para-nitrophenyl cellobioside (pNPC) as a substrate. The cellulase chimeras were amplified from the shuffling vector using primers PPY100 and PPY103 and subcloned into the T7-expression vectors pAED4 between NdeI and HindIII sites. The cellulase chimeras were over expressed in *E. coli* and purified using a Nickel affinity column. Protein concentration was determined using the extinction coefficient of the parent genes $\epsilon=76890$ and absorption at $A_{280}$. To determine the kinetic constants for the hydrolysis of pNPC, the cellulase chimeras were incubated at room temperature in phosphate buffer (25 mM $K_2HPO_4$, 100 mM NaCl, pH=7) containing various concentrations of the substrate, and the release of p-nitrophenol ($\epsilon_{pH=7}=4000M^{-1}$ cm$^{-1}$, $A_{420}$) was recorded continuously in a SpectraMax Plus 384 spectrophotometer.

Results

TABLE 3

| Cellulase | $k_{cat}$ (sec$^{-1}$) | $K_M$ (mM) | $K_{cat}/K_M$ (sec$^{-1}$mM$^{-1}$) |
| --- | --- | --- | --- |
| Cellulase N | $1.3 * 10^3$ | 3.4 | 374 |
| Cellulase A | $1.4 * 10^3$ | 7.2 | 193 |
| Cellulase T | $1.1 * 10^3$ | 4.6 | 237 |
| Cellulase VI | | | |
| Colony 1 | $1.6 * 10^4$ | 1.3 | $1.2 * 10^4$ |
| Colony 2 | $4.3 * 10^3$ | 3.2 | $1.3 * 10^3$ |

The coding regions of the cellulase genes for Colony 1 and Colony 2 were sequenced and determined to be SEQ ID NO: 1 and SEQ ID NO:2, respectively. Of note, because a parental strain of colony 1 (cellulase 4; CELLVAR1) was not considered, the increase in activity was determined to be 33-fold, which was an error.

14. EXAMPLE

Directed Evolution of Cellulases Via Chemical Complementation

A reverse yeast three-hybrid strain was developed that performs efficiently in liquid culture, thereby enabling cellulase selection in liquid culture which allows for small increases in catalytic activity to be amplified and reduces the amount of small molecule required per experiment. Once the yeast three-hybrid strain was developed, cellulase activity from *Humicola insolens* Cel7B, which catalyzes the hydrolysis of β-1,4-linked glucosidic bonds in cellulose, was detected using the URA3 counter selection. In the experiments described in this section, it is demonstrated that chemical complementation can read out cellulase activity and can produce a 200-fold enrichment in active cellulases from a 1:100 active:inactive cellulase pool after one round of selection. The URA3 counter selection was then applied to the directed evolution of cellulases using three cellulases from *Erwinia carotovora*: CelN and CelA and CeV (Olsen, O. et al., 1996, Biotechnology (NY) 14: 71-6; Park, et al., 1997, Biochem. Biophys. Res. Commun. 241: 636-41; Bell, et al., 2004, Proc. Natl. Acad. Sci. USA 101: 11105-10). Using DNA family shuffling as the mutagenesis and chemical complementation as the selection platform, cellulase variants were isolated with 3.6-fold and 5.3-fold increases (Cellulase 1 (CELLVAR2) and Cellulase 2 of Table 1A, respectively) in cellulase activity on p-nitrophenyl cellobioside (pNPC). This selection methodology enables a high-throughput assay that may be used for directed evolution or cloning of cellulase variants with increased catalytic activity for the conversion of biomass to fuel ethanol (FIG. 24).

14.1 Methods

Reporter Yeast Strain Construction

The URA3 gene from pMW112 was recombined at the ura3-52 locus of FY251 (MATa trp1Δ63 his3Δ200 ura3-52 leu2Δ 1 Gal+) and selected on plates lacking uracil to give strain VC2169Y. Vectors pBC398 and pKB521 carrying the GR-B42 and LexA-DHFR constructs were transformed into VC2169Y to give strain VC2291Y. The LexA(4op)-URA3 reporter construct was obtained by fusion PCR of the LexA (4op) from pMW112 and the Spo13-URA3 fusion gene from MaV95 (Vidal et al., 1996, Proc. Natl. Acad. Sci. USA 93: 10315-20). The reporter construct was inserted into pPPY2148 to create pPPY2176. The reporter construct was amplified with oligos carrying 30 bp homology to the URA3 promoter and the URA3 gene, recombined at the URA3 locus of VC2291Y, and selected on 5-FOA plates to give the reverse yeast three-hybrid strain VC2204Y. Recombination was confirmed phenotypically and by colony PCR.

Cellulase Enrichment Assay.

A library containing 1:100 ratio of active cellulase Cel7B to inactive cellulase (Cel7B:E197A) variants was transformed into the reverse yeast three-hybrid strain to give a library size of 104. Nine random colonies were analyzed to establish the library integrity. The library was plated under non-selective conditions lacking the corresponding auxotrophs and incubated at 30° C. After three days, the cells were resuspended in sterile distilled water to an OD600=1 and 10 μl were used to carry out the enrichment assay in synthetic media containing 2% galactose, 2% raffinose, 0.2% 5-FOA, and 1 μM Mtx-Cel-Dex, and lacking histidine, tryptophan, and leucine, in a final volume of 200 μl. After 5 days of selection, a sample was plated under non-selective conditions lacking the corresponding auxotrophs and nine random colonies were analyzed by colony PCR and restriction digest. A NcoI site was incorporated into the Cel7B:E197A variant when the glutamic acid nucleophile was mutated to an alanine in order to facilitate the restriction analysis.

Cellulase Mutagenesis.

The DNA shuffling and expression vector pPPY2148 was constructed by digesting p425Met25 (ATCC 87323) with HindIII and PstI and introducing an 800 bp stuffer flanked by SfiI sites. A C-terminus 6-Histag was added to the catalytic domains, signal peptides removed, of CelN, CelA, and CelV, and subcloned into pPPY2148 to create vectors pPPY2230, pPPY2234, and pPPY2236 respectively. The cellulase genes were shuffled using standard procedures with slight modification (Zhao & Arnold, 1997, Nucleic. Acids. Res. 25: 1307-8). The shuffled product was re-amplified using oligos containing 30 bp homology to the promoter and terminator regions of the shuffling vector and the product was purified in a 2% agarose gel.

Yeast Transformation and Cellulase Selection.

The reverse yeast three-hybrid strain, VC2204Y, was transformed with the 12.5 μg of shuffled cellulases and 3.6 μg of cut vector via electroporation using high transformation efficiency procedures with slight variations to give a library of $10^8$ (Colby, et al., 2004, Methods Enzymol. 388: 348-58). The library was resuspended in 1 ml YPD and recovered in a 30° C. shaker for 1 hour. After recovery, 10 μl were used to determine the library size and the rest was resuspended in selection media (synthetic media at pH 5 containing 2% galactose, 2% raffinose, 0.2% 5-FOA, and 1 μM Mtx-Cel-Dex, lacking histidine, tryptophan, and leucine) to a final volume of 2 ml. The selection was run for nine days, and samples were taken on days 5, 6 and 8. To isolate selected variants, samples of the selection were diluted and plated under non-selective conditions.

Secondary Screen for Aldehyde Formation Using CMC.

The secondary screen for aldehyde formation using CMC was adapted to be carried out in a 96-well plate format (Jue et al., 1985, J. Biochem. Biophys. Methods. 11: 109-15). The twenty-two colonies isolated before selection and the twenty-two colonies isolated after 5 days of selection were grown in 10 ml synthetic media lacking leucine for two days. The same number of cells (2×107) from each cell culture were arrayed on a 96-well plate and lysed using 100 μl YPER (Novagen). The cell extract (80 μl) was transferred onto a second 96-well plate containing 120 μl 2% CMC (low viscosity, Sigma) in 0.1M sodium acetate buffer pH 5, and the reaction was incubated at 37° C. for 24 hrs. The next day, 10 μl of the reaction mixture were incubated with 90 μl of 0.1% tetrazolium blue (0.5M potassium sodium tartrate, 0.05M sodium hydroxide) and heated at 98° C. for 10 min. The reaction was cooled to room temperature and absorption at 660 nm was taken immediately.

In Vitro Kinetic Characterization with pNPC.

The three starting cellulases and the improved cellulase variants were subcloned into the *E. coli* T7 vector, pAED4, between NdeI and HindIII sites to give vectors pPPY2256 (CelN), pPPY2258 (CelA), pPPY2257 (CelV), pPPY2291 (Cel_3.7), and pPPY2292 (Cel_5.7). The cellulases were purified using Quick spin Ni-NTA affinity column (Qiagen). Protein concentration was determined using the extinction coefficient of the starting genes ($\epsilon$=76670) and absorption at 280 nm. To determine the kinetic constants for the hydrolysis of pNPC, the cellulase chimeras were incubated at room temperature in phosphate buffer (25 mM K2HPO4, 100 mM NaCl, pH 7) containing seven different concentrations of pNPC ranging from 12 mM to 0.185 mM. The release of p-nitrophenol ($\epsilon$pH 7=4000M−1 cm−1, A420) was recorded continuously in a SpectraMax Plus 384 spectrophotometer at 420 nm.

14.2 Results

In the yeast three-hybrid system the DBD and the AD are split in half and each half is fused to a protein receptor for one of the small molecules. In the Mtx-Dex yeast three-hybrid system, the DBD is fused to the Mtx receptor protein dihydrofolate reductase (DBD-DHFR) and the AD is fused to the Dex receptor protein glucocorticoid receptor (AD-GR). In the presence of Mtx-Dex, AD-GR is recruited to DBD-DHFR, which is bound upstream of the reporter gene, effectively reconstituting the transcriptional activator, and leading to transcription of the downstream reporter gene.

To adapt the yeast three-hybrid system to read out cellulase catalysis, the linkage between Mtx and Dex is replaced with the substrate for the reaction, cellulose, and the cellulase enzyme is added as the fourth component to the system. For the cellulase growth selection, LexA is used as the DBD and B42 as the AD. Both the DBD-DHFR and AD-GR fusion proteins are expressed from a Gal1 promoter in a 2μ plasmid. The reporter gene is URA3, which in the presence of 5-fluoroorotic acid (5-FOA) produces 5-fluorouracil (5-FU) and so is toxic. Cell survival is achieved by cleavage of the heterodimeric small molecule, disrupting expression of the URA3 gene (FIG. 25). For the directed evolution of cellulases, the catalytic domains, signal peptides removed, of the three starting cellulases, *E. carotovora*, CelN, CelA, and CelV, were shuffled and introduced into a 2μ yeast expression vector under the repressible Met25 promoter Mtx-Cel-Dex Substrate.

The cellulose substrate for the chemical complementation selection must incorporate the Mtx and Dex ligands, yet still be efficient substrates for cellulases. Since *E. carotovora* CeA, CelN, and CelV, belong to the family 5 subfamily 2 glycosylhydrolase, we took advantage of the extensive crystallographic data on the cellulase *Bacillus agaradharens* Cel5A, which shares 68% amino acid sequence identity with the starting cellulases, to guide the design of the Mtx-Cel-Dex substrate (Davies, et al., 1998, Biochemistry 37: 1926-32; Davies, et al., 1998, Biochemistry 37: 11707-13; Varrot, et al., 2000, J. Mol. Biol. 297: 819-28; Varrot, et al., 2001, Acta Crystallogr. D Biol. Crystallogr. 57: 1739-42; Varrot & Davies, 2003, Acta Crystallogr. D Biol. Crystallogr. 59: 447-52). The high-resolution structure of *B. agaradharens* Cel5A predicts five subsites in the active site that accommodate five glucose units (−3, −2, −1, 1, 2). Given that in other cellulases four subsites (−2, −1, 1, 2) contribute most to the binding energy, with the fifth contributing only slightly, the cellulase substrate was constructed with four saccharides (Schou et al., 1993, Eur. J. Biochem. 217: 947-53). The synthesis of Mtx-Cel-Dex was carried out chemoenzymatically. Mtx-Lac-F and Dex-Cel were synthesized using previously published strategies and the linkage between the two halves was performed by Cel7B:E197A glycosynthase (Lin et al., 2004, J. Am. Chem. Soc. 126:15051-9).

Reverse Yeast Three-Hybrid Strain Construction.

Previously, chemical complementation has been adapted to detect bond cleavage reactions as a screen using lacZ as the reporter gene (Baker, K. et al., 2002, Proc. Natl. Acad. Sci. USA 99: 16537-42). Modifying chemical complementation to detect bond cleavage reactions as a growth selection is not trivial because, in a counter-selection, basal transcription of the toxic reporter gene may stress the cells, not only affecting their growth but also decreasing the dynamic range of the system. To tailor chemical complementation to detect cellulase activity as a growth selection, a counter-selection yeast strain had to be developed in which enzyme catalysis relieves transcription of a toxic reporter gene. In yeast, the URA3 gene product, OMP decarboxylase, converts 5-FOA to 5-FU, which is toxic to the cell, allowing for counter selection in the presence of 5-FOA. With the idea of carrying the counter selection in liquid culture, we developed a URA3 reverse yeast three-hybrid strain that performs efficiently in this medium. Precedent in the literature of a URA3 reverse yeast two-hybrid strain supported the feasibility of constructing a URA3 reverse yeast three-hybrid strain (Vidal, et al., 1996, Proc. Natl. Acad. Sci. USA 93: 10315-20; Huang, et al., 1997, Proc. Natl. Acad. Sci. USA 94: 13396-401).

To reduce the basal expression of the toxic URA3 reporter gene, the gene was placed under control of the tightly regulated Spo13 promoter (Vidal, et al., 1996, Proc. Natl. Acad. Sci. USA 93: 10315-20), in front of which four LexA operons (LexA(4op)) would have to be placed in order for the DBD to be recruited upstream of the reporter gene. One-step introduction of a LexA(4op)-Spo13-URA3 construct into our chemical complementation yeast strain was not convenient because our yeast strain has a ura3-52 background, conferring a Ura phenotype. Simple introduction of the LexA(4op)-Spo13-URA3 construct into this strain would also lead to a Ura$^-$ phenotype. As there is no phenotypic change, this introduction cannot be selected or screened. Therefore, we resorted to a three-step approach to construct the reverse yeast three-hybrid strain (FIG. 26A).

First, we recombined the URA3 gene at the ura3-52 locus of our chemical complementation yeast strain, FY251, and selected for Ura$^+$ phenotype on medium lacking uracil to create VC2169. Next, the vectors carrying the DBD-DHFR and GR-B42 constructs were introduced into VC2169 and selected on plates lacking uracil, histidine, and tryptophan to create VC2291. Finally, we introduced the LexA(4op) and the Spo13 promoter upstream of the URA3 gene and selected for Ura$^-$ phenotype on medium containing 5-FOA. This selection provided numerous reverse three-hybrid colonies. Three colonies were used to optimize the reverse yeast three-hybrid system for the highest fold increase in activation in the presence of 10 μM Mtx-Dex by measuring the difference between cell survival and cell death. Mtx-Dex was used, instead of Mtx-Cel-Dex, for the optimization of the system as the cellulose linker is not necessary for the system's functioning, and the synthesis of Mtx-Dex is simpler than that of Mtx-Cel-Dex. The system was optimized by varying the level of galactose, which affects the concentration of DBD-DHFR and AD-GR in the system, and 5-FOA, which controls the toxicity level of the reporter gene. Galactose levels ranging from 1 to 2% and 5-FOA concentrations ranging from 0.1 to 0.5% were tested simultaneously. The largest fold activation was obtained with synthetic media containing 2% galactose, 2% raffinose, 0.2% 5-FOA, and 10 μM Mtx-Dex, and lacking histidine and tryptophan. We observed that 5-FOA concentrations beyond 0.3% are detrimental for cell growth, while reducing the concentration to 0.1% leads to cell growth independent of Mtx-Dex. At 0.2% 5-FOA, cell growth was Mtx-Dex dependent and the inherent toxicity of 5-FOA was not overly detrimental to the cell, thus allowing us to indirectly increase the stringency of the URA3 counter selection by increasing the 5-FOA concentration up to 0.3% if necessary. With the optimized conditions for the reverse three-hybrid system in hand, we collected two hundred and ten colonies from the reverse yeast three-hybrid selection to isolate the reverse yeast three-hybrid strain with the largest fold activation in liquid medium. We found that the increase in activation was strain dependent and that five days of selection generated strains with increases in activation spanning 0.7 to 5-fold. The ten strains with the highest increase in activation were tested in triplicate in the presence of 0 and 10 μM Mtx-Dex. To determine the minimum small molecule concentration necessary to elicit transcription activation we tested the strain with the highest fold increase in activation, VC2204, with 0, 1, 5, and 10 μM Mtx-Dex (FIG. 26B). The reverse three-hybrid strain showed an on-off behavior between 1-10 μM Mtx-Dex, meaning that with 1 μM Mtx-Dex all binding sites for the small-molecule are saturated, thus allowing us to carry the URA3 counter selection experiments at 1 μM small molecule concentration. We then tested VC2204 with 1 μM Mtx-Cel-Dex, the small-molecule to be used in the cellulase selection, to confirm activation of the system. At 1 μM Mtx-Cel-Dex, the reverse yeast three hybrid system shows a only 2-fold increase in activation, which we attribute to poor cell permeability of the Mtx-Cel-Dex substrate (FIG. 26B). However, knowing that small changes in enzyme activity are amplified in liquid selections, we believed that a 2-fold increase in activation would be sufficient to detect cellulase activity.

Chemical Complementation Links Cellulase Activity to URA3 Transcription In Vivo.

The reverse yeast three-hybrid system was modified to detect cellulase activity by introducing the cellulase from *H. insolens* Cel7B as a fourth component to the system. Using Mtx-Cel-Dex as the substrate for the cellulase, we optimized the URA3 counter selection to detect *H. insolens* Cel7B activity by changing the pH of the media, which controls enzyme behavior inside the cell. The activity of the cellulase in the URA3 counter selection was tested in media ranging from pH 4 through pH 7 in order to optimize the behavior of the cellulase inside the cell. Maximal cellulase activity was detected at pH 5. The final conditions for the URA3 counter selection were synthetic media at pH 5 containing 2% galactose, 2% raffinose, 0.2% 5-FOA, and 1 µM Mtx-Cel-Dex, and lacking histidine, tryptophan, and leucine. Using the optimized conditions for the URA3 counter selection, we showed that expression of *H. insolens* Cel7B in the presence of Mtx-Cel-Dex conferred a growth advantage to the reverse yeast three-hybrid selection strain, presumably because the Cel7B cellulase catalyzed the cleavage of Mtx-Cel-Dex, thus halting the expression of the toxic URA3 reporter gene. We performed this experiment in liquid culture as we were planning to carry out the directed evolution of cellulases in liquid culture. FIG. 27A shows cell density measured as absorption at 600 nm in the absence of Mtx-Cel-Dex and the presence of empty vector, in the presence of 1 µM Mtx-Cel-Dex and presence of active Cel7B, in the presence of 1 µM Mtx-Cel-Dex and the presence of an inactive mutant of Cel7B (Cel7B: E197A), obtained by mutation of the nucleophilic glutamic acid to alanine, and in the presence of 1 uM Mtx-Dex and the presence of empty vector. Under selection conditions, presence of empty vector in the absence of Mtx-Cel-Dex leads to cell growth, hence an enhanced absorption at 600 nm. Next, we showed that transcription activation is dependent on the catalytic activity of Cel7B. The reverse yeast three-hybrid strain expressing either Cel7B or the inactive cellulase variant Cel7B:E197A was grown in the presence of 1 uM Mtx-Cel-Dex. Cellulase activity cleaves Mtx-Cel-Dex, disrupting dimerization and halting transcription of the URA3 reporter gene, leading to increased cell growth and hence an increase in $OD_{600}$. The inactive cellulase mutant Cel7B:E197A does not cleave the Mtx-Cel-Dex substrate, leading to transcription of the toxic URA3 reporter gene and hence a lack of increase in $OD_{600}$. Finally, presence of empty vector in the presence of 1 µM Mtx-Dex leads to cell death, hence a lack of increase in $OD_{600}$. This second control was performed as a redundancy, with the more readily synthesized Mtx-Dex instead of Mtx-Cellulose-Dex as the more stringent control, inactive cellulase, was performed in the presence of Mtx-Cellulose-Dex. Together these data indicate that Cel7B activity can be detected using chemical complementation.

To further confirm that the URA3 counter selection could effectively detect cellulase activity in liquid culture, we carried out an enrichment assay for cellulase activity (FIG. 27B). A library containing 1:100 ratio of Cel7B to inactive Cel7B: E197A variants was transformed into the reverse yeast three-hybrid strain. To facilitate the colony analysis, a unique NcoI restriction site was introduced in the Cel7B:E197A variant at the A197 position. Before selection, nine colonies were analyzed by colony PCR and restriction mapping to determine the integrity of the library. As expected from a 1:100 ratio, all nine colonies were Cel7B:E197A. After five days of selection in liquid culture, a sample of the selection was plated, and nine random colonies were analyzed. Of these nine colonies, six contained Cel7B and three contained the Cel7B:E197A inactive cellulase variant, which corresponds to an enrichment of 200-fold enrichment after a single round of selection.

Directed Evolution of Cellulases.

The URA3 counter selection was used to evolve cellulases with increased catalytic efficiency. We used DNA family shuffling as the mutagenesis technique because it is technically simple and has been used to obtain the largest increases in catalytic activity in recent years (Castle, et al., 2004, Science 304: 1151-4; Park, et al., 2006, Science 311: 535-8). Therefore, we acquired three cellulases, *E. carotovora* CelN, CelA, and CelV, which share 77-90% sequence identity at the nucleotide level, to generate a library of cellulase chimeras. To reach a large library size, we took advantage of the efficient recombination machinery of *S. cerevisiae* to introduce the library of shuffled cellulases into the expression vector via in vivo homologous recombination (Colby, et al., 2004, Methods Enzymol. 388: 348-58; Abecassis, et al., 2000, Nucleic. Acids. Res. 28: E88). The shuffled cellulase library was amplified using primers carrying 30 base pairs identical to the promoter and terminator regions of the expression vector to ensure successful recombination. The shuffled cellulase library was co-transformed with linearized expression vector via electroporation to produce a library of $10^8$.

The selection was run for a total of nine days. Twenty-two variants were isolated before selection and twenty-two variants were isolated after five days of selection. To determine whether longer exposure to selection conditions leads to the isolation of cellulase variants with even higher catalytic activities, we also isolated eight variants after six days of selection and eight variants after eight days of selection. It is worth noting that we could have isolated any number of cellulase variants on any day of the selection as the selection was run in liquid culture and required only the taking of a small sample and its plating under non-selective conditions to isolate more cellulase variants. Sequencing of the 40 variants isolated after selection showed an average of 5 to 12 crossovers. To determine whether the URA3 counter selection was indeed selecting for variants with increased cellulase activity, we retransformed the 62 variants into the URA3 counter selection strain and tested the crude cell extract for cellulase activity using a colorimetric screen based on the quantification of aldehyde formation using carboxymethylcellulose (CMC) as the substrate (Jue et al., 1985, *J. Biochem. Biophys. Methods*. 11: 109-15). As FIG. 27C shows, the mean cellulase activity of the twenty-two variants isolated after five days of selection is higher than the mean cellulase activity of variants isolated before selection. This difference is statistically significant ($p<0.005$), indicating that that the URA3 counter selection is indeed selecting for cellulase variants with increased catalytic activity. There is no statistical difference, however, between the cellulase activities of colonies isolated after five days of selection and those isolated after six and eight days of selection.

In Vitro Characterization of Evolved Cellulase Variants.

We carried out the in vitro kinetic characterization of four cellulases isolated on day eight using pNPC, the standard substrate for measuring cellulase kinetics. The four variants were overexpressed in *E. coli* and purified using a Ni-NTA affinity column. Two variants had very low expression levels with the conditions used and no in vitro kinetics were measured. The other two variants, Cel_3.7 (cellulase 1) and Cel_5.7 (cellulase 2) showed very good expression levels and 3.7-fold (cellulase 1) and 5.7-fold (cellulase 2) increases in catalytic efficiency, respectively, over the best starting cellulase, CelN. Table 4 shows the kinetics for the starting cellulase genes and the improved cellulase variants.

TABLE 4

Kinetics of the parent genes CelN, CelA, CelV and the evolved variant on pNPC

| Cellulase | $k_{cat}$ (sec$^{-1}$) | Km (M) | $K_{cat}$/Km (M$^{-1}$sec$^{-1}$) |
|---|---|---|---|
| Cellulase N | $1.3 \times 10^3$ | $3.4 \times 10^{-3}$ | $3.7 \times 10^5$ |
| Cellulase A | $1.4 \times 10^3$ | $7.2 \times 10^{-3}$ | $1.92 \times 10^5$ |
| Cellulase V | $1.1 \times 10^3$ | $4.6 \times 10^{-3}$ | $2.4 \times 10^5$ |
| Cel__3.7 (cellulase 1) | $4.3 \times 10^3$ | $3.2 \times 10^{-3}$ | $1.4 \times 10^6$ |
| Cel__5.7 (cellulase 2) | $5.2 \times 10^3$ | $2.47 \times 10^{-3}$ | $2.1 \times 10^6$ |

CELV = CELT from before. Between last year and now they actually name that variant CELV.

Sequencing of the improved cellulase variants revealed nucleotide segments from CelV, CelA and CelN. Cel__3.7 (cellulase 1) contains nine crossovers. When compared to the most active starting cellulase, CelN, Cel__3.7 (cellulase 1) differs by nine point mutations: S126N, D157E, Q186L L193M, V254I, T288A, E295A, G30A, and G304S. A homology model of Cel__3.7 (cellulase 1) was made, utilizing the B. agaradherans Cel5A structure (SwissProt: O85465; PDB: 1h5v) with the inhibitor methyl 4,4II,4III,4IV-tetrathio-α-cellopentoside bound to the active site, using Swiss-Model (FIG. 28A). The eight mutations accessible with the homology model map onto the surface of the enzyme, away from the extended carbohydrate binding site. Although the B. agaradharens Cel5A X-ray structure does not cover the region where the ninth mutation is positioned, we manually extended the chain by three more residues and concluded that the last mutation is on the N-terminus of the TIM barrel and away from the C-terminus catalytic region.

When Cel__5.7 (cellulase 2) is compared to the most active starting cellulase, CelN, Cel__5.7 differs by eight point mutations: A86V, S126N, E154D, T172S, C208R, T262S, A267T, and A272T. A homology model of Cel__5.7 (cellulase 2) was made, again utilizing the same structure of B. agaradherans Cel5A, using Swiss-Model (FIG. 28b)[38]. Four mutations are in the C-terminus loops that compose the extended carbohydrate binding site, while the other 4 map onto the surface of the enzyme. Although mutation T172S is located in C-terminus loop 5, it is 15 Å away from closest hexose ring in the substrate inhibitor. Mutations T262S, A267T, A272T are located in C-terminus loop 8. The mutation T262S is the closest to the substrate inhibitor, 6 Å away from the 6'-OH of the hexose ring in the −3 subsite. Interestingly, only one mutation is present in both of the evolved variants, S126N. This mutation is located at the N-terminus of the barrel and points towards the solvent.

Various publications are cited herein, the contents of which are hereby incorporated by reference in their entireties.

| EC | Enzyme | Linkage | Substrate | Notes |
|---|---|---|---|---|
| 3.2.1.1 | Alpha-amylase | 1,4-alpha-D-glucosidic | maltopentaose | |
| 3.2.1.2 | Beta-amylase | 1,4-beta-D-glucosidic | maltotetraose | |
| 3.2.1.3 | Glucan 1,4-alpha-glucosidase | terminal 1,4-linked alpha-D-glucose | cyclodextrin | |
| 3.2.1.4 | Cellulase | 1,4-beta-D-glucosidic | cellotetraose | |
| 3.2.1.6 | Endo-1,3(4)-beta-glucanase | 1,3- or 1,4-beta-D-glucans, requires C-3 substitution of glucose whose reducing group is involved in the hydrolyzed linkage | NAG-NAG-BMA-MAN-MAN-MAN-MAN | |
| 3.2.1.7 | Inulinase | 2,1-beta-D-fructosidic | inulin | |
| 3.2.1.8 | Endo-1,4-beta-xylanase | 1,4-beta-D-xylosidic | xylobiose | |
| 3.2.1.10 | Oligo-1,6-glucosidase | 1,6-alpha-D-glucosidic | isomaltose | |
| 3.2.1.11 | Dextranase | 1,6-alpha-D-glucosidic | dextran | |
| 3.2.1.14 | Chitinase | N-acetyl-beta-D-glucosaminide 1,4-beta- | chitin | |
| 3.2.1.15 | Polygalacturonase | 1,4-alpha-D-galactosiduronic | pectate | |
| 3.2.1.17 | Lysozyme | 1,4-beta-linkages between N-acetylmuramic acid and N-acetyl-D-glucosamine residues in a peptidoglycan, and between N-acetyl-D-glucosamine residues in chitodextrins | | |
| 3.2.1.18 | Exo-alpha-sialidase | alpha-(2->3)-, alpha-(2->6)-, alpha-(2->8)-glycosidic linkages of terminal sialic residues | | |
| 3.2.1.20 | Alpha-glucosidase | terminal, non-reducing 1,4-linked alpha-D-glucose | | |
| 3.2.1.21 | Beta-glucosidase | terminal, non-reducing beta-D-glucose | dimboa-beta-d-glucoside | |
| 3.2.1.22 | Alpha-galactosidase | terminal, non-reducing alpha-D-galactose | melibiose | |
| 3.2.1.23 | Beta-galactosidase | terminal non-reducing beta-D-galactose residues in beta-D-galactosides | lactose | |
| 3.2.1.24 | Alpha-mannosidase | terminal, non-reducing alpha-D-mannose residues in alpha-D-mannosides | | |
| 3.2.1.25 | Beta-mannosidase | terminal, non-reducing beta-D-mannose | | |
| 3.2.1.26 | Beta-fructofuranosidase | terminal non-reducing beta-D-fructofuranoside | raffinose | |
| 3.2.1.28 | Alpha,alpha-trehalase | alpha,alha-trehalose | alpha,alha-trehalose | |
| 3.2.1.31 | Beta-glucuronidase | beta-D-glucuronoside | beta-D-glucuronoside | |
| 3.2.1.32 | Xylan endo-1,3-beta-xylosidase | 1,3-beta-D-glycosidic linkages in 1,3-beta-D-xylans | | |
| 3.2.1.33 | Amylo-alpha-1,6-glucosidase | 1->6)-alpha-D-glucosidic branch linkages in glycogen phosphorylase limit dextrin | | |
| 3.2.1.35 | Hyaluronoglucosaminidase | 1->4-linkages between N-acetyl-beta-D-glucosamine and D-glucuronate residues in hyaluronate | hyaluronan | |
| 3.2.1.36 | Hyaluronoglucuronidase | 1,3-linkages between beta-D-glucuronate and N-acetyl-D-glucosamine residues in hyaluronate | hyaluronan | |

-continued

| EC | Enzyme | Linkage | Substrate | Notes |
|---|---|---|---|---|
| 3.2.1.37 | Xylan 1,4-beta-xylosidase | 1,3-beta-D-glycosidic linkages in 1,3-beta-D-xylans | | |
| 3.2.1.38 | Beta-D-fucosidase | terminal non-reducing beta-D-fucose residues in beta-D-fucosides | | |
| 3.2.1.39 | Glucan endo-1,3-beta-D-glucosidase | 1,3-beta-D-glycosidic linkages in 1,3-beta-D-glucans | laminarin, laminaribiose | |
| 3.2.1.40 | Alpha-L-rhamnosidase | terminal non-reducing alpha-L-rhamnose residues in alpha-L-rhamnosides | | |
| 3.2.1.41 | Pullulanase | (1->6)-alpha-D-glucosidic linkages in pullulan and in amylopectin and glycogen, and the alpha- and beta-limit dextrins of amylopectin and glycogen | pullulan, maltotriose | |
| 3.2.1.42 | GDP-glucosidase | GDP-glucose | GDP-glucose | |
| 3.2.1.43 | Beta-L-rhamnosidase | terminal, non-reducing beta-L-rhamnose residues in beta-L-rhamnosides | | |
| 3.2.1.44 | Fucoidanase | 1,2-alpha-L-fucoside linkages in fucoidan | fucoidan | |
| 3.2.1.45 | Glucosylceramidase | D-glucosyl-N-acylsphingosine | D-glucosyl-N- | |
| 3.2.1.46 | Galactosylceramidase | D-galactosyl-N-acylsphingosine | D-galactosyl-N-acylsphingosine | |
| 3.2.1.47 | Galactosylgalactosylglucosylceramidase | D-galactosyl-D-galactosyl-D-glucosyl-N-acylsphingosine | D-galactosyl-D-galactosyl-D-glucosyl-N- | |
| 3.2.1.48 | Sucrose alpha-glucosidase | sucrose, maltose | sucrose, maltose | |
| 3.2.1.49 | Alpha-N-acetylgalactosaminidase | terminal non-reducing N-acetyl-D-galactosamine residues in N-acetyl-alpha-D-galactosaminides | N-acetyl-d-glucosamine | |
| 3.2.1.50 | Alpha-N-acetylglucosaminidase | erminal non-reducing N-acetyl-D-glucosamine residues in N-acetyl-alpha-D-glucosaminides | | |
| 3.2.1.51 | Alpha-L-fucosidase | alpha-L-fucoside | alpha-L-fucoside | |
| 3.2.1.52 | Beta-N-acetylhexosaminidase | terminal non-reducing N-acetyl-D-hexosamine residues in N-acetyl-beta-D-hexosaminides | Di(n-acetyl-d-glucosamine) | |
| 3.2.1.53 | Beta-N-acetylgalactosaminidase | terminal non-reducing N-acetyl-D-galactosamine residues in N-acetyl-beta-D-galactosaminides | | |
| 3.2.1.54 | Cyclomaltodextrinase | cyclomaltodextrin | cyclomaltodextrin | |
| 3.2.1.55 | Alpha-N-arabinofuranosidase | terminal non-reducing alpha-L-arabinofuranoside residues in alpha-L-arabinosides | arabinoxylan | |
| 3.2.1.56 | Glucuronosyl-disulfoglucosamine glucuronidase | 3-D-glucuronosyl-N(2)-,6-disulfo-beta-D-glucosamine | 3-D-glucuronosyl-N(2)-,6-disulfo-beta-D-glucosamine | |
| 3.2.1.57 | Isopullulanase | panose | panose | |
| 3.2.1.58 | Glucan 1,3-beta-glucosidase | beta-D-glucose units from the non-reducing ends of 1,3-beta-D-glucans | 2,4-dinitrophenyl 2-deoxy-2-fluoro-beta-d-glucopyranoside | |
| 3.2.1.59 | Glucan endo-1,3-alpha-glucosidase | 1,3-alpha-D-glucosidic linkages in isolichenin, pseudonigeran and nigeran | | |
| 3.2.1.60 | Glucan 1,4-alpha-maltotetraohydrolase | 1,4-alpha-D-glucosidic linkages in amylaceous polysaccharides | maltotetraose | |
| 3.2.1.61 | Mycodextranase | 1,4-alpha-D-glucosidic linkages in alpha-D-glucans containing both 1,3- and 1,4-bonds | | |
| 3.2.1.62 | Glycosylceramidase | glycosyl-N-acylsphingosine | glycosyl-N-acylsphingosine | |
| 3.2.1.63 | 1,2-alpha-L-fucosidase | methyl-2-alpha-L-fucopyranosyl-beta-D-galactoside | methyl-2-alpha-L-fucopyranosyl-beta-D-galactoside | |
| 3.2.1.64 | 2,6-beta-fructan 6-levanbiohydrolase | 2,6-beta-D-fructofuranan | 2,6-beta-D-fructofuranan | |
| 3.2.1.65 | Levanase | 2,6-beta-D-fructofuranosidic linkages in 2,6-beta-D-fructans (levans) containing more than 3 fructose units | kestose? | |
| 3.2.1.66 | Quercitrinase | quercitrin | quercitrin | |
| 3.2.1.67 | Galacturan 1,4-alpha-galacturonidase | (1,4-alpha-D-galacturonide)(n) | | |
| 3.2.1.68 | Isoamylase | (1->6)-alpha-D-glucosidic branch linkages in glycogen, amylopectin and their beta-limit dextrins | amylopectin | |
| 3.2.1.70 | Glucan 1,6-alpha-glucosidase | (1->6)-alpha-D-glucosidic linkages in 1->6-alpha-D-glucans | | |
| 3.2.1.71 | Glucan endo-1,2-beta-glucosidase | 1,2-glucosidic linkages in 1,2-beta-D-glucans | | |
| 3.2.1.72 | Xylan 1,3-beta-xylosidase | non-reducing termini of 1,3-beta-D-xylans | | |
| 3.2.1.73 | Licheninase | 1,4-beta-D-glucosidic linkages in beta-D-glucans containing 1,3- and 1,4-bonds | lichenin? | |
| 3.2.1.74 | Glucan 1,4-beta-glucosidase | 1,4-beta-D-glucans | | |
| 3.2.1.75 | Glucan endo-1,6-beta-glucosidase | 1,4-alpha-D-glucosidic linkages in, amylaceous polysaccharides | | |
| 3.2.1.76 | L-iduronidase | 1,6-beta-D-glucans | lutean, pustulan | |
| 3.2.1.77 | Mannan 1,2-(1,3)-alpha-mannosidase | 1,4-beta-D-mannosidic | mannan, galactomannan, glucomannan | |

-continued

| EC | Enzyme | Linkage | Substrate | Notes |
|---|---|---|---|---|
| 3.2.1.78 | Mannan endo-1,4-beta-mannosidase | 1,4-beta-D-mannosidic | mannan, galactomannan, glucomannan | |
| 3.2.1.80 | Fructan beta-fructosidase | terminal, non-reducing 2,1- and 2,6-linked beta-D-fructofuranose | inulin, levan, sucrose | |
| 3.2.1.81 | Beta-agarase | 1,4-beta-D-galactosidic linkages in agarose | | |
| 3.2.1.82 | Exo-poly-alpha-galacturonosidase | pectic acid | pectic acid | |
| 3.2.1.83 | Kappa-carrageenase | 1,4-beta-D- between D-galactose 4-sulfate and 3,6-anhydro-D-galactose | kappa-carrageenans | |
| 3.2.1.84 | Glucan 1,3-alpha-glucosidase | terminal 1,3-alpha-D-glucosidic | | |
| 3.2.1.85 | 6-phospho-beta-galactosidase | 6-phospho-beta-D-galactoside | 6-phospho-beta-D-galactoside | |
| 3.2.1.86 | 6-phospho-beta-glucosidase | 6-phospho-beta-D-glucosyl-(1,4)-D-glucose | 6-phospho-beta-D-glucosyl-(1,4)-D-glucose | |
| 3.2.1.87 | Capsular-polysaccharide endo-1,3-alpha-galactosidase | 1,3-alpha-D-galactosidic linkages in Aerobacter aerogenes capsular polysaccharide | | |
| 3.2.1.88 | Beta-L-arabinosidase | beta-L-arabinoside | | |
| 3.2.1.89 | Arabinogalactan endo-1,4-beta-galactasidase | 1,4-beta-D-galactosidic linkages in arabinogalactans | arabinogalactan | |
| 3.2.1.91 | Cellulose 1,4-beta-cellobiosidase | 1,4-beta-D-glucosidic linkages in cellulose and cellotetraose | cellotetraose | |
| 3.2.1.92 | Peptidoglycan beta-N-acetylmuramidase | terminal, non-reducing N-acetylmuramic | | |
| 3.2.1.93 | Alpha, alpha-phosphotrehalase | Alpha, alpha-trehalose 6-phosphate | | |
| 3.2.1.94 | Glucan 1,6-alpha-isomaltosidase | 1,6-alpha-D-glucosidic | | |
| 3.2.1.95 | Dextran 1,6-alpha-isomaltotriosidase | 1,6-alpha-D-glucosidic | dextran | |
| 3.2.1.96 | Mannosyl-glycoprotein endo-beta-N-acetylglucosaminidase | N,N'-diacetylchitoblosyl | high-mannose glycopeptides and glycoproteins containing the -(Man(GlcNAc)(2))Asn-glycopeptides, glycoproteins | |
| 3.2.1.97 | Glycopeptide alpha-N-acetylgalactosaminidase | terminal D-galactosyl-N-acetyl-alpha-D-galactosaminidic | | |
| 3.2.1.98 | Glucan 1,4-alpha-maltohexaosidase | 1,4-alpha-D-glucosidic | amylaceous | |
| 3.2.1.99 | Arabinan endo-1,5-alpha-L-arabinosidase | 1,5-alpha-arabinofuranosidic | 1,5-arabinans | |
| 3.2.1.100 | Mannan 1,4-mannobiosidase | 1,4-beta-D-mannosidic | 1,4-mannans | |
| 3.2.1.101 | Mannan endo-1,6-alpha-mannosidase | 1,6-alpha-D-mannosidic | 1,6-mannans | |
| 3.2.1.102 | Blood-group-substance endo-1,4-beta-galactosidase | 1,4-beta-D-galactosidic | blood group A and b substances | |
| 3.2.1.103 | Keratan-sulfate endo-1,4-beta- | 1,4-beta-D-galactosidic | keratan sulfate | |
| 3.2.1.104 | Steryl-beta-glucosidase | cholesteryl-beta-D-glucoside | cholesteryl-beta-D- | |
| 3.2.1.105 | Strictosidine beta-glucosidase | strictosidine | strictosidine | |
| 3.2.1.106 | Mannosyl-oligosaccharide glucosidase | non-reducing terminal glucose | Glc(3)Man(9)GlcNAc(2) | |
| 3.2.1.107 | Protein-glucosylgalactosylhydroxylysine glucosidase | protein alpha-D-glucosyl-1,2-beta-D-galactosyl-L-hydroxylysine | protein alpha-D-glucosyl-1,2-beta-D-galactosyl-L-hydroxylysine | |
| 3.2.1.108 | Lactase | lactose | lactose | |
| 3.2.1.109 | Endogalactosaminidase | 1,4-alpha-D-galactosaminidic | poly(D-galactosamine) (e.g. hyaluronan) | |
| 3.2.1.110 | Mucinaminylserine mucinaminidase | D-galactosyl-3-(N-acetyl-beta-D-galactosaminyl)-L-serine | D-galactosyl-3-(N-acetyl-beta-D-galactosaminyl)-L-serine | |
| 3.2.1.111 | 1,3-alpha-L-fucosidase | 1,3-linkages between alpha-L-fucose and N-acetylglucosamine | glycoproteins | |
| 3.2.1.112 | 2-deoxyglucosidase | 2-deoxy-alpha-D-glucoside | 2-deoxy-alpha-D-glucoside | |
| 3.2.1.113 | Mannosyl-oligosaccharide 1,2-alpha- | terminal 1,2-linked alpha-D-mannose | Man(9)(GlcNAc)(2) | |
| 3.2.1.114 | Mannosyl-oligosaccharide 1,3-1,6-alpha-mannosidase | terminal 1,3- and 1,6-linked alpha-D-mannose | Man(5)(GlcNAc)(3) | |
| 3.2.1.115 | Branched-dextran exo-1,2-alpha- | 1,2-alpha-D-glucosidic, at branch point | dextran | |
| 3.2.1.116 | Glucan 1,4-alpha-maltotriohydrolase | 1,4-alpha-D-glucosidi | amylaceous | |
| 3.2.1.117 | Amygdalin beta-glucosidase | (R)-amygdalin | (R)-amygdalin | |
| 3.2.1.118 | Prunasin beta-glucosidase | (R)-prunasin | (R)-prunasin | |
| 3.2.1.119 | Vicianin beta-glucosidase | (R)-vicianin | (R)-vicianin | |
| 3.2.1.120 | Oligoxyloglucan beta-glycosidase | 1,4-beta-D-glucosidic | oligoxyloglucans | |
| 3.2.1.121 | Polymannuronate hydrolase | D-mannuronide | polymannuronate | |
| 3.2.1.122 | Maltose-6'-phosphate glucosidase | maltose 6'-phosphate | maltose 6'-phosphate | |
| 3.2.1.123 | Endoglycosylceramidase | oligoglycosylglucosylceramide | oligoglycosylglucosylcerami | |
| 3.2.1.124 | 3-deoxy-2-octulosonidase | beta-ketopyranosidic | 3-deoxy-D-manno-2-octulosonate in capsular polysaccharides | |
| 3.2.1.125 | Raucaffricine beta-glucosidase | raucaffricine | raucaffricine | |
| 3.2.1.126 | Coniferin beta-glucosidase | coniferin | coniferin | |
| 3.2.1.127 | 1,6-alpha-L-fucosidase | 1,6-between alpha-L-fucose and N-acetyl-D-glucosamine | glycopeptides | |
| 3.2.1.128 | Glycyrrhizinate beta-glucuronidase | glycyrrhizinate | glycyrrhizinate | |
| 3.2.1.129 | Endo-alpha-sialidase | (2->8)-alpha-sialosyl | oligo- or poly(sialic) acids | |
| 3.2.1.130 | Glycoprotein endo-alpha-1,2-mannosidase | alpha-D-glucosyl-(1,3)-D-mannosyl | GlcMan(9)(GlcNAc)(2) | |
| 3.2.1.131 | Xylan alpha-1,2-glucuronosidase | alpha-D-1,2-(4-O-methyl)glucuronosyl | hardwood xylan | |

| EC | Enzyme | Linkage | Substrate | Notes |
|---|---|---|---|---|
| 3.2.1.132 | Chitosanase | beta-1,4- between D-glucosamine residues | beta-1,4-linkages between D-glucosamine residues | |
| 3.2.1.133 | Glucan 1,4-alpha-maltohydrolase | (1->4)-alpha-D-glucosidic | | |
| 3.2.1.134 | Difructose-anhydride synthase | Bis-D-fructose 2',1:2,1'-dianhydride | Bis-D-fructose 2',1:2,1'-dianhydride | |
| 3.2.1.135 | Neopullulanase | pullulan | pullulan | |
| 3.2.1.136 | Glucuronoarabinoxylan endo-1,4-beta- | 1,4-beta-D-xylosyl | some | |
| 3.2.1.137 | Mannan exo-1,2-1,6-alpha-mannosidase | 1,2-alpha-D- and 1,6-alpha-D- | yeast mannan | |
| 3.2.1.139 | Alpha-glucuronidase | alpha-D-glucuronoside | alpha-D-glucuronoside | |
| 3.2.1.140 | Lacto-N-biosidase | Beta-D-Gal-(1->3)-beta-D-GlcNAc-(1->3)-beta-D-Gal-(1->4)-D-Glc | Beta-D-Gal-(1->3)-beta-D-GlcNAc-(1->3)-beta-D-Gal-(1->4)-D-Glc | |
| 3.2.1.141 | 4-alpha-D-((1->4)-alpha-D-glucano)trehalose trehalohydrolase | alpha-(1->4)-D-glucosidic | 4-alpha-D-((1->4)-alpha-D-glucanosyl)(n) trehalose | |
| 3.2.1.142 | Limit dextrinase | (1->6)-alpha-D-glucosidic | alpha- and beta-limit dextrins of amylopectin and glycogen, and in amylopectin and pullulan | |
| 3.2.1.143 | Poly(ADP-ribose) glycohydrolase | poly(ADP-ribose) at glycosidic (1''-2') | | |
| 3.2.1.144 | 3-deoxyoctulosonase | 3-deoxyoctulosonyl-lipopolysaccharide | 3-deoxyoctulosonyl-lipopolysaccharide | |
| 3.2.1.145 | Galactan 1,3-beta-galactosidase | terminal, non-reducing beta-D-galactose | (1->3)-beta-D-galactopyranans | |
| 3.2.1.146 | Beta-galactofuranosidase | alpha 6-O-(beta-D-xylopyranosyl)-beta-D-glucopyranoside | alpha 6-O-(beta-D-xylopyranosyl)-beta-D-glucopyranoside | |
| 3.2.1.147 | Thioglucosidase | thioglucoside | thioglucoside | |
| 3.2.1.149 | Beta-primeverosidase | alpha 6-O-(beta-D-xylopyranosyl)-beta-D-glucopyranoside | alpha 6-O-(beta-D-xylopyranosyl)-beta-D-glucopyranoside | |
| 3.2.1.150 | Oligoxyloglucan reducing-end-specific | | | |
| 3.2.1.151 | Xyloglucan-specific endo-beta-1,4- | 1,4-beta-D-glucosidic | xyloglucan | |
| 3.2.1.152 | Mannosylglycoprotein endo-beta-mannosidase | alpha-D-mannosyl-(1->6)-beta-D-mannosyl-(1->4)-beta-D-N-acetylglucosaminyl-(1->4)-beta-D-N-acetylglucosaminyl | | |
| 3.2.1.153 | Fructan beta-(2,1)-fructosidase | terminal, non-reducing 2,1-linked beta-D-fructofuranose | fructan | |
| 3.2.1.154 | Fructan beta-(2,6)-fructosidase | terminal, non-reducing 2,6-linked beta-D-fructofuranose | fructan | |
| 3.2.1.155 | Xyloglucan-specific exo-beta-1,4-glucanase | 1,4-beta-D-glucosidic | xyloglucan | |
| 3.2.1.156 | Oligosaccharide reducing-end xylanase | 1,4-beta-D-xylose residues from reducing end of oligosaccharides | | |
| 3.2.1.157 | Iota-carrageenase | 1,4-beta-D- between D-galactose 4-sulfate and 3,6-anhydro-D-galactose-2-sulfate | iota-carrageenans | |
| 3.2.1.158 | Alpha-agarase | 1,3-alpha-L-galactosidic | agarose | |
| 3.2.1.159 | Alpha-neoagaro-oligosaccharide hydrolase | 1,3-alpha-L-galactosidic | neoagaro-oligosaccharides | |
| 3.2.1.160 | Xyloglucan-specific exo-beta-1,4-glucanase | xyloglucan | xyloglucan | |
| 3.2.1.161 | Beta-apiosyl-beta-glucosidase | 7-(beta-D-apiofuranosyl-(1->6)-beta-D-glucopyranosyloxy)isoflavonoid | 7-(beta-D-apiofuranosyl-(1->6)-beta-D-glucopyranosyloxy)isoflavonoid | |
| 3.2.1.162 | Lambda-carrageenase | beta-1,4- in the backbone of lambda-carrageenan | lambda-carrageenan | |
| 4.2.2.1 | Hyaluronate lyase | hyaluronate | hyaluronate | |
| 4.2.2.2 | Pectate lyase | (1->4)-alpha-D-galacturonan | (1->4)-alpha-D-galacturonan | |
| 4.2.2.3 | Poly(beta-D-mannuronate) lyase | beta-D-mannuronate containing polysaccharides | | |
| 4.2.2.5 | Chondroitin Ac lyase | 1,4-beta-D-hexosaminyl and 1,3-beta-D-glucuronosyl | | |
| 4.2.2.6 | Oligogalacturonide lyase | 4-(4-deoxy-beta-D-gluc-4-enuronosyl)-D-galacturonate | 4-(4-deoxy-beta-D-gluc-4-enuronosyl)-D-galacturonate | |
| 4.2.2.7 | Heparin lyase | 1,4-linked D-glucuronate or L-iduronate residues and 1,4-alpha-linked 2-sulfoamino-2-deoxy-6-sulfo-D-glucose | | |
| 4.2.2.8 | Heparin-sulfate lyase | between N-acetyl-D-glucosamine and uronate | | |
| 4.2.2.9 | Pectate disaccharide-lyase | 4-(4-deoxy-alpha-D-galact-4-enuronosyl)-D-galacturonate | pectate | |
| 4.2.2.10 | Pectin lyase | (1->4)-alpha-D-galacturonan methyl ester | | |
| 4.2.2.11 | Poly(alpha-L-guluronate) lyase | terminal alpha-L-guluronate | | |
| 4.2.2.12 | Xanthan lyase | terminal beta-D-mannosyl-beta-D-1,4-glucuronosyl | xanthan | |
| 4.2.2.13 | Exo-(1->4)-alpha-D-glucan lyase | linear alpha-glucan | linear alpha-glucan | |
| 4.2.2.14 | Glucuronan lyase | (1->4)-beta-D-glucuronans | | |

-continued

| EC | Enzyme | Linkage | Substrate | Notes |
|---|---|---|---|---|
| 4.2.2.15 | Anhydrosialidase | N-acetylneuraminic acid glycosides | | |
| 4.2.2.16 | Levan fructotransferase (DFA-IV-forming) | terminal D-fructosyl-D-fructosyl disaccharide | | |
| 4.2.2.17 | Inulin fructotransferase (DFA-I-forming) | terminal D-fructosyl-D-fructosyl disaccharide | | |
| 4.2.2.18 | Inulin fructotransferase (DFA-III-forming) | terminal D-fructosyl-D-fructosyl disaccharide | | |
| 4.2.2.19 | Chondroitin B | dermatan sulfate containing 1,4-beta-D-hexosaminyl and 1,3-beta-D-glucurosonyl or 1,3-alpha-L-iduronosyl | | |
| 4.2.2.20 | Chondroitin-sulfate-ABC endolyase | beta-1,4-galactosaminic between N-acetylgalactosamine and either D-glucuronic acid or L-iduronic acid | | |
| 4.2.2.21 | Chondroitin-sulfate-ABC exolyase | non-reducing ends of both polymeric chondroitin sulfates and their oligosaccharide fragments | | |

We claim:

1. A system for directing evolution of a biological entity of interest comprising a plurality of yeast host cells, wherein individual host cells contain:
   (i) a nucleic acid target corresponding to the entity of interest;
   (ii) at least one diversifying nucleic acid carried in the host cell genome or in an episome, said diversifying nucleic acid comprising or flanked by
      (a) one or more recognition sequences recognized by a homing endonuclease; and
      (b) a region homologous to the target which promotes homologous recombination with the target; and
   (iii) said endonuclease, expression of which is under the control of an inducible promoter, where induction of expression of the endonuclease results in cleavage at the recognition sequence which promotes recombination between the diversifying nucleic acid and the target; wherein the system comprises a plurality of different diversifying nucleic acids and wherein said system further comprises a reporter gene or chemical complementation system for selecting for a mutant target exhibiting a desired activity.

2. The system of claim 1, wherein individual host cells contain a plurality of different diversifying nucleic acids.

3. The system of claim 1, where the one or more diversifying nucleic acid is integrated into the yeast genome.

4. The system of claim 2, where the one or more diversifying nucleic acid is integrated into the yeast genome.

5. The system of claim 1, where the one or more diversifying nucleic acids in contained in a 2μ plasmid.

6. The system of claim 2, where the one or more diversifying nucleic acids in contained in a 2μ plasmid.

7. The system of claim 1, where the yeast host cells are replicating.

8. The system of claim 1, where the yeast host cells are engaged in sexual reproduction.

9. The system of claim 2, where the yeast host cells are replicating.

10. The system of claim 2, where the yeast host cells are engaged in sexual reproduction.

11. The system of claim 1, which comprises a primary population of host cells containing a diversity of mutant targets.

12. The system of claim 1, which comprises a secondary population of host cells resulting from genetic exchange between two or more primary populations of cells.

13. The system of claim 2, which comprises a primary population of host cells containing a diversity of mutant targets.

14. The system of claim 2, which comprises a secondary population of host cells resulting from genetic exchange between two or more primary populations of cells.

15. The system of claim 1, where the endonuclease is HO endonuclease.

16. The system of claim 1, where the endonuclease is I-SceI endonuclease.

* * * * *

SEQUENCE LISTING

```
<160> NUMBER OF SEQ ID NOS: 60

<210> SEQ ID NO 1
<211> LENGTH: 945
<212> TYPE: DNA
<213> ORGANISM: Artificial Sequence
<220> FEATURE:
<223> OTHER INFORMATION: Synthetic oligonucleotide

<400> SEQUENCE: 1
atggccacgc cagtagaaac gcatggtcag ctgtccatcg aaaacgggcg actggtggat      60
gaacagggga aaagggtgca actgagaggg gtcagttcgc acggtttgca gtggtttggc     120
gactatgtca acaaagactc gataaaatgg ctgcgtgacg actgggggat caatgtgttt     180
cgcgttgcca tgtacacggc ggagaatggt tatattgcta acccttccct cgccaataag     240
gtaaaagagg ccgttgcggc ggcgcaaagc ctcggcgtct acatcatcat cgactggcac     300
attttgtcgg ataacgatcc caatacttat aaagcacagg caaaaatctt ctttgccgaa     360
atggctgggc tgtatggcag ctcaccgaac gtgatttatg aaatcgccaa tgagccaaac     420
ggtggcgtga cgtggaacgg acagattcgg ccttatgcgc tggaagtgac tgacaccatc     480
cgtagcaaag atcctgataa ccttattatc gtcggtaccg gcacctggag tcaggatatc     540
cacgatgcag cggataacca actgcccgat ctgaataccc tatacgcgct gcatttctat     600
gcgggcacgc acgggcaatt cctgtgcgat cgtattgact atgcgcaaag ccgtggcgcg     660
gcgattttcg tcagcgagtg gggcaccagc gatgcatccg caacggtgg gccgttcctg      720 cctgaatcgc agacctggat cgatttcctg aataaccgtg gcgtaagctg ggtgaactgg     780
tcactaagcg ataagtctga gacgtctgcg gcgctgactc caggggcgag caaatcaggc    840
ggctggacgg agcagaattt gtcgacgtca ggcaaatttg tcagagagca gattcgtgcg     900
ggggcgggtc tgagcggtgg tgatcaccat caccatcacc attaa                     945

<210> SEQ ID NO 2
<211> LENGTH: 945
<212> TYPE: DNA
<213> ORGANISM: Artificial Sequence
<220> FEATURE:
<223> OTHER INFORMATION: Synthetic oligonucleotide
```

<400> SEQUENCE: 2

```
atggccacgc cagtagaaac gcatggtcag ctgtccatcg aaaacgggcg actggtggat      60
gaacagggga aagggtgca actgagaggg gtcagttcgc acggtttgca gtggtttggc     120
gactatgtca acaaagactc gatgaagtgg ctgcgtgatg actgggggat taatgtattc     180
cgcgtcgcca tgtacacggc ggcggatggt tatatttcga atccttccct cgccaataag     240
gtaaaagagg ccgttgcggc ggcgcaaagc ctcggcgttt acatcatcat cgactggcac     300
attttgtcgg ataacgatcc taatatttat aaagcacagg caaaaacctt ctttgccgaa     360
atggcgggc tgtacggtaa ttcgccgaac gtgatttatg aaatcgccaa tgaacctaac     420
ggcggcgtga cctggaacgg gcagattcgg ccttatgcgc tggaagtgac tgaaactatc     480
cgtagtaaag atcctgataa tctgattatc gttggcacgg gtacctggag tcaggatatc     540
catgatgcgg cggacaatct gttgcccgat ccgaatacga tgtacgcgct gcatttctat     600
gcgggcacgc acgggcaatt cctgtgcgat cgtattgact atgcgcaaag ccgtggcgcg     660
gcgattttcg tcagcgagtg gggcaccagc gatgcatccg caacggtgg gccgttcctg     720
cctgaatcgc agacctggat cgatttcctg aataaccgtg gcataagctg ggtgaactgg     780
tcgcttaccg ataagtcaga ggcgtccgcc gcgctggctc aggggcgag taaatcaggc     840
ggttggacgg agcagaattt gtcggcgtca ggaaaatttg tcagagcaca gattcgcgcg     900
gctgcgaatc taagcggtgg cgatcaccat caccatcacc attaa                    945
```

<210> SEQ ID NO 3
<211> LENGTH: 314
<212> TYPE: PRT
<213> ORGANISM: Artificial Sequence
<220> FEATURE:
<223> OTHER INFORMATION: Synthetic polypeptide

<400> SEQUENCE: 3

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Ile
         35                  40                  45

Lys Trp Leu Arg Asp Asp Trp Gly Ile Asn Val Phe Arg Val Ala Met
     50                  55                  60

Tyr Thr Ala Glu Asn Gly Tyr Ile Ala Asn Pro Ser Leu Ala Asn Lys
 65                  70                  75                  80

Val Lys Glu Ala Val Ala Ala Ala Gln Ser Leu Gly Val Tyr Ile Ile
                 85                  90                  95

Ile Asp Trp His Ile Leu Ser Asp Asn Asp Pro Asn Thr Tyr Lys Ala
            100                 105                 110

Gln Ala Lys Ile Phe Phe Ala Glu Met Ala Gly Leu Tyr Gly Ser Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Leu Asn
```

```
            180                 185                 190
Thr Leu Tyr Ala Leu His Phe Tyr Ala Gly Thr His Gly Gln Phe Leu
            195                 200                 205

Cys Asp Arg Ile Asp Tyr Ala Gln Ser Arg Gly Ala Ala Ile Phe Val
            210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Ser Asp Lys Ser Glu Thr Ser Ala Ala Leu
            260                 265                 270

Thr Pro Gly Ala Ser Lys Ser Gly Gly Trp Thr Glu Gln Asn Leu Ser
            275                 280                 285

Thr Ser Gly Lys Phe Val Arg Glu Gln Ile Arg Ala Gly Ala Gly Leu
            290                 295                 300

Ser Gly Gly Asp His His His His His His
305                 310

<210> SEQ ID NO 4
<211> LENGTH: 314
<212> TYPE: PRT
<213> ORGANISM: Artificial Sequence
<220> FEATURE:
<223> OTHER INFORMATION: Synthetic polypeptide

<400> SEQUENCE: 4

Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
50                  55                  60

Tyr Thr Ala Ala Asp Gly Tyr Ile Ser Asn Pro Ser Leu Ala Asn Lys
65                  70                  75                  80

Val Lys Glu Ala Val Ala Ala Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Leu Leu Pro Asp Pro Asn
            180                 185                 190

Thr Met Tyr Ala Leu His Phe Tyr Ala Gly Thr His Gly Gln Phe Leu
        195                 200                 205

Cys Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
```

```
                225                 230                 235                 240
Pro Glu Ser Gln Thr Trp Ile Asp Phe Leu Asn Asn Arg Gly Ile Ser
                    245                 250                 255

Trp Val Asn Trp Ser Leu Thr Asp Lys Ser Glu Ala Ser Ala Ala Leu
                260                 265                 270

Ala Pro Gly Ala Ser Lys Ser Gly Gly Trp Thr Gln Asn Leu Ser
            275                 280                 285

Ala Ser Gly Lys Phe Val Arg Ala Gln Ile Arg Ala Ala Ala Asn Leu
            290                 295                 300

Ser Gly Gly Asp His His His His His His
305                 310

<210> SEQ ID NO 5
<211> LENGTH: 945
<212> TYPE: DNA
<213> ORGANISM: Artificial Sequence
<220> FEATURE:
<223> OTHER INFORMATION: Synthetic oligonucleotide

<400> SEQUENCE: 5
atggccacac cggtggaaac gcatggccaa ctgtccattg aaaatgggcg actggtggat      60
gaacagggga aagggtgcaa ctgagagggg gtcagttcgc acggtttgca gtggtttggc     120
gactatgtca acaaagactc gatgaagtgg ctgcgtgatg actggggat  taatgtattc     180
cgcgtcgcca tgtacacggc ggcggatggt tatatttcga atccttccct cgccaataag     240
gtcaaagaag ccgttgcggt ggcacaaagc ctcggcgttt acatcatcat cgactggcat     300
atcttgtcgg ataacgatcc caatatttat aaagcacagg caaaaacctt ctttgccgaa     360
atggcgggc tgtacggtaa ttcgccgaac gtgatttatg aaatcgccaa tgaacctaac      420
ggcggcgtga catggaacgg gcagattcgg cctatgcgc tggatgttac tgacactatc      480
cgtagcaaag atcctgataa ccttattatc gtcggcagcg ggacctggag ccaggacatc     540
catgacgcgg cggataatca gctgcccgat ccgaatacgc tgtacgcgct gcatttctat     600
gcgggtacgc acgggcagtt cctgcgcgat cgtattgact atgcgcaaag ccgtggcgcg     660
gcgattttcg tcagcgagtg gggcaccagc gatgcatccg caacggtgg ccgttcctg       720
cctgaatcgc agacctggat cgatttcctg aataaccgtg gtgtaagctg gtaaactgg      780
tcactaagcg ataagtctga cgtctgcg gcgctgactc caggggcgag taaatcaggc       840
ggttggacgg agcagaatct gtcgacgtca ggaaatttg tcagagagca gattcgtgca     900
ggtgcgaatc tgggcggtgg cgatcaccat caccatcacc attaa                    945

<210> SEQ ID NO 6
<211> LENGTH: 313
<212> TYPE: PRT
<213> ORGANISM: Artificial Sequence
<220> FEATURE:
<223> OTHER INFORMATION: Synthetic Polypeptide

<400> SEQUENCE: 6

Ala Thr Pro Val Glu Thr His Gly Gln Leu Ser Ile Glu Asn Gly Arg
1               5                   10                  15

Leu Val Asp Glu Gln Gly Lys Arg Val Gln Leu Arg Gly Val Ser Ser
                20                  25                  30

His Gly Leu Gln Trp Phe Gly Asp Tyr Val Asn Lys Asp Ser Met Lys
            35                  40                  45

Trp Leu Arg Asp Asp Trp Gly Ile Asn Val Phe Arg Val Ala Met Tyr
```

|  |  | 50 |  |  |  | 55 |  |  |  | 60 |  |
|---|---|---|---|---|---|---|---|---|---|---|---|

Thr Ala Ala Asp Gly Tyr Ile Ser Asn Pro Ser Leu Ala Asn Lys Val
65                  70                  75                  80

Lys Glu Ala Val Ala Val Ala Gln Ser Leu Gly Val Tyr Ile Ile Ile
                85                  90                  95

Asp Trp His Ile Leu Ser Asp Asn Asp Pro Asn Ile Tyr Lys Ala Gln
            100                 105                 110

Ala Lys Thr Phe Phe Ala Glu Met Ala Gly Leu Tyr Gly Asn Ser Pro
        115                 120                 125

Asn Val Ile Tyr Glu Ile Ala Asn Glu Pro Asn Gly Gly Val Thr Trp
    130                 135                 140

Asn Gly Gln Ile Arg Pro Tyr Ala Leu Asp Val Thr Asp Thr Ile Arg
145                 150                 155                 160

Ser Lys Asp Pro Asp Asn Leu Ile Ile Val Gly Ser Gly Thr Trp Ser
                165                 170                 175

Gln Asp Ile His Asp Ala Ala Asp Asn Gln Leu Pro Asp Pro Asn Thr
            180                 185                 190

Leu Tyr Ala Leu His Phe Tyr Ala Gly Thr His Gly Gln Phe Leu Arg
        195                 200                 205

Asp Arg Ile Asp Tyr Ala Gln Ser Arg Gly Ala Ala Ile Phe Val Ser
    210                 215                 220

Glu Trp Gly Thr Ser Asp Ala Ser Gly Asn Gly Pro Phe Leu Pro
225                 230                 235                 240

Glu Ser Gln Thr Trp Ile Asp Phe Leu Asn Asn Arg Gly Val Ser Trp
                245                 250                 255

Val Asn Trp Ser Leu Ser Asp Lys Ser Glu Thr Ser Ala Ala Leu Thr
            260                 265                 270

Pro Gly Ala Ser Lys Ser Gly Trp Thr Glu Gln Asn Leu Ser Thr
        275                 280                 285

Ser Gly Lys Phe Val Arg Glu Gln Ile Arg Ala Gly Ala Asn Leu Gly
    290                 295                 300

Gly Gly Asp His His His His His His
305                 310

<210> SEQ ID NO 7
<211> LENGTH: 834
<212> TYPE: DNA
<213> ORGANISM: Artificial Sequence
<220> FEATURE:
<223> OTHER INFORMATION: Synthetic Oligonucleotide

<400> SEQUENCE: 7

```
atggccacgc cagtagaaac gcatggtcag ctgtccatcg aaaacgggcg actggtggat      60
gaacagggga aaagggtgca actgagaggg gtcagttcgc acggtttgca gtggtttggc     120
gactatgtca acaaagactc gatgaagtgg ctgcgtgatg actgggggat taatgtattc     180
cgcgtcgcca tgtacacggc ggcggatggt tatatttcga atccttccct cgccaataag     240
gtaaaagagg ccgttgcggc ggcgcaaagc ctcggcgttt acatcatcat cgactggcac     300
attttgtcgg ataacgatcc caatatttat aaagcacagg caaaaaacctt ctttgccgaa     360
atggcgggc tgtacggtaa ttcgccgaac gtgatttatg aaatcgccaa tgaacctaac     420
ggcggcgtga cctggaacgg gcagattcgg ccttatgcgc tggaagtgac tgaaactatc     480
cgtagtaaag atcctgataa tctgattatc gttggcacgg gtacctggag tcaggatatc     540
catgatgcgg cggacaatct gttgcccgat ccgaatacga tgtacgcgct gcatttctat     600
```

```
gcgggcacgc acgggcaatt cctgtgcgat cgtattgact atgcgcaaag ccgtggcgcg    660
gcgattttcg tcagcgagtg gggcaccagc gatgcatccg caacggtgg gccgttcctg    720 cctgaatcgc agacctggat cgatttcctg aataaccgtg gcataagctg ggtgaactgg    780
tcgcttaccg ataagtcaga ggcgtccgcc gcgctggctc caggggcga gtaa           834
```

<210> SEQ ID NO 8
<211> LENGTH: 277
<212> TYPE: PRT
<213> ORGANISM: Artificial Sequence
<220> FEATURE:
<223> OTHER INFORMATION: Synthetic Polypeptide

<400> SEQUENCE: 8

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
 65                  70                  75                  80

Val Lys Glu Ala Val Ala Ala Gln Ser Leu Gly Val Tyr Ile Ile
                 85                  90                  95

Ile Asp Trp His Ile Leu Ser Asp Asn Asp Pro Asn Ile Tyr Lys Ala
                100                 105                 110

Gln Ala Lys Thr Phe Phe Ala Glu Met Ala Gly Leu Tyr Gly Asn Ser
            115                 120                 125

Pro Asn Val Ile Tyr Glu Ile Ala Asn Glu Pro Asn Gly Val Thr
            130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Leu Leu Pro Asp Pro Asn
            180                 185                 190

Thr Met Tyr Ala Leu His Phe Tyr Ala Gly Thr His Gly Gln Phe Leu
        195                 200                 205

Cys Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
                245                 250                 255

Trp Val Asn Trp Ser Leu Thr Asp Lys Ser Glu Ala Ser Ala Ala Leu
            260                 265                 270

Ala Pro Gly Gly Glu
        275
```

<210> SEQ ID NO 9
<211> LENGTH: 945
<212> TYPE: DNA
<213> ORGANISM: Artificial Sequence
<220> FEATURE:

<223> OTHER INFORMATION: Synthetic Oligonucleotide

<400> SEQUENCE: 9

```
atggccacgc cagtagaaac gcatggtcag ctgtccatcg aaaacgggcg actggtggat      60
gaacagggga aagggtgca actgagaggg gtcagttcgc acggtttgca gtggtttggc      120
gactatgtca acaaagactc gataaaatgg ctgcgtgacg actggggat caatgtgttt      180
cgcgttgcca tgtacacggc ggagaatggt tatattgcta acccttccct cgccaataag      240
gtaaaagagg ccgttgcggc ggcgcaaagc ctcggcgtct acatcatcat cgactggcac      300
attttgtcgg ataacgatcc caatacttat aaagcacagg caaaaatctt ctttgccgaa      360
atggctgggc tgtatggcag ctcaccgaac gtgatttatg aaatcgccaa tgagccaaac      420
ggtggcgtga cgtggaacgg acagattcgg ccttatgcgc tggaagtgac tgacaccatc      480
cgtagcaaag atcctgataa ccttattatc gtcggtaccg gcacctggag tcaggatatc      540
cacgatgcag cggataacca actgcccgat ctgaataccc tatacgcgct gcatttctat      600
gcgggcacgc acgggcaatt cctgtgcgat cgtattgact atgcgcaaag ccgtggcgcg      660
gcgattttcg tcagcgagtg gggcaccagc gatgcatccg caacggtgg gccgttcctg      720
cctgaatcgc agacctggat cgatttcctg aataaccgtg gcgtaagctg ggtgaactgg      780
tcactaagcg ataagtctga acgtctgcg gcgctgactc aggggcgag caaatcaggc       840
ggctggacgg agcagaattt gtcgacgtca ggcaaatttg tcagagagca gattcgtgcg      900
ggggcgggtc tgagcggtgg tgatcaccat caccatcacc attaa                      945
```

<210> SEQ ID NO 10
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 10

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Ile
         35                  40                  45

Lys Trp Leu Arg Asp Asp Trp Gly Ile Asn Val Phe Arg Val Ala Met
     50                  55                  60

Tyr Thr Ala Glu Asn Gly Tyr Ile Ala Asn Pro Ser Leu Ala Asn Lys
 65                  70                  75                  80

Val Lys Glu Ala Val Ala Ala Gln Ser Leu Gly Val Tyr Ile Ile
                 85                  90                  95

Ile Asp Trp His Ile Leu Ser Asp Asn Asp Pro Asn Thr Tyr Lys Ala
            100                 105                 110

Gln Ala Lys Ile Phe Phe Ala Glu Met Ala Gly Leu Tyr Gly Ser Ser
        115                 120                 125

Pro Asn Val Ile Tyr Glu Ile Ala Asn Glu Pro Asn Gly Val Thr
        130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Thr Gly Thr Trp
                165                 170                 175
```

```
Ser Gln Asp Ile His Asp Ala Ala Asp Asn Gln Leu Pro Asp Leu Asn
            180                 185                 190

Thr Leu Tyr Ala Leu His Phe Tyr Ala Gly Thr His Gly Gln Phe Leu
        195                 200                 205

Cys Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Ser Asp Lys Ser Glu Thr Ser Ala Ala Leu
            260                 265                 270

Thr Pro Gly Ala Ser Lys Ser Gly Gly Trp Thr Glu Gln Asn Leu Ser
        275                 280                 285

Thr Ser Gly Lys Phe Val Arg Glu Gln Ile Arg Ala Gly Ala Gly Leu
    290                 295                 300

Ser Gly Gly Asp His His His His His His
305                 310

<210> SEQ ID NO 11
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 11
atggccacgc cagtagaaac acatggccaa ctgtccatcg aaaatgggcg actggtggat      60
gaacagggga aagggtgca actgagaggg gtcagttcgc acggtttgca gtggtttggc     120
gactatgtca caaagattc gatgaagtgg ctgcgtgatg actgggggat taatgtattc     180
cgcgtcgcca tgtacacggc ggcggatggt tatatttcga atccttccct cgccaataag     240
gtaaaagagg ccgttgcggt ggcacaaagc ctcggcgttt acatcatcat cgactggcat     300
atcttgtcgg ataacgatcc caatacttat aaagcacagg caaaaacctt ctttgctgaa     360
atggctgggc tgtatggcag ctcaccgaac gtgatttatg aaatcgccaa tgagccaaac     420
ggtggcgtga cctggaacgg gcagattcgg ccttatgcgc tggaagtgac tgacaccatc     480
cgtagcaaag atcccgataa ccttattatc gtcggcagcg ggacctggag ccaggatatc     540
catgatgcag cggataacca actgcccgat ccgaatacgc tgtacgcgct gcatttctat     600
gcgggcacgc acgggcagtt cctgcgcgat cgcattgatt atgcacaaag ccgcggtgcc     660 gcgattttg tcagcgagtg gggaaccagc gatgcgtccg gcaatggcgg ccgttcctg      720 cctgaatcgc agacctggat cgatttcctg aataaccgtg gcgtaagctg ggtgaactgg     780
tcgcttaccg ataaatcaga ggcgtccgcc gcgctggctc cgggagcgag caaatctggt     840
ggctggacgg agcagaatct gtcgacgtca ggcaaatttg tcagagagca gattcgtgca     900
ggtgcgaatc tgggcggtgg cgatcaccat caccatcacc attaa                    945

<210> SEQ ID NO 12
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 12
```

Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
            85                  90                  95

Ile Asp Trp His Ile Leu Ser Asp Asn Asp Pro Asn Thr Tyr Lys Ala
        100                 105                 110

Gln Ala Lys Thr Phe Phe Ala Glu Met Ala Gly Leu Tyr Gly Ser Ser
            115                 120                 125

Pro Asn Val Ile Tyr Glu Ile Ala Asn Glu Pro Asn Gly Gly Val Thr
        130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asn Gln Leu Pro Asp Pro Asn
        180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
        210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
                260                 265                 270

Ala Pro Gly Ala Ser Lys Ser Gly Gly Trp Thr Glu Gln Asn Leu Ser
            275                 280                 285

Thr Ser Gly Lys Phe Val Arg Glu Gln Ile Arg Ala Gly Ala Asn Leu
        290                 295                 300

Gly Gly Gly Asp His His His His His His
305                 310

<210> SEQ ID NO 13
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 13
atggccacgc cagtagaaac gcatggccaa ctgtccatcg aaaatgggcg actggtggat     60
gagcagggaa aaagagtgca actgagagga atcagctcga acgggttgca gtggtttggt    120
gactacgtca acaaagattc gatgaagtgg ctgcgtgatg actgggggat taacgtattc    180
cgtgttgcca tgtacacggc ggcggatggt tatatttcga atccttccct cgccaataag    240
gtcaaagaag ccgttgcggt ggcacaaagc ctcggcgtct acatcatcat cgactggcat    300

```
atcttgtcgg ataacgatcc taatatttat aaagcacagg caaaaaccctt ctttgccgaa      360 atggcggggc tgtacggtaa ttcgccgaac gtgattatg aaatcgccaa tgaacctaac       420
ggcggcgtga catggaacgg gcaaattcgg ccttatgcgc tggatgttac tgacaccatc      480
cgtagcaaag atcccgataa cctcattatc gtcggtaccg gcacctggag tcaggatatc      540
cacgatgcag cggataacca actgcccgat ccgaatacgc tgtatgcgct gcatttctat      600
gccggtacgc acgggcagtt cctgcgcgat cgcattgact atgcacaaag ccgcggtgct      660
gcaattttcg tcagcgagtg gggaacaagc gatgcgtccg caacggtgg gccgttcctg       720 ccagaatcgc aaacctggat cgatttcctg aataaccgtg cataagctg ggttaactgg       780 tcgcttaccg ataaatcaga ggcgtctgcg gcgctggcac cgggagcgag caaatctggc      840
ggttggacag agcagaattt gtcggcgtca ggaaaattg tcagagcaca gattcgcgcg       900
gctgcgaatc tgggcggtgg cgatcaccat caccatcacc attaa                      945
```

<210> SEQ ID NO 14
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 14

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Ile Ser
            20                  25                  30

Ser Asn Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Asp Val Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
```

```
                    245                 250                 255
Trp Val Asn Trp Ser Leu Thr Asp Lys Ser Glu Ala Ser Ala Ala Leu
            260                 265                 270

Ala Pro Gly Ala Ser Lys Ser Gly Gly Trp Thr Glu Gln Asn Leu Ser
        275                 280                 285

Ala Ser Gly Lys Phe Val Arg Ala Gln Ile Arg Ala Ala Asn Leu
    290                 295                 300

Gly Gly Gly Asp His His His His His His
305                 310
```

<210> SEQ ID NO 15
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 15

```
atggccacgc cagtagaaac gcatggccaa ctgtccattg aaaatgggcg actggtggac      60
gaacagggga aagggtgca actgagaggg gtcagttcgc acggtttgca gtggtttggt     120
gactacgtca acaagattc gatgaagtgg ctgcgtgatg actgggggat taatgtattc     180
cgcgtcgcca tgtacacggc ggcggatggt tatatttcga atccttccct cgccaataag     240
gtaaaagagg ccgttgcggc ggcgcaaagc tcggcgtttc acatcatcat cgactggcat     300
atcttgtcgg ataacgatcc taatatttat aaagcacagg caaaaacctt ctttgccgaa     360
atggcggggc tgtacggtaa ttcgccgaac gtgatttatg aaatcgccaa tgaacctaac     420
ggcggcgtga catggaacgg gcaaattcgg ccttatgcgc tggaagtgac tgaaactatc     480
cgtagtaaag atcctgataa ccttattatc gtcggcagcg ggacctggag ccaggacatc     540
catgatgcgg cagacaatca gttgcccgat ccgaatacga tgtacgcgct gcatttctat     600
gccggcacgc acgggcagtt cctgcgcgat cgtatcgatt atgcgcaaag ccgcggcgcc     660
gcgattttg tcagcgagtg gggcacaagc gatgcgtccg gcaacggcgg accgttcctg     720
cctgaatcgc agacctggat cgatttcctg aacaaccgtg tgtgagctg ggttaactgg     780
tcgcttaccg ataagtcaga ggcgtctgcg gcgctggcac cgggagcgag caaatcaggt     840
ggctggacgg agcagaatct gtcgacgtca ggcaaatttg tcagagagca gattcgtgca     900
ggtgcgaatc tgggcggtgg cgatcaccat caccatcacc attaa                    945
```

<210> SEQ ID NO 16
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 16

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
```

```
                65                  70                  75                  80
Val Lys Glu Ala Val Ala Ala Gln Ser Leu Gly Val Tyr Ile Ile
                    85                  90                  95

Ile Asp Trp His Ile Leu Ser Asp Asn Asp Pro Asn Ile Tyr Lys Ala
                    100                 105                 110

Gln Ala Lys Thr Phe Phe Ala Glu Met Ala Gly Leu Tyr Gly Asn Ser
                115                 120                 125

Pro Asn Val Ile Tyr Glu Ile Ala Asn Glu Pro Asn Gly Gly Val Thr
            130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Gln Leu Pro Asp Pro Asn
                180                 185                 190

Thr Met Tyr Ala Leu His Phe Tyr Ala Gly Thr His Gly Gln Phe Leu
                195                 200                 205

Arg Asp Arg Ile Asp Tyr Ala Gln Ser Arg Gly Ala Ala Ile Phe Val
            210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
                260                 265                 270

Ala Pro Gly Ala Ser Lys Ser Gly Gly Trp Thr Glu Gln Asn Leu Ser
            275                 280                 285

Thr Ser Gly Lys Phe Val Arg Glu Gln Ile Arg Ala Gly Ala Asn Leu
            290                 295                 300

Gly Gly Gly Asp His His His His His His
305                 310

<210> SEQ ID NO 17
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 17
atggccacgc cagtagaaac gcatggtcag ctgtccatcg aaaacgggcg actggtggat        60
gaacagggga aagggtgcac tgagagggg gtcagttcgc acggtttgca gtggtttggt       120
gactacgtca acaaagattc gatgaaatgg ctgcgcgatg actggggat  taacgtattc       180 cgtgttgcca tgtacacggc agcggatggc tatatttcca atccttccct gcgaataag       240 gtcaaagaag ccgttgcggt ggcacaaagc ctcggcgttt acatcatcat cgactggcac       300
attttgtcgg ataacgatcc taatatttat aaagcacagg caaaaacctt ctttgccgaa       360 atggcgggc  tgtacggtaa ttcgccgaac gtgatttatg aaatcgccaa tgagccaaac       420
ggtggcgtga cctggaacgg gcagattcgg cctatgcgc  tggaagccac tgacaccatc       480
cgtagcaaag atcccgataa ccttattatc gtcggcagcg ggacctggag ccaggatatc       540
catgatgcgg cagacaatca gttgcccgat ccgaatactc tgtatgcgct gcatttctat       600
gcgggtacgc acgggcagtt cctgcgcgat cgtattgact atgcacaaag ccgcggtgct       660
```

```
gcaattttcg tcagcgagtg gggcaccagc gatgcatccg gcaacggtgg gccgttcctg    720
cctgaatcgc agacctggat cgatttcctg aataaccgtg cgtaagctg ggtgaactgg     780 tcgcttaccg ataagtcaga ggtgtccgcc gcgctggctc aggggcgag taaatcaggc     840 ggttggacgg agcagaatct gtcgacgtca ggaaaatttg tcagagcaca gattcgcgcg    900
gctgcgaatc taagcggtgg cgatcaccat caccatcacc attaa                    945
```

<210> SEQ ID NO 18
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 18

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
 65                  70                  75                  80

Val Lys Glu Ala Val Ala Val Ala Gln Ser Leu Gly Val Tyr Ile Ile
                 85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Ala Thr Asp Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Val Ser Ala Ala Leu
            260                 265                 270

Ala Pro Gly Ala Ser Lys Ser Gly Gly Trp Thr Glu Gln Asn Leu Ser
        275                 280                 285

Thr Ser Gly Lys Phe Val Arg Ala Gln Ile Arg Ala Ala Ala Asn Leu
    290                 295                 300

Ser Gly Gly Asp His His His His His His
305                 310
```

<210> SEQ ID NO 19
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 19

```
atggccacgc cagtagaaac acatggccaa ctgtccatcg aaaacgggcg actggtggat      60
gaacagggga aagggtgca actgagaggg gtcagttcgc acggtttgca gtggtttggt     120
gactatgtca acaaagactc gatgaagtgg ctgcgcgatg actgggggat taacgtattc     180
cgtgttgcca tgtacacggc agcggatggc tatatttcca atccttccct gcgaataag     240
gtcaaagaag ccgttgcggt ggcacaaagc ctcggcgtct acatcatcat cgactggcac     300
attttgtcgg ataacgatcc taatatttat aaagcacagg caaaaacctt cttcgccgaa     360
atggctgggc tgtacggtaa ctcgccgaac gtgatttatg aaatcgccaa tgaacctaac     420
ggtggcgtga cctggaacgg gcaaattcgg ccttatgcgc tggaagtgac tgaaactatc     480
cgtagtaaag atcctgataa ccttattatc gtcggcagcg ggacctggag ccaggacatc     540
catgatgcgg cggacaatct gttgcccgat ccgaatacga tgtacgcgct gcatttctat     600
gcgggtacgc acgggcagtt cctgcgcgat cgcattgatt atgcacaaag ccgcggtgcc     660
gcgacttttg tcagcgagtg gggcacaagc gatgcgtccg gcaatggcgg accgttcctg     720
cctgaatcgc agacctggat cgatttcctg aataaccgtg gcgtaagctg ggttaactgg     780
tcgcttaccg ataaatcaga ggcgtctgcg gcgctggctc cagggggcgag caaatcaggt     840
ggctggacgg agcagaattt gtcaacgtca ggcaaatttg tcagagagca gattcgtgcg     900
ggtgcagacc tgagtggtgg cgttcaccat caccatcacc attaa                     945
```

<210> SEQ ID NO 20
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 20

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
 65                  70                  75                  80

Val Lys Glu Ala Val Ala Val Ala Gln Ser Leu Gly Val Tyr Ile Ile
                 85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140
```

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Ser Gly Thr Trp
            165                 170                 175

Ser Gln Asp Ile His Asp Ala Ala Asn Leu Leu Pro Asp Pro Asn
        180                 185                 190

Thr Met Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Thr Phe Val
        210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
            245                 250                 255

Trp Val Asn Trp Ser Leu Thr Asp Lys Ser Glu Ala Ser Ala Ala Leu
            260                 265                 270

Ala Pro Gly Ala Ser Lys Ser Gly Gly Trp Thr Glu Gln Asn Leu Ser
        275                 280                 285

Thr Ser Gly Lys Phe Val Arg Glu Gln Ile Arg Ala Gly Ala Asp Leu
        290                 295                 300

Ser Gly Gly Val His His His His His His
305                 310

<210> SEQ ID NO 21
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 21
atggccacac cggtggaaac acatggccaa ctgtccatcg aaaatgggcg actggtggat      60
gagcagggaa aagggtgca actgagaggg gtcagttcgc acgggttgca gtgggttggt     120
gactacgtca acaaagactc gatgaagtgg ctgcgtgatg actgggggat taacgtattc     180
cgtgttgcca tgtacacggc agcggatggc tatatttcca atccttccct tgcgaataag     240
gtcaaagaag ccgttgcggt ggcacaaagc ctcggcgttt acatcatcat cgactggcac     300
attttgtcgg ataacgatcc taatatttat aatgcacagg caaaaacctt ctttgctgaa     360 atggcgggc tgtacggtaa ttcgccgaac gtgatttatg aaatcgccaa tgagccaaac     420
ggtggcgtga cctggaacgg acagattcgg ccttatgcgc tggaagtgac tgacaccatc     480
cgtagcaaag atcccgataa cctcattatc gtcggtaccg gcacctggag tcaggatatc     540
cacgatgcag cggataacca actgcccgat ccgaataccc tatacgcgct gcatttctat     600
gcgggcacgc acgggcagtt cctgcgcgat cgtatcgatt atgcgcaaag ccgtggcgcg     660
gcgattttcg tcagcgagtg gggcaccagc gatgcatccg gcaacggtgg gccgttcctg     720
cctgaatcgc agacctggat cgatttcctg aataaccgtg gcgtaagctg ggtgaactgg     780
tcgcttaccg ataagtcaga ggcgtccgcc gcgctggctc aggggcgag caaatctggc     840 ggttggacag agcagaattt gtcggcgtca ggaaaatttg tcagagcaca gattcgcgcg     900
gctgcgaatc taagcggtgg cgatcaccat caccatcacc attaa                     945

<210> SEQ ID NO 22
<211> LENGTH: 314

```
<212> TYPE: PRT
<213> ORGANISM: Artificial Sequence
<220> FEATURE:
<223> OTHER INFORMATION: Synthetic Polypeptide

<400> SEQUENCE: 22

Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Val Gly Asp Tyr Val Asn Lys Asp Ser Met
        35                  40                  45

Lys Trp Leu Arg Asp Asp Trp Gly Ile Asn Val Phe Arg Val Ala Met
50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
                85                  90                  95

Ile Asp Trp His Ile Leu Ser Asp Asn Asp Pro Asn Ile Tyr Asn Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Ala Pro Gly Ala Ser Lys Ser Gly Gly Trp Thr Glu Gln Asn Leu Ser
        275                 280                 285

Ala Ser Gly Lys Phe Val Arg Ala Gln Ile Arg Ala Ala Ala Asn Leu
290                 295                 300

Ser Gly Gly Asp His His His His His His
305                 310

<210> SEQ ID NO 23
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 23
atggccacgc cagtagaaac acatggccaa ctgtccatcg aaaacgggcg actggtggat      60
```

```
gaacagggga aaagggtgca actgggaggg gtcagttcgc acggtttgca gtggtttggt    120
gactatgtca acaaagactc gatgaagtgg ctgcgcgatg actgggggat aacgtattc     180
cgtgttgcca tgtacacggc agcggatggc tatatttcca atccttccct gcgaataag     240
gtcaaagaag ccgttgcggt ggcacaaagc ctcggcgtct acatcatcat cgactggcac    300
attttgtcgg ataacgatcc taatatttat aaagcacagg caaaaacctt cttcgccgaa    360
atggctgggc tgtatggtaa ctcgccgaac gtgatttatg aaatcgccaa tgaacctaac    420
ggtggcgtga cctggaacgg gcaaattcgg ccttatgcgc tggaagtgac tgaaactatc    480
cgtagtaaag atcctgataa ccttattatc gtcggcagcg ggacctggag ccaggacatc    540
catgatgcgg cggacaatct gttgcccgat ccgaatacga tgtacgcgct gcatttctat    600
gcgggtacgc acgggcagtt cctgcgcgat cgcattgatt atgcacaaag ccgcggtgcc    660
gcgattttg tcagcgagtg gggcacaagc gatgcgtccg gcaatggcgg accgttcctg     720
cctgaatcgc agacctggat cgatttcctg aataaccgtg gcgtaagctg ggttaactgg    780
tcgcttaccg ataaatcaga ggcgtctgcg gcgctggctc aggggcgag caaatcaggt     840
ggctggacgg agcagaattt gtcaacgtca ggcaaatttg tcagagagca gattcgtgcg    900
ggtgcagacc tgagtggtgg cgttcaccat caccatcacc attaa                   945
```

<210> SEQ ID NO 24
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 24

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Gly Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Leu Leu Pro Asp Pro Asn
            180                 185                 190

Thr Met Tyr Ala Leu His Phe Tyr Ala Gly Thr His Gly Gln Phe Leu
        195                 200                 205
```

```
Arg Asp Arg Ile Asp Tyr Ala Gln Ser Arg Gly Ala Ala Ile Phe Val
210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
                260                 265                 270

Ala Pro Gly Ala Ser Lys Ser Gly Gly Trp Thr Glu Gln Asn Leu Ser
                275                 280                 285

Thr Ser Gly Lys Phe Val Arg Glu Gln Ile Arg Ala Gly Ala Asp Leu
                290                 295                 300

Ser Gly Gly Val His His His His His His
305                 310

<210> SEQ ID NO 25
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 25
atggccacgc cagtagaaac gcatggccag ctgtccatcg aaaacgggcg actggtggat      60
gaacagggga aagggtgca actgagaggg gtcagttcgc acggtttgca gtggtttggt     120
gactacgtca caaagattc gatgaaatgg ctgcgcgatg actgggggat taacgtattc     180
cgtgttgcca tgtacacggc agcggatggc tatatttcca atccttccct tgcgaataag     240
gtcaaagaag ccgttgcggt ggcacaaagc ctcggcgttt acatcatcat cgactggcac     300
attttgtcgg ataacgatcc taatatttat aaagcacagg caaaaacctt ctttgccgaa     360
atggcgggc tgtacggtaa ttcgccgaac gtgatttatg aaatcgccaa tgagccaaac     420
ggtggcgtga cctggaacgg gcagattcgg ccttatgcgc tggaagccac tgacaccatc     480
cgtagcaaag atcccgataa ccttattatc gtcggcagcg ggacctggag ccaggatatc     540
catgatgcgg cagacaatca gttgcccgat ccgaatactc tgtatgcgct gcatttctat     600
gcgggtacgc acgggcagtt cctgcgcgat cgtattgact atgcacaaag ccgcggtgct     660
gcaattttcg tcagcgagtg gggcaccagc gatgcatccg gcaacggtgg gccgttcctg     720
cctgaatcgc agacctggat cgatttcctg aataaccgtg gcgtaagctg ggtgaactgg     780
tcgcttaccg ataagtcaga ggtgtccgcc gcgctggctc aggggcgag taaatcaggc     840
ggttggacgg agcagaatct gtcgacgtca ggaaaatttg tcagagcaca gattcgcgcg     900
gctgcgaatc taagcggtgg cgatcaccat caccatcacc attaa                   945

<210> SEQ ID NO 26
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 26

Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Val Ser
                20                  25                  30
```

```
Ser His Gly Leu Gln Trp Phe Gly Asp Tyr Val Asn Lys Asp Ser Met
         35                  40                  45
Lys Trp Leu Arg Asp Asp Trp Gly Ile Asn Val Phe Arg Val Ala Met
 50                  55                  60
Tyr Thr Ala Ala Asp Gly Tyr Ile Ser Asn Pro Ser Leu Ala Asn Lys
 65                  70                  75                  80
Val Lys Glu Ala Val Ala Val Ala Gln Ser Leu Gly Val Tyr Ile Ile
                 85                  90                  95
Ile Asp Trp His Ile Leu Ser Asp Asn Asp Pro Asn Ile Tyr Lys Ala
                100                 105                 110
Gln Ala Lys Thr Phe Phe Ala Glu Met Ala Gly Leu Tyr Gly Asn Ser
            115                 120                 125
Pro Asn Val Ile Tyr Glu Ile Ala Asn Glu Pro Asn Gly Gly Val Thr
        130                 135                 140
Trp Asn Gly Gln Ile Arg Pro Tyr Ala Leu Glu Ala Thr Asp Thr Ile
145                 150                 155                 160
Arg Ser Lys Asp Pro Asp Asn Leu Ile Ile Val Gly Ser Gly Thr Trp
                165                 170                 175
Ser Gln Asp Ile His Asp Ala Ala Asp Asn Gln Leu Pro Asp Pro Asn
                180                 185                 190
Thr Leu Tyr Ala Leu His Phe Tyr Ala Gly Thr His Gly Gln Phe Leu
            195                 200                 205
Arg Asp Arg Ile Asp Tyr Ala Gln Ser Arg Gly Ala Ala Ile Phe Val
        210                 215                 220
Ser Glu Trp Gly Thr Ser Asp Ala Ser Gly Asn Gly Gly Pro Phe Leu
225                 230                 235                 240
Pro Glu Ser Gln Thr Trp Ile Asp Phe Leu Asn Asn Arg Gly Val Ser
                245                 250                 255
Trp Val Asn Trp Ser Leu Thr Asp Lys Ser Glu Val Ser Ala Ala Leu
                260                 265                 270
Ala Pro Gly Ala Ser Lys Ser Gly Gly Trp Thr Glu Gln Asn Leu Ser
            275                 280                 285
Thr Ser Gly Lys Phe Val Arg Ala Gln Ile Arg Ala Ala Ala Asn Leu
        290                 295                 300
Ser Gly Gly Asp His His His His His
305                 310

<210> SEQ ID NO 27
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 27
atggccacgc cagtagaaac gcatggccaa ctgtccattg aaaatgggcg actggtggat      60
gagcagggaa aaagagtgca actgagaggg gtcagttcgc acggtttgca gtggtttggc     120
gactatgtca acaaagattc gatgagatgg ccgcgcgatg actgggggat tgacgtattc     180
cgtgttgcca tgtacacggc ggcggatggt tatatttcga atccttccct cgccaataag     240
gtcaaagaag ccgttgcggt ggcacaaagc ctcggcgtct acatcatcat cgactggcac     300
attttgtcgg ataacgatcc caatacttat aaagcacagg caaaaacctt ctttgccgaa     360
atggcggggc tgtatggcag ctcaccgaac gtgatttatg aaatcgccaa tgagccaaac     420
ggtggcgtga cacggaacgg gcaaattcgg ccttatgcgc tggatgtgac tgaaactatc     480
```

-continued

```
cgtagtaaag atcctgataa tccgattatc gtcggcagcg ggacctggag ccaggacatc    540
cacgatgcgg cggacaatct gttgcccgat ccgaatacga tgtacgcgct gcatttctat    600
gccggtacgc acgggcagtt cctgtgtgat cgtatcgatt atgcgcaaag ccgcggtgct    660
gcaattttcg tcagcgagtg gggcacaagc gatgcgtccg caacggtgg gccgttcctg     720 cctgaatcgc agacctggat cgatttcctg aacaaccgtg gtgtgagctg ggttaactgg    780
tcgcttaccg ataaatcaga ggcgtctgcg gcgctggcac cgggagcgag caaatctggc    840
ggttggacag agcagaattt gtcggcgtca ggaaaatttg tcagagcaca gattcgcgcg    900
gctgcgaatc taagcggtgg cgatcaccat caccatcacc attaa                    945
```

<210> SEQ ID NO 28
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 28

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Arg Trp Pro Arg Asp Asp Trp Gly Ile Asp Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
                85                  90                  95

Ile Asp Trp His Ile Leu Ser Asp Asn Asp Pro Asn Thr Tyr Lys Ala
            100                 105                 110

Gln Ala Lys Thr Phe Phe Ala Glu Met Ala Gly Leu Tyr Gly Ser Ser
        115                 120                 125

Pro Asn Val Ile Tyr Glu Ile Ala Asn Glu Pro Asn Gly Gly Val Thr
    130                 135                 140

Arg Asn Gly Gln Ile Arg Pro Tyr Ala Leu Asp Val Thr Glu Thr Ile
145                 150                 155                 160

Arg Ser Lys Asp Pro Asp Asn Pro Ile Ile Val Gly Ser Gly Thr Trp
                165                 170                 175

Ser Gln Asp Ile His Asp Ala Ala Asp Asn Leu Leu Pro Asp Pro Asn
            180                 185                 190

Thr Met Tyr Ala Leu His Phe Tyr Ala Gly Thr His Gly Gln Phe Leu
        195                 200                 205

Cys Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Ala Pro Gly Ala Ser Lys Ser Gly Gly Trp Thr Glu Gln Asn Leu Ser
```

Ala Ser Gly Lys Phe Val Arg Ala Gln Ile Arg Ala Ala Ala Asn Leu
          275                 280                 285

Ala Ser Gly Lys Phe Val Arg Ala Gln Ile Arg Ala Ala Ala Asn Leu
    290                 295                 300

Ser Gly Gly Asp His His His His His His
305                 310

<210> SEQ ID NO 29
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 29

```
atggccacgc cagtagaaac gcatggtcag ctgtccatcg aaaacgggcg actggtggat    60
gaacagggga aagggtgcaa actgagaggg gtcagttcgc acggtttgca gtgggttggt   120
gactatgtca acaaagattc gatgaaatgg ctgcgtgacg actgggggat caatgtgttt   180
cgcgttgcca tgtacacggc ggagaatggt tatattgcta cccttctct cgccaataaa   240
gtaaaagagg ctgttgcggc ggcgcaaagc cttggcgtct acatcatcat cgactggcat   300
atcttgtcgg ataacgatcc taatatttat aaagcacagg caaaaacctc ctttgccgaa   360
atggcggggc tgtatggtaa ctcgccgaac gtgatttatg aaatcgccaa tgagccaaac   420
ggcagtgtga catggaacgg gcaaattcgg ccttatgcgc tggaagccac tgacaccatc   480
cgtagcaaag atcccgataa ccttattatc gtcggcagcg ggacctggag ccaggacatc   540
catgatgcgc ggacaatctc gttgcccgat ccgaatacgc tgtacgcgct gcatttctat   600
gcgggcacgc acgggcagtt cctgcgcgat cgcattgatt atgcacaaag ccgcggtgcc   660
gcgatttttg tcagcgagtg gggcacaagc gatgcgtccg caacggtgg ccgttcctg   720
cctgaatcgc agacctggat cgatttcctg aacaaccgtg gtgtgagctg gttaactgg   780
tcgcttaccg ataaatcaga ggcgtctgcg gcgctgactc caggggcgag taaatcaggc   840
ggttggacgg agcagaatct gtcgacgtca ggcaaatttg tcagagagca gattcgtgca   900
ggtgcgaatc taagcggtgg cgatcaccat caccatcacc attaa                   945
```

<210> SEQ ID NO 30
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 30

Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Val Ser
            20                  25                  30

Ser His Gly Leu Gln Trp Val Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Glu Asn Gly Tyr Ile Ala Asn Pro Ser Leu Ala Asn Lys
65                  70                  75                  80

Val Lys Glu Ala Val Ala Ala Gln Ser Leu Gly Val Tyr Ile Ile
                85                  90                  95

Ile Asp Trp His Ile Leu Ser Asp Asn Asp Pro Asn Ile Tyr Lys Ala

```
            100                 105                 110
Gln Ala Lys Thr Ser Phe Ala Glu Met Ala Gly Leu Tyr Gly Asn Ser
        115                 120                 125

Pro Asn Val Ile Tyr Glu Ile Ala Asn Glu Pro Asn Gly Ser Val Thr
    130                 135                 140

Trp Asn Gly Gln Ile Arg Pro Tyr Ala Leu Glu Ala Thr Asp Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Leu Leu Pro Asp Pro Asn
            180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Thr Pro Gly Ala Ser Lys Ser Gly Gly Trp Thr Glu Gln Asn Leu Ser
        275                 280                 285

Thr Ser Gly Lys Phe Val Arg Glu Gln Ile Arg Ala Gly Ala Asn Leu
    290                 295                 300

Ser Gly Gly Asp His His His His His His
305                 310

<210> SEQ ID NO 31
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 31
atggccacgc cagtagaaac gcatggtcag ctgtccatcg aaaacgggcg actggtggat    60
gaacagggga aaagggtgca actgagaggg gtcagttcgc acggtttgca gtggtttggc   120
gactatgtca caaagactc gatgaagtgg ctgcgtgatg actgggggat taacgtattc   180
cgtgttgcca tgtacacggc agcggatggc tatatttcca atccttccct cgccaataag   240
gtaaaagagg ccgttgcggt ggcacaaagc ctcggcgttt acatcatcat cgactggcac   300
attttgtcgg ataacgatcc taatatttat aaagcacagg caaaaacctt ctttgccgaa   360 atggcgggc tgtatggtaa ctcgccgaac gtgatttatg aaatcgccaa tgaacctaac   420
ggtgccgtga cctggaacgg gcaaattcgg ccttatgcgc tggatgttac tgaaactatc   480
cgtagtaaag atcctgataa tctgattatc gttggcacgg gtacctggag tcaggatatt   540
catgacgcgg cggataatca gctgcccgat ccgaatacgc tgtacgcgct gcatctctat   600
gccggtacgc acgggcaatt cctgtgcgat cgtattgact atgcgcaaag ccgcggcgcc   660 gcgattttg tcagcgagtg ggggacaagc gatgcgtccg gcaatggcgg gccgttcctg   720
cctgaatcgc agacctggat cgatttcctg aataaccgtg cgtaagctg ggtgaactgg   780 tcgcttaccg ataagtcaga ggcgtccgcc gcgctggctc aggggcgag caaatcaggt   840
```

```
ggctggacgg agcagaatat gtcgacgtca ggcaaatttg tcagagagca gattcgtgca    900
ggtgcgaatc taagcggtgg cgatcaccat caccatcacc attaa                    945
```

<210> SEQ ID NO 32
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 32

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
 65                  70                  75                  80

Val Lys Glu Ala Val Ala Val Ala Gln Ser Leu Gly Val Tyr Ile Ile
                 85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Asp Val Thr Glu Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Leu Tyr Ala Gly Thr His Gly Gln Phe Leu
        195                 200                 205

Cys Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Ala Pro Gly Ala Ser Lys Ser Gly Gly Trp Thr Glu Gln Asn Met Ser
        275                 280                 285

Thr Ser Gly Lys Phe Val Arg Glu Gln Ile Arg Ala Gly Ala Asn Leu
    290                 295                 300

Ser Gly Gly Asp His His His His His
305                 310
```

<210> SEQ ID NO 33
<211> LENGTH: 945
<212> TYPE: DNA
<213> ORGANISM: Artificial Sequence

```
<220> FEATURE:
<223> OTHER INFORMATION: Synthetic Oligonucleotide
<221> NAME/KEY: misc_feature
<222> LOCATION: 757
<223> OTHER INFORMATION: n = A,T,C or G

<400> SEQUENCE: 33
atggccacgc cagtagaaac gcatggtcag ctgtccatcg aaaacgggcg actggtggac      60
gaacagggga aaagggtgca actgagaggg gtcagttcgc acggtttgca gtggtttggc     120
gactatgtca acaaagactc gatgaagtgg ctgcgtgatg actgggggat caatgtgttt     180
cgcgttgcca tgtacacggc ggcggatggt tatatttcga atccttccct cgccaataag     240
gtaaaagagg ccgttgcggc ggcgcaaagc ctcggcgttt acatcatcat cgactggcac     300
attttgtcgg ataacgatcc caatacttat aaagcgcagg caaaaacctt ctttgctgaa     360
atggcgggc tgtatggcag ctcaccgaac gtgatttatg aaatcgccaa tgagccaaac     420
ggtggcgtga cctggaacgg gcagattcgg ccttatgcgc tggaagtgac tgacaccatc     480
cgtagcaaag atcctgataa ccttattatc gtcggtaccg gcacctggag tcaggatatc     540
cacgatgcag cggataacca actgcccgat ccgaataccc tatacgcgct gcatttctat     600
gcgggcacgc acgggcaatt cctgtgcgat cgtattgact atgcgcaaag ccgtggcgcg     660
gcgattttcg tctgcgagtg gggcaccagc gatgcgtccg gcaatggcgg gccgttcctg     720
cctgaatcgc agacctggat cgatttcctg aataacngtg gcgtaagctg ggtgaactgg     780
tcgcttagcg ataaatcaga ggcgtccgcc gcgctggctc caggcgcgag taaatcaggt     840
ggctggacgg agcagaatct gtcgacgtca ggcaaatttg tcagagagca gattcgtgca     900
ggtgcgaatc tgggcggtgg cgatcaccat caccatcacc attaa                     945

<210> SEQ ID NO 34
<211> LENGTH: 314
<212> TYPE: PRT
<213> ORGANISM: Artificial Sequence
<220> FEATURE:
<223> OTHER INFORMATION: Synthetic Polypeptide
<221> NAME/KEY: VARIANT
<222> LOCATION: 253
<223> OTHER INFORMATION: Xaa = Any Amino Acid

<400> SEQUENCE: 34

Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
 65                  70                  75                  80

Val Lys Glu Ala Val Ala Ala Ala Gln Ser Leu Gly Val Tyr Ile Ile
                 85                  90                  95

Ile Asp Trp His Ile Leu Ser Asp Asn Asp Pro Asn Thr Tyr Lys Ala
            100                 105                 110

Gln Ala Lys Thr Phe Phe Ala Glu Met Ala Gly Leu Tyr Gly Ser Ser
        115                 120                 125

Pro Asn Val Ile Tyr Glu Ile Ala Asn Glu Pro Asn Gly Gly Val Thr
    130                 135                 140
```

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Thr Gly Thr Trp
            165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
            195                 200                 205

Cys Asp Arg Ile Asp Tyr Ala Gln Ser Arg Gly Ala Ala Ile Phe Val
        210                 215                 220

Cys Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Xaa Gly Val Ser
            245                 250                 255

Trp Val Asn Trp Ser Leu Ser Asp Lys Ser Glu Ala Ser Ala Ala Leu
            260                 265                 270

Ala Pro Gly Ala Ser Lys Ser Gly Gly Trp Thr Glu Gln Asn Leu Ser
            275                 280                 285

Thr Ser Gly Lys Phe Val Arg Glu Gln Ile Arg Ala Gly Ala Asn Leu
            290                 295                 300

Gly Gly Gly Asp His His His His His His
305                 310

<210> SEQ ID NO 35
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 35
atggccacgc cagtagaaac gcatggccaa ctgtccattg aaaatgggcg actggtggat     60
gagcagggaa aaagagtgca actgagagga atcagctcga acgggttgca gtgggttggt    120
gattacgtaa acaaagattc gatgaagtgg ccgcgtgatg actgggggat taatgtgttt    180
cgcgttgcca tgtacacggc ggcggatggc tatatttcga atccttccct cgccaataag    240
gtcaaagaag ccgttgcggt ggcacaaagc ctcggcgtct acatcatcat cgactggcat    300
attttgtcgg acaacgatcc taatatttat aaagcacagg caaaaacctt ctttgccgaa    360
atggcggggc tgtatggcaa ctcgccgaat gtgatttatg aatcgccaa tgagccaaac    420
ggcggcgtga catggaacgg gcaaattcgg ccttatgcgc tggaagtgac tgaaactatc    480
cgtagtaaag atcctgataa tctgattatc gtcggcagcg ggacctggag ccaggatatt    540
catgacgcgg cggataatca gctgcccgat ccgaatacgc tgtacgcgct gcatttctat    600
gctggcatgc acgggcaatt cctgtgcgat cgtattgact atgcgcaaag ccgtggcgcg    660
gcgattttcg tcatcgagtg gggcaccagc gatgcatccg gcaacggtgg gccgttcctg    720
cctgaatcgc agacctggat cgatttcctg aacaaccgtg gcataagctg ggtaaactgg    780
tcactaagcg ataagtctga cgtctgcg gcgctggctc taggggcgag taaatcaggc    840
ggctggacag agcagaattt gtcggcgtca ggaaaatttg tcagagagca gattcgtgca    900
ggtgcgaatc tgggcggtgg cgatcaccat caccatcacc attaa                    945

<210> SEQ ID NO 36
<211> LENGTH: 314

```
<212> TYPE: PRT
<213> ORGANISM: Artificial Sequence
<220> FEATURE:
<223> OTHER INFORMATION: Synthetic Polypeptide

<400> SEQUENCE: 36
```

Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Ile Ser
            20                  25                  30

Ser Asn Gly Leu Gln Trp Val Gly Asp Tyr Val Asn Lys Asp Ser Met
        35                  40                  45

Lys Trp Pro Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Gly Ile Ala Asn Glu Pro Asn Gly Val Thr
    130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Met His Gly Gln Phe Leu
        195                 200                 205

Cys Asp Arg Ile Asp Tyr Ala Gln Ser Arg Gly Ala Ala Ile Phe Val
    210                 215                 220

Ile Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
                245                 250                 255

Trp Val Asn Trp Ser Leu Ser Asp Lys Ser Glu Thr Ser Ala Ala Leu
            260                 265                 270

Ala Leu Gly Ala Ser Lys Ser Gly Gly Trp Thr Glu Gln Asn Leu Ser
        275                 280                 285

Ala Ser Gly Lys Phe Val Arg Glu Gln Ile Arg Ala Gly Ala Asn Leu
    290                 295                 300

Gly Gly Gly Asp His His His His His His
305                 310

```
<210> SEQ ID NO 37
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 37
```
atggccacgc cagtagaaac gcatggtcag ctgtccatcg aaaacgggcg actggtggat     60

```
gaacggggga aaagggtgca actgagaggg gtcagttcgc acggtttaca gtggtttggc      120
gactatgtca acaaagactc gatgaagtgg ctgcgtgatg actgggggat taatgtattc      180
cgcgtcgcca tgtacacggc ggcggatggt tatatttcga atccttccct cgccaataag      240
gtcaaagaag ccgttgcggc ggcgcaaagc ctcggcgttt acatcatcat cgactggcac      300
attttgtcgg ataacgatcc taatatttat aaagcacagg caaaaatctt ctttgccgaa      360 atggcgggc tgtacggtaa ttcgccgaac gtgatttatg aattcgccaa tgaacctaac      420
ggcggcgtga cctggaacgg gcagattcgg ccttatgcgc tggaagtgac tgaaactatc      480
cgtagtaaag atcctgataa tctgattatc gtcggtaccg gcacctggag tcaggatatc      540
cacgatgcag cggataacca actgcccgat ctgaataccc tatacgcgct gcatttctat      600
gcgggcacgc acgggcaatt cctgtgcgat cgtattgact atgcgcaaag ccgtggcgcg      660
gcgattttcg tccgcgagtg gggcaccagc gatgcatccg gcaacggtgg gccgttcctg      720
cctgaatcgc agacctggat cgatttcctg aataaccgtg gcgtaagctg ggtgaactgg      780
tcgcttaccg ataagtctga gacgtctgcg gcgctgactc aggggcgag caaatcaggc      840 ggctggacgg agcagaattt gtcggcatca ggaaaatttg tcagagcaca gattcgcgcg      900
gctgcgaatc taagcggtgg cgatcaccat caccatcacc attaa                     945
```

<210> SEQ ID NO 38
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 38

```
Met Ala Thr Pro Val Glu Thr His Gly Gln Leu Ser Ile Glu Asn Gly
 1               5                   10                  15

Arg Leu Val Asp Glu Arg Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Ala Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Ile Phe Phe Ala Glu Met Ala Gly Leu Tyr Gly Asn Ser
        115                 120                 125

Pro Asn Val Ile Tyr Glu Phe Ala Asn Glu Pro Asn Gly Gly Val Thr
    130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Leu Asn
            180                 185                 190

Thr Leu Tyr Ala Leu His Phe Tyr Ala Gly Thr His Gly Gln Phe Leu
        195                 200                 205
```

```
Cys Asp Arg Ile Asp Tyr Ala Gln Ser Arg Gly Ala Ala Ile Phe Val
        210                 215                 220

Arg Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Thr Ser Ala Ala Leu
                260                 265                 270

Thr Pro Gly Ala Ser Lys Ser Gly Gly Trp Thr Glu Gln Asn Leu Ser
                275                 280                 285

Ala Ser Gly Lys Phe Val Arg Ala Gln Ile Arg Ala Ala Ala Asn Leu
                290                 295                 300

Ser Gly Gly Asp His His His His His His
305                 310
```

<210> SEQ ID NO 39
<211> LENGTH: 771
<212> TYPE: DNA
<213> ORGANISM: Artificial Sequence
<220> FEATURE:
<223> OTHER INFORMATION: Synthetic Oligonucleotide

<400> SEQUENCE: 39

```
atgtttcgcg ttgccatgta cacggcggcg gatggttata tttcgaatcc ttccctcgcc      60
aataaggtca agaagccgt tgcggtggcg caaagcctcg gcgtctacat catcatcgac     120
tggcacattt tgtcggataa cgatcctaat atttataaag cacaggcaaa aaccttcttt     180
gccgaaatgg cggggctgta cggtaattcg ccgaacgtga tttatgaaat cgccaatgaa     240
cctaacggcg gcgtgacctg gaacgggcag attcggcctt atgcgctgga agtgactgaa     300
actatccgta gcaaagatcc tgataacctt attatcgtcg gcagcgggac ctggagccag     360
gacatccatg acgcggcgga taatcagctg cccgatccga atacgctgta cgcgctgcat     420
ttctatgcgg gcacgcacgg gcagttcctg cgcgatcgta ctgactatgc gcaaagccgt     480
ggcgcggcga ttttcgtcag cgagtggagc accagcgatg catccggcaa cggtgggccg     540
ttcctgcctg aatcgcagac ctggatcgat ttcctgaata accgtggcat aagctgggtg     600
aactggtcgc ttaccgataa gtcagaggcg tccgccgcgc tggctccagg ggcgagtaaa     660
tcaggcggtt ggacggagca gaatttgtcg acgtcaggca aatttgtcag agagcagatt     720
cgtgcggggg cgggtctgag cggtggcgat caccatcacc atcaccatta a             771
```

<210> SEQ ID NO 40
<211> LENGTH: 256
<212> TYPE: PRT
<213> ORGANISM: Artificial Sequence
<220> FEATURE:
<223> OTHER INFORMATION: Synthetic Polypeptide

<400> SEQUENCE: 40

```
Met Phe Arg Val Ala Met Tyr Thr Ala Ala Asp Gly Tyr Ile Ser Asn
1               5                   10                  15

Pro Ser Leu Ala Asn Lys Val Lys Glu Ala Val Ala Val Ala Gln Ser
                20                  25                  30

Leu Gly Val Tyr Ile Ile Ile Asp Trp His Ile Leu Ser Asp Asn Asp
                35                  40                  45

Pro Asn Ile Tyr Lys Ala Gln Ala Lys Thr Phe Phe Ala Glu Met Ala
                50                  55                  60
```

```
Gly Leu Tyr Gly Asn Ser Pro Asn Val Ile Tyr Glu Ile Ala Asn Glu
 65                  70                  75                  80

Pro Asn Gly Gly Val Thr Trp Asn Gly Gln Ile Arg Pro Tyr Ala Leu
                 85                  90                  95

Glu Val Thr Glu Thr Ile Arg Ser Lys Asp Pro Asp Asn Leu Ile Ile
            100                 105                 110

Val Gly Ser Gly Thr Trp Ser Gln Asp Ile His Asp Ala Ala Asp Asn
        115                 120                 125

Gln Leu Pro Asp Pro Asn Thr Leu Tyr Ala Leu His Phe Tyr Ala Gly
    130                 135                 140

Thr His Gly Gln Phe Leu Arg Asp Arg Thr Asp Tyr Ala Gln Ser Arg
145                 150                 155                 160

Gly Ala Ala Ile Phe Val Ser Glu Trp Ser Thr Ser Asp Ala Ser Gly
                165                 170                 175

Asn Gly Gly Pro Phe Leu Pro Glu Ser Gln Thr Trp Ile Asp Phe Leu
            180                 185                 190

Asn Asn Arg Gly Ile Ser Trp Val Asn Trp Ser Leu Thr Asp Lys Ser
        195                 200                 205

Glu Ala Ser Ala Ala Leu Ala Pro Gly Ala Ser Lys Ser Gly Gly Trp
    210                 215                 220

Thr Glu Gln Asn Leu Ser Thr Ser Gly Lys Phe Val Arg Glu Gln Ile
225                 230                 235                 240

Arg Ala Gly Ala Gly Leu Ser Gly Gly Asp His His His His His His
                245                 250                 255
```

<210> SEQ ID NO 41
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 41

```
atggccacgc cagtagaaac gcatggtcag ctgtccatcg aaaacgggcg actggtggat      60
gaacagggga aagggtgca  actgagaggg gtcagttcac acggtttgca gtggtttggc     120
gactatgtca caaagactc  gatgaagtgg ctgcgtgatg actggggat  taatgtattc     180
cgcgtcgcca tgtacacggc ggcggatggt tatatttcga tccttccct  cgccaataag     240
gtaaaagagg ccgttgcggc ggcgcaaagc ctcggcgttt acatcatcat cgactggcat     300
atcttgtcgg ataacgatcc caatatttat aaagcacagg caaaaacctt ctttgccgaa     360
atggcgggc  tgtacggtaa ttcgccgaac gtgatttatg aaatcgccaa tgaacctaac     420
ggcggcgtga cctggaacgg cagattcgg  ccttatgcgc tggaagtgac tgaaactatc     480
cgtagtaaag atcctgataa tctgattatc gttgacacgg gtacctggag tcaggatatc     540
catgatgcgg cggacaatct gttgcccgat ccgaatacga cgtacgcgct gcatttctat     600
gcgggcacgc acgggcagtt cctgcgcgat cgtattgact atgcgcaaag ccgtggcgcg     660
gcgattttcg tcagcgagtg gggcaccagc gatgcatccg gcaacggtgg gccgttcctg     720
cctgaatcgc agacctggat cgatttcctg aataaccgtg gcataagctg ggtgaactgg     780
tcgcttaccg ataagtctga gacgtctgcg gcgctgactc aggggcgag  caaatcaggc     840
ggctggacgg agcagaattt gtcgacgtca ggcaaatttg tcagagaaca gattcgtgcg     900
ggggcgggtc tgagcggtgg cgatcaccat caccatcacc attaa                     945
```

<210> SEQ ID NO 42
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 42

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Asp Thr Gly Thr Trp
                165                 170                 175

Ser Gln Asp Ile His Asp Ala Ala Asp Asn Leu Leu Pro Asp Pro Asn
            180                 185                 190

Thr Thr Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
                245                 250                 255

Trp Val Asn Trp Ser Leu Thr Asp Lys Ser Glu Thr Ser Ala Ala Leu
            260                 265                 270

Thr Pro Gly Ala Ser Lys Ser Gly Gly Trp Thr Glu Gln Asn Leu Ser
        275                 280                 285

Thr Ser Gly Lys Phe Val Arg Glu Gln Ile Arg Ala Gly Ala Gly Leu
    290                 295                 300

Ser Gly Gly Asp His His His His His His
305                 310
```

<210> SEQ ID NO 43
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 43

```
atggccacgc cagtagaaac gcatggtcag ctgtccatcg aaaacgggcg actggtggat      60
gaacagggga aaagggtgca attgagaggg gtcagttcgc acggtttgca gtggtttggc     120
gactatgtca acaaagactc gatgaagtgg ctgcgtgatg actgggggat taatgtattc     180
cgcgtcgcca tgtacacggc ggcggatggt tatatttcga atccttccct cgccaataag     240
gtcaaagagg ccgttgcggc ggcgcaaagc ctcggcgttt acatcatcat cgactggcat     300
atcttgtcgg ataacgatcc caatatttat aaagcacagg caaaaacctt ctttgccgaa     360
atggcgggc tgtacggtaa ttcgccgaac gtgatttatg aaatcgccaa tgagccaaac     420
ggtggcgtga cgtggaacgg acagattcgg ccttatgcgc tggaggtgac tgacactatc     480
cgtagcaaag atcctgataa ccttattatc gtcggcagcg ggacctggag ccaggacatc     540
catgacgcgg cggataatca gctgcccgat ccggatacgc tgtacgcgct gcatttctat     600
gcgggcacgc acgggcaatt cctgtgcgat cgtattgact atgcgcaaag ccgtggcgcg     660
gcgattttcg tcagcgagtg gggcaccagc gatgcatccg caacggtgg gccgttcctg     720
cctgaatcgc agacctggat cgatttcctg aataaccgtg gcataagctg ggtgaactgg     780
tcgcttaccg ataagtcaga ggcgtccgcc gcgctggctc caggggcgag taaatcaggc     840
ggctggacgg agcagaattt gtcgacgtca ggcaaatttg tcagagagca gattcgtgcg     900
ggggcgggtc tgagcggtgg cgatcaccat caccatcacc attaa                     945
```

<210> SEQ ID NO 44
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 44

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Ala Gln Ser Leu Gly Val Tyr Ile Ile
            85                  90                  95

Ile Asp Trp His Ile Leu Ser Asp Asn Asp Pro Asn Ile Tyr Lys Ala
        100                 105                 110

Gln Ala Lys Thr Phe Phe Ala Glu Met Ala Gly Leu Tyr Gly Asn Ser
    115                 120                 125

Pro Asn Val Ile Tyr Glu Ile Ala Asn Glu Pro Asn Gly Gly Val Thr
            130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Gln Leu Pro Asp Pro Asp
            180                 185                 190

Thr Leu Tyr Ala Leu His Phe Tyr Ala Gly Thr His Gly Gln Phe Leu
```

```
                 195                 200                 205
Cys Asp Arg Ile Asp Tyr Ala Gln Ser Arg Gly Ala Ala Ile Phe Val
    210                 215                 220
Ser Glu Trp Gly Thr Ser Asp Ala Ser Gly Asn Gly Gly Pro Phe Leu
225                 230                 235                 240
Pro Glu Ser Gln Thr Trp Ile Asp Phe Leu Asn Asn Arg Gly Ile Ser
                245                 250                 255
Trp Val Asn Trp Ser Leu Thr Asp Lys Ser Glu Ala Ser Ala Ala Leu
            260                 265                 270
Ala Pro Gly Ala Ser Lys Ser Gly Gly Trp Thr Glu Gln Asn Leu Ser
        275                 280                 285
Thr Ser Gly Lys Phe Val Arg Glu Gln Ile Arg Ala Gly Ala Gly Leu
    290                 295                 300
Ser Gly Gly Asp His His His His His His
305                 310
```

<210> SEQ ID NO 45
<211> LENGTH: 766
<212> TYPE: DNA
<213> ORGANISM: Artificial Sequence
<220> FEATURE:
<223> OTHER INFORMATION: Synthetic Oligonucleotide

<400> SEQUENCE: 45

```
atggccacgc cagtagaaac gcatggtcag ctgtccatcg aaaacgggcg actggtggat      60
gaacagggga aagggtgca actgagaggg gtcagttcgc acggtttgca gtggtttggc     120
gactatgtca caaagactc gatgaagtgg ctgcgtgatg actgggggat taatgtattc     180
cgcgtcgcca tgtacacggc ggcggatggt tatatttcga atccttccct cgccaataag     240
gtaaaagagg ccgttgcggc ggcgcaaagc ctcggcgttt acatcatcat cgactggcac     300
attttgtcgg ataacgatcc cagtatttat aaagcacagg caaaaaccct ctttgccgaa     360
atggcggggc tgtacggtaa ttcgccgaac gtgatttatg aaatcgccaa tgaacctaac     420
ggcggcgtga catggaacgg gcagattcgg ccttatgcgc tggaagtgac tgaaactatc     480
cgtagtaaag atcctgataa tctgattatc gttggcacgg gtacctggag tcaggatatc     540
catgatgcgg cggacaatct gttgcccgat ccgaatacga tgtacgcgct gcatttctat     600
gcgggcacgc acggacaatt cctgtgcgat cgtattgact atgcgcaaag ccgtggcgcg     660
gcgattttcg tcagcgagtg gggcaccagc gatgcatccg gcaacggtgg gccgttcctg     720
cctgaatcgc agacctggat cgatttcctg aataaccgtg gcataa                    766
```

<210> SEQ ID NO 46
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 46

```
Met Ala Thr Pro Val Glu Thr His Gly Gln Leu Ser Ile Glu Asn Gly
1               5                   10                  15
Arg Leu Val Asp Glu Gln Gly Lys Arg Val Gln Leu Arg Gly Val Ser
            20                  25                  30
Ser His Gly Leu Gln Trp Phe Gly Asp Tyr Val Asn Lys Asp Ser Met
        35                  40                  45
Lys Trp Leu Arg Asp Asp Trp Gly Ile Asn Val Phe Arg Val Ala Met
```

```
                   50                  55                  60
Tyr Thr Ala Ala Asp Gly Tyr Ile Ser Asn Pro Ser Leu Ala Asn Lys
 65                  70                  75                  80

Val Lys Glu Ala Val Ala Ala Gln Ser Leu Gly Val Tyr Ile Ile
                 85                  90                  95

Ile Asp Trp His Ile Leu Ser Asp Asn Asp Pro Ser Ile Tyr Lys Ala
                100                 105                 110

Gln Ala Lys Thr Phe Phe Ala Glu Met Ala Gly Leu Tyr Gly Asn Ser
                115                 120                 125

Pro Asn Val Ile Tyr Glu Ile Ala Asn Glu Pro Asn Gly Val Thr
                130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Leu Leu Pro Asp Pro Asn
                180                 185                 190

Thr Met Tyr Ala Leu His Phe Tyr Ala Gly Thr His Gly Gln Phe Leu
                195                 200                 205

Cys Asp Arg Ile Asp Tyr Ala Gln Ser Arg Gly Ala Ala Ile Phe Val
210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
                245                 250                 255

Trp Val Asn Trp Ser Leu Thr Asp Lys Ser Glu Ala Ser Ala Ala Leu
                260                 265                 270

Ala Pro Gly Ala Ser Lys Ser Gly Gly Trp Thr Glu Gln Asn Leu Ser
                275                 280                 285

Ala Ser Gly Lys Phe Val Arg Ala Gln Ile Arg Ala Ala Ala Asn Leu
                290                 295                 300

Ser Gly Gly Asp His His His His His His
305                 310

<210> SEQ ID NO 47
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 47
atggccacgc cagtagaaac gcatggccaa ctgtccatcg aaaacgggcg actggtggat      60
gaacagggga aaagggtgca actgagaggg gtcagttcgc acggtttgca gtggtttggt     120
gactacgtca acaaagattc gatgaaatgg ctgcgcgatg actgggggat taacgtattc     180
cgtgttgcca tgtacacggc ggagaatggt tatatttcga atccttccct cgccaataag     240
gtaaaagaag ccgttgcggt ggcacaaagc ctcggcgtct acatcatcat cgactggcat     300
atcttgtcgg ataacgatcc taatatttat aaagcacagg caaaaatctt ctttgccgaa     360 atggcgggc tgtatggcaa ctcgccgaac gtggtttatg aaatcgccaa tgaacctgac     420
ggcggcgtga cctggaacgg gcaaattcgg ccttatgcgc tggaagccac tgacactatc     480
cgtagcaaag atcctgataa ccttattatc gtcggcagcg ggacctggag ccaggacatc     540
catgatgcgg cggacaatct gttgcccgat ccgaatacga tgtacgcgct gcatttctat     600
```

```
gcgggtacac acgggcagtt cctgcgcgat cgtatcgatt atgcgcaaag ccgcggtgcc      660 gcgattttg tcagcgagtg gggcaccagc gatgcatccg caacggcgg accgttcctg       720 cctgaatcgc agacctggat cgatttcctg aacaaccgtg gcgtaagctg ggtgaactgg     780
tcgcttaccg ataaatcaga ggcgtctgcg gcgctggcac cggggggcgag caaatctggc    840 ggttggacgg agcagaattt gtcggcgtca ggaaaatttg tcagagcaca gattcgcgcg    900
gctgcgaatc taagcggtgg cgatcaccat caccatcacc attaa                    945
```

<210> SEQ ID NO 48
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 48

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
                 20                  25                  30

Ser His Gly Leu Gln Trp Phe Gly Asp Tyr Val Asn Lys Asp Ser Met
             35                  40                  45

Lys Trp Leu Arg Asp Asp Trp Gly Ile Asn Val Phe Arg Val Ala Met
 50                  55                  60

Tyr Thr Ala Glu Asn Gly Tyr Ile Ser Asn Pro Ser Leu Ala Asn Lys
 65                  70                  75                  80

Val Lys Glu Ala Val Ala Val Ala Gln Ser Leu Gly Val Tyr Ile Ile
                 85                  90                  95

Ile Asp Trp His Ile Leu Ser Asp Asn Asp Pro Asn Ile Tyr Lys Ala
            100                 105                 110

Gln Ala Lys Ile Phe Phe Ala Glu Met Ala Gly Leu Tyr Gly Asn Ser
            115                 120                 125

Pro Asn Val Val Tyr Glu Ile Ala Asn Glu Pro Asp Gly Gly Val Thr
        130                 135                 140

Trp Asn Gly Gln Ile Arg Pro Tyr Ala Leu Glu Ala Thr Asp Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Leu Leu Pro Asp Pro Asn
            180                 185                 190

Thr Met Tyr Ala Leu His Phe Tyr Ala Gly Thr His Gly Gln Phe Leu
            195                 200                 205

Arg Asp Arg Ile Asp Tyr Ala Gln Ser Arg Gly Ala Ala Ile Phe Val
        210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Ala Pro Gly Ala Ser Lys Ser Gly Gly Trp Thr Glu Gln Asn Leu Ser
        275                 280                 285

Ala Ser Gly Lys Phe Val Arg Ala Gln Ile Arg Ala Ala Ala Asn Leu
        290                 295                 300
```

Ser Gly Gly Asp His His His His His His
305                 310

<210> SEQ ID NO 49
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 49

```
atggccacgc cagtagaaac gcatggccaa ctgtccattg aaaatgggcg actggtggat      60
gaacagggga aaagggtgca actgagaggg gtcagttcgc acggtttgca gtggtttggt    120
gactacgtca acaaagattc gatgaaatgg ctgcgtgacg actgggggat caatgtgttt    180
cgcgttgcca tgtacacggc ggagaatggt tatatttcca atccttccct tgcgaataag    240
gtcaaagaag ccgttgcggc ggcgcaaagc ctcggcgttt acatcatcat cgactggcac    300
attttgtcgg ataacgatcc caatacttat aaagcacagg caaaaacctt ctttgccgaa    360
atggcggggc tgtacggtaa ttcgccgaac gtgatttatg aaatcgccaa tgagccaaac    420
ggtggcgtga cctggaacgg gcagattcgg ccttatgcgc tggaagtgac tgacaccatc    480
cgtagcaaag atcccgataa cctcattatc gtcggtaccg gcacctggag tcaggatatc    540
cacgatgcag cggataacca actgcccgat ccgaataccc tatacgcgct gcatttctat    600
gctggcacgc acgggcagtt cctgcgcgat cgcattgact atgcgcaaag ccgcggtgcc    660
gcgattttg tcagcgagtg gggcaccagc gatgcatccg gcaatggcgg gccgttcctg    720
ccagaatcgc aaacctggat cgatttcctg aataaccgtg gcgtaagctg ggtgaactgg    780
tcgcttaccg ataagtcaga ggcgtctgcg gcgctgactc caggggcgag taaatcaggc    840
ggttggacgg agcagaatct gtcgacgtca ggaaaatttg tcagagcaca gattcgcgcg    900
gctgcgaatc tgggcggtgg cgatcaccat caccatcacc attaa                    945
```

<210> SEQ ID NO 50
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 50

Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Glu Asn Gly Tyr Ile Ser Asn Pro Ser Leu Ala Asn Lys
65                  70                  75                  80

Val Lys Glu Ala Val Ala Ala Ala Gln Ser Leu Gly Val Tyr Ile Ile
                85                  90                  95

Ile Asp Trp His Ile Leu Ser Asp Asn Asp Pro Asn Thr Tyr Lys Ala
            100                 105                 110

Gln Ala Lys Thr Phe Phe Ala Glu Met Ala Gly Leu Tyr Gly Asn Ser
        115                 120                 125

```
Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Thr Pro Gly Ala Ser Lys Ser Gly Gly Trp Thr Glu Gln Asn Leu Ser
        275                 280                 285

Thr Ser Gly Lys Phe Val Arg Ala Gln Ile Arg Ala Ala Ala Asn Leu
    290                 295                 300

Gly Gly Gly Asp His His His His His His
305                 310

<210> SEQ ID NO 51
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 51
atggccacgc cagtagaaac acatggccaa ctgtccatcg aaaatgggcg actggtggac      60
gaacagggga aaagggtgca actgagaggg gtcagttcgc acggtttgca gtggtttggc    120
gactatgtca caaagactc gatgaagtgg ctgcgtgatg actggggtat aaatgtgttc     180
cgcgtcgcta tgtacacggc ggagaatggt tatatttcga tccttccct cgccaataag    240 gtaaaagagg ccgttgcggc ggcgcaaagc cttggcatct acatcattat cgactggcac    300
attttgtcgg ataacgatcc taatatttat aaagcgcagg caaaaacctt ctttgctgaa    360 atggcgggc tgtatggtaa ttcgccgaac gtgatttatg aaatcgccaa tgaacctaac    420
ggcggcgtga catggaacgg gcagattcgg ccttatgcgc tggaagccac tgacaccatc    480
cgtagcaaag atcccgataa cctcattatc gtcggtaccg gcacctggag tcaggatatt    540
catgacgcgg cagacaatca gctgcccgat ccgaatacgc tgtacgcgct gcatttctat    600
gcgggtacgc acgggcagtt cctgcgcgat cgtatcgatt atgcgcaaag ccgcggtgct    660
gcaattttcg tcagcgagtg gggcaccagc gatgcatccg gcaacggtgg gccgttcctg    720
cctgaatcgc agacctggat cgatttcctg aacaaccgtg gtgtgagctg ggttaactgg    780
tcgcttaccg ataaatcaga ggcgtccgcc gcgctggctc aggggcgag taaatcagac    840 ggttggacgg agcagaatct gtcgacgtca ggaaaatttg tcagagcaca gattcgcgcg    900
gctgcgaatc taagcggtgg cgatcaccat caccatcacc attaa                    945
```

<210> SEQ ID NO 52
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 52

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Asp Ser Met
        35                  40                  45

Lys Trp Leu Arg Asp Asp Trp Gly Ile Asn Val Phe Arg Val Ala Met
    50                  55                  60

Tyr Thr Ala Glu Asn Gly Tyr Ile Ser Asn Pro Ser Leu Ala Asn Lys
65                  70                  75                  80

Val Lys Glu Ala Val Ala Ala Gln Ser Leu Gly Ile Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Ala Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Ala Ser Ala Ala Leu
            260                 265                 270

Ala Pro Gly Ala Ser Lys Ser Asp Gly Trp Thr Glu Gln Asn Leu Ser
        275                 280                 285

Thr Ser Gly Lys Phe Val Arg Ala Gln Ile Arg Ala Ala Ala Asn Leu
    290                 295                 300

Ser Gly Gly Asp His His His His His His
305                 310
```

<210> SEQ ID NO 53
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 53

```
atggccacgc cagtagaaac gcatggtcag ctgtccatcg aaaacgggcg actggtggat      60
gaacagggga aaagggtgca actgagaggg gtcagttcgc acggtttgca gtggtttggc     120
gactatgtca acaaagactc gatgaaatgg ctgcgtgatg actgggggat taatgtattc     180
cgtgttgcca tgtacacggc agcggatggc tatatttcca atccttccct gcgaataag      240
gtcaaagaag ccgttgcggt ggcgcaaagc cttggcatct acatcatcat cgactggcac     300
attttgtcgg ataacgatcc taatatttat aaagcgcagg caaaaacctt ctttgctgaa     360
atggcgggc tgtacggtaa ttcgccgaac gtgatttatg aaatcgccaa tgaacctaac      420
ggcggcgtga catggaacgg gcagattcgg ccttatgcgc tggatgttac tgacactatc     480
cgtagcaaag atcctgataa ccttattatc gtcggtaccg gcacctggag tcaggatatt     540
catgacgcgg cggataatca gctgcccgat ccgaatacgc tgtacgcgct gcatttctat     600
gcgggcacgc acgggcagtt cctgcgcgat cgcattgact atgcacaaag ccgcggtgct     660
gcaatttttg tcagcgagtg gggcacaagc gatgcatccg caacggtgg gccgttcctg      720
cctgaatcgc agacctggat cgatttcctg aataaccgtg gtataagctg gtaaactgg      780
tcgcttaccg ataagtctga gcatccgcg gcgctggcac cgggagcgag caaatctggt      840
ggttggacag agcagaattc gtcggcgtca ggaaaatttg tcagagagca ggttcgtgcg      900
ggtgcagacc tgagtggtgg cgatcaccat caccatcacc attaa                     945
```

<210> SEQ ID NO 54
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 54

```
Met Ala Thr Pro Val Glu Thr His Gly Gln Leu Ser Ile Glu Asn Gly
  1               5                  10                  15

Arg Leu Val Asp Glu Gln Gly Lys Arg Val Gln Leu Arg Gly Val Ser
             20                  25                  30

Ser His Gly Leu Gln Trp Phe Gly Asp Tyr Val Asn Lys Asp Ser Met
         35                  40                  45

Lys Trp Leu Arg Asp Asp Trp Gly Ile Asn Val Phe Arg Val Ala Met
     50                  55                  60

Tyr Thr Ala Ala Asp Gly Tyr Ile Ser Asn Pro Ser Leu Ala Asn Lys
 65                  70                  75                  80

Val Lys Glu Ala Val Ala Val Ala Gln Ser Leu Gly Ile Tyr Ile Ile
                 85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Asp Val Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190
```

Thr Leu Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
            245                 250                 255

Trp Val Asn Trp Ser Leu Thr Asp Lys Ser Glu Thr Ser Ala Ala Leu
                260                 265                 270

Ala Pro Gly Ala Ser Lys Ser Gly Gly Trp Thr Glu Gln Asn Ser Ser
        275                 280                 285

Ala Ser Gly Lys Phe Val Arg Glu Gln Val Arg Ala Gly Ala Asp Leu
    290                 295                 300

Ser Gly Gly Asp His His His His His His
305                 310

<210> SEQ ID NO 55
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 55
atggccacgc cagtagaaac gcatggccaa ctgtccatcg aaaatgggcg actggtggat     60
gagcagggaa aaagagtgca actgagaggg gtcagttcgc acggtttgca gtggtttggt    120
gactatgtca caaagactc gatgaagtgg ctgcgtgatg actgggggat taacgtattc    180
cgtgttgcca tgtacacggc agcggatggc tatatttcca atcctcccct tgcgaataag    240
gtcaaagaag ccgttgcggt ggcacaaagc ctcggcgtct acatcatcat cgactggcat    300
atcttgtcgg ataacgatcc taatatttat aaagcacagg caaaaacctt ctttgccgaa    360 atggcgggc tgtacggtaa ttcgccgaac gtgatttatg aaatcgccaa tgaacctaac    420
ggcggcgtga catggaacgg gcaaattcgg ccttatgcgc tggaagtgac tgacactatc    480
cgtagcaaag atcctgataa ccttattatc gtcggcagcg ggacctggag ccaggacatc    540
catgatgcgg cagacaatca gttgcccgat ccgaatacgc tgtacgcgct gcatttctat    600
gcgggcacgc acgggcaatt cctgtgcgat cgtattgact atgcgcaaag ccgtggcgcg    660
gcgattttcg tcagcgagtg gggcaccagc gatgcatccg gcaacggcgg accgttcctg    720
cctgaatcgc aaacctggat cgatttcctg aataaccgtg gcataagctg ggttaactgg    780
tcgcttagcg ataagtctga gacgtctgcg gcgctgactc caggggcgag taaatcaggc    840
ggttggacgg agcagaatct gtcggcgtca ggaaaacttg tcagagcaca gattcgtgca    900
ggtgcgaatc tgggcggtgg cgatcaccat caccatcacc attaa                    945

<210> SEQ ID NO 56
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 56

Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Val Ser
         20                  25                  30

Ser His Gly Leu Gln Trp Phe Gly Asp Tyr Val Asn Lys Asp Ser Met
     35                  40                  45

Lys Trp Leu Arg Asp Asp Trp Gly Ile Asn Val Phe Arg Val Ala Met
 50                  55                  60

Tyr Thr Ala Ala Asp Gly Tyr Ile Ser Asn Pro Pro Leu Ala Asn Lys
 65                  70                  75                  80

Val Lys Glu Ala Val Ala Val Ala Gln Ser Leu Gly Val Tyr Ile Ile
                 85                  90                  95

Ile Asp Trp His Ile Leu Ser Asp Asn Asp Pro Asn Ile Tyr Lys Ala
             100                 105                 110

Gln Ala Lys Thr Phe Phe Ala Glu Met Ala Gly Leu Tyr Gly Asn Ser
         115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Ser Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
        195                 200                 205

Cys Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Ile Ser
                245                 250                 255

Trp Val Asn Trp Ser Leu Ser Asp Lys Ser Glu Thr Ser Ala Ala Leu
            260                 265                 270

Thr Pro Gly Ala Ser Lys Ser Gly Gly Trp Thr Glu Gln Asn Leu Ser
        275                 280                 285

Ala Ser Gly Lys Leu Val Arg Ala Gln Ile Arg Ala Gly Ala Asn Leu
    290                 295                 300

Gly Gly Gly Asp His His His His His
305                 310

<210> SEQ ID NO 57
<211> LENGTH: 945
<212> TYPE: DNA
<213> ORGANISM: Artificial Sequence
<220> FEATURE:
<223> OTHER INFORMATION: Synthetic Oligonucleotide
<221> NAME/KEY: misc_feature
<222> LOCATION: 799, 852, 855, 884, 886
<223> OTHER INFORMATION: n = A,T,C or G

<400> SEQUENCE: 57
atggccacgc cagtagaaac gcatggtcag ctgtccatcg aaaacgggcg actggtggat    60
gaacagggga aaagggtgca actgagaggg gtcagttcgc acggtttgca gtggtttggt   120
gactacgtca acaaaggttc gatgaaatgg ctgcgcgatg actgggggat taacgtattc   180
cgtgttgcca tgtacacggc ggcggatggt tatatttcga atcctcccct cgccaataag   240
gtaaaagaag ccgttgcggt ggcacaaagc ctcggcgtct acatcatcat cgactggcat   300

```
atcttgtcgg ataacgatcc taatatttat aaagcacagg caaaaacctt ctttgccgaa    360
atggcggggc tgtacggtaa ttcgccgaac gtgatttatg aaatcgccaa tgaacctaac    420
ggcggcgtga catggaacgg gcaaattcgg ccttatgcgc tggaagtgac tgaaactatc    480
cgtagtaaag atcctgataa tctgattatc gttggcacgg gtacctggag tcaggatatt    540
catgacgcgg cggataatca gctgcccgat ccgaatacga tgtacgcgct gcatttctat    600
gcgggtacgc acgggcagtt cctgcgcgat cgcattgatt atgcacaaag ccgcggtgcc    660
gcgattttg tcagcgagtg gggcaccagc gatgcatccg caacggtgg gccgttcctg    720
cctgaatcgc agacctggat cgatttcctg aataaccgtg cgtaagctg ggtgaactgg    780
tcgcttaccg ataaatcana ggcgtccgcc gcgctggctc aggggcgag taaatctggc    840
ggttggacgg ancanaatct gtcgacgtca ggcaaatttg tcananagca gattcgtgca    900
ggtgcgaatc tgggcggtgg cgatcaccat caccatcacc attaa              945
```

<210> SEQ ID NO 58  
<211> LENGTH: 314  
<212> TYPE: PRT  
<213> ORGANISM: Artificial Sequence  
<220> FEATURE:  
<223> OTHER INFORMATION: Synthetic Polypeptide  
<221> NAME/KEY: VARIANT  
<222> LOCATION: 267, 284, 285, 295, 296  
<223> OTHER INFORMATION: Xaa = Any Amino Acid

<400> SEQUENCE: 58

```
Met Ala Thr Pro Val Glu Thr His Gly Gln Leu Ser Ile Glu Asn Gly
 1               5                  10                  15

Arg Leu Val Asp Glu Gln Gly Lys Arg Val Gln Leu Arg Gly Val Ser
            20                  25                  30

Ser His Gly Leu Gln Trp Phe Gly Asp Tyr Val Asn Lys Gly Ser Met
        35                  40                  45

Lys Trp Leu Arg Asp Asp Trp Gly Ile Asn Val Phe Arg Val Ala Met
    50                  55                  60

Tyr Thr Ala Ala Asp Gly Tyr Ile Ser Asn Pro Ser Leu Ala Asn Lys
65                  70                  75                  80

Val Lys Glu Ala Val Ala Val Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
        115                 120                 125

Pro Asn Val Ile Tyr Glu Ile Ala Asn Glu Pro Asn Gly Gly Val Thr
    130                 135                 140

Trp Asn Gly Gln Ile Arg Pro Tyr Ala Leu Glu Val Thr Glu Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Met Tyr Ala Leu His Phe Tyr Ala Gly Thr His Gly Gln Phe Leu
        195                 200                 205

Arg Asp Arg Ile Asp Tyr Ala Gln Ser Arg Gly Ala Ala Ile Phe Val
    210                 215                 220

Ser Glu Trp Gly Thr Ser Asp Ala Ser Gly Asn Gly Gly Pro Phe Leu
```

```
                225                 230                 235                 240
Pro Glu Ser Gln Thr Trp Ile Asp Phe Leu Asn Asn Arg Gly Val Ser
                    245                 250                 255

Trp Val Asn Trp Ser Leu Thr Asp Lys Ser Xaa Ala Ser Ala Ala Leu
                260                 265                 270

Ala Pro Gly Ala Ser Lys Ser Gly Gly Trp Thr Xaa Xaa Asn Leu Ser
                275                 280                 285

Thr Ser Gly Lys Phe Val Xaa Xaa Gln Ile Arg Ala Gly Ala Asn Leu
            290                 295                 300

Gly Gly Gly Asp His His His His His His
305                 310
```

<210> SEQ ID NO 59
<211> LENGTH: 945
<212> TYPE: DNA
<213> ORGANISM: Artificial Sequence
<220> FEATURE:
<223> OTHER INFORMATION: Synthetic Oligonucleotide

<400> SEQUENCE: 59

```
atggccacgc cagtagaaac gcatggtcag ctgtccatcg aaaacgggcg actggtggat    60
gaacagggga aagggtgca actgagaggg gtcagttcgc acggtttgca gtggtttggt   120
gactacgtca caaagattc gataaaatgg ctgcgtgacg actgggggat caatgtgttt   180
cgcgttgcca tgtacacggc ggagaatggt tatattgcta cccttctct cgccaataag   240
gtaaaagagg ccgttgcggc ggcgcaaagc ctcggcgttt acatcatcat cgactggcat   300
atcttgtcgg ataacgatcc taatatttat aaagcacagg caaaaacctt ctttgccgaa   360
atggctgggc tgtacggtaa ttcgccgaac gtgatttatg aaatcgccaa tgaacctaac   420
ggcggcgtga catggaacgg gcaaattcgg ccttatgcgc tggaagtgac tgacaccatc   480
cgtagcaaag atcccgataa cctcattatc gtcggtaccg gcacctggag tcaggatatc   540
cacgatgcag cggataacca actgcccgat ccgaataccc tatacgcgct gcatttctat   600
gccggtacgc acgggcagtt cctgcgcgat cgtattgact atgcacaaag ccgcggtgcc   660
gcgattttcg tcagcgagtg gggcacaagc gatgcgtccg gcaacggcgg accgttcctg   720
cctgaatcgc agacctggat cgatttcctg aataaccgtg gcgtaagctg gtgaactgg   780
tcgcttaccg ataagtcaga gacgtctgcg gcgctggcac cgggagcgag caaatctggc   840
ggttggacag agcagaattt gtcggcgtca gcaaatttg tcagagagca gattcgtgca   900
ggtgcgaatc tgggcggtgg cgatcaccat caccatcacc attaa                   945
```

<210> SEQ ID NO 60
<211> LENGTH: 314
<212> TYPE: PRT
<213> ORGANISM: Artificial Sequence
<220> FEATURE:
<223> OTHER INFORMATION: Synthetic Polypeptide

<400> SEQUENCE: 60

```
Met Ala Thr Pro Val Glu Thr His Gly Gln Leu Ser Ile Glu Asn Gly
1               5                   10                  15

Arg Leu Val Asp Glu Gln Gly Lys Arg Val Gln Leu Arg Gly Val Ser
                20                  25                  30

Ser His Gly Leu Gln Trp Phe Gly Asp Tyr Val Asn Lys Asp Ser Ile
            35                  40                  45

Lys Trp Leu Arg Asp Asp Trp Gly Ile Asn Val Phe Arg Val Ala Met
```

```
        50              55              60
Tyr Thr Ala Glu Asn Gly Tyr Ile Ala Asn Pro Ser Leu Ala Asn Lys
65                  70                  75                  80

Val Lys Glu Ala Val Ala Ala Ala Gln Ser Leu Gly Val Tyr Ile Ile
                85                  90                  95

Ile Asp Trp His Ile Leu Ser Asp Asn Asp Pro Asn Ile Tyr Lys Ala
            100                 105                 110

Gln Ala Lys Thr Phe Phe Ala Glu Met Ala Gly Leu Tyr Gly Asn Ser
            115                 120                 125

Pro Asn Val Ile Tyr Glu Ile Ala Asn Glu Pro Asn Gly Gly Val Thr
            130                 135                 140

Trp Asn Gly Gln Ile Arg Pro Tyr Ala Leu Glu Val Thr Asp Thr Ile
145                 150                 155                 160

Arg Ser Lys Asp Pro Asp Asn Leu Ile Ile Val Gly Thr Gly Thr Trp
                165                 170                 175

Ser Gln Asp Ile His Asp Ala Ala Asp Asn Gln Leu Pro Asp Pro Asn
            180                 185                 190

Thr Leu Tyr Ala Leu His Phe Tyr Ala Gly Thr His Gly Gln Phe Leu
            195                 200                 205

Arg Asp Arg Ile Asp Tyr Ala Gln Ser Arg Gly Ala Ala Ile Phe Val
210                 215                 220

Ser Glu Trp Gly Thr Ser Asp Ala Ser Gly Asn Gly Gly Pro Phe Leu
225                 230                 235                 240

Pro Glu Ser Gln Thr Trp Ile Asp Phe Leu Asn Asn Arg Gly Val Ser
                245                 250                 255

Trp Val Asn Trp Ser Leu Thr Asp Lys Ser Glu Thr Ser Ala Ala Leu
                260                 265                 270

Ala Pro Gly Ala Ser Lys Ser Gly Gly Trp Thr Glu Gln Asn Leu Ser
            275                 280                 285

Ala Ser Gly Lys Phe Val Arg Glu Gln Ile Arg Ala Gly Ala Asn Leu
            290                 295                 300

Gly Gly Gly Asp His His His His His His
305                 310
```